US010472382B2

(12) United States Patent
Gordon et al.

(10) Patent No.: US 10,472,382 B2
(45) Date of Patent: *Nov. 12, 2019

(54) METHODS AND COMPOSITIONS FOR INCORPORATING NUCLEOTIDES

(71) Applicant: QIAGEN SCIENCES, LLC, Germantown, MD (US)

(72) Inventors: Steven Gordon, Weston, MA (US); Jerzy Olejnik, Brookline, MA (US)

(73) Assignee: QIAGEN SCIENCES, LLC, Germantown, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 16/193,639

(22) Filed: Nov. 16, 2018

(65) Prior Publication Data

US 2019/0119315 A1    Apr. 25, 2019

Related U.S. Application Data

(60) Continuation of application No. 15/480,043, filed on Apr. 5, 2017, now Pat. No. 10,174,066, which is a continuation of application No. 15/144,079, filed on May 2, 2016, now Pat. No. 9,644,237, which is a continuation of application No. 14/518,114, filed on Oct. 20, 2014, now Pat. No. 9,399,799, which is a division of application No. 13/305,415, filed on Nov. 28, 2011, now Pat. No. 9,017,973, which is a continuation of application No. 12/405,779, filed on Mar. 17, 2009, now abandoned.

(60) Provisional application No. 61/037,845, filed on Mar. 19, 2008.

(51) Int. Cl.
| | |
|---|---|
| *C07H 19/00* | (2006.01) |
| *G01N 21/05* | (2006.01) |
| *G01N 21/64* | (2006.01) |
| *C12Q 1/6869* | (2018.01) |
| *C12Q 1/6874* | (2018.01) |
| *G01N 21/03* | (2006.01) |

(52) U.S. Cl.
CPC .......... *C07H 19/00* (2013.01); *C12Q 1/6869* (2013.01); *C12Q 1/6874* (2013.01); *G01N 21/05* (2013.01); *G01N 21/645* (2013.01); *G01N 21/6428* (2013.01); *C12Q 2535/101* (2013.01); *G01N 2021/0346* (2013.01); *G01N 2021/058* (2013.01); *G01N 2021/6417* (2013.01); *G01N 2021/6419* (2013.01); *G01N 2021/6421* (2013.01); *G01N 2021/6439* (2013.01); *G01N 2021/6441* (2013.01); *G01N 2021/6471* (2013.01); *G01N 2201/062* (2013.01); *G01N 2201/0627* (2013.01); *G01N 2201/12* (2013.01)

(58) Field of Classification Search
CPC .................................................... C07H 19/00

USPC ...................... 536/4.1, 26.1, 26.6
See application file for complete search history.

(56) References Cited

U.S. PATENT DOCUMENTS

| | | | |
|---|---|---|---|
| 5,143,854 A | 9/1992 | Pirrung et al. | 436/518 |
| 5,302,509 A | 4/1994 | Cheeseman | 435/6 |
| 5,547,839 A | 8/1996 | Dower et al. | 435/6 |
| 5,571,639 A | 11/1996 | Hubbell et al. | 430/5 |
| 5,733,729 A | 3/1998 | Lipshutz et al. | 435/6.11 |
| 5,746,982 A | 5/1998 | Saneii et al. | 422/134 |
| 5,795,716 A | 8/1998 | Chee et al. | 435/6.11 |
| 6,066,454 A | 5/2000 | Lipshutz et al. | 506/8 |
| 6,107,061 A | 8/2000 | Johnson | 435/91.1 |
| 6,228,593 B1 | 5/2001 | Lipshutz et al. | 506/8 |
| 6,255,083 B1 | 7/2001 | Williams | 435/91.1 |
| 6,309,836 B1 | 10/2001 | Kwiatkowski | 435/6 |
| 6,355,420 B1 | 3/2002 | Chan | 435/6.12 |
| 6,485,944 B1 | 11/2002 | Church et al. | 435/91.2 |
| 6,546,340 B2 | 4/2003 | Lipshutz et al. | 702/20 |
| 6,598,013 B1 | 7/2003 | Domnisoru et al. | 702/191 |
| 6,664,079 B2 | 12/2003 | Ju et al. | 435/6.18 |
| 6,957,149 B2 | 10/2005 | Lipshutz et al. | 702/20 |
| 7,057,026 B2 | 6/2006 | Barnes et al. | 536/23.1 |
| 7,209,836 B1 | 4/2007 | Schermer et al. | 702/19 |
| 7,883,869 B2 | 2/2011 | Ju et al. | 435/91.1 |
| 9,399,799 B2 * | 7/2016 | Gordon | G01N 21/05 |
| 9,644,237 B2 * | 5/2017 | Gordon | G01N 21/05 |
| 10,174,066 B2 * | 1/2019 | Gordon | G01N 21/05 |
| 2003/0105195 A1 | 6/2003 | Holcomb | 524/102 |

(Continued)

FOREIGN PATENT DOCUMENTS

| | | |
|---|---|---|
| WO | WO 2005024010 | 3/2005 |
| WO | WO 2005040425 | 6/2005 |
| WO | WO 2009054922 | 4/2009 |

OTHER PUBLICATIONS

Azoulay et al., "A New Drug-release Method Using the Staudinger Ligation." *Bioorganic & Medicinal Chemistry Letters* 16(12): 3147-3149 (2006).

Bi et al., "Design and Synthesis of a Chemically Cleavable Fluorescent Nucleotide, 3'-O-Allyl-dGTP-allyl-Bodipy-FL-510, as a Reversible Terminator for DNA Sequencing by Synthesis." *J. Am. Chem Soc.* 128(8) 2542-3 (2006).

(Continued)

*Primary Examiner* — Jezia Riley
(74) *Attorney, Agent, or Firm* — Medlen & Carroll, LLP

(57) ABSTRACT

The invention provides methods and compositions, including, without limitation, algorithms, computer readable Media, computer programs, apparatus, and systems for determining the identity of nucleic acids in nucleotide sequences using, for example, data obtained from sequencing by synthesis methods. The methods of the invention include correcting one or more phenomena that are encountered during nucleotide sequencing, such as using sequencing by synthesis methods. These phenomena include, without limitation, sequence lead, sequence lag, spectral crosstalk, and noise resulting from variations in illumination and/or filter responses.

8 Claims, 66 Drawing Sheets

Specification includes a Sequence Listing.

(56) References Cited

U.S. PATENT DOCUMENTS

| | | | |
|---|---|---|---|
| 2003/0120471 A1 | 6/2003 | Izmailov et al. | 703/11 |
| 2004/0248161 A1 | 12/2004 | Rothberg et al. | 435/6.1 |
| 2006/0160075 A1 | 7/2006 | Balasubramanian et al. | 435/6 |
| 2006/0240439 A1 | 10/2006 | Smith | 435/6.12 |
| 2007/0117104 A1 | 5/2007 | Buzby | 435/6.11 |
| 2007/0166705 A1 | 7/2007 | Milton et al. | 435/6.11 |
| 2007/0194249 A1 | 8/2007 | Gavrilov et al. | 250/459.1 |
| 2010/0317012 A1 | 12/2010 | Ju et al. | 435/6 |
| 2014/0234832 A1 | 8/2014 | Olejnk | 435/6.1 |

OTHER PUBLICATIONS

Borchardt and Cohen, "Stereopopulation Control. II. Rate Enhancement of Intramolecular Nucleophilic Displacement." *J. Am. Chem. Soc.* 94(26): 9166-9174 (1972).

Carl et al., "A Novel Connector Linkage Applicable in Prodrug Design" *J. Med. Chem.* 24(5):479-480 (1981).

Duimstra et al., "A Gadolinium Chelate for Detection of B-Glucuronidase: A Self-Immolative Approach." *J. Am. Chem. Soc* 127(37): 12847-12855) (2005).

Eltoukhy et al., "Modeling and Base-Calling for DNA Sequencing-By-Synthesis." *IEEE International Conference on Acoustics, Speech and signal processing* 2:1032-1035 (2006).

Margulies et al., "Genome Sequencing in Microfabricated High-Density Picolotre Reactors." *Nature*, 437:376-380 (2005).

Metzker, "Emerging Technologies in DNA Sequencing." *Genome Res.*, 15(12): 1767-1776 (2005).

Murata et al., "A Novel Linker for Solid-Phase Synthesis Cleavable Under Neutral Conditions." *Tetrahedron Letters* 47(13): 2147-2150 (2006).

Ruparel et al., "Design and Synthesis of a 3'-O-allyl Photocleavable Fluorescent Nucleotide as a Reversible Terminator for DNA Sequencing by Synthesis." *Proc. Natl. Acad. Sci.* 102(17) 5932-7 (2005).

Shendure et al. "Advanced Sequencing Technologies: Methods and Goals." *Nature Reviews Genetics*, 5: 335-344 (2004).

Turcatti et al., "A New Class of Cleavable Fluorescent Nucleotides: Synthesis and Optimization as Reversible Terminators for DNA Sequencing by Synthesis." *Nucleic Acids Res.*, 36(4):e25 (2008).

Wada et al., "2-(Azidomethyl)benzoyl as a New Protecting Group in Nucleosides." *Tetrahedron Letters* 42(6): 1069-1072 (2001).

Wang et al., Development of a Novel Redox-Sensitive Protecting Group for Amines Which Utilizes a Facilitated Lactonization Reaction. *J. Org. Chem.* 60(3): 539-543 (1995).

Wang et al., "Structural Analysis of a Facile Lactonization System Facilitated by a "Trimethyl Lock"." *Bioorg. Chem.* 24: 39-49 (1996).

Wang et al., "Synthesis of a Novel Esterase-Sensitive Cyclic Prodrug System for Peptides That Utilizes a "Trimethyl Lock"—Facilitated Lactonization Reaction." *J. Org. Chem.* 62(5): 1363-1367 (1997).

Xu et al., "(2-Azidomethyl)phenylacetyl as a New, Reductively Cleavable Protecting Group for Hydroxyl Groups in Carbohydrate Synthesis." *Carbohydrate Research* 337(2): 87-91 (2002).

Seo, et al., "Four-color DNA sequencing by synthesis on a chip using photocleavable fluorescent nucleotides." *PNAS*, 102(1), 5926-5931 (2005).

Zavgorodny, et al.,"S,X-Acetals in NucleosideChemistry. III1. Synthesis of 2'-and 3'-Ozidomethyl Derivatives of Ribonucleosides." *Nucleosides, Nucleotides & Nucleic Acids*, 19(10-12), 1977-1991 (2000).

Hovinen, et al., "Novel Solid Supports for the Preparation of 3'-Derivatized Oligonucleotides: Introduction of 3'-Alkylphosphate Tether Groups Bearing Amino, Carboxy, Calboxamido, and Mercapto Functionalities." Tetrahedron 50(24):7203-7218 (1994).

McDonnell, et al., "Zinc ejection as a new rationale for the use of cystamine and related disulfide-containing antiviral agents in the treatment of AIDS." J Med Chem. 40:1969-1976 (1997).

Lee, et al., "Reactivity of acetylenyl-terminated self-assembled monolayers on gold: triazole formation." *Langmuir* 20(10):3844-7 (2004).

Giddings et al., "An Adaptive Object Oriented Strategy for Base Calling in DNA Sequence Analysis." *Nucleic Acids Research* 21:4530-4540 (1993).

Izmailov et al., "A General Approach to the Analysis of Errors and Failure Modes in the Base Calling Function in Automated Flourescent DNA Sequencing." *Electrophoresis* 23:2720-2728 (2002).

Nakamura, et al., "Conformational Changes in Seventeen Cystine Disulfide Bridges of Bovine Serum Albumin Proved by Raman Spectroscopy." *FEBS Lett*, 417(3):375-378 (1997).

\* cited by examiner

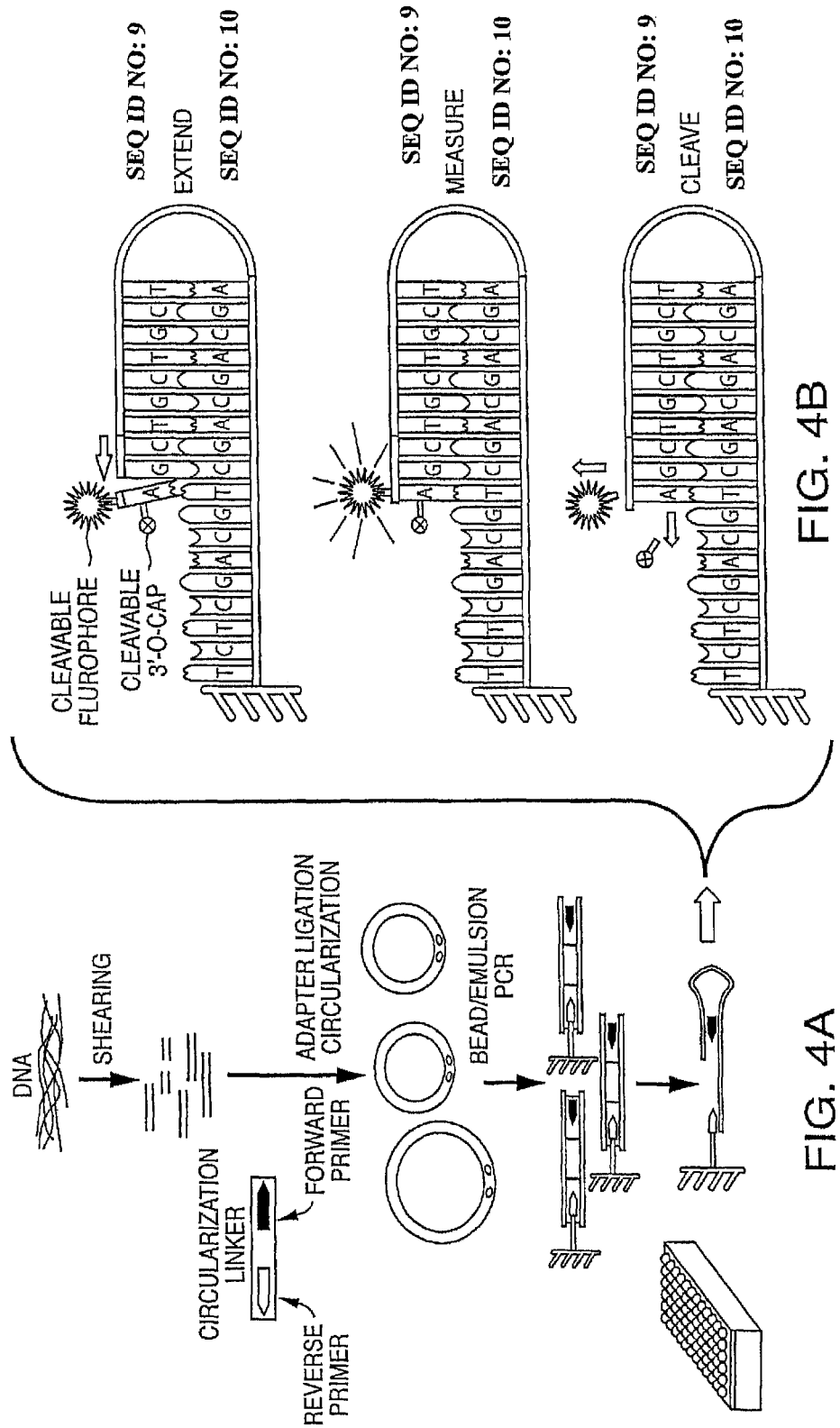

SYNTHETIC DNA TEMPLATES USED IN THE SEQUENCING EXPERIMENT.

SEQ ID NO: 1  5'-NH2-CAT CAC TCT CAC ATG TCA GAC TCG AGC TGAATT CCG CGT TCG CGG AAT TCA GC-3'

TEMPLATE 20

SEQ ID NO: 2  5'-NH2-GCG AAA AAG AAG AGA TGG GGT GAA GGC TGA ATT CCG CGT TCG CGG AAT TCA GC-3'

TEMPLATE 21

SEQ ID NO: 3  5'-NH2-TGA TTT CGC TTT TAC CCT ACA CTC TGC TGA ATT CCG CGT TCG CGG AAT TCA GC-3'
TEMPLATE 22

SEQ ID NO: 4  5'-NH2-ATC GCC CTA TAT TCT AAC TTG ACT CGC TGA ATT CCG CGT TCG CGG AAT TCA GC-3'
TEMPLATE 23

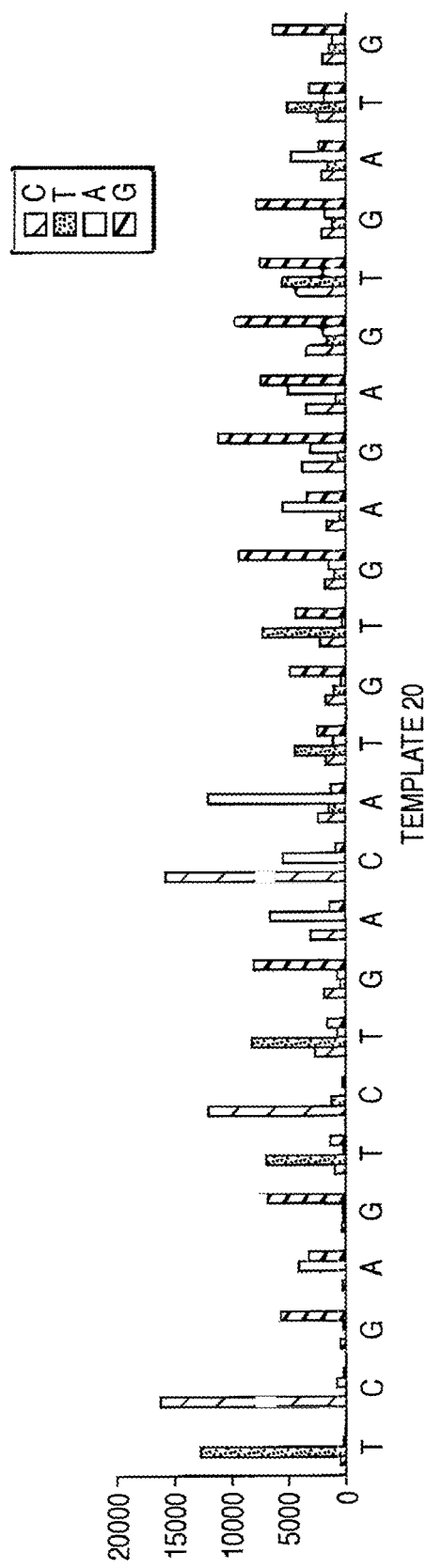
FIG. 24A  TEMPLATE 20  SEQ ID NO 6
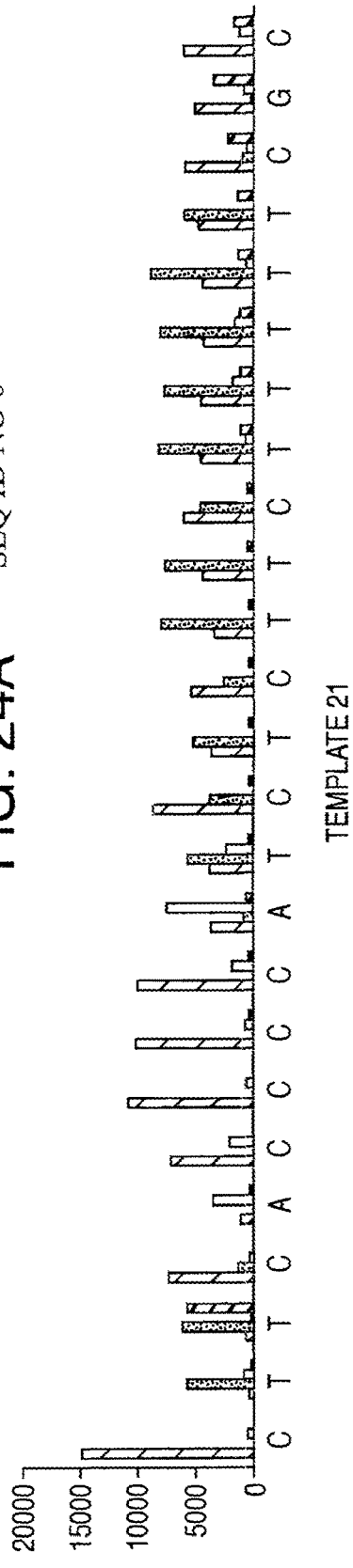
FIG. 24B  TEMPLATE 21  SEQ ID NO 7

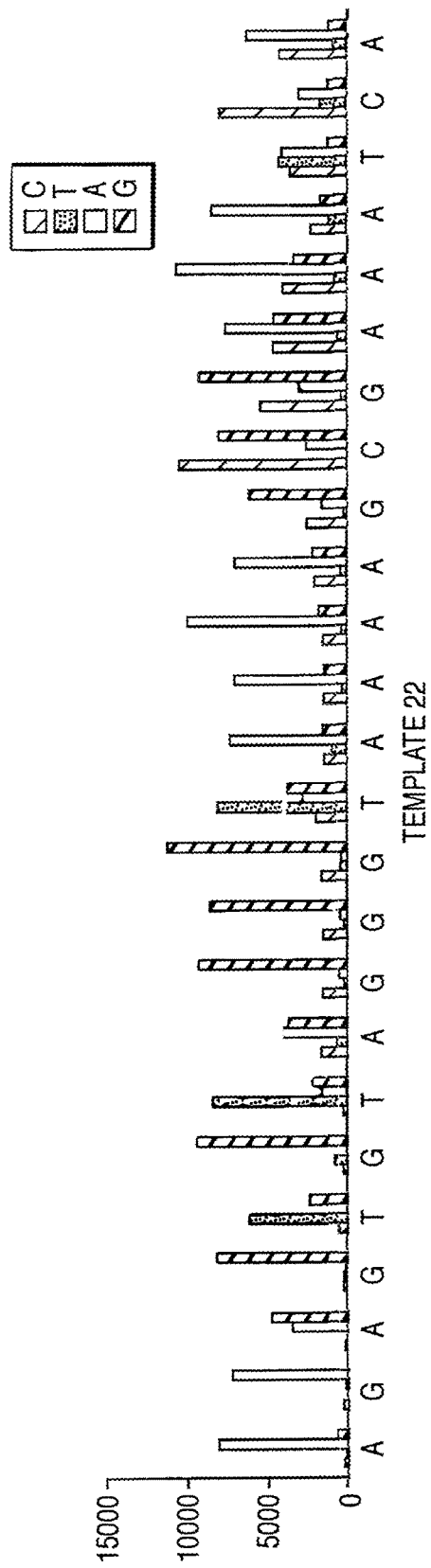
FIG. 24C  TEMPLATE 22  SEQ ID NO 8
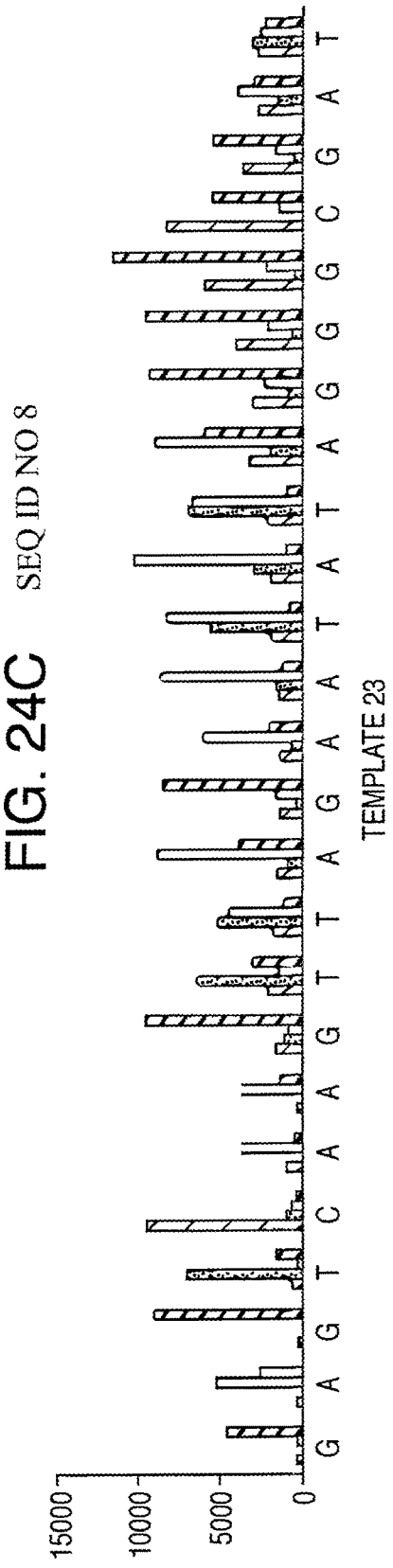
FIG. 24D  TEMPLATE 23  SEQ ID NO 9

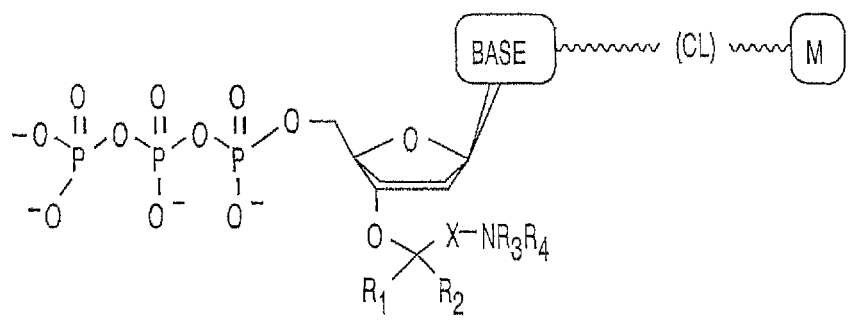
X = O, NH; $R_1, R_2, R_3, R_4,$ = H, ALKYL GROUP
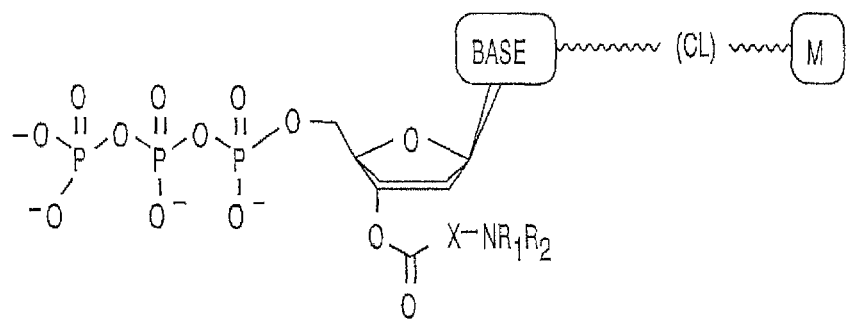
X = O, NH; $R_1, R_2,$ = H, ALKYL GROUP
FIG. 27

CONDITIONS: HONO/OTHER NO+ SOURCES, H2O2/HORSE RADISH PEROXIDASE, OTHER MILD OXIDIZING AGENTS THAT GENERATE REACTIVE OXYGEN SPECIES.

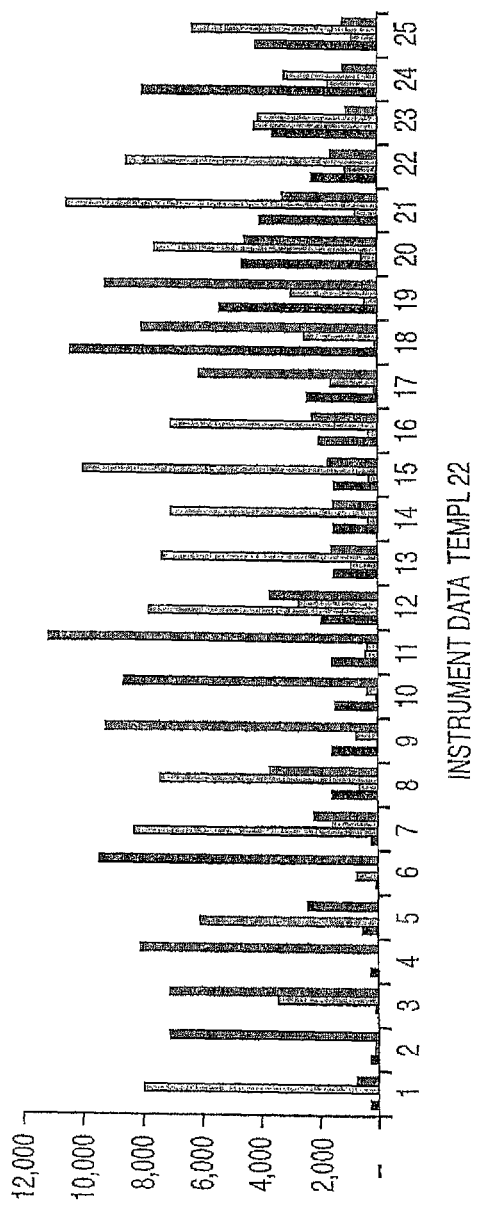
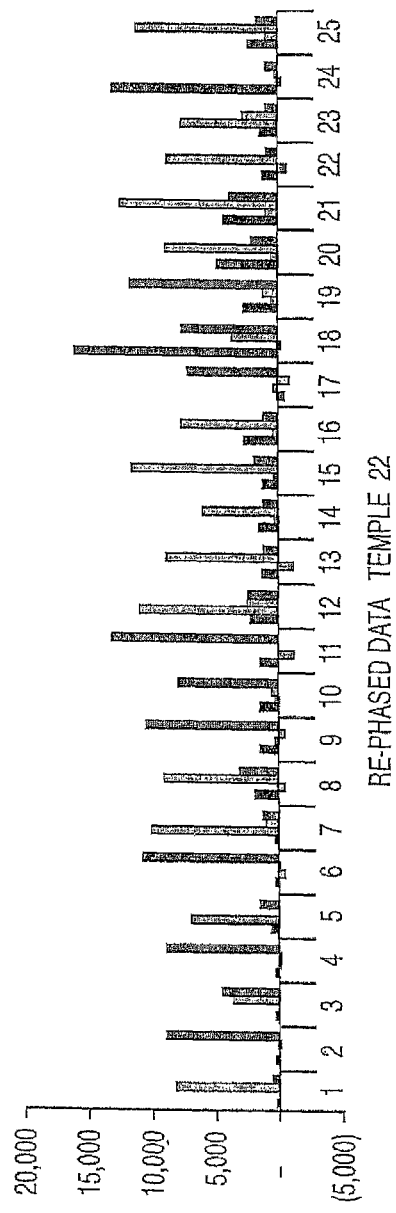
FIG. 34A
FIG. 34B

FIGURE 35

FIGURE 39
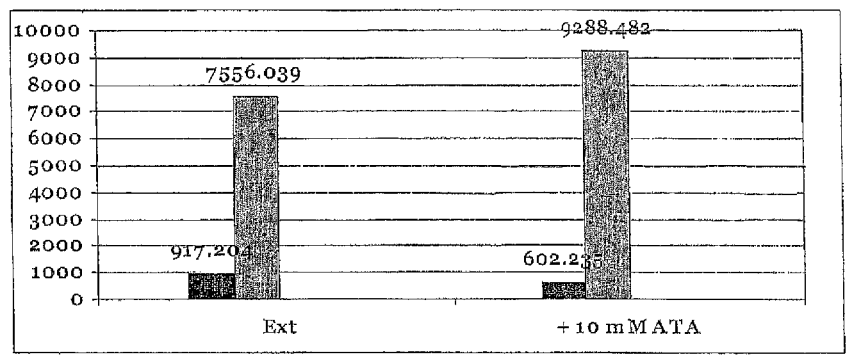
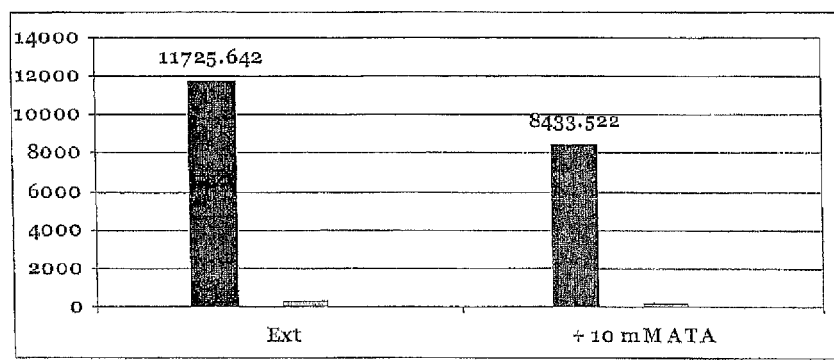
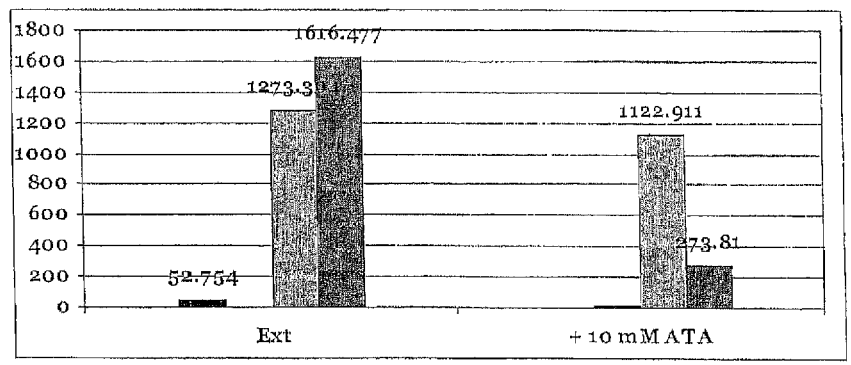
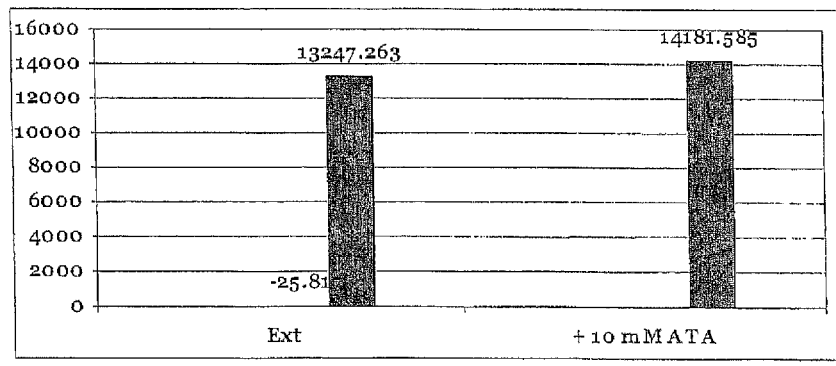

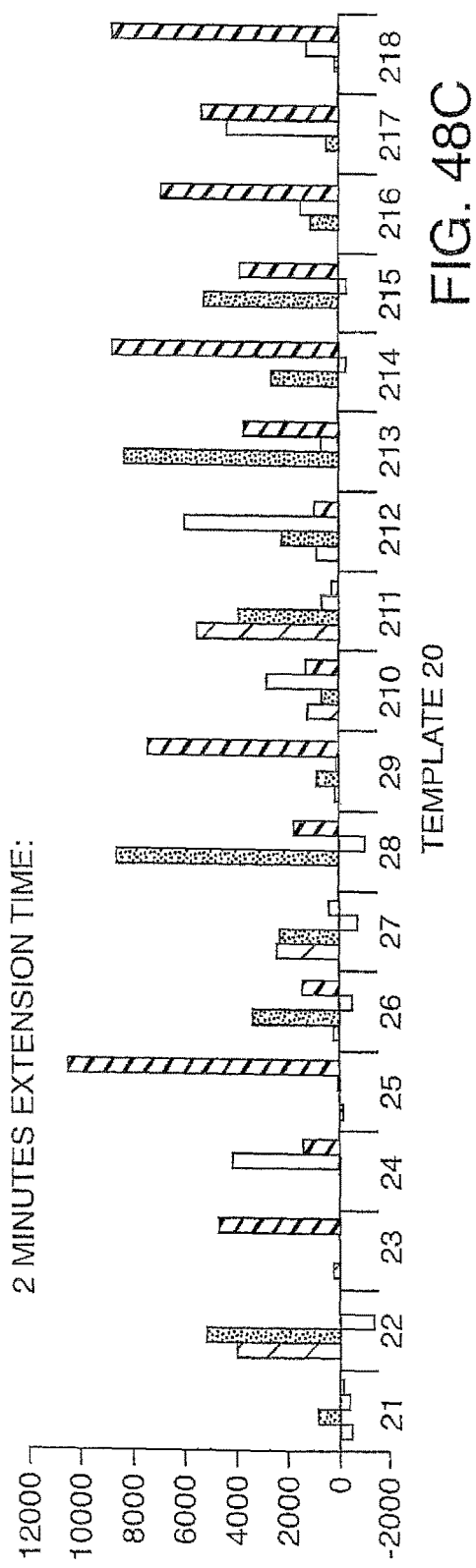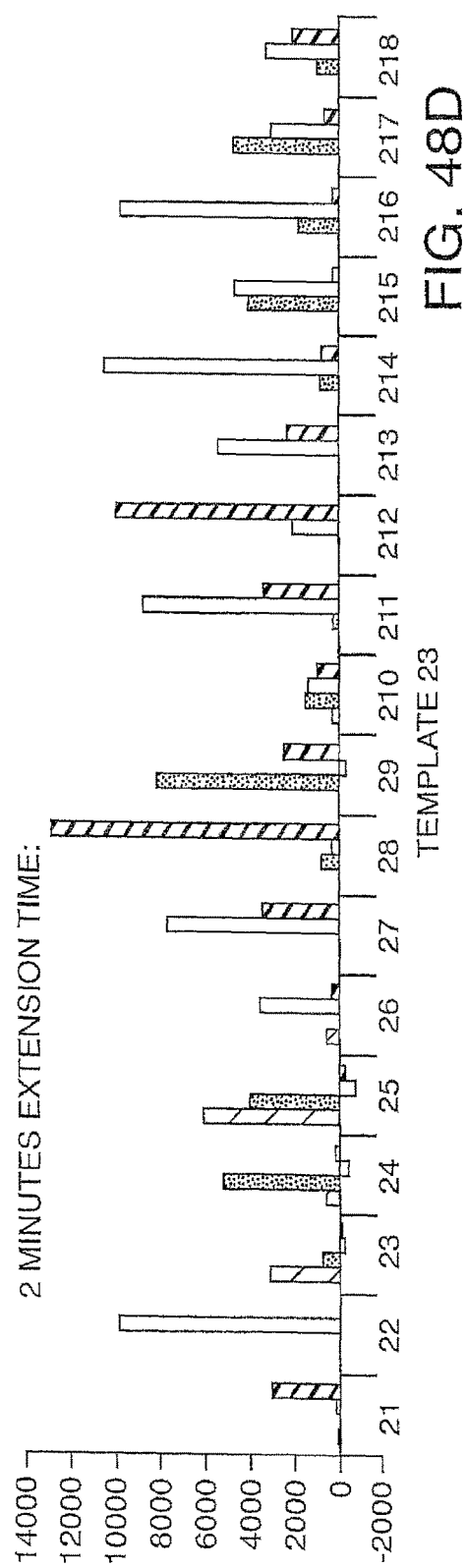

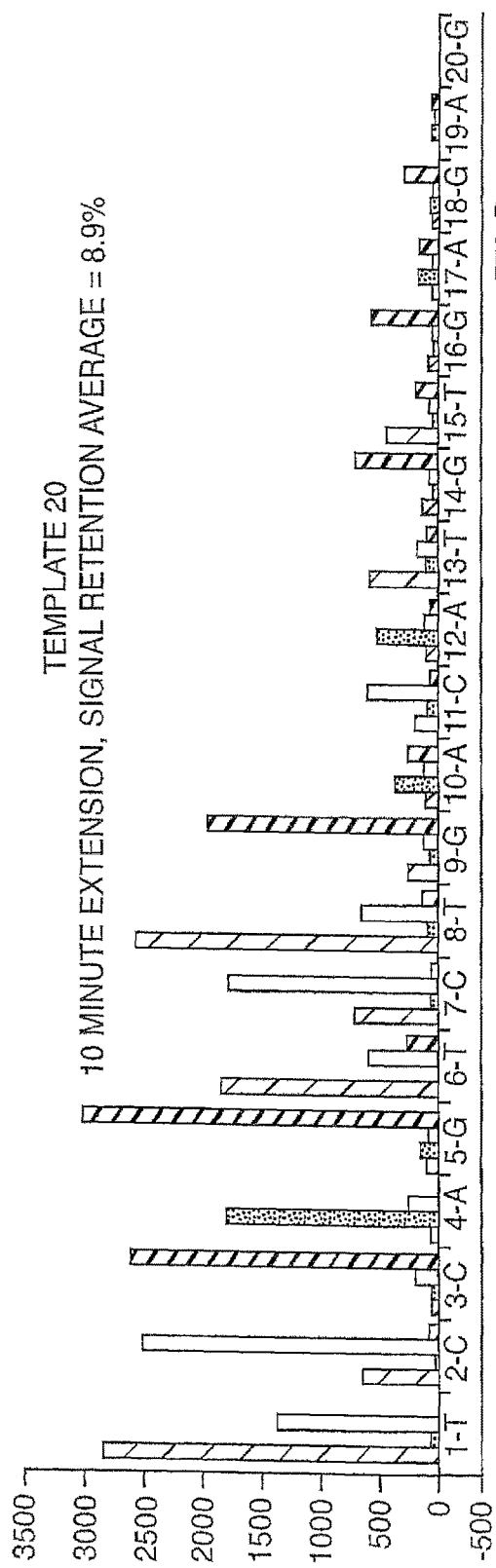
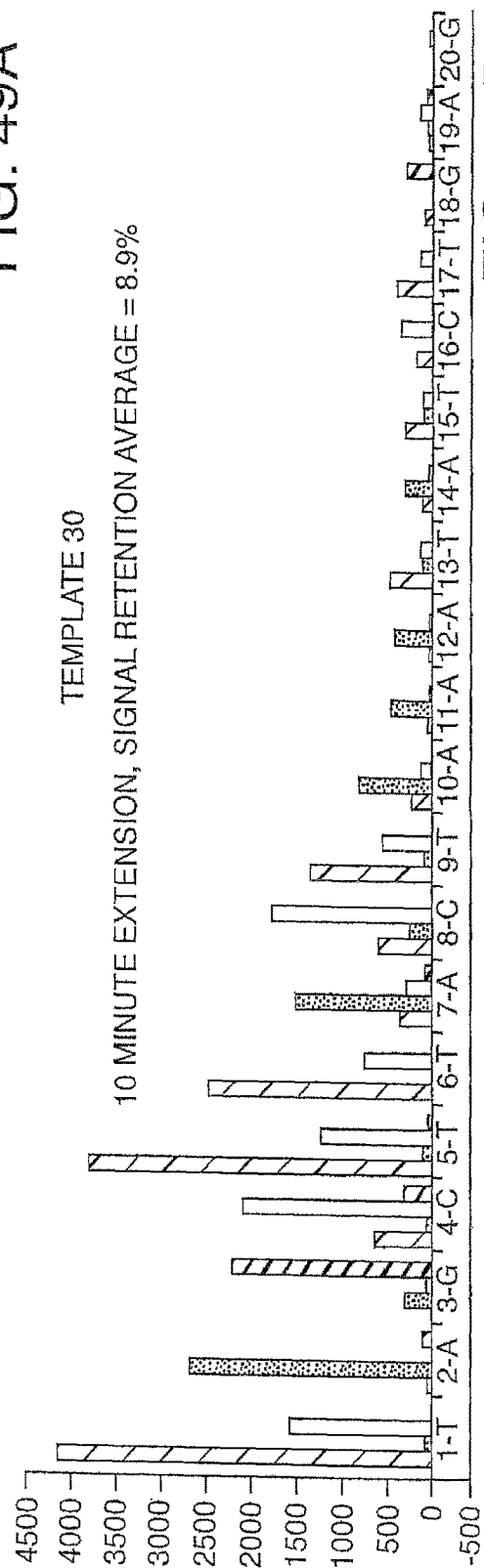
FIG. 49A
FIG. 49B

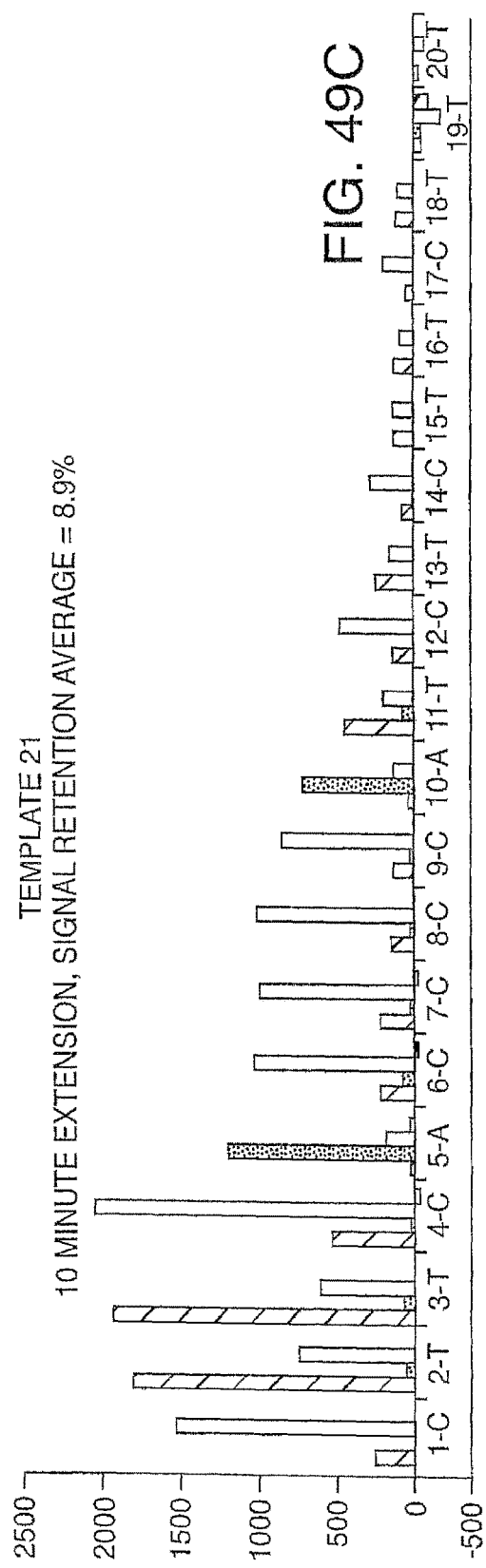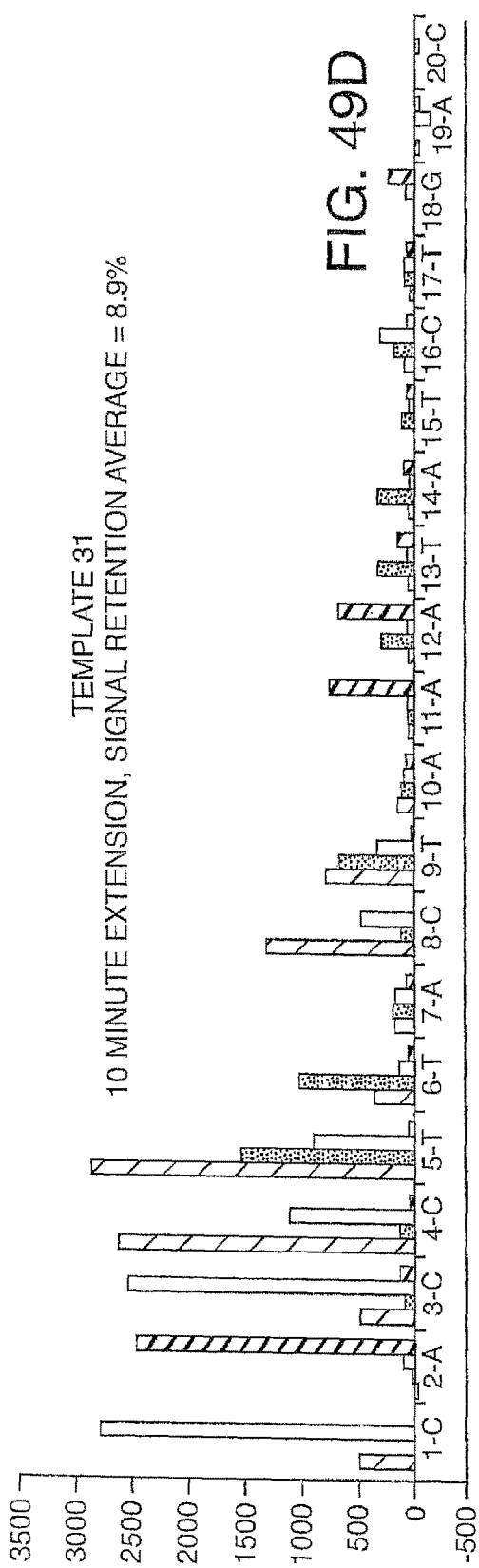

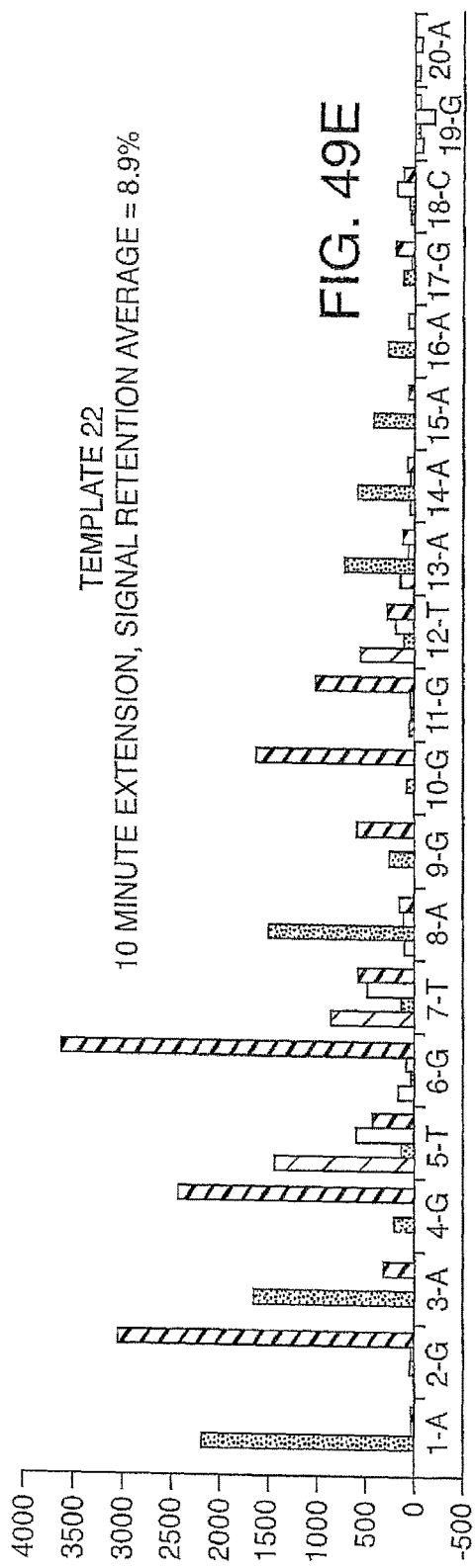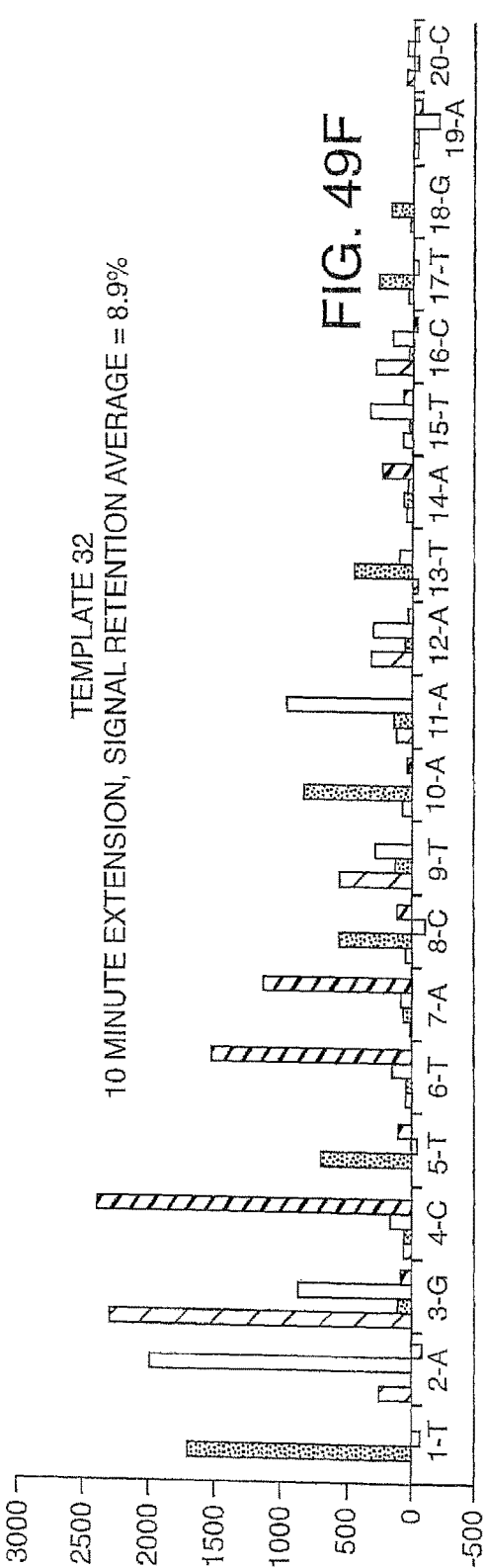

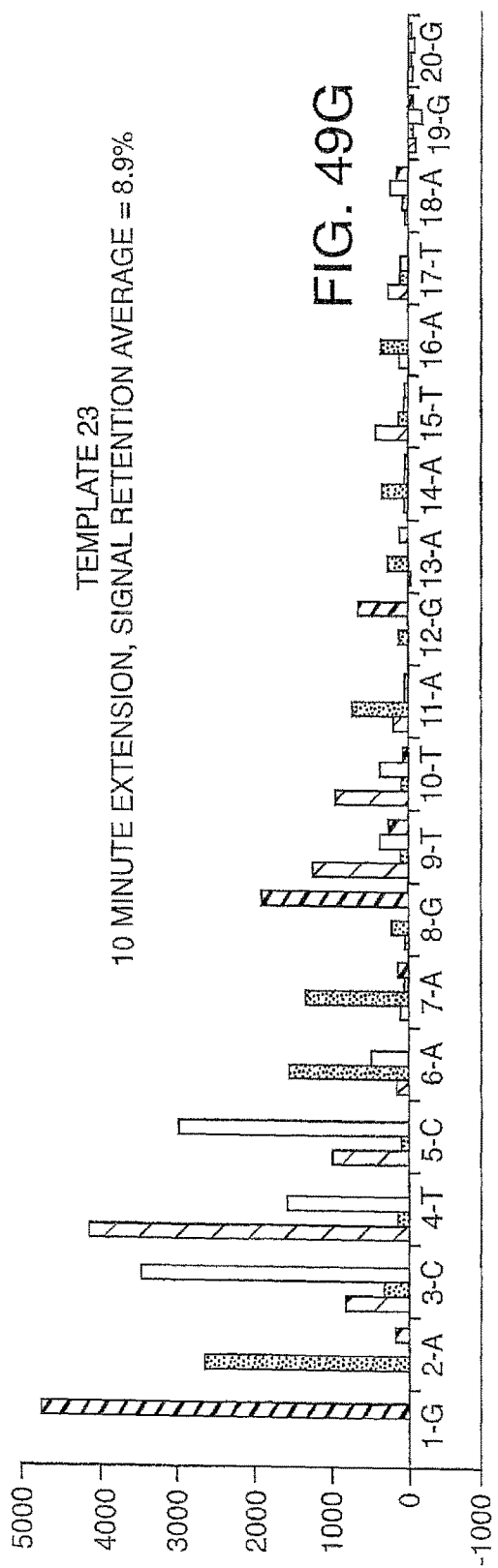
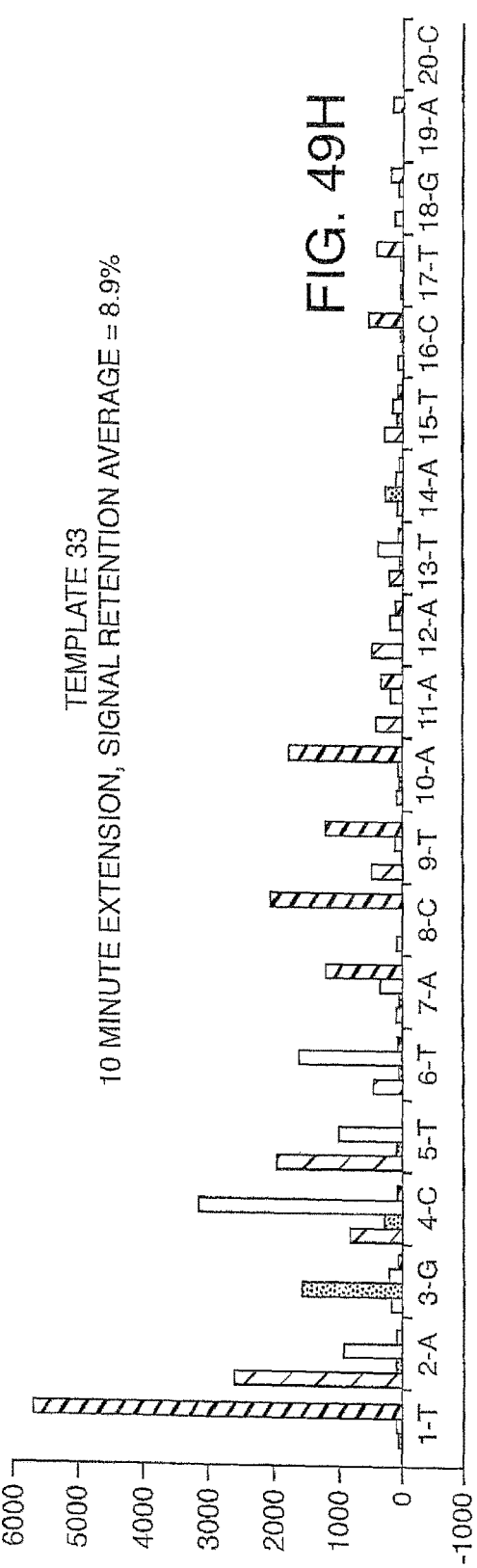

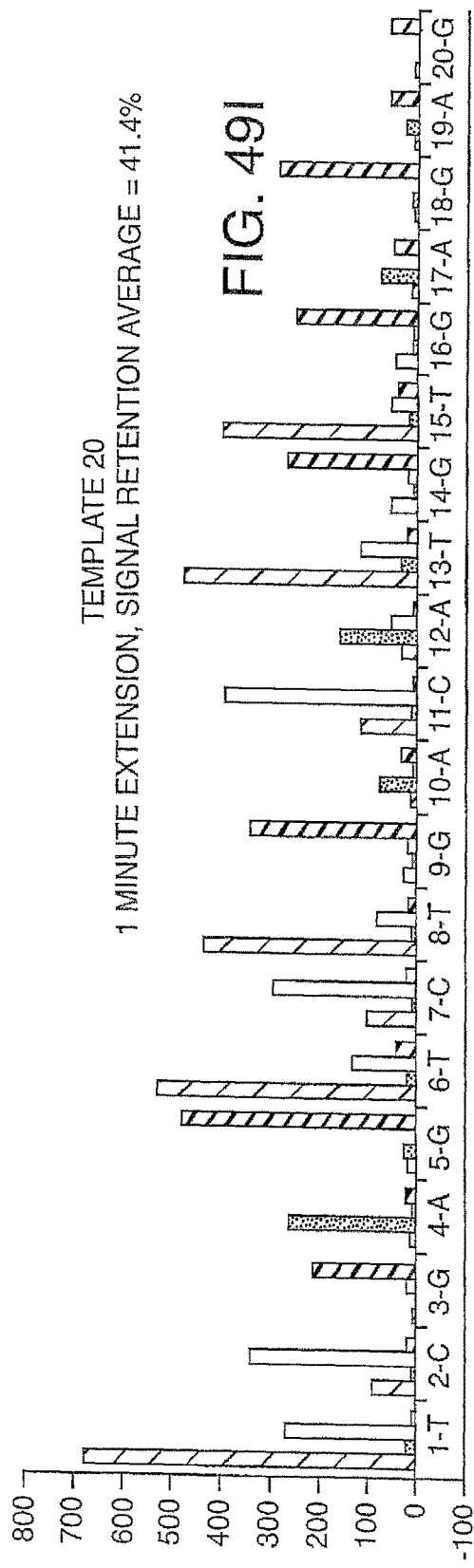
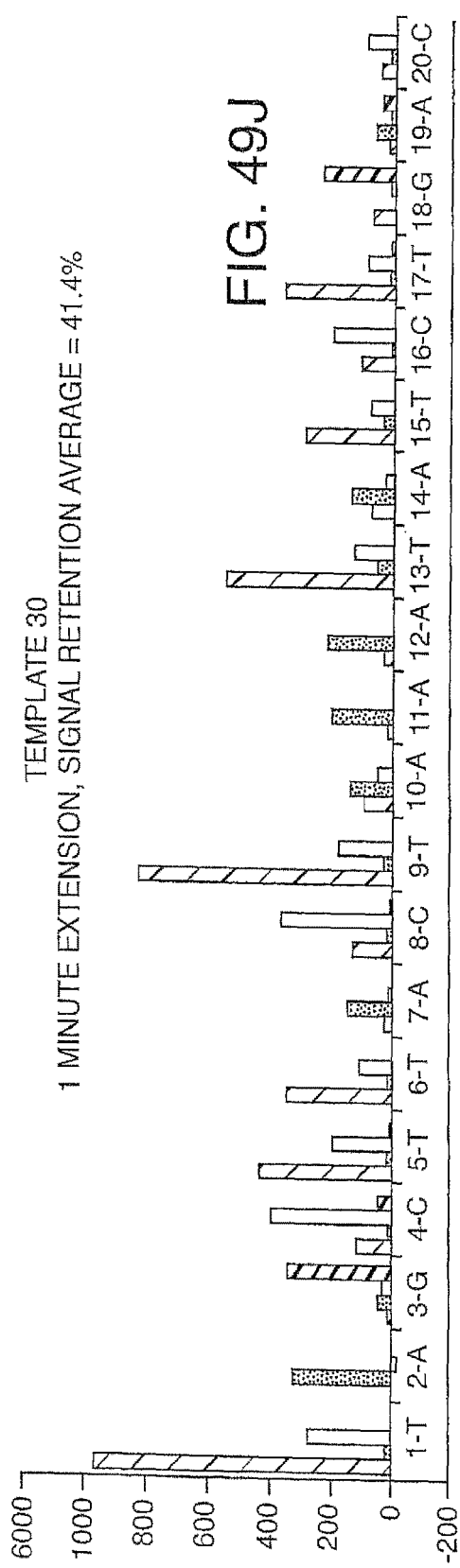

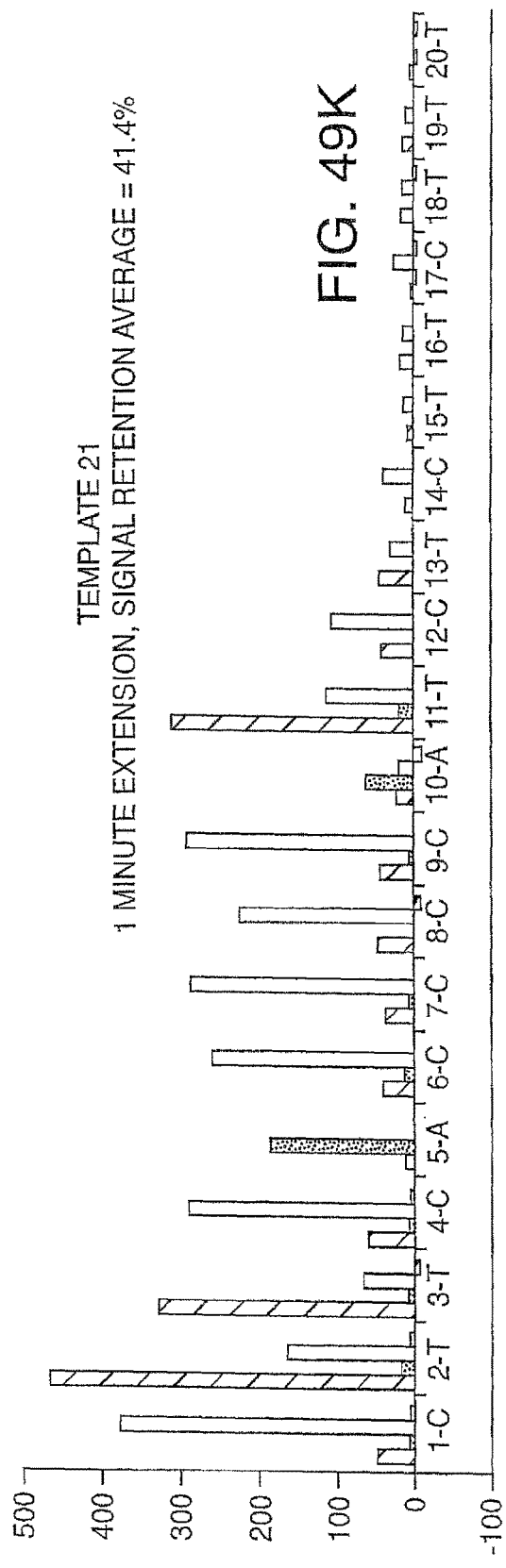
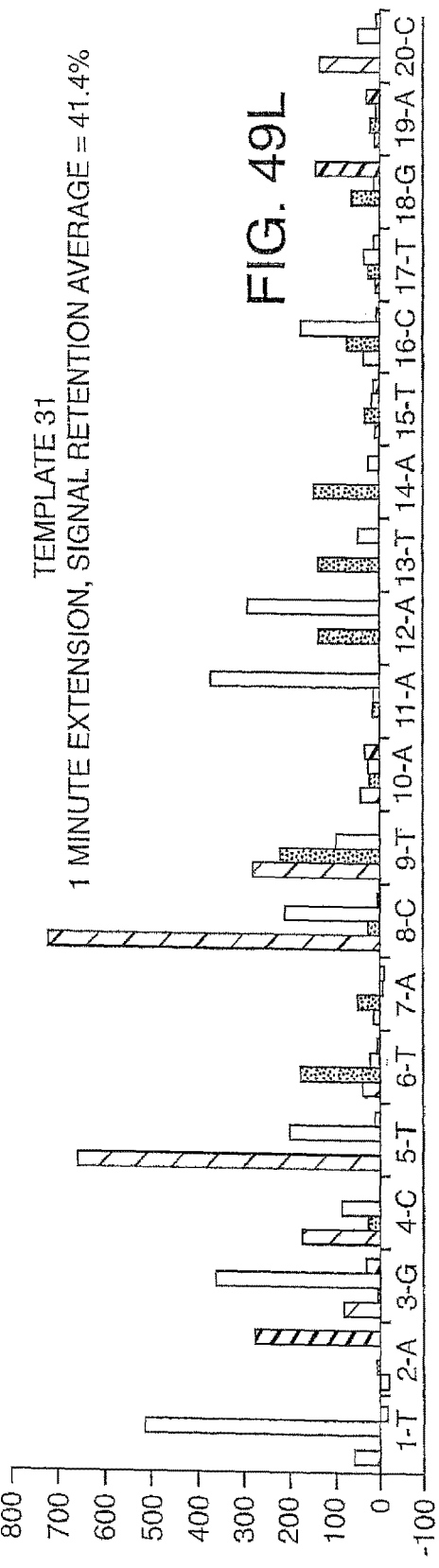

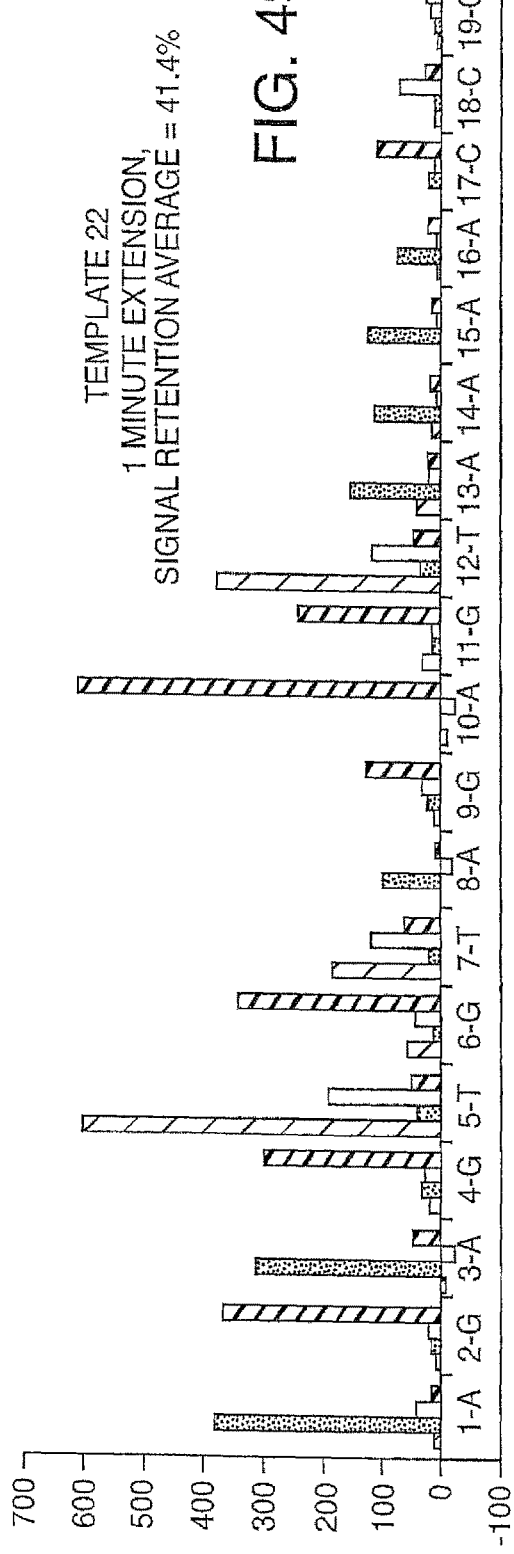
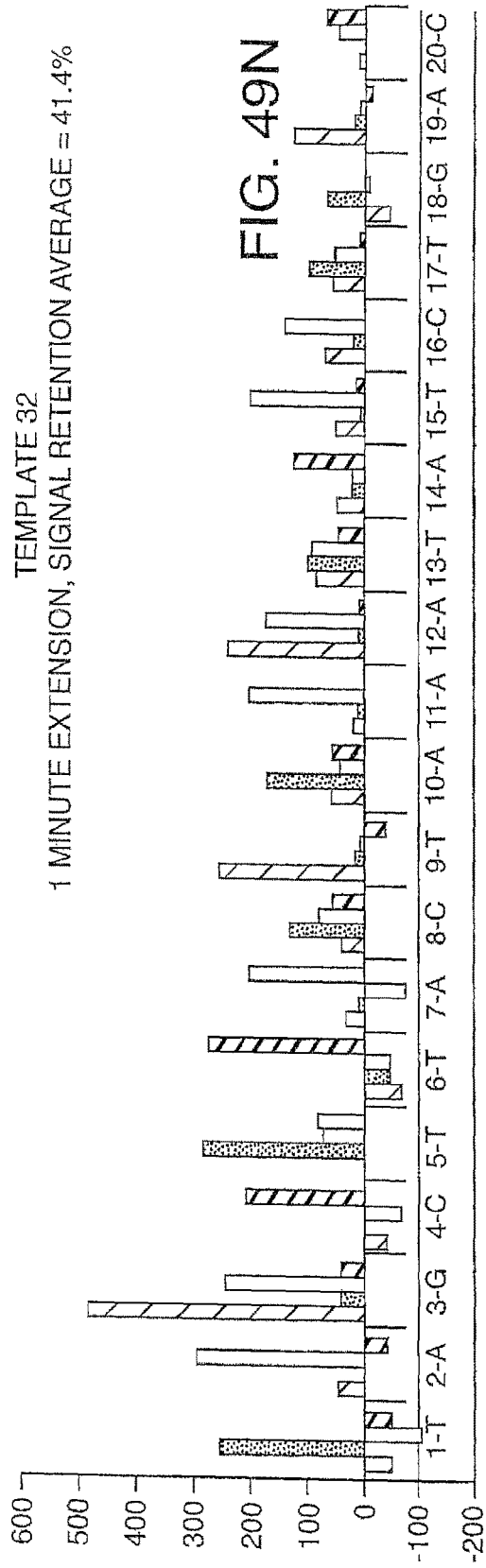

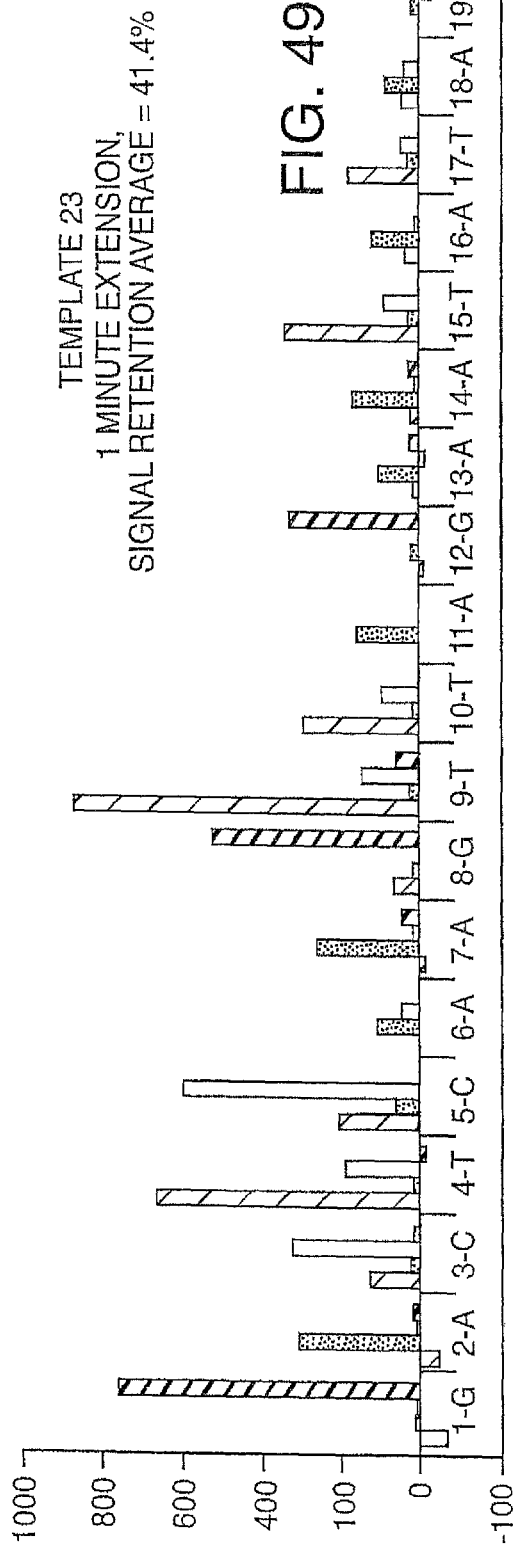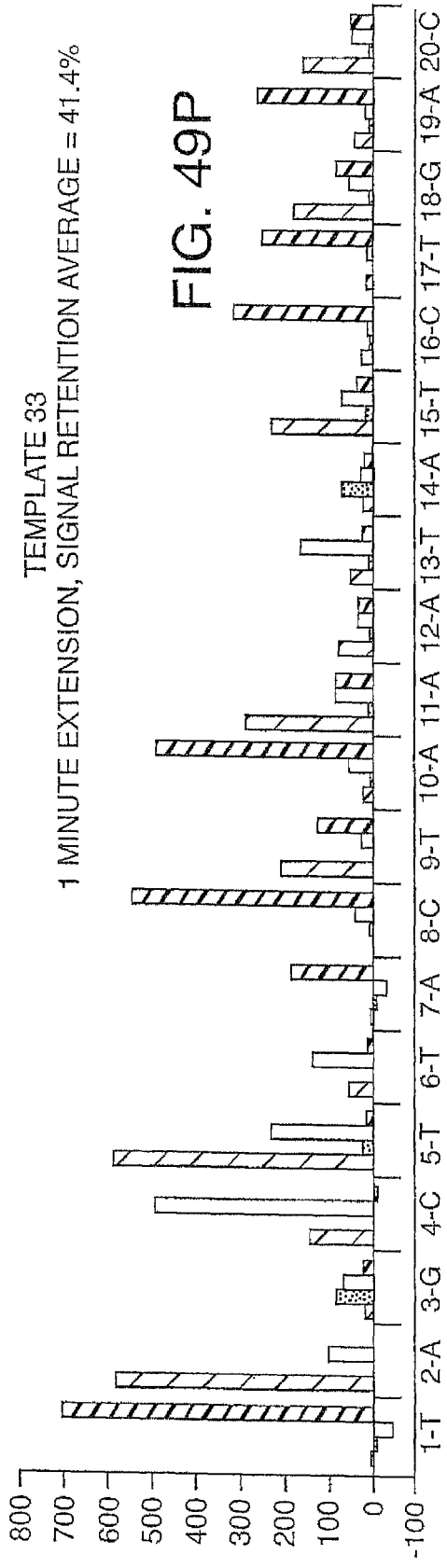

METHODS AND COMPOSITIONS FOR INCORPORATING NUCLEOTIDES

FIELD OF THE INVENTION

The invention relates to methods, compositions, devices, systems and kits are described including, without limitation, reagents, mixtures, data processing steps, algorithms, computer readable media, and computer programs, for determining the identity of nucleic acids in nucleotide sequences using, for example, data obtained from sequencing by synthesis methods.

BACKGROUND OF THE INVENTION

Over the past 25 years, the amount of DNA sequence information that has been generated and deposited into Genbank has grown exponentially. Many of the next-generation sequencing technologies use a form of sequencing by synthesis (SBS), wherein specially designed nucleotides and DNA polymerases are used to read the sequence of chip-bound, single-stranded DNA templates in a controlled manner. To attain high throughput, many millions of such template spots are arrayed across a sequencing chip and their sequence is independently read out and recorded.

Devices, equations, and computer systems for forming and using arrays of material on a substrate for DNA sequencing are known (e.g., Ju et al., U.S. Pat. No. 6,664,079; Pirrung et al., U.S. Pat. No. 5,143,854; Hubbell et al., U.S. Pat. No. 5,71,639; Lipshutz et al., U.S. Pat. Nos. 6,957,149, 5,733,729, 6,066,454, 6,228,593 and 6,546,340; Chee et al., U.S. Pat. No. 5,795,716; Donanisoru et al., U.S. Pat. No. 6,598,013; Schermer et al., U.S. Pat. No. 7,209,836; Gavrilov et al., U.S. Pat. Application No. 2007/0194249; Eltoukhy et al. In: IEEE International Conference on Acoustics, Speech and signal processing, (2006) 2:1032-1035; Margulies et al. (2005) Nature 437:376-380; and Gerardo et al. (2008) Nucleic Acids Res. (2008) 36(4):e25). However, there is a continued need for methods and compositions for increasing the fidelity of sequencing nucleic acid sequences.

SUMMARY OF THE INVENTION

The invention provides methods, compositions, devices, systems and kits are described including, without limitation, reagents, mixtures, data processing steps, algorithms, computer readable media, and computer programs, for determining the identity of nucleic acids in nucleotide sequences using, for example, data obtained from sequencing by synthesis methods. The methods of the invention include reducing and/or correcting one or more phenomena that are encountered during nucleotide sequencing, such as using sequencing by synthesis methods. These phenomena include, without limitation, sequence lead, sequence lag, spectral crosstalk, light from neighboring spots, and noise resulting from variations in illumination and/or filter responses.

In one embodiment, the present invention contemplates a set of data processing steps that may be used to analyze images of a hexagonal array of spots or beads on a surface. In one embodiment, the steps comprise a) field flattening and background subtraction, b) spot location in the array, c) image sharpening, d) spot brightness determination, e) neighbor influence elimination, and f) color crosstalk elimination. Each of these steps is described in more detail below. Of course, in one embodiment, the present invention contemplates using a subset of these steps (in the same order or in a different order) as well as additional processing steps. The result of the analysis may be used to make measurements of the output of four different fluorescent dyes for each spot in the array. The methods described may also be generalized for a rectangular or other shaped arrays rather than a hexagonal array.

In one embodiment, the invention provides a method for determining an identity of a nucleic acid at an interrogation position in a nucleotide sequence from data acquired from one or more channels, comprising a) obtaining a data set for one or more probe intensities at one or more nucleic acid positions in the sequence, wherein each probe corresponds to a nucleic acid, b) determining the ratio contribution to probe intensity at the interrogation position from probe intensities at the interrogation position and at one or both of i) at least one subsequent nucleic acid positions in the sequence, and ii) at least one preceding nucleic acid positions in the sequence, and c) applying the ratio contribution to probe intensity to the data set to arrive at an identity for a nucleic acid at the interrogation position in the nucleotide sequence. In a particular embodiment, the step of determining the ratio contribution to probe intensity comprises measuring the rate (that is, the fraction of template molecules in an ensemble of identical template molecules) at which a lag, such as $G_i$, occurs at one or more nucleotide position in the nucleotide sequence, such as at each nucleotide position in the nucleotide sequence. In another embodiment, the step of determining the ratio contribution to probe intensity comprises measuring the rate (fraction) at which a lead, such as $D_i$, occurs at one or more nucleotide positions in the nucleotide sequence. In yet another embodiment, the method further comprises calling a nucleic acid at the interrogation position in the nucleotide sequence. In a further embodiment, the method comprises repeating steps b) and c) to arrive at an identity for a nucleic acid at more than one interrogation position in the nucleotide sequence.

While not intending to limit the invention's method to particular steps, in one embodiment, the method further comprises a) applying a sequence lead-lag compensation equation to determine the ratio contribution to probe intensity from probe at i) the interrogation position, ii) each position preceding the interrogation position, and iii) each position subsequent to the interrogation position, and b) summing up the ratio contribution to probe intensity. In an alternative embodiment, the step of applying of the ratio contribution to probe intensity comprises a) comparing probe intensities from the one or more channels at the interrogation position, b) selecting the highest probe intensity of the compared probe intensities, and c) calling a nucleic acid, which corresponds to the selected probe, at the interrogation position.

It is not intended to limit the invention to a particular mathematical formula. Nonetheless, in one embodiment, the method comprises applying a sequence lead-lag compensation equation to the ratio contribution to probe intensity at a plurality of positions in the sequence. In one particular embodiment, the sequence lead-lag compensation equation is determined by applying equation $$\begin{bmatrix} I_{M1} \\ I_{M2} \\ \vdots \\ I_{MN} \end{bmatrix} = K_{Lead/Lag} \begin{bmatrix} I_{A1} \\ I_{A2} \\ \vdots \\ I_{AN} \end{bmatrix}$$

where
- $I_{M1}$ is a probe intensity measured at position 1 in the sequence,
- $I_{M2}$ is a probe intensity measured at position 2 in the sequence,
- $I_{MN}$ is a probe intensity measured at position N in the sequence,
- $I_{A1}$ is the actual probe intensity at position 1 in the sequence,
- $I_{A2}$ is the actual probe intensity at position 2 in the sequence,
- $I_{AN}$ is the actual probe intensity at position N in the sequence, where $$K_{Lead/Lag} = \begin{bmatrix} R_{Lag/Lead,1} & R_{+1Lead,1} & R_{+2Lead,1} & R_{+3Lead,1} & \cdots & R_{+(N-1)Lag,1} \\ R_{-1Lag,2} & R_{Lag/Lead,2} & R_{+1Lead,2} & R_{+2Lead,2} & \cdots & R_{+(N-2)Lag,2} \\ R_{-2Lag,3} & R_{-1Lag,3} & R_{Lag/Lead,3} & R_{+1Lead,3} & \cdots & R_{+(N-3)Lag,3} \\ R_{-3Lag,4} & R_{-2Lag,4} & R_{-1Lag,4} & R_{Lag/Lead,4} & \cdots & R_{+(N-4)Lag,4} \\ \vdots & \vdots & \vdots & \vdots & \ddots & \vdots \\ R_{-(N-1)Lag,N} & R_{-(N-2)Lag,N} & R_{-(N-3)Lag,N} & R_{-(N-4)Lag,N} & \cdots & R_{Lag/Lead,N} \end{bmatrix}$$

where
- $R_{Lag/Lead,1}$ is the ratio between reduced probe intensity for nucleic acid at position 1 to actual probe intensity at the nucleic acid at position 1,
- $R_{+1Lead,1}$ is the ratio contribution to probe intensity at nucleic acid position 1 from probe at nucleic acid position 2,
- $R_{+2Lead,1}$ is the ratio contribution to probe intensity at nucleic acid position 1 from probe at nucleic acid position 3,
- $R_{+3Lead,1}$ is the ratio contribution to probe intensity at nucleic acid position 1 from probe at nucleic acid position 4,
- $R_{+(N-1)Lead,1}$ is the ratio contribution to probe intensity at nucleic acid position 1 from probe at nucleic acid position 1+(N−1),
- $R_{-1Lag,2}$ is the ratio contribution to probe intensity at nucleic acid position 2 from probe at nucleic acid position 1,
- $R_{Lag/Lead,2}$ is the ratio between reduced probe intensity for nucleic acid at position 2 to actual probe intensity at the nucleic acid at position 2,
- $R_{+1Lead,2}$ is the ratio contribution to probe intensity at nucleic acid position 2 from probe at nucleic acid position 3,
- $R_{+2Lead,2}$ is the ratio contribution to probe intensity at nucleic acid position 2 from probe at nucleic acid position 4,
- $Rd_{+(N-2)Lead,2}$ is the ratio contribution to probe intensity at nucleic acid position 2 from probe at nucleic acid position 2+(N−2),
- $R_{-2Lag,3}$ is the ratio contribution to probe intensity at nucleic acid position 3 from probe at nucleic acid position 1,
- $R_{-1Lag,3}$ is the ratio contribution to probe intensity at nucleic acid position 3 from probe at nucleic acid position 2,
- $R_{Lag/Lead,3}$ is the ratio between reduced probe intensity for nucleic acid at position 3 to actual probe intensity at the nucleic acid at position 3,
- $R_{+1Lead,3}$ is the ratio contribution to probe intensity at nucleic acid position 3 from probe at nucleic acid position 4,
- $R_{+(N-3)Lead,3}$ is the ratio contribution to probe intensity at nucleic acid position 3 from probe at nucleic acid position 3+(N−3),
- $R_{3Lag,4}$ is the ratio contribution to probe intensity at nucleic acid position 4 from probe at nucleic acid position 1,
- $R_{-2Lag,4}$ is the ratio contribution to probe intensity at nucleic acid position 4 from probe at nucleic acid position 2,
- $R_{-1Lag,4}$ is the ratio contribution to probe intensity at nucleic acid position 4 from probe at nucleic acid position 3,
- $R_{Lag/Lead,4}$ is the ratio between reduced probe intensity for nucleic acid at position 4 to actual probe intensity at the nucleic acid at position 4,
- $R_{+(N-4)Lead,4}$ is the ratio contribution to probe intensity at nucleic acid position 4 from probe at nucleic acid position 4+(N−4),
- $R_{-(N-1)Lag,N}$ the ratio contribution to probe intensity at nucleic acid position N from probe at nucleic acid position N−(N−1),
- $R_{-(N-2)Lag,N}$ is the ratio contribution to probe intensity at nucleic acid position N from probe at nucleic acid position N−(N−2),
- $R_{-(N-3)Lag,N}$ is the ratio contribution to probe intensity at nucleic acid position N from probe at nucleic acid position N−(N−3),
- $R_{-(N-4)Lag,N}$ is the ratio contribution to probe intensity at nucleic acid position N from probe at nucleic acid position N−(N−4), and
- $R_{Lag/Lead,N}$ is the ratio between reduced probe intensity for nucleic acid at position N to actual probe intensity at the nucleic acid at position N.

In a further embodiment, the sequence lead-lag compensation equation is determined by applying equation $$\begin{bmatrix} I_{M1} \\ I_{M2} \\ \vdots \\ I_{MN} \end{bmatrix} = K_{Lead/Lag} \begin{bmatrix} I_{A1} \\ I_{A2} \\ \vdots \\ I_{AN} \end{bmatrix}$$

In a particular embodiment, the nucleic acid comprises a base selected from the group of adenine (A), guanine (G), cytosine (C), thymine (T), and uracil (U), and the probe is detectable using any means such as color in the visible spectrum (e.g., fluorescence), radioactivity, and the like.

While not intending to limit the invention's methods to particular steps, in one embodiment, the methods further comprise field flattening of background data for the data set. This may be accomplished by, for example, a) obtaining a first data set for a plurality of pixel intensities of a first raw image of a probe at a first concentration on a solid support, wherein the first raw image is produced using a first spectral filter for detecting a first probe, b) obtaining a second data set for a plurality of pixel intensities of a second smoothed image of the probe uniformly spread on the solid support or other uniformly radiating substrate, wherein the second smoothed image is produced using a low pass filter, c) determining a field flattening intensity value for a plurality of pixels of the first raw image, and d) generating a third field flattened image of the probe on the solid support using the field flattening intensity of the plurality of pixels, wherein the correlation of intensity of a plurality of pixels to their spatial location on the third field flattened image is reduced compared to the intensity of a plurality of pixels at a corresponding location on the first raw image. In a particular embodiment, the background intensities are removed from both the first and second data sets so that the lowest intensity data point is at 0.

Although the field flattening methods are not intended to be limited to any particular equation, in one embodiment, the field flattening intensity value of a pixel is determined by equation $$F_{x,y} = R_{x,y} M_{x0,y0} / M_{x,y}$$

where $F_{x,y}$ is a field flattening intensity value, $R_{x,y}$ is the intensity of a pixel of the plurality of pixels on the first raw image, $M_{x,y}$ is the intensity of a pixel of the plurality of pixels on the second smoothed image at a corresponding spatial location to the pixel on the first raw image, and $M_{x0,y0}$ is the intensity of a reference pixel on the second smoothed image or is an arbitrary scale factor.

In one embodiment, the scale factor $M_{x0,y0}$ may also include a factor accounting for different exposure times or lighting intensities. In another embodiment, such as where a camera system has a proportional response to changes in exposure times or lighting conditions, the following equation may be used $$M_{x0,y0} = M_0 E_{(second\ image)} / E_{(first\ image)}$$

where $E_{(first\ image)}$ is the exposure or lighting level used during measurement of the first image, $E_{(second\ image)}$ is the exposure or lighting level used for the second image and $M_0$ is an arbitrary constant. In a further embodiment, the method further comprises repeating steps a) to d), using a second spectral filter for detecting a second probe. In an alternative embodiment, the method further comprises repeating steps a) to d), using the probe at a second concentration on the solid support. The solid support is exemplified, but not limited to, a microscope slide and silicon chip.

Also without limiting the invention's methods to particular steps, in one embodiment, the methods further comprise reducing spectral crosstalk in the one or more channels, by a) determining spectral crosstalk factors for each of the one or more probes in its corresponding channel from one or more adjacent channels, b) applying the spectral crosstalk factors to determine a spectral crosstalk matrix, and c) applying the spectral crosstalk matrix to the data set for the one or more probe intensities. In a particular embodiment, the step of reducing spectral crosstalk comprises a) determining probe intensity for one or more probes from one or more channels, wherein each channel corresponds to a probe, b) determining the ratios of the probe intensities in the one or more channels to arrive at signature ratios for the probe intensity in the channels, c) applying the signature ratios in a matrix equation, and d) inverting the matrix equation to arrive at an inverted matrix. In one embodiment, the method further comprises e) applying the inverted matrix to data from the one or more channels.

While not intending to limit reducing spectral crosstalk to any particular equation, in one embodiment, the step of determining spectral crosstalk matrix comprises using equation $$\begin{bmatrix} M_A \\ M_B \\ M_C \\ M_D \end{bmatrix} = K \begin{bmatrix} A \\ B \\ C \\ D \end{bmatrix}$$

where $$K = \begin{bmatrix} 1 & R_{AB} & 0 & 0 \\ R_{BA} & 1 & R_{BC} & 0 \\ 0 & R_{CB} & 1 & R_{CD} \\ 0 & 0 & R_{DC} & 1 \end{bmatrix}$$

and where $M_A$ is the observed intensity in the channel for probe A,
$M_B$ is the observed intensity in the channel for probe B,
$M_C$ is the observed intensity in the channel for probe C,
$M_D$ is the observed intensity in the channel for probe D,
A is the actual probe intensity of probe A,
B is the actual probe intensity of probe B,
C is the actual probe intensity of probe C,
D is the actual probe intensity of probe D,
$R_{AB}$ is the ratio between (a) the portion of intensity in the channel for probe A that is contributed by probe B, and (b) the actual probe intensity of probe B,
$R_{BA}$ is the ratio between (a) the portion of intensity in the channel for probe B that is contributed by probe A, and (b) the actual probe intensity of probe A,
$R_{BC}$ is the ratio between (a) the portion of intensity in the channel for probe B that is contributed by probe C, and (b) the actual probe intensity of probe C,
$R_{CB}$ is the ratio between (a) the portion of intensity in a channel for probe C that is contributed by probe B, and (b) the actual probe intensity of probe B,
$R_{CD}$ is the ratio between (a) the portion of intensity in a channel for probe C that is contributed by probe D, and (b) the actual probe intensity of probe D, and
$R_{DC}$ is the ratio between (a) the portion of intensity in a channel for probe D that is contributed by probe C, and (b) the actual probe intensity of probe C.

The above equation is solved to determine spectral crosstalk matrix $K^{-1}$ and an estimate of the actual intensities of the probes (A, B, C and D) using equation $$\begin{bmatrix} A \\ B \\ C \\ D \end{bmatrix} = K^{-1} \begin{bmatrix} M_A \\ M_B \\ M_C \\ M_D \end{bmatrix}$$

In an alternative embodiment, the equation is solved to determine and/or estimate for actual probe intensities A, B, C and. D.

The invention further provides an algorithm for processing data for nucleic acids in a nucleotide sequence, wherein the data is acquired from one or more channels, the algorithm comprising a) determining the ratio contribution to probe intensity in the one or more channels for one or more interrogation positions, from probe intensities at the interrogation position and at one or both of i) at least one subsequent nucleic acid positions in the sequence, and ii) at least one preceding nucleic acid positions in the sequence, b) processing data from the one or more channels to correct for sequence lead and sequence lag, and c) reconstructing the data in the one or more channels. In one embodiment, the step of processing data comprises applying the ratio contribution to probe intensity to determine, for the probe at the one or more interrogation positions, a sequence lead-lag compensation equation. Without limiting the invention to any particular equation, in one embodiment, the sequence lead-lag compensation equation is determined by applying equation $$\begin{bmatrix} I_{M1} \\ I_{M2} \\ \vdots \\ I_{MN} \end{bmatrix} = K_{Lead/Lag} \begin{bmatrix} I_{A1} \\ I_{A2} \\ \vdots \\ I_{AN} \end{bmatrix}$$

where $I_{M1}$ is a probe intensity measured at position 1 in the sequence, $I_{M2}$ is a probe intensity measured at position 2 in the sequence, $I_{MN}$ is a probe intensity measured at position N in the sequence, $I_{A1}$ is the actual probe intensity at position 1 in the sequence, $I_{A2}$ is the actual probe intensity at position 2 in the sequence, $I_{AN}$ is the actual probe intensity at position N in the sequence, In an alternative embodiment, the sequence lead-lag compensation equation is determined by applying equation $$K_{Lead/Lag} = \begin{bmatrix} R_{Lag/Lead,1} & R_{+1Lead,1} & R_{+2Lead,1} & R_{+3Lead,1} & \cdots & R_{+(N-1)Lead,1} \\ R_{-1Lag,2} & R_{Lag/Lead,2} & R_{+1Lead,2} & R_{+2Lead,2} & \cdots & R_{+(N-2)Lead,2} \\ R_{-2Lag,3} & R_{-1Lag,3} & R_{Lag/Lead,3} & R_{+1Lead,3} & \cdots & R_{+(N-3)Lead,3} \\ R_{-3Lag,4} & R_{-2Lag,4} & R_{-1Lag,4} & R_{Lag/Lead,4} & \cdots & R_{+(N-4)Lead,4} \\ \vdots & \vdots & \vdots & \vdots & \ddots & \vdots \\ R_{-(N-1)Lag,N} & R_{-(N-2)Lag,N} & R_{-(N-3)Lag,N} & R_{-(N-4)Lag,N} & \cdots & R_{Lag/Lead,N} \end{bmatrix}$$

where $R_{Lag/Lead,1}$ is the ratio between reduced probe intensity for nucleic acid at position 1 to actual probe intensity at the nucleic acid at position 1, $R_{+1Lead,1}$ is the ratio contribution to probe intensity at nucleic acid position 1 from probe at nucleic acid position 2, $R_{+2Lead,1}$ is the ratio contribution to probe intensity at nucleic acid position 1 from probe at nucleic acid position 3, $R_{+3Lead,1}$ is the ratio contribution to probe intensity at nucleic acid position 1 from probe at nucleic acid position 4, $R_{+(N-1)Lead,1}$ is the ratio contribution to probe intensity at nucleic acid position 1 from probe at nucleic acid position 1+(N−1), $R_{-1Lag,2}$ is the ratio contribution to probe intensity at nucleic acid position 2 from probe at nucleic acid position 1, $R_{Lag/Lead,2}$ is the ratio between reduced probe intensity for nucleic acid at position 2 to actual probe intensity at the nucleic acid at position 2, $R_{+1Lead,2}$ is the ratio contribution to probe intensity at nucleic acid position 2 from probe at nucleic acid position 3, $R_{+2Lead,2}$ is the ratio contribution to probe intensity at nucleic acid position 2. from probe at nucleic acid position 4, $R_{+(N-2)Lead,2}$ is the ratio contribution to probe intensity at nucleic acid position 2 from probe at nucleic acid position 2+(N−2), $R_{-2Lag,3}$ is the ratio contribution to probe intensity at nucleic acid position 3 from probe at nucleic acid position 1, $R_{-1Lag,3}$ is the ratio contribution to probe intensity at nucleic acid position 3 from probe at nucleic acid position 2, $R_{Lag/Lead,3}$ is the ratio between reduced probe intensity for nucleic acid at position 3 to actual probe intensity at the nucleic acid at position 3, $R_{+1Lead,3}$ is the ratio contribution to probe intensity at nucleic acid position 3 from probe at nucleic acid position 4, $R_{+(N-3)Lead,3}$ is the ratio contribution to probe intensity at nucleic acid position 3 from probe at nucleic acid position 3+(N−3), $R_{-3Lag,4}$ is the ratio contribution to probe intensity at nucleic acid position 4 from probe at nucleic acid position 1, $R_{-2Lag,4}$ is the ratio contribution to probe intensity at nucleic acid position 4 from probe at nucleic acid position 2, $R_{-1Lag,4}$ is the ratio contribution to probe intensity at nucleic acid position 4 from probe at nucleic acid position 3, $R_{Lag/Lead,4}$ is the ratio between reduced probe intensity for nucleic acid at position 4 to actual probe intensity at the nucleic acid at position 4, $R_{+(N-4)Lead,4}$ is the ratio contribution to probe intensity at nucleic acid position 4 from probe at nucleic acid position 4+(N−4), $R_{-(N-1)Lag,N}$ is the ratio contribution to probe intensity at nucleic acid position N from probe at nucleic acid position N−(N−1), $R_{-(N-2)Lag,N}$ is the ratio contribution to probe intensity at nucleic acid position N from probe at nucleic acid position N−(N−2), $R_{-(N-3)Lag,N}$ is the ratio contribution to probe intensity at nucleic acid position N from probe at nucleic acid position N−(N−3), $R_{-(N-4)Lag,N}$ is the ratio contribution to probe intensity at nucleic acid position N from probe at nucleic acid position N−(N−4), and $R_{Lag/Lead,N}$ is the ratio between reduced probe intensity for nucleic acid at position N to actual probe intensity at the nucleic acid at position N.

In another alternative embodiment, the sequence lead-lag compensation equation is determined by applying equation $$\begin{bmatrix} I_{M1} \\ I_{M2} \\ \vdots \\ I_{MN} \end{bmatrix} = K_{Lead/Lag} \begin{bmatrix} I_{A1} \\ I_{A2} \\ \vdots \\ I_{AN} \end{bmatrix}$$

While not necessary, it may be desirable to also include field flattening of background data in the algorithm and/or reducing spectral crosstalk between the data comprised in a plurality of channels. Dephasing correction (i.e., correction for lead-lag effects), field flattening and spectral crosstalk correction may be carried out in any order. Thus, in one embodiment, the field flattening is carried out before spectral crosstalk correction. In an alternative embodiment, spectral crosstalk correction is carried out before dephasing correction.

The invention also provides a computer readable medium containing a computer program for performing one or more of the method steps disclosed herein.

Also provided by the invention is a computer program product for processing data for nucleic acids in a nucleotide sequence to determine an identity of a nucleic acid at an interrogation position in the nucleotide sequence, the computer program product comprising a) computer code that inputs data from one or more channels for one or more probe intensities, wherein each channel corresponds to a probe, and each probe corresponds to a nucleic acid, b) computer code that applies to the input data a sequence lead-lag compensation equation to correct for sequence lead and sequence lag, c) computer code that compares probe intensities in the one or more channels that have been corrected for sequence lead and sequence lag, d) computer code that determines the highest probe intensity of the compared probe intensities, and e) computer code that identifies a nucleic acid at the interrogation position according to the highest probe intensity. Optionally, the computer program product may further comprise computer code that applies field flattening of background data and/or that reduces spectral crosstalk between data comprised in the one or more channels.

The invention also provides an apparatus that processes data for nucleic acids in a nucleotide sequence to determine an identity of a nucleic acid at an interrogation position in the nucleotide sequence, the apparatus comprising a) means for inputting data from one or more channels for one or more probe intensities, wherein each channel corresponds to a probe, and each probe corresponds to a nucleic acid, b) means for applying to the input data a sequence lead-lag compensation equation to correct for sequence lead and sequence lag, c) means for comparing probe intensities in the one or more channels that have been corrected for sequence lead and sequence lag, d) means for determining the highest probe intensity of the compared probe intensities, and e) means for identifying a nucleic acid at the interrogation position according to the highest probe intensity. Though not necessary, it may be desirable to also include means for applying field flattening of background data and/or for reducing spectral crosstalk between data comprised in the one or more channels.

Additionally provided herein is a system for processing data to determine an identity of a nucleic acid at an interrogation position in the nucleotide sequence, the system comprising a) a processor, and b) a computer readable medium readable by the processor, the computer readable medium storing a computer program that comprises i) code that receives as input a plurality of probe intensities at various positions in a nucleotide sequence, ii) code that applies to the input data a sequence lead-lag compensation equation to correct for sequence lead and sequence lag, and iii) code that identifies a nucleic acid at one or more interrogation position according to the corrected data. While not necessary, it may be desirable to additionally include in the computer readable medium code that applies field flattening of background data and/or that reduces spectral crosstalk between data comprised in the one ore more channels.

The invention also provides a method for field flattening an image of a probe on a solid support, comprising a) obtaining a first data set for a plurality of pixel intensities of a first raw image of a probe at a first concentration on a solid support, wherein the first raw image is produced using a first spectral filter for detecting a first probe, b) obtaining a second data set for a plurality of pixel intensities of a second smoothed image of the probe on the solid support, wherein the second smoothed image is produced using a low-pass filter, c) determining a field flattening intensity value for a plurality of pixels of the first raw image, and d) generating a third field flattened image of the probe on the solid support using the field flattening intensity of the plurality of pixels, wherein the correlation of intensity of a plurality of pixels to their spatial location on the third field flattened image is reduced compared to the intensity of a plurality of pixels at a corresponding location on the first raw image. Without intending to limit the invention to any particular equation, in one embodiment, the field flattening intensity value of a pixel is determined by equation $$F_{x,y} = R_{x,y} M_{x0,y0} / M_{x,y}$$

where $F_{x,y}$ is a field flattening intensity value, $R_{x,y}$ is the intensity of a pixel of the plurality of pixels on the first raw image, $M_{x,y}$ is the intensity of a pixel of the plurality of pixels on the second smoothed image at a corresponding spatial location to the pixel on the first raw image, and $M_{x0,y0}$ is the intensity of a reference pixel on the second smoothed image, or is any other scale factor of interest.

In one embodiment, it may be desirable to repeat steps a) to d), using a second spectral filter for detecting a second probe. Alternatively, or in addition, it may be desirable to repeat steps a) to d), using the probe at a second concentration on the solid support. In one embodiment, the probe is fluorescent and corresponds to a nucleic acid that comprises a base selected from the group of adenine (A), guanine (G), cytosine (C), thymine (T), and uracil (U). The solid support may comprise a microscope slide, silicon chip, and the like.

The invention also provides a method for reducing spectral crosstalk in one or more channels that deliver data for determining the identity of a nucleic acid at an interrogation position in a nucleotide sequence, comprising a) obtaining a data set for one or more probe intensities at one or more nucleic acid positions in the sequence, wherein each probe corresponds to a nucleic acid, b) determining spectral crosstalk factors for each of the one or more probes in its corresponding channel from one or more adjacent channels, c) applying the spectral crosstalk factors to determine a spectral crosstalk matrix, and d) applying the spectral crosstalk matrix to the data set to arrive at an identity for a nucleic acid at the interrogation position in the nucleotide sequence. In one embodiment, the step of determining spectral crosstalk factors comprises determining a ratio between (a) the portion of probe intensity in a first channel of a first probe that is contributed by a second probe in a second channel adjacent to the first channel, and (b) the actual probe intensity of the second probe in the second channel. In a particular embodiment, the method further comprises determining the ratio between (a) the portion of probe intensity in the first channel of the first probe that is contributed by a third probe in a third channel adjacent to the first channel, and (b) the actual probe intensity of the third probe in the third channel Without limiting the type of equation used, in one embodiment, the step of determining spectral crosstalk matrix comprises using equation $$\begin{bmatrix} M_A \\ M_B \\ M_C \\ M_D \end{bmatrix} = K \begin{bmatrix} A \\ B \\ C \\ D \end{bmatrix}$$

where $$K = \begin{bmatrix} 1 & R_{AB} & 0 & 0 \\ R_{BA} & 1 & R_{BC} & 0 \\ 0 & R_{CB} & 1 & R_{CD} \\ 0 & 0 & R_{DC} & 1 \end{bmatrix}.$$

and where
$M_A$ is the observed probe intensity of probe A,
$M_B$ is the observed probe intensity of probe B,
$M_C$ is the observed probe intensity of probe C,
$M_D$ is the observed probe intensity of probe D,
A is the actual probe intensity of probe A,
B is the actual probe intensity of probe B,
C is the actual probe intensity of probe C,
D is the actual probe intensity of probe D,
$R_{AB}$ is the ratio between (a) the portion of intensity in the channel for probe A that is contributed by probe 13, and (b) the actual probe intensity of probe B,
$R_{BA}$ is the ratio between (a) the portion of intensity in the channel for probe B that is contributed by probe A, and (b) the actual probe intensity of probe A,
$R_{BC}$ is the ratio between (a) the portion of intensity in the channel for probe B that is contributed by probe C, and (b) the actual probe intensity of probe C,
$R_{CB}$ is the ratio between (a) the portion of intensity in a channel for probe C that is contributed by probe B, and (b) the actual probe intensity of probe B,
$R_{CD}$ is the ratio between (a) the portion of intensity in a channel for probe C that is contributed by probe D, and (b) the actual probe intensity of probe D, and
$R_{DC}$ the ratio between (a) the portion of intensity in a channel for probe D that is contributed by probe C, and (b) the actual probe intensity of probe C.
In a further embodiment, the equation is solved to determine spectral crosstalk matrix $K^{-1}$ and an estimate of the actual intensity or probes (A, B, C and D) using equation $$\begin{bmatrix} A \\ B \\ C \\ D \end{bmatrix} = K^{-1} \begin{bmatrix} M_A \\ M_B \\ M_C \\ M_D \end{bmatrix}$$

In a particular embodiment, the order of the data correction methods described herein is 1) field flattening, 2) color crosstalk correction and 3) dephasing correction. When field flattening precedes color crosstalk correction, then the same crosstalk parameters may be used for the entire image. When color crosstalk correction precedes dephasing correction, the dephasing correction will be more accurate as the intensity data from the different channels will more precisely represent actual probe intensities.

As noted above, the present invention contemplates reducing some of these phenomenon that make accurate base calling difficult. One problem addressed in one embodiment of the present invention is the problem created by using a cleaving agent. In one embodiment, a cleaving agent scavenger is employed to address leftover cleaving agent which might prematurely cleave in the next cycle. Thus, the present invention contemplates in one embodiment a method of incorporating labeled nucleotides into nucleic acid, comprising: a) providing a plurality of nucleic acid template molecules, a polymerase, a cleaving agent, a cleaving agent scavenger, and a plurality of nucleotide analogues wherein each nucleotide analogue is labeled with a unique label and contains a removable chemical moiety capping the 3'-OH group; b) incorporating a first nucleotide analogue with said polymerase; c) detecting the label of the incorporated nucleotide analogue; d) removing the chemical moiety of the incorporated nucleotide analogue capping the 3'-OH group with said cleaving agent; and f) incorporating a second nucleotide analogue in the presence of said cleaving agent scavenger. With regard to step f), the scavenger can, by way of example, be put into the solution used to incorporate nucleotides in the next round (indeed, in one embodiment, the present invention contemplates compositions comprising 1) the scavenger(s) and one or more labeled or unlabeled nucleotides, 2) the scavenger(s) and polymerase, 3) the scavenger(s) and one or more nucleotides with or without 3-OH capping groups). Alternatively, the scavenger can be in a separate solution that is used prior to the incorporation solution (with residual scavenger present at the time of incorporation). In one embodiment, the present invention contemplates wash steps after step b) and after step d).

It is not intended that the present invention be limited by the nature of the chemistry of the removable chemical moiety. A variety of chemistries are contemplated (and described below in more detail). In one embodiment, said removable chemical moiety comprises a disulfide bond. In another embodiment, said removable chemical moiety comprises an azido group (e.g. .an azidomethyl ether). It is preferred that said moiety capping the 3'-OH is not a fluorescent moiety.

It is also not intended that the present invention be limited by the nature of the cleaving agent. In the case of azido-group-containing nucleotides (e.g. 3'-O-azidomethyl ether nucleotides), several types of cleaving agents can be used. In principle, any reducing agent capable of converting the azido group into an amine is suitable for this purpose. The amine undergoes spontaneous conversion to hydroxyl group to enable next nucleotide incorporation. Examples of cleaving agents include: a) Catalytic hydrogenation over $PtO_2$ or Pd/C; b) Reduction with $LiAlH_4$, $HCO_2NH_4$-10% Pd/C, $NaBH_4/COCl_2.6H_2O$, $Zn/NH_4Cl$, $Fe/NH_4Cl$; and c) Reduction with phosphines; e.g., tri-n-butyl-phosphine, triphenyl phosphine and its sulfonated versions (i.e., tris(3-sulfophenyl)-phosphine, TPPTS), and tri(carboxyethyl)phosphine (TCEP) and its salts. Most preferred cleaving reagents are soluble in water and are highly selective reducing agents. Water soluble phosphines are particularly preferred. In one embodiment, said cleaving agent is a phosphine Tris(2-carboxy-ethyl)phosphine.

It is also not intended that the present invention be limited by the nature of the cleaving agent scavenger. A variety of chemistries are contemplated (and are described below and in the figures) and more than one type of chemistry can be used together (e.g. two different scavengers). In a preferred embodiment, said cleaving agent scavenger does not contain a nucleic acid base. In one embodiment, said cleaving agent scavenger comprises a disulfide bond (e.g. cystamine or one of the other disulfide-containing compounds shown in FIG. 37). Cystamine is also known as 2,2'-Dithiobisethanamine, 2-Aminoethyl disulfide, or Decarboxycystine, and is available commercially from Sigma-Aldrich. Alternatively, the present invention contemplates in one embodiment that said cleaving agent scavenger comprises an azido group (e.g. an azidomethyl group, an azidoethyl ether group, etc.). In a preferred embodiment, said scavenger is 11-Azido-3,6,9-trioxaundecan-1-amine (which is also known as: 1-Amino-11-azido-3,6,9-trioxaundecane, 2-{2-[2-(2-Azidoethoxy)ethoxy]ethoxy}ethylamine, or O-(2-Aminoethyl)-O'-(2-azidoethyl)-diethylene glycol, and which is available commercially from Sigma-Aldrich).

It is not intended that the present invention be limited by where the first and second nucleotides are incorporated. In one embodiment, they are incorporated into a primer [e.g. prior to step b), the present invention contemplates in one embodiment hybridizing a primer to said plurality of nucleic acid template molecules, such that said first nucleotide analogue is incorporated into said primer at step b)]. In another embodiment, they are incorporated into the template molecules [e.g. said nucleic acid template molecules comprise a self-priming hairpin, such that said first nucleotide analogue is incorporated into said template molecules at step b)].

In some embodiments, two cites of cleavage are contemplated, i.e. cleavage occurs at two locations on the nucleotide analogue. Thus, in one embodiment, the present invention contemplates a method of incorporating labeled nucleotides into nucleic acid, comprising: a) providing a plurality of nucleic acid template molecules, a polymerase, a cleaving agent, a cleaving agent scavenger, and a plurality of nucleotide analogues selected from the group consisting of cytosine, thymine, deaza-adenine and deaza-guanine, wherein each nucleotide analogue comprises a unique label attached through a cleavable linker to a 5-position of cytosine or thymine or to a 7-position of deaza-adenine or deaza-guanine, and wherein each nucleotide analogue contains a removable chemical moiety capping the 3'-OH group; b) incorporating a first nucleotide analogue with said polymerase; c) detecting the label of the incorporated nucleotide analogue; d) removing the chemical moiety of the incorporated nucleotide analogue capping the 3'-OH group and cleaving the cleavable linker with said cleaving agent; and e) incorporating a second nucleotide analogue in the presence of said cleaving agent scavenger.

Again, it is not intended that the present invention be limited by where the first and second nucleotides are incorporated. In one embodiment, they are incorporated into a primer [e.g. prior to step b), the present invention contemplates in one embodiment hybridizing a primer to said plurality of nucleic acid template molecules, such that said first nucleotide analogue is incorporated into said primer at step b)]. In another embodiment, they are incorporated into the template molecules [e.g. said nucleic acid template molecules comprise a self-priming hairpin, such that said first nucleotide analogue is incorporated into said template molecules at step b)].

Again, it is not intended that the present invention be limited by the nature of the chemistry of the removable chemical moiety. A variety of chemistries are contemplated (and described below in more detail) and the chemistry need not be the same chemistry as used in the cleavable linker attaching the label. In one embodiment, said removable chemical moiety comprises a disulfide bond. In another embodiment, said removable chemical moiety comprises an azido group (e.g. .an azidomethyl ether). It is preferred that said moiety capping the 3'-OH is not a fluorescent moiety.

Similarly, a variety of chemistries are contemplated for the cleavable linker attaching the label to the nucleotide analogue (and these are described in more detail below). In one embodiment, said cleavable linker comprises a disulfide bond. As noted above, the present invention contemplates embodiments wherein the chemistries for the cleavage at the two cites is the same, as well as embodiments where it is different. For example, in one embodiment, said removable chemical moiety comprises an azido group (e.g. an azidomethyl ether) and said cleavable linker (which attaches the label) comprises a disulfide bond. In another embodiment, this is reversed (the cleavable linker comprises an azido group and the removable chemical moiety comprises a disulfide bond.

Again, it is also not intended that the present invention be limited by the nature of the cleaving agent. However, in one embodiment, said cleaving agent is a phosphine (e.g. Tris (2-carboxy-ethyl)phosphine). Again, a variety of cleaving agent scavengers are contemplated (discussed above). In a preferred embodiment, said cleaving agent scavenger does not contain a nucleic acid base.

In one embodiment, the present invention contemplates incorporating nucleotides having only one location for cleavage (e.g. the cleavable linker attaching the label). Thus, in one embodiment, the present invention contemplates a method of incorporating labeled nucleotides into nucleic acid, comprising: a) providing a plurality of nucleic acid template molecules, a polymerase, a cleaving agent, a cleaving agent scavenger, and a plurality of nucleotide analogues wherein each nucleotide analogue is labeled with a unique label, said label attached by a cleavable linker; b) incorporating a first nucleotide analogue with said polymerase; c) detecting the label of the incorporated nucleotide analogue; d) removing the label of the incorporated nucleotide analogue by cleaving the cleavable linker with said cleaving agent; and e) incorporating a second nucleotide analogue in the presence of said cleaving agent scavenger.

Again, it is not intended that the present invention be limited by where the first and second nucleotides are incorporated. In one embodiment, they are incorporated into a primer [e.g. prior to step b), the present invention contemplates in one embodiment hybridizing a primer to said plurality of nucleic acid template molecules, such that said first nucleotide analogue is incorporated into said primer at step b)]. In another embodiment, they are incorporated into the template molecules [e.g. said nucleic acid template molecules comprise a self-priming hairpin, such that said first nucleotide analogue is incorporated into said template molecules at step b)].

Again, a variety of chemistries are contemplated for the cleavable linker (e.g. wherein said cleavable linker comprises a disulfide bond, azido group, or some other chemical group). However, in a preferred embodiment, the chemistry of the cleavable linker dictates the chemistry of the scavenger (e.g. wherein wherein said cleaving agent scavenger comprises a disulfide bond, it is preferred that the scavenger also comprise a disulfide bond, such as where said scavenger is cystamine or other similar compound).

In one embodiment, the present invention contemplates carrying out nucleotide incorporation in a device, including automated devices. Solutions comprising various combinations of biomolecules are contemplated; such solutions can be, in one embodiment, conveniently be stored in reservoirs which are in fluid communication with a reaction chamber (e.g. flow cells, microchannels, etc.). A series of steps can be carried out to introduce these solutions (and the reagents they contain) into the reaction chamber (e.g. by valving) to carry out the reaction(s). Thus, in one embodiment, the present invention contemplates a method of incorporating labeled nucleotides into nucleic acid, comprising: a) providing i) a reaction chamber (e.g. a flow cell) comprising plurality of nucleic acid template molecules bound to a solid support, ii) a first solution comprising polymerase and a plurality of nucleotide analogues wherein each nucleotide analogue is labeled with a unique label and contains a removable chemical moiety capping the 3'-OH group, iii) a second solution comprising a cleaving agent, and iv) a cleaving agent scavenger; b) introducing said first solution into said reaction chamber under conditions wherein a first nucleotide analogue is incorporated by said polymerase; c) detecting the label of the incorporated nucleotide analogue; d) introducing said second solution into said reaction change under conditions such that the chemical moiety of the incorporated nucleotide analogue capping the 3'-OH group is removed by said cleaving agent; and e) introducing said cleaving agent scavenger into said reaction chamber.

It is not intended that the present invention be limited by the way in which the cleaving agent scavenger is stored or introduced into the reaction chamber. In one embodiment, said cleaving agent scavenger is in a third solution and said scavenger is introduced into said reaction chamber in step e) by introducing said third solution. In another embodiment, the above-indicated method further comprises the step f) re-introducing said first solution into said reaction chamber under conditions such that a second nucleotide analogue is incorporated by said polymerase (and this first solution may contain the scavenger if desired). In another embodiment, separate steps [i.e. step e) and step f)] are not required; rather, a single step is contemplated wherein said cleaving agent scavenger is in said first solution and said introducing of step e) comprises introducing said first solution comprising said scavenger (in this embodiment, a second nucleotide analogue is incorporated in the presence of said cleaving agent scavenger). In some embodiments, additional wash steps are employed to remove reagents between steps [e.g. wash steps after step b), and step d)], although the usefulness of the scavenger has been discovered empirically, since residual cleaving agent is difficult to remove with a practical number of washes (discussed more below).

Again, it is not intended that the present invention be limited by where the first and second nucleotides are incorporated. In one embodiment, they are incorporated into a primer [e.g. prior to step b), the present invention contemplates in one embodiment hybridizing a primer to said plurality of nucleic acid template molecules, such that said first nucleotide analogue is incorporated into said primer at step b)]. In another embodiment, they are incorporated into the template molecules [e.g. said nucleic acid template molecules comprise a self-priming hairpin, such that said first nucleotide analogue is incorporated into said template molecules at step b)].

Again, it is not intended that the present invention be limited by the nature of the chemical moiety capping the 3'-OH on the nucleotide analogue. In one embodiment, said removable chemical moiety comprises a disulfide bond. In one embodiment, said removable chemical moiety comprises an azido group (e.g. an azidomethyl ether). It is preferred that said moiety capping the 3'-OH is not a fluorescent moiety.

Again, it is also not intended that the present invention be limited by the nature of the cleaving agent. However, in one embodiment, said cleaving agent is a phosphine (e.g. Tris (2-carboxy-ethyl)phosphine). Again, a variety of cleaving agent scavengers are contemplated (discussed above). In a preferred embodiment, said cleaving agent scavenger does not contain a nucleic acid base.

In some embodiments, the reaction in the device is directed at cleavage at two locations on the nucleotide analogue(s). Thus, in one embodiment, the present invention contemplates a method of incorporating labeled nucleotides into nucleic acid, comprising: a) providing i) a reaction chamber comprising plurality of nucleic acid template molecules bound to a solid support, ii) a first solution comprising polymerase and a plurality of nucleotide analogues selected from the group consisting of cytosine, thymine, deaza-adenine and deaza-guanine, wherein each nucleotide analogue comprises a unique label attached through a cleavable linker to a 5-position of cytosine or thymine or to a 7-position of deaza-adenine or deaza-guanine, and wherein each nucleotide analogue is labeled with a unique label and contains a removable chemical moiety capping the 3'-OH group, iii) a second solution comprising a cleaving agent, and iv) a cleaving agent scavenger; b) introducing said first solution into said reaction chamber under conditions wherein a first nucleotide analogue is incorporated by said polymerase; c) detecting the label of the incorporated nucleotide analogue; d) introducing said second solution into said reaction change under conditions such that the chemical moiety of the incorporated nucleotide analogue capping the 3'-OH group is removed and said cleavable linker is cleaved by said cleaving agent; and e) introducing said cleaving agent scavenger into said reaction chamber (e.g. flow cell or the like).

Again, it is not intended that the present invention be limited by the way in which the cleaving agent scavenger is stored or introduced into the reaction chamber. In one embodiment, said cleaving agent scavenger is in a third solution and said scavenger is introduced into said reaction chamber in step e) by introducing said third solution. In another embodiment, the above-indicated method further comprises the step f) re-introducing said first solution into said reaction chamber under conditions such that a second nucleotide analogue is incorporated by said polymerase (and this first solution may contain the scavenger if desired). In another embodiment, separate steps [i.e. step e) and step f)] are not required; rather, a single step is contemplated wherein said cleaving agent scavenger is in said first solution and said introducing of step e) comprises introducing said first solution comprising said scavenger (in this embodiment, a second nucleotide analogue is incorporated in the presence of said cleaving agent scavenger). In some embodiments, additional wash steps are employed to remove reagents between steps [e.g. wash steps after step b).

Again, it is not intended that the present invention be limited by where the first and second nucleotides are incorporated. In one embodiment, they are incorporated into a primer [e.g. prior to step b), the present invention contemplates in one embodiment hybridizing a primer to said plurality of nucleic acid template molecules, such that said first nucleotide analogue is incorporated into said primer at step b)]. In another embodiment, they are incorporated into the template molecules [e.g. said nucleic acid template molecules comprise a self-priming hairpin, such that said first nucleotide analogue is incorporated into said template molecules at step b)).

Again, it is not intended that the present invention be limited by the nature of the chemical moiety capping the 3'-OH on the nucleotide analogue. In one embodiment, said removable chemical moiety comprises a disulfide bond. In one embodiment, said removable chemical moiety comprises an azido group (e.g. an azidomethyl ether). It is preferred that said moiety capping the 3'-OH is not a fluorescent moiety.

Again, the chemistry of the cleavable linker (which attaches the label) may be the same or different vis-à-vis the removable chemical capping moiety. Thus, in one embodiment, the linker and the capping group comprise a disulfide bond. Yet, in another embodiment, said removable chemical moiety comprises an azido group and said cleavable linker comprises a disulfide bond (or the reverse, i.e. the capping group comprises a disulfide bond and the cleavable linker comprises an azido group).

Again, it is also not intended that the present invention be limited by the nature of the cleaving agent. However, in one embodiment, said cleaving agent is a phosphine (e.g. Tris (2-carboxy-ethyl)phosphine). Again, a variety of cleaving agent scavengers are contemplated (discussed above). In a preferred embodiment, said cleaving agent scavenger does not contain a nucleic acid base.

In some embodiments, the present invention contemplates a reaction in the device wherein only a single cite of cleavage on the nucleotide analogue is targeted (e.g. a cleavable linker attaching the label). Thus, in one embodiment, the present invention contemplates a method of incorporating labeled nucleotides into nucleic acid, comprising: a) providing i) a reaction chamber comprising plurality of nucleic acid template molecules bound to a solid support, ii) a first solution comprising polymerase and a plurality of nucleotide analogues wherein each nucleotide analogue is labeled with a unique label, said label attached via a cleavable linker, iii) a second solution comprising a cleaving agent, and iv) a cleaving agent scavenger; b) introducing said first solution into said reaction chamber under conditions wherein a first nucleotide analogue is incorporated by said polymerase; c) detecting the label of the incorporated nucleotide analogue; d) introducing said second solution into said reaction change under conditions such that the label of the incorporated nucleotide analogue is removed by cleaving said cleavable linker with said cleaving agent; and e) introducing said cleaving agent scavenger into said reaction chamber.

Again, it is not intended that the present invention be limited by where the first and second nucleotides are incorporated. In one embodiment, they are incorporated into a primer [e.g. prior to step b), the present invention contemplates in one embodiment hybridizing a primer to said plurality of nucleic acid template molecules, such that said first nucleotide analogue is incorporated into said primer at step b)]. In another embodiment, they are incorporated into the template molecules [e.g. said nucleic acid template molecules comprise a self-priming hairpin, such that said first nucleotide analogue is incorporated into said template molecules at step b)].

A variety of chemistries for the cleavable linker are contemplated. In one embodiment, said cleavable linker comprises a disulfide bond, In one embodiment, the chemistry used in the cleavable linker controls the chemistry of the scavenger. For example, in one embodiment, where the linker comprises a disulfide bond, said cleaving agent scavenger comprises a disulfide bond. In one embodiment, where the linker comprises an azido group, said cleaving agent scavenger comprises an azido group. In a preferred embodiment, said cleaving agent scavenger does not contain a nucleic acid base.

The present invention contemplates methods, kits, devices, systems and compositions. In one embodiment, the present invention contemplates a composition comprising cleaving agent scavenger and one or more nucleotide analogues (unlabeled or labeled as herein described). In one embodiment, said composition further comprises polymerase. In one embodiment, the present invention contemplates a composition comprising cleaving agent scavenger and polymerase, and (optionally) one or more nucleotide analogues (unlabeled or labeled as herein described).

In one embodiment, the present invention contemplates a reaction chamber (e.g. a flow cell, flew channels, etc.) comprising a solution, said solution comprising cleaving agent scavenger and one or more nucleotide analogues (labeled or unlabeled as herein described). In one embodiment, said solution further comprises polymerase. In one embodiment, said solution comprises cleaving agent scavenger and polymerase, and (optionally) one or more nucleotide analogues (unlabeled or labeled as herein described).

In one embodiment, the present invention contemplates kits, said kits comprising a solution comprising cleaving agent scavenger and one or more nucleotide analogues (labeled or unlabeled as herein described) and (optionally) polymerase. Alternatively, said kits comprise a solution comprising cleaving agent scavenger and polymerase, and (optionally) one or more nucleotide analogues (unlabeled or labeled as herein described). Preferably, such kits also provide instructions for carrying out incorporation reactions, as well as wash buffers and the like.

In one embodiment, the present invention contemplates a system comprising reservoirs in fluid communication with a reaction chamber, at least one of said reservoirs comprising a solution comprising cleaving agent scavenger and one or more nucleotide analogues (labeled or unlabeled as herein described) and (optionally) polymerase. Alternatively, at least one of said reservoirs comprises a solution comprising cleaving agent scavenger and polymerase, and (optionally) one or more nucleotide analogues (unlabeled or labeled as herein described). Preferably, such solutions can be introduced by automated means (e.g. valving).

As described herein, the present invention contemplates embodiments wherein nucleotides used in extension reactions contain linkers, spacers and chemical groups. The presence of these spacers and groups may affect the ability of the sequencing polymerases to incorporate the subsequent nucleotide. The present invention contemplates a number of ways to minimize or eliminate this undesirable effect, including but not limited to: a) reducing the amount of labeled nucleotides incorporated in the template; b) reducing the size of the spacer arm or eliminate it completely by carefully designing nucleotide analogs; and c) change the reactivity of the spacer arm groups or their charge by performing a chemical "capping" step, where specific reagent is added to react only with groups on the spacer arm.

Reducing the amount of labeled nucleotides that are incorporated can be accomplished by reducing the concentration of labeled nucleotides in the extension solution, and/or by mixing labeled nucleotides (reversible terminators) with non-labeled reversibly terminating nucleotides (e.g. where the non-labeled nucleotides are employed in ratios between 1:1 and 1000:1 relative to the labeled nucleotides, but more preferably in ratios between 10:1 and 100:1). In contrast to labeled nucleotides, non-labeled reversible terminator nucleotides after cleavage convert to native nucleotide (and therefore do not present problems for polymerases). Thus, in one embodiment, the present invention contemplates a composition comprising i) a first plurality of nucleotide analogues wherein each nucleotide analogue is labeled with a unique label and contains a removable chemical moiety capping the 3'-OH group; and ii) a second plurality of nucleotide analogues wherein each nucleotide analogue is unlabeled and contains a removable chemical moiety capping the 3'-OH group. In one embodiment, the composition further comprises polymerase. In a preferred embodiment, said nucleotide analogues are in solution. In one embodiment, the second plurality of nucleotide analogues is present in said solution at a high concentration than said first plurality of nucleotide analogues. In one embodiment, said second plurality of nucleotide analogues is present at a concentration between 1 uM and 100 uM. In one embodiment, said first plurality of nucleotide analogues is present at a concentration between 1 nM and 1 uM.

It is not intended that the composition be limited by the number or nature of nucleotide analogues in said composition. However, in a preferred embodiment, said first plurality of nucleotide analogues comprises four different nucleotide analogues (for example, in one embodiment, the four nucleotides are either (i) aA, aC, aG, and aT, or (ii) aA, aC, aG, and aU). In a preferred embodiment, said second plurality of (unlabeled) nucleotide analogues comprises four different nucleotide analogues (for example, either (i) aA, aC, aG, and aT, or (ii) aA, aC, aG, and aU).

It is also not intended that the composition be limited by the nature of the label. However, in one embodiment, each of said four different nucleotide analogues comprises a unique (preferably cleavable) label, said label selected from the group consisting of BODIPY, Rhodamine, Carboxyrhodamine, and Cyanine (see FIG. 36, which shows these labels in the context of a cleavable disulfide bond).

It is also not intended that the composition be limited by the chemistry of the removable chemical moiety, which may, by way of example, comprise a disulfide bond or an azido group (e.g. an azidomethyl ether). The chemistry may be the same or different vis-à-vis the cleavable linker. For example, said removable chemical moiety comprises an azido group and said cleavable linker comprises a disulfide bond.

In one embodiment, the present invention contemplates a composition comprising i) a first plurality of nucleotide analogues comprising four different (for example, in one embodiment, the four nucleotides are either (i) aA, aC, aG, and aT, or (ii) aA, aC, aG, and aU) nucleotide analogues, wherein each different nucleotide analogue is labeled with a unique (preferably cleavable) label and contains a removable chemical moiety capping the 3'-OH group; and ii) a second plurality of nucleotide analogues comprising four different (for example, in one embodiment, the four nucleotides are either (i) aA, aC, aG, and aT, or (ii) aA, aC, aG, and aU) nucleotide analogues, wherein each nucleotide analogue is unlabeled and contains a removable chemical moiety capping the 3'-OH group. Again, this composition may further comprise a polymerase and it is preferred that the reagents (e.g. said nucleotide analogues and optionally said polymerase) are in solution.

It is not intended that the composition be limited by the particular linkages. However, in a preferred embodiment, the nucleotide analogues selected from the group consisting of cytosine, thymine, deaza-adenine and deaza-quanine and each comprising a unique (preferably) label attached through a cleavable linker to a 5-position of cytosine or thymine or to a 7-position of deaza-adenine or deaza-guanine.

In one embodiment, the second plurality of nucleotide analogues is present in said solution at a high concentration than said first plurality of nucleotide analogues. In one embodiment, said second plurality of nucleotide analogues is present at a concentration between 1 uM and 100 uM. In one embodiment, said first plurality of nucleotide analogues is present at a concentration between 1 nM and 1 uM.

In one embodiment, the present invention contemplates kits, said kits comprising a mixture of labeled and unlabeled nucleotide analogues (preferably both containing groups capping the 3'-OH—such as an azido group) and (optionally) polymerase. In one embodiment, the present invention contemplates a mixture of 4 labeled and 4 unlabeled nucleotide analogues as herein described) and (optionally) polymerase. The mixture can be provided dry or in solution in the kit (along with appropriate instructions for extension reactions). Preferably, the unlabeled nucleotide analogues are present in the mixture in a greater amount than the labeled nucleotide analogues.

The above-indicated solutions provide advantages in incorporation reactions. Thus, in one embodiment, the present invention contemplates a method of incorporating labeled nucleotides into nucleic acid, comprising: a) providing i) a reaction chamber comprising plurality of nucleic acid template molecules bound to a solid support, ii) a solution comprising a first plurality of nucleotide analogues wherein each nucleotide analogue is labeled with a unique (preferably cleavable) label and contains a removable chemical moiety capping the 3'-OH group, and a second plurality of nucleotide analogues wherein each nucleotide analogue is unlabeled and contains a removable chemical moiety capping the 3'-OH group; and iii) polymerase; b) introducing said solution into said reaction chamber under conditions wherein a nucleotide analogue of said first plurality of nucleotide analogues is incorporated by said polymerase (e.g. the polymerase can be added separately or together with other reagents; regardless, it is preferred that said polymerase is in said solution prior to step b); and c) detecting the label of the incorporated nucleotide analogue. The method may comprise additional steps (cleavage of the capping group, washing, etc.) and may repeat steps (e.g. in order to incorporate subsequent, e.g. a second, third, fourth, etc., nucleotide analogues).

It is not intended that the present invention be limited by where the first (or subsequent) nucleotides are incorporated. In one embodiment, they are incorporated into a primer [e.g. prior to step b), the present invention contemplates in one embodiment hybridizing a primer to said plurality of nucleic acid template molecules, such that said first nucleotide analogue is incorporated into said primer at step b)]. In another embodiment, they are incorporated into the template molecules [e.g. said nucleic acid template molecules comprise a self-priming hairpin, such that said first nucleotide analogue is incorporated into said template molecules at step b)].

In one embodiment, the second plurality of nucleotide analogues is present in said solution at a high concentration than said first plurality of nucleotide analogues. In one embodiment, said second plurality of nucleotide analogues is present at a concentration between 1 uM and 100 uM. In one embodiment, said first plurality of nucleotide analogues is present at a concentration between 1 nM and 1 uM.

In a preferred embodiment, said first plurality of nucleotide analogues comprises four different nucleotide analogues and said second plurality of nucleotide analogues comprises four different nucleotide analogues. In one embodiment, each of said four different nucleotide analogues of said first plurality of labeled analogues comprises a unique label, said label selected from the group consisting of BODIPY, Rhodamine, Carboxyrhodamine, and Cyanine.

Again, it is not intended that the present invention be limited by the nature of the chemical moiety capping the 3'-OH on the nucleotide analogue or the (preferably cleavable) linker attaching the label. In one embodiment, said removable chemical moiety comprises a disulfide bond, In one embodiment, said removable chemical moiety comprises an azido group (e.g. an azidomethyl ether). In one embodiment, said removable chemical moiety comprises an azido group and said cleavable linker comprises a disulfide bond. In another embodiment, these chemistries are reversed. Again, it is preferred that said moiety capping the 3'-OH is not a fluorescent moiety.

Increasing the number of bases that can be sequenced, i.e. increasing read lengths is desirable. However, as one proceeds to larger and larger read lengths, one often encounters a reduction in signal. In one embodiment, the present invention contemplates reducing extension times (e.g. extension times of 5-15 minutes are reduced to 1-2 minutes) in order to maintain signal strength at longer read lengths (greater than 20 bases, more preferably greater than 30 bases, etc.). This reduction in extension times eat be combined with other methods herein described (e.g. the use of mixtures of labeled and unlabeled nucleotides) to improve performance and increase the retention in signal. Signal retention is defined as the ratio of signals at the end of the run to the signals at the beginning of the run.

BRIEF DESCRIPTION OF THE DRAWINGS

FIGS. 2 A-C schematically show one embodiment of a flow cell (200).

FIGS. 4A-B show a schematic for steps involved in sample preparation FIG. 4A and highly parallel sequencing steps FIG. 4B for embodiments of the invention.

FIG. 24A-D shows sequencing results using four different 25 nt DNA templates.

FIG. 27 shows exemplary nucleotide structures with 3'-OH group protection that can be cleaved by mild oxidation reactions.

FIG. 34A-B panel 34A shows 25-base-long sequence data and panel 34B shows the same data after applying the lead/lag compensation algorithm.

FIG. 35 provides examples of chemical structures of the reversibly terminating nucleotides used in sequencing. These examples include: 3'-O-azidomethyl nucleotides, 3'-O-aminoxy nucleotides, 3'-O-allyl nucleotides; and disulfide nucleotides.

FIG. 39 shows detection of incorporated nucleotides in an extension reaction done in the presence of a second scavenger (ATA).

FIG. 41A shows an embossing surface 80 with extensions 81 and a slide (or chip) 82. FIG. 41B shows the application of the embossing surface into the slide (or chip) showing a compressed structure 83. FIG. 41C shows the separated embossing surface and the newly embossed slide (or chip) with indentations. FIG. 41D shows the acceptance of microbeads 84 comprising nucleic acid 85 into the embossed indentations 86 of the slide (or chip).

FIGS. 48A-D show that using a mixture of labeled and unlabeled nucleotides (e.g. a mixture of labeled and non-labeled reversible terminators) and controlling extension time can improve performance (e.g. increase retention of signal) on an automated sequencing device, With additional control provided (e.g. by reducing extension time from 15 minutes to 2 minutes), the incorporation rate of labeled nucleotides can be controlled and results in improved fidelity and performance. FIGS. 48A and 48B show the results for 15 minutes. FIGS. 48C and 48B show the results for 2 minutes.

FIGS. 49A-P show that using a mixture of labeled and unlabeled nucleotides (e.g. a mixture of labeled and non-labeled reversible terminators) and controlling extension time can improve performance (e.g. increase retention of signal) on an automated sequencing device. FIGS. 49A, 49B, 49C, 49D, 49E, 49F, 49G and 49H show the results with 10 minute extension (for templates 20, 30, 21, 31, 22, 32, 23 and 33, respectively). FIGS. 49I, 49J, 49K, 49L, 49M, 49N, 49O and 49P show the results with 1 minute extension (for templates 20, 30, 21, 31, 23 and 33, respectively). With additional control provided (e.g. by reducing extension time from 10 minutes to 1 minute), the incorporation rate of labeled nucleotides can be controlled and results in improved fidelity and performance. Signal retention is defined as the ratio of signals at the end of the run to the signals at the beginning of the run.

DEFINITIONS

Figure 1:
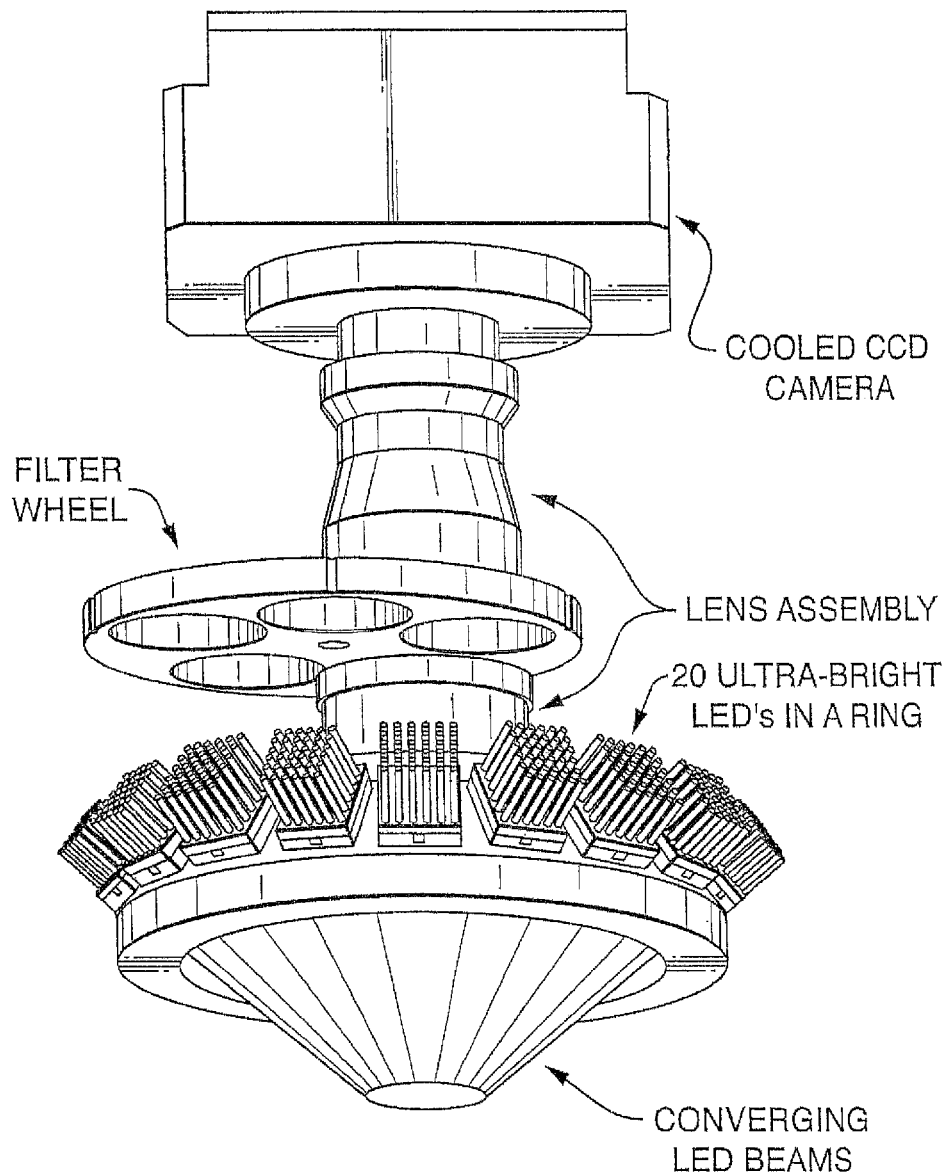
FIG. 1 schematically shows one embodiment of the imaging system of the present invention, said embodiment comprising a) a circular array of LEDs configured such that the emitted light converges on a region or platform (e.g. a position for a sample, flow cell, etc.) so as to excite fluorescence of fluorescent material, b) a lens assembly positioned above the region so as to capture at least a portion of said fluorescence, c) a filter wheel comprising bandpass filters, and d) light collection means (in this case a cooled CCD camera), wherein said filter wheel is positioned between the region where the light converges and the light collection means.

To facilitate understanding of the invention, a number of terms are defined below, and others are found elsewhere in the specification.

The term "plurality" means two or more.

The term "nucleotide sequence" refers to a polymer comprising deoxyribonucleotides (in DNA) or ribonucleotides (in RNA).

The tetra "interrogation position" when made in reference to a nucleotide sequence refers to a location of interest in the sequence, such as the location at which the identity of a nucleic acid is sought to be determined.

The term "preceding nucleic acid" when made in reference to a first nucleic acid in relation to a second nucleic acid that is located at an interrogation position in a nucleotide sequence refers to a nucleic acid that is inserted during synthesis into the nucleotide sequence before the insertion of the second nucleic acid at the interrogation position. The term "subsequent nucleic acid" when made in reference to a third nucleic acid in relation to the second nucleic acid at the interrogation position refers to a nucleic acid that is inserted during synthesis into the nucleotide sequence after the insertion of the second nucleic acid at the interrogation position.

The terms "probe" and "label" are interchangeably used to describe a chemical moiety that, when attached to a composition of interest, acts as a marker for the presence of the composition of interest. Probes are exemplified by fluorescent moieties such as 5-carboxyfluorescein, 6-carboxyrhodamine-6G, N,N,N',N'-tetramethyl-6-carboxyrhodamine, and 6-carboxy-X-rhodamine. Probes also include a fluorescence energy transfer tag that comprises an energy transfer donor and an energy transfer acceptor. The energy transfer donor is exemplified by 5-carboxyfluorescein and cyanine, and the energy transfer acceptor is exemplified by dichlorocarboxyfluorescein, dichloro-6-carboxyrhodamine-6G, dichloro-N,N,N',N'-tetramethyl-6-carboxyrhodamine, and dichloro-6-carboxy-X-rhodamine. The mass tag is exemplified by a 2-nitro-a-methyl-benzyl group, 2-nitro-a-methyl-3-fluorobenzyl group, 2-nitro-a-methyl-3,4-difluorobenzyl group, and 2-nitro-a-methyl-3,4-dimethoxybenzyl group.

The term "probe corresponds to a nucleotide" means that the probe serves as a marker for the presence of the nucleotide. Thus, detecting the presence of the probe also detects the presence of the nucleotide.

The term "field flattening" when in reference to pixel intensity of an image refers to reducing differences in pixel intensity between two or more pixels at different spatial locations on the image of a uniformly radiating surface.

The terms "reducing," "decreasing" and grammatical equivalents when in reference to the level of a molecule and/or phenomenon (e.g., light intensity, chemical concentration, correlation between two event, etc.) in a first sample relative to a second sample, mean that the quantity of molecule and/or phenomenon in the first sample is lower than in the second sample by any amount that is statistically significant using any art-accepted statistical method of analysis. In some embodiments, the quantity of molecule and/or phenomenon in the first sample is at least 10% lower than, at least 25% lower than, at least 50% lower than, at least 75% lower than, and/or at least 90% lower than the quantity of the same molecule and/or phenomenon in a second sample. The term "reducing" includes, but does not require, a 100% lowering in the quantity of the molecule and/or phenomenon in the first sample compared to the second sample.

The terms "increasing," "elevating" and grammatical equivalents when in reference to the level of a molecule and/or phenomenon (e.g., light intensity, chemical concentration, correlation between two event, etc.) in a first sample relative to a second sample, mean that the quantity of molecule and/or phenomenon in the first sample is higher than in the second sample by any amount that is statistically significant using any art-accepted statistical method of analysis. In some embodiments, the quantity of the molecule and/or phenomenon in the first sample is at least 10% greater than, at least 25% greater than, at least 50% greater than, at least 75% greater than, and/or at least 90% greater than the quantity of the same molecule and/or phenomenon in a second sample.

"Spectral" is a term that refers to electromagnetic radiation. In one embodiment, the electromagnetic radiation is in the visible light region (wavelength of approximately 400-700 nanometers), such as that emitted by fluorescent moieties.

The terms "spectral filter" and "color filter" are interchangeably used to refer to a filter for detection of a particular range of electromagnetic wavelengths, such as in the visible region.

The terms "spectral crosstalk" and "color crosstalk" refer to any phenomenon by which a spectral signal, or a digital signal that corresponds to a spectral signal, that is transmitted and measured in one channel of transmission creates an undesired effect in another channel. For example, spectral crosstalk may occur when exciting only a green dye, resulting in a signal that is visible in the yellow channel as well as in the green channel. Using methods disclosed herein, if this spectral crosstalk is calibrated, it may be removed from subsequent measurements even if the dyes are mixed in unknown quantities.

The term "low pass filter" refers to a filter that passes slowly spatially varying intensity signals but reduces signals with higher spatial variation than a desired cutoff value. Exemplary software for carrying out these steps is shown Appendix C, which is a source code for creating a flat map calibration image.

The term "computer readable medium" refers to a medium, such as a compact optical disc, that is used to store and retrieve digital data.

One element is in "fluid communication" or "fluidic communication" with another element when it is attached through a channel, tube or other conduit that permits the passage of liquid, gas, vapor and the like. "Tubing" can be made of a variety of materials, including put not limited to various plastics, metals and composites. Tubing can be rigid or flexible. Tubing can be "attached" in a detachable mode or a fixed mode. Tubing is typically attached by sliding into or over (both of which are examples of "slidably engaging") other tubing or connectors.

DESCRIPTION OF THE INVENTION

For further clarity, the invention is described below under the following headings
A. Sequencing by Synthesis; B. Device Embodiments and Elements; C. Nucleotides; D. Reducing Lead And Lag; E. Dephasing; F. Field Flattening; G. Spot Location in the Array; H. Image Sharpening; I. Spot Brightness Determination; J. Neighbor Influence Elimination; K. Spectral Crosstalk Calibration; L. Base Calls; and M. Software Appendices A-C
A. Sequencing by Synthesis The invention relates to methods and compositions for determining the identity of nucleic acids in nucleotide sequences using, for example, data obtained from sequencing by synthesis methods. Methods of DNA sequencing are generally described in Metzker, Genome Res. (2005) 15(12): 1767-1776 and Shendure et al. (2004) Nature Reviews Genetics 5: 335-344. The Sanger sequencing method or chain termination or dideoxy method is a technique that uses an enzymatic procedure to synthesize DNA chains of varying length in different reactions that contain diluted concentrations of individual dideoxy nucleotides mixed in with normal nucleotides. DNA replication is stopped at positions that are occupied by one of the dideoxy nucleotide bases resulting in a distribution of nucleotide fragments since the normal nucleotides will properly incorporate. Unnatural ddNTP terminators replace the OH with an H at the 3'-position of the deoxyribose molecule and irreversibly terminate DNA polymerase activity. The resulting fragment lengths are determined to decipher the ultimate sequence. Electrophoretic separation of the deoxyribonucleotide triphosphate (dNTP) fragments may be accomplished with single-base resolution.

In sequencing by synthesis, nucleotides conjugated with fluorescent markers that incorporate into a growing double-stranded nucleic acid from the single strand are detected. For example, one may immobilize template DNA on a solid surface by its 5' end. One may accomplish this by annealing a sequencing primer to a consensus sequence and introducing DNA polymerase and fluorescent nucleotide conjugates (alternatively, a self-priming hairpin can be introduced by PCR or ligation to the template). One detects nucleotide incorporation using a laser microarray scanner or fluorescent microscope by correlating a particular fluorescent marker to a specific nucleotide. After each nucleotide is incorporated and the fluorescent signal is detected, one bleaches or removes the fluorescent moiety from the nucleotide conjugate so as to prevent the accumulation of a background signal.

In one embodiment, the present invention contemplates DNA sequencing by synthesis using an automated instrument, as well as methods and compositions useful for sequencing using such an instrument. In one embodiment, the instrument comprises a flow cell (FIGS. 2A and 2B) with at least two fluidics ports, a substrate with sequenceable nucleic acid molecules attached to the substrate, reagent and waste reservoirs and fluidic system connecting the reservoirs to the flowcell (FIG. 3). The flowcell is interfaced with a detection system to monitor the incorporation of the nucleotides.

In one embodiment, the sequencing by synthesis is carried out using reversibly terminating nucleotides and polymerase. The nucleotides comprise a protective group at their 3'-OH which prevents multiple incorporations and allows for accurate decoding of the sequence. Once incorporated the protective groups can be cleaved with high efficiency and specificity to allow subsequent nucleotide incorporations. The nucleotides may also comprise a detectable label which can be cleaved after the detection.

In one embodiment, the present invention contemplates a series of method steps, which an instrument for automated sequencing by synthesis may carry out. In one embodiment, the process is comprised of the following reagent reservoirs: 1) Extend A (reversibly terminated labeled nucleotides and polymerase); 2) Extend B (reversibly terminated unlabeled nucleotides and polymerase, but lacking labeled nucleotide analogues); 3) Wash solution 1 (e.g. in one embodiment comprising a detergent, such as polysorbate 20, in a citrate solution, such as saline sodium citrate); 4) Cleave solution; 5) Wash solution 2 (e.g. in one embodiment, comprising a detergent, such as polysorbate 20 in a buffer comprising tris(hydroxymethyl)aminomethane or "Tris"). Of course, the present invention is not limited to particular concentrations of reagents in these solutions (and other buffers and detergents can be employed). Nonetheless, in order to achieve high throughput rates, the incorporation reactions and the cleavage reactions are desired to be fast. In one embodiment, high reaction rates are achieved by increasing the concentration of reagents, agitation, pH or temperature (or the combination of all these factors). The incorporation rate in addition is dependent on the specific activity and processivity of the polymerase used. In one particular embodiment (which is provided by way of a non-limiting example), the reagents solutions have the following compositions and concentration ranges:
1) Extend A—reversibly terminated (3'-O-Azidomethyl) labeled (1 nM to 1 uM) and non-labeled nucleotides (1 uM to 100 uM) and a first polymerase (1-500 ug/ml)); 2) Extend B—reversibly terminated non-labeled nucleotides (1 uM to 100 uM) and a second polymerase (1-500 ug/ml)); 3) Wash solution 1 (3.times.SSC, 0.02% Tween® 20); 4) Cleave solution (50-100 mM TCEP); 5) Wash solution 2 (100 mM Tris-HCl, 0.02% Tween® 20, 10 mM KCl, 20 mM (NH2)2SO4. In one embodiment, the first polymerase incorporates labeled nucleotides better than the second polymerase, which incorporates unlabeled nucleotides more efficiently. Examples of commercially available polymerases that can be used include Therminator™ I-III. These polymerases are derived from *Thermococcus* sp. and carry mutations allowing for incorporation of modified nucleotides. Examples of these polymerases are listed in Table below:

| Therminator I | NEB cat. # M0261L | 9°N A485L (exo−) DNA Polymerase |
|---|---|---|
| Therminator II | NEB cat. # M0266L | 9°N A485L/Y409V (exo−) DNA Polymerase |
| Therminator III | NEB cat. # M0333L | 9°N L408S/Y409A/P410V (exo−) DNA Polymerase |

Other polymerases derived from 9 deg N parent polymerase or *Thermococcus* sp. could also be used. Other suitable polymerase families could conceivably be used after introducing mutation controlling the steric gate and enabling reversible terminators incorporation.

In one embodiment, the sequenceable DNA (preferably loaded on the chip or slide) is subjected to these solutions and compositions in the instrument, and the sequencing is performed using automated protocol. Again, it is not intended that the present invention be limited to a precise protocol or series of method steps. The order and number of steps can vary, as well as the time taken for each step. By way of a non-limiting example, in one embodiment, the instrument protocol comprises (and is configured) as follows:

1. Extend A—0.5-5 minutes (delivery+agitation)
2. Extend B 1-20 minutes (delivery+agitation)
3. Wash 2—5-10 minutes (10-20× delivery and agitation followed by flow cell evacuation)
4. Image
5. Cleave—1-5 minutes (delivery+agitation)
6. Wash 1—5 10 minutes (10-20× delivery and agitation followed by flow cell evacuation)
7. Wash 2—5-10 minutes (10-20× delivery and agitation followed by flow cell evacuation)
8. Go to step 1

The cycle may be repeated as desired and images may be taken and subsequently analyzed to decode the DNA sequence present at each location.

In one embodiment of the above indicated cycle, eight nucleotide analogues are employed: four (A, T, C, G) cleavably labeled and reversibly terminated; four (A, T, G, C) unlabeled but reversibly terminated. In one embodiment, the concentration of the labeled analogues is at a relatively low concentration [e.g. just enough to be incorporated into a substantial portion (e.g. so the label is visible and detected) of the plurality of primers, whether they be detached primers or self-priming hairpins on the template]. By contrast, the unlabeled analogues, in one embodiment, are employed in a relatively high concentration (e.g. in order to drive the extensions to completion, and avoid primers, whether they be detached primers or self-priming hairpins, that lack incorporation of a first nucleotide analogue). It has been found empirically that the use of unlabeled nucleotides improves read lengths, and reduces lead and lag (discussed below).

One example of a currently optimized protocol running on Beta instrument using 3'-O-azidomethyl/disulfide labeled nucleotides and non-labeled 3'-O-azidomethyl nucleotides is shown

| Nucleotide | Labeled nucleotides [nM] | Un-labeled nucleotides [nM] |
|---|---|---|
| dCTP | 30 | 250 |
| dATP | 20 | 250 |
| dGTP | 30 | 250 |
| TTP | 30 | 250 | in the Table (above), wherein un-labeled nucleotides are employed in ratios between 8.33 to 1 and 12.5 to 1 (relative to labeled nucleotides). In one embodiment, the labeling (i.e. incorporation) step uses Kapa RevTerm polymerase (from Kapa Biosystems, Woburn, mA) at 2 μg/ml and is performed at 55 deg C. for 1-2 minutes. This is followed by synchronization step where only non-labeled nucleotides are used at 25 μM concentration and a polymerase derived from 9 deg N (*Thermococcus* sp). at 25 μg/ml is used. This step is also carried out at 55 deg C. Thus, unlabeled nucleotide analogues can be employed together with labeled nucleotides, as well as in steps where no labeled nucleotides are employed.

B. Device

In one embodiment, the present invention contemplates using an optical system, for exciting and measuring fluorescence on or in samples comprising fluorescent materials (e.g., fluorescent labels, dyes or pigments). In a further embodiment, a device is used to detect fluorescent labels on nucleic acid. In another embodiment, the device comprises a fluorescent detection system and a flow cell for processing biomolecules (e.g., nucleic acid samples) arrayed on a "chip" or other surface (e.g., microscope slide, etc.). The flow cell permits the user to perform biological reactions, including but not limited to, hybridization and sequencing of nucleic acids.

It is not intended that the present invention be limited to particular light sources. By way of example only, the system can employ ultra-bright LEDs (such as those available from Philips Lumileds Lighting Co., San lose, Calif.) of different colors to excite dyes attached to the arrayed nucleic acids. These LEDs are more cost effective and have a longer life than conventionally used gas or solid state lasers. Other non-lasing sources of lights such as incandescent or fluorescent lamps may also be used.

FIG. 1 shows a useful configuration of the LEDs, whereby the emitted light converges on a region or platform (e.g., suitable for positioning the flow cell or sample). However, linear arrays of LEDs can also be used.

It is not intended that the present invention be limited to particular light collection devices. By way of example only, the system may employ a high sensitivity CCD camera (such as those available from Roper Scientific, Inc., Photometric division, Tucson Ariz. or those available from Apogee Instruments, Roseville, Calif.) to image the fluorescent dyes and make measurements of their intensity. The CCD cameras may also be cooled to increase their sensitivity to low noise level signals. These may also be CMOS, vidicon or other types of electronic camera systems.

Since LED illumination light is not a collimated beam as from lasers, it is therefore an appropriate choice for imaging a larger area of many nucleic acid spots. To get sufficient light and therefore fluorescent signals over the larger area, the area seen by each pixel of the camera must be of sufficient size to allow enough fluorescent dye molecules to create a sufficient signal (for example, an Apogee U13 CCD available has 1.3 megapixels of 16 microns in size, while the Apogee U32 has 3.2 megapixels of 6.8 microns in size).

To increase capacity and efficiency, the present invention contemplates in one embodiment, a two flow cell system (e.g. while one chip in a first flow cell is undergoing one or more reaction steps, a second chip in a second flow cell is being scanned and imaged) with a single camera. In yet another embodiment of an imaging system, two flow cells and two cameras are employed.

Figure 2A:
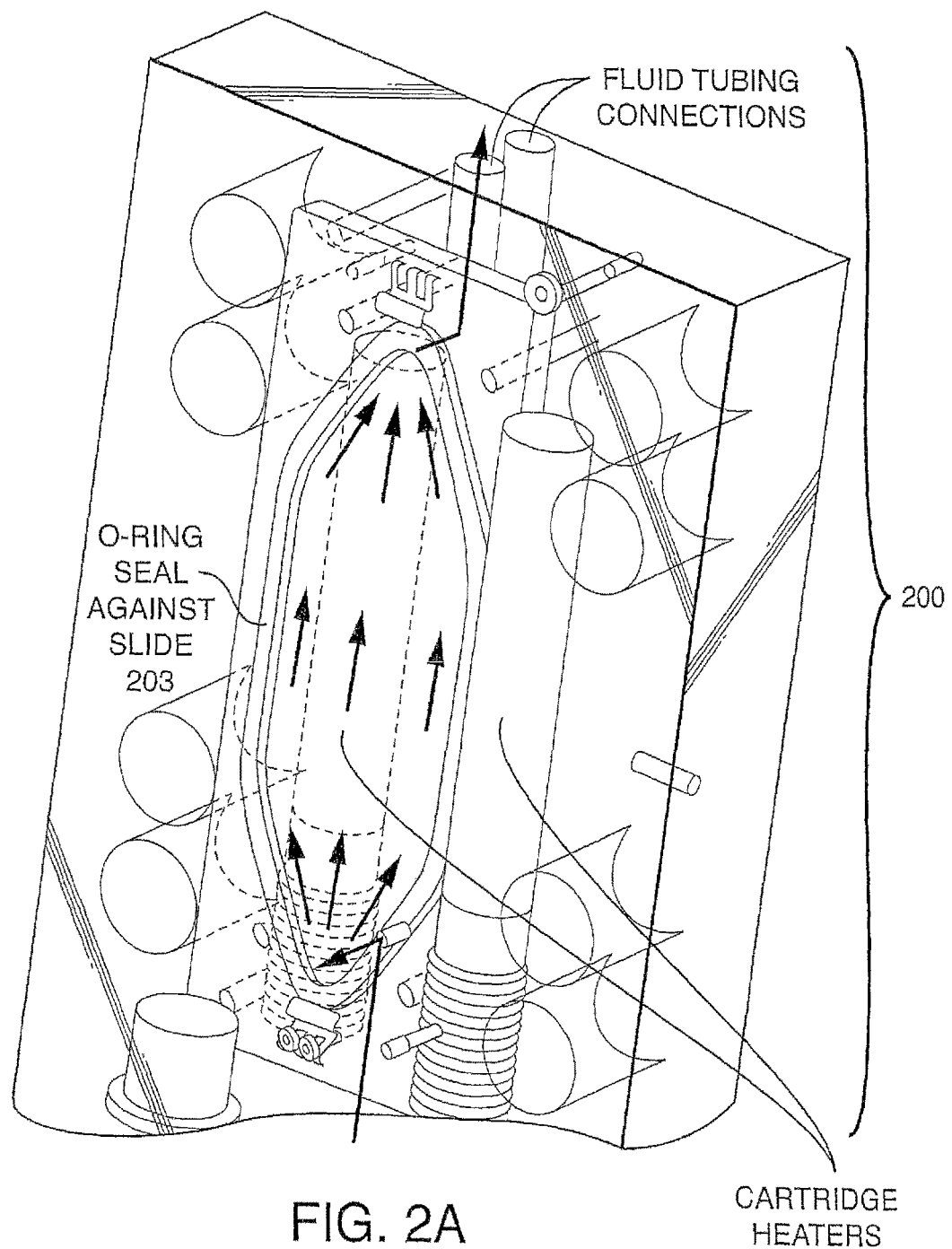
FIG. 2A shows a three dimensional translucent view of a flow cell, comprising fluid tubing connections, cartridge heaters, and O-ring seal.
Figure 2B:
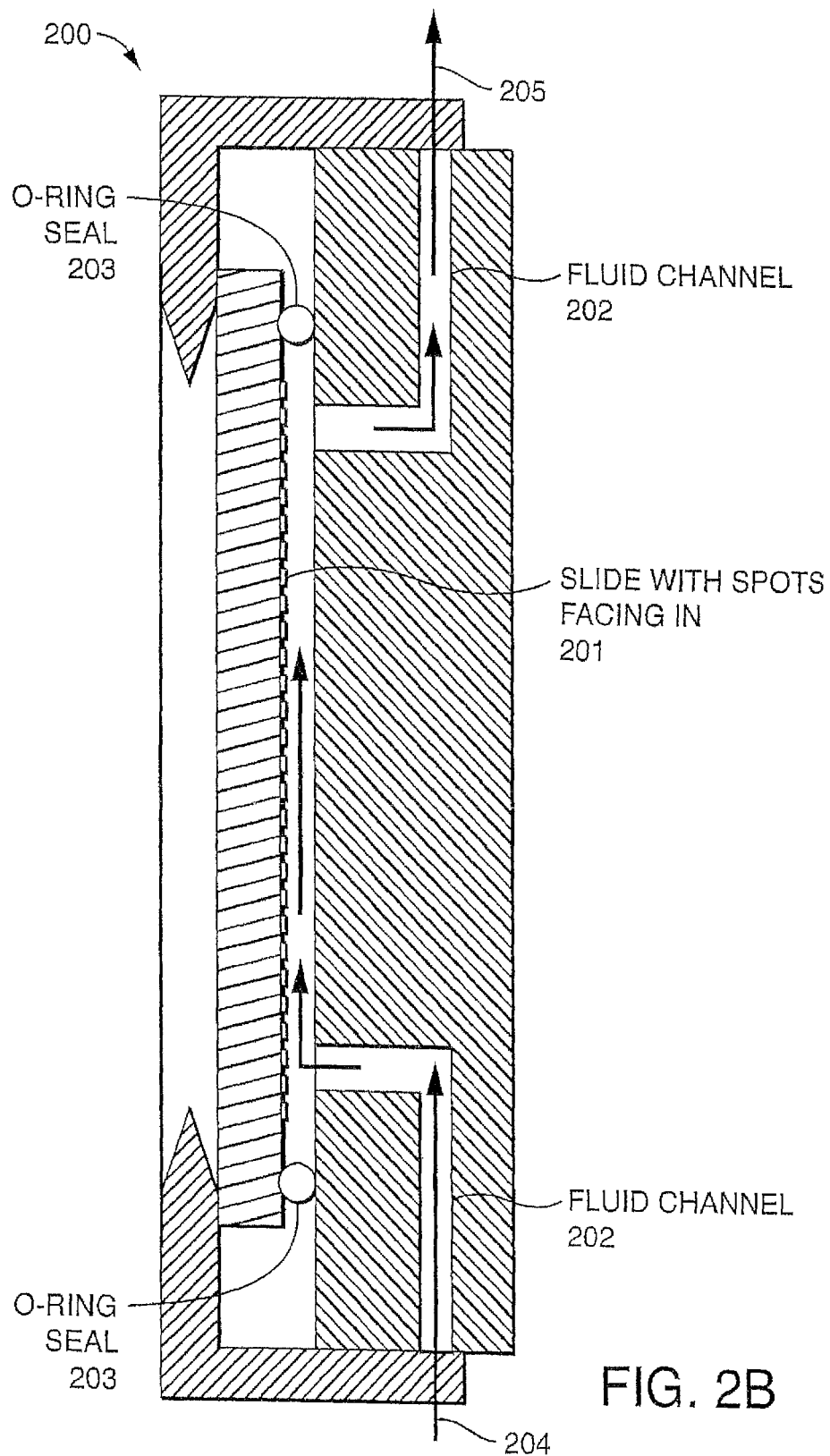
FIG. 2B is a two dimensional thawing of a side view of a flow cell (200), showing an array or slide (201) with spaced spots on the surface (representing positions for biomolecules and/or anchoring molecules), said array positioned (e.g. inverted) in a fluid channel (202) such that solutions of buffers and/or reagents can be introduced over the surface under conditions whereby reactions and/or washing can be achieved. The arrows show one particular direction of fluid flow, with entrance (204) and exit ports (205), as well as one particular method of sealing (O-ring seal 203).
Figure 2C:
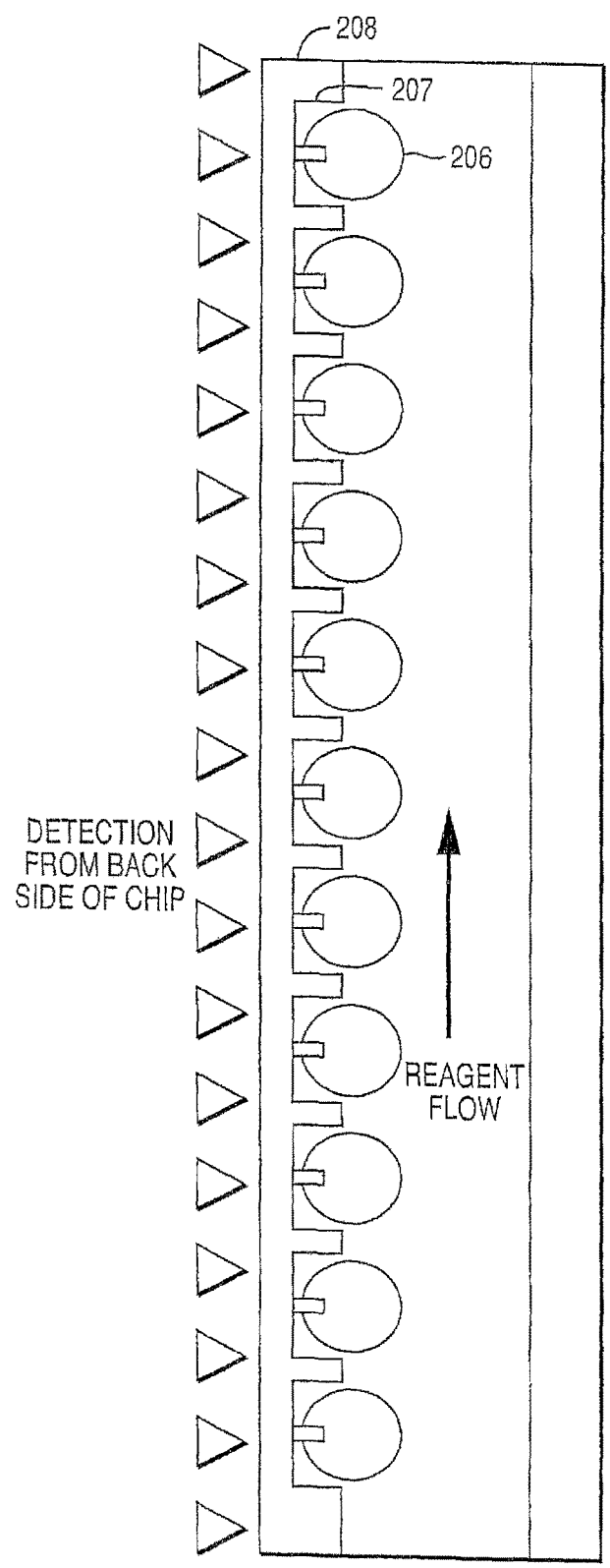
FIG. 2C is a drawing depicting beads (206) in the wells (207) of the slide (or chip 208), which preferably comprises nucleic acid to be sequenced (not shown), said slide positioned in a flow cell for contact with reagents in the solution traveling through the flow cell. The single dark arrow shows reagent flow in the flow cell. The many light arrow heads represent detection (e.g. light imaging) from the back of the slide (or chip).
Figure 3A:
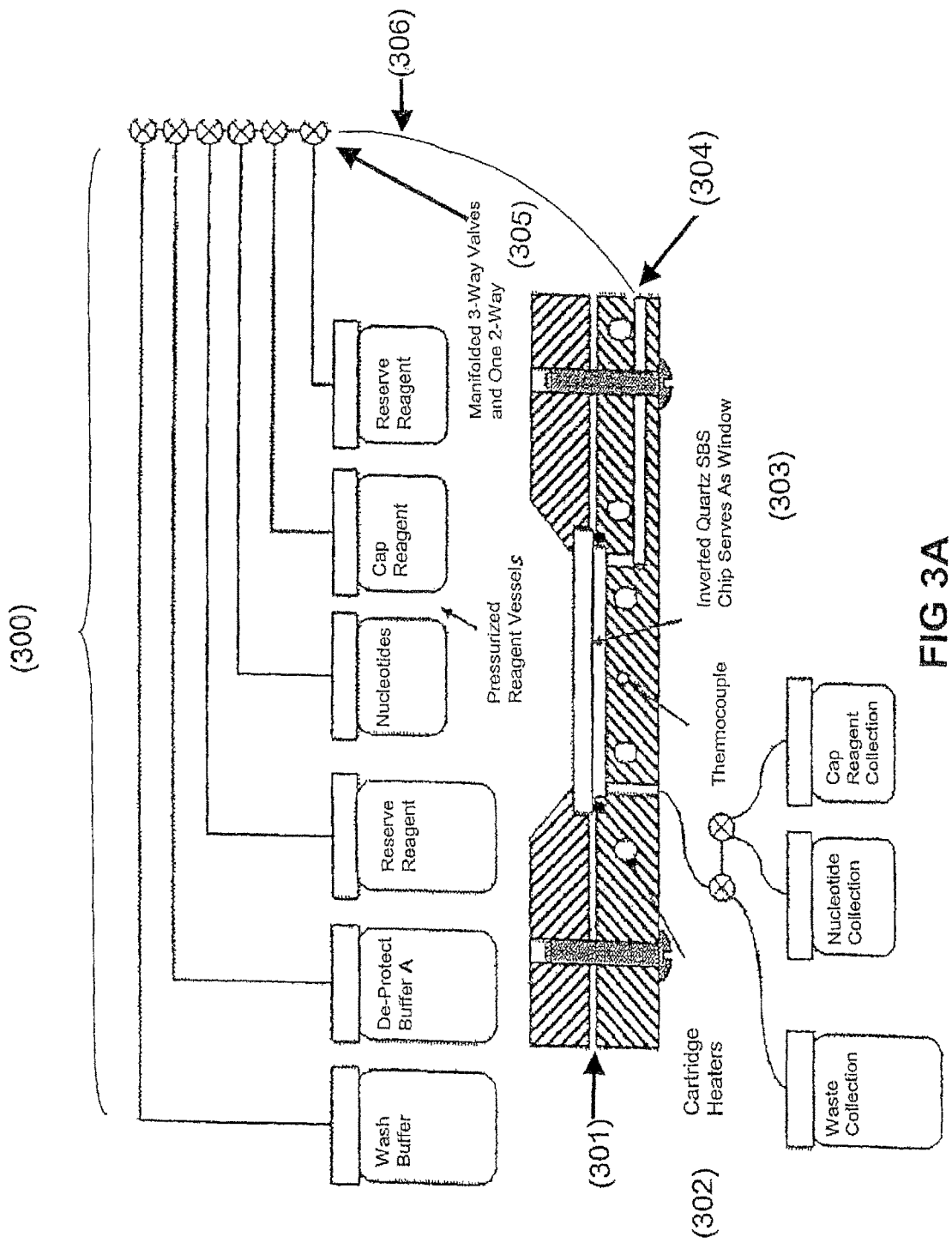
FIG. 3A schematically shows one embodiment of a fluidics system (300), comprising a variety of illustrative reagent and buffer reservoirs in communication (via tubing (306) or other channeling into a manifold comprising valves (305)) with one embodiment of a flow cell (comprising a side entrance port (301) and one or more heaters 302), wherein the array or chip (303) is inverted and the exit port (304) is on the bottom, thereby permitting the fluid channel to be drained at least in part by gravity so that waste can be readily collected into a reservoir. 3B shows another embodiment of the system (310), showing the flow cell (311) in relationship to the illumination and optics (312).
Figure 3B:
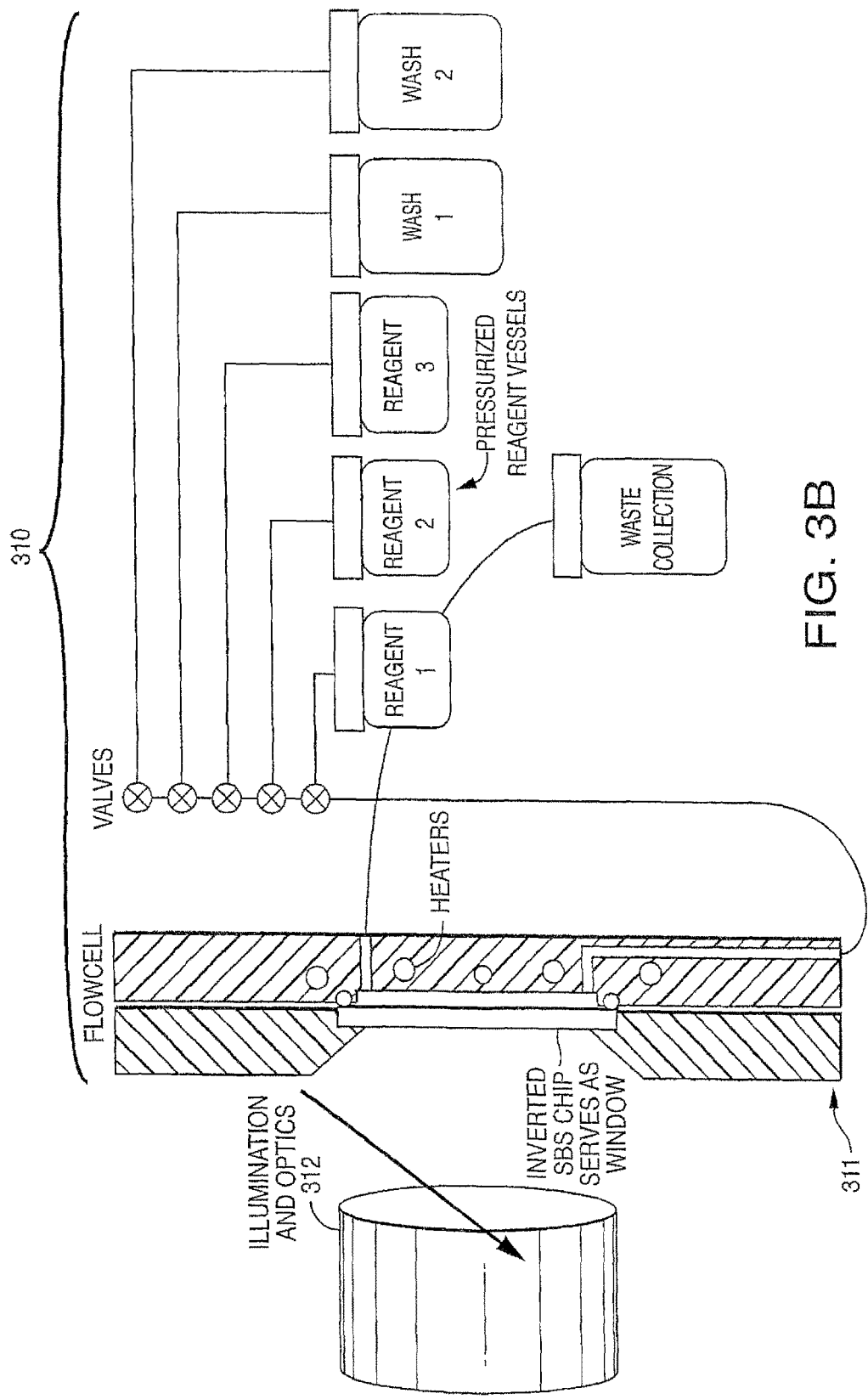

In one embodiment, the chip containing the array of nucleic acid spots is processed in a transparent flow cell incorporated within the instrument, which flows reagent past the spots and produces the signals required for sequencing (see FIGS. 2A and 2B). In a particular embodiment, the chip remains in the flow cell while it is imaged by the LED detector. The flow cell and associated reagents adds the nucleic acids, enzymes, buffers, etc. that are required to produce the fluorescent signals for each sequencing step, then the flow cell delivers the required reagents to remove the fluorescent signals in preparation for the next cycle. Measurement by the detector occurs between these two steps. In order for reactions to take place, the flow channels are configured to be of sufficient dimensions. For example, the flow-cell fluid channel found by the array and the flat surface of the flow cell are at least 0.1 mm in depth (more particularly 0.5 min in depth) and the volume formed by the chip, the block and the seal is at least 100 microliters in volume (more particularly, between 100 and 700 microliters, and still more particularly, between 150 and 300 microliters, e.g. 200 microliters, in volume).

In one embodiment, the flow cell is motionless (i.e., not moved during reactions or imaging). On the other hand, the flow cell can readily be mounted on a rotary or one or more linear stages, permitting movement. For example, in a two flow cell embodiment, the two flow cells may move up and down (or side to side) across the imaging system. Movement may be desired where additional processes are desired (e.g., where exposure to UV light is desired for photochemical reactions within the flow cell, such as removal of photocleavable fluorescent labels), when multiple flow cells share a single camera, or when the field of view of the detection system is smaller than the desired area to be measured on the flow cell. The detector system may also be moved instead of or in addition to the flow cell.

In a further embodiment, the flow cell is in fluid communication with a fluidics system (see illustrative system shown in FIG. 3. In one embodiment, each bottle is pressurized with a small positive gas pressure. Opening the appropriate valve allows reagent to flow from the source bottle through the flow cell to the appropriate collection vessel(s). In one embodiment, the nucleotides and polymerase solutions are recovered in a separate collection bottle for re-use in a subsequent cycle. In one embodiment, hazardous waste is recovered in a separate collection bottle. The bottle and valve configuration allow the wash fluid to flush the entire valve train for the system as well as the flow cell. In one embodiment, the process steps comprise: 1) flushing the system with wash reagent, 2) introducing nucleotides (e.g. flowing a nucleotide cocktail) and polymerase, 3) flushing the system with wash reagent, 4) introducing de-blocking reagent (enzyme or compounds capable of removing protective groups in order to permit nucleic acid extension by a polymerase), 5) imaging, 6) introducing label removing reagent (enzyme or compounds capable of removing fluorescent labels), and 7) flushing the system with wash reagent.

The system can be made to include a user interface system. The Labview (National Instruments, Austin, Tex.) system is available and provides software for computer controlled systems. Galil Motion Control (Rocklin, Calif.) provides motion control systems that can be interfaced to control the instrument.

C. Nucleotides

The invention's compositions and methods contemplate using nucleotide sequences that contain nucleotides. The terms "nucleotide" and "nucleic acid" refer to constituents of nucleic acids (DNA and RNA) that contain a purine or pyrimide base, such as adenine (A), guanine (G), cytosine (C), uracil (U), or thymine (T)), covalently linked to a sugar, such as D-ribose (in RNA) or D-2-deoxyribose (in DNA), with the addition of from one to three phosphate groups that are linked in series to each other and linked to the sugar. The term "nucleotide" includes native nucleotides and modified nucleotides.

"Native nucleotide" refers to a nucleotide occurring in nature, such as in the DNA and RNA of cells. In contrast, "modified nucleotide" refers to a nucleotide that has been modified by man, such as using chemical and/or molecular biological techniques compared to the native nucleotide. The terms also include nucleotide analogs attached to one or more probes to facilitate the determination of the incorporation of the corresponding nucleotide into the nucleotide sequence. In one embodiment, nucleotide analogues are synthesized by linking a unique label through a cleavable linker to the nucleotide base or an analogue of the nucleotide base, such as to the 5-position of the pyrimidines (T, C and U) and to the 7-position of the purines (G and A), to use a small cleavable chemical moiety to cap the 3'-OH group of the deoxyribose or ribose to make it nonreactive, and to incorporate the nucleotide analogues into the growing nucleotide sequence strand as terminators, such as reversible terminators and irreversible terminators. Detection of the unique label will yield the sequence identity of the nucleotide. Upon removing the label and the 3'-OH capping group, the polymerase reaction will proceed to incorporate the next nucleotide analogue and detect the next base. Exemplary fluorescent moieties and fluorescent semiconductor crystals are described in Ju et al., U.S. Pat. No. 6,664,079, hereby incorporated by reference.

Other nucleotide analogs that contain markers, particularly cleavable markers, are also contemplated, such as those configured using allyl groups, azido groups, and the like, and which are further described below. The nucleotide compositions of the invention are particularly useful in massively parallel DNA Sequencing By Synthesis (SBS) approaches utilizing fluorophores as markers.

a. Allyl Analogs

Cleavable fluorescent nucleotides with photo-cleavable linkers having reversible terminator allyl groups have been described in Ruparel et al. (2005) Proc. Natl. Acad. Sci. 102(17) 5932-7. Similar, fluorescent nucleotide conjugates have been described in Bi et al. (2006) J. Am. Chem. Soc. 128(8) 2542-3. In one embodiment, the invention contemplates using nucleotide analogs with cleavable markers conveniently configured with allyl groups. In a particular embodiment, the exposed amine groups of incorporated nucleotides are capped during sequencing. In other embodiments, the nucleotide derivatives comprise two or more allyl ethers and synthetic intermediates thereto.

Figure 5:
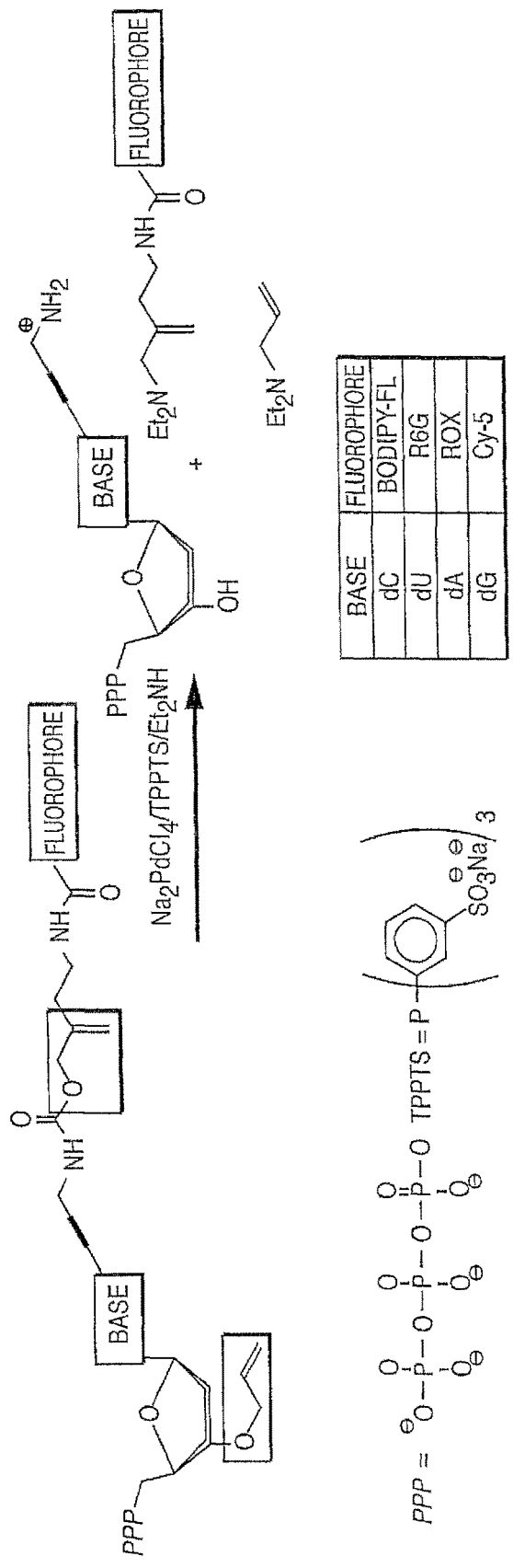
FIG. 5 shows a general structure of embodiments of cleavable fluorophore nucleotide conjugates with reversible terminator functionality. The 3'-OH group is reversibly blocked by an allyl ether function and the fluorophore is attached via a cleavable allyl carbamate linker (both shown in frames). After incorporation and signal readout, the fluorophore and the 3-O-allyl protective groups are cleaved by aqueous solution of Pd (0).

Sample preparation and parallel sequencing steps are exemplified, but not limited, to those illustrated in FIGS. 4 and 5. FIG. 4 Panel A shows how one isolates and prepares the DNA prior to sequencing and Panel B shows the sequencing cycle. One isolates DNA from a biological source and shears it by a mechanical device to the desired average size. One end-repairs, A-tails, and circularizes the fragments using a dT-tailed linker about 100 nucleotides in length. The linker consists of two outward directed primer recognition sequences and an arbitrary sequence of about 100 bases between the priming sites. After ligation, one decomposes noncircular sequences by treatment with an endonuclease. One dilutes the circular DNA fragments to prepare them for bead-based emulsion PCR using a biotinylated forward primer and a bead-attached reverse primer carrying an azido group on. its 5'-end. One performs emulsion PCR. An aqueous mix containing all the necessary components for PCR plus primer-bound beads and template DNA are stirred together with an oil/detergent mix to create microemulsions. The aqueous compartments contain an average of less than one template molecule and less than one bead. The microemulsions are temperature-cycled as in a conventional PCR. If a DNA template and bead are present together in a single aqueous compartment, the bead-bound oligonucleotides act as primers for amplification. One breaks the emulsion and subjects the mixture to an enrichment step by using streptavidin coated magnetic beads. One denatures the nucleic acid immobilized on the beads generating single stranded amplicons to which a self-priming hairpin moiety is then ligated.

The beads are then arrayed on a chip surface and the sequencing by synthesis reactions are performed. Each cycle comprises steps that are used to read out the DNA sequence (See FIG. 4, Panel B). One subjects the array segment to the fluorescent nucleotide conjugate with a hydroxyl-protecting group on the 3' end. One scans the array and the fluorescent output of each of the fluorescent markers and measures the output for each position. One exposes the array to conditions for cleavage of the fluorescent marker and the hydroxyl-protecting group. The entire process is repeated with another set of nucleotide bases unit the sequence of each position is determined. As the sequence data is generated, one collects the sequence information and aligns the reference sequences for diagnosis. One may use computer software and a database of previously known mutations and corresponding sequences to correlate them to the sequence with known mutations.

The PCR approach described above ensures that instead of sequencing of the entire pool of templates, one performs clonal or digital sequencing, resulting in much higher sensitivity for detection of mutations. For example, if a spontaneous mutation is present at only 5% of the population and the remaining 95% of the gene copies are wild types it is difficult to detect the mutated DNA using a conventional pool sequencing approach because of insufficient sensitivity. In the applicants' approach, one dilutes the input sample so that each PCR emulsion bubble contains at most a single template, which is then subjected to sequencing. If one performs this process on 1,000 unique clones, then one on average detects mutant sequences (present in 5% of amplicons) in 50 reactions and wild type sequence in 95% of the reactions.

b. Azido Analogs

Nucleotide analogs that contain cleavable markers configured using azido groups are also useful in the invention's methods and compositions. The nucleotide analogs are exemplified by nucleotide compositions comprising compounds of the following general structure:

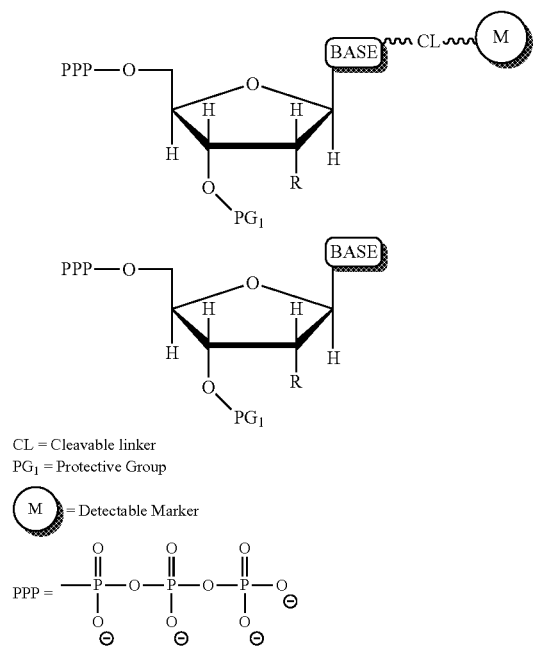

Where PG1 stands for protective group that is selectively removable and, and CL stands for cleavable linker, which is also selectively cleavable, and R is selected from the group of H, OH, F, $NH_2$. Several particular embodiments of this invention are contemplated. In one embodiment these nucleotide compositions can be incorporated into the nucleic acid by nucleic acids modifying enzymes in a controlled fashion to decode the identity of the bases encoded by the marker moiety M. Once the identity of the base has been decoded, then the marker moiety can be cleaved off and removed. This invention contemplates the use of the cleavable linkers based on the "trimethyl lock" mechanism or the "1,6-rearrangement" mechanism. The 3'-O-protective groups which act as reversible terminators can also be cleaved off to enable addition of the next nucleotide. This invention contemplates the use of azidomethyl, methylaminoxy, disulfide and allyl groups as reversible 3'-OH terminators.

Methods for synthesizing exemplary nucleotide analogs that contain cleavable markers configured using azido groups are described in Examples 2-11 and shown in FIGS. 20-26.

The invention contemplates the use of the cleavable linkers based on the "trimethyl lock" mechanism or the "1,6-rearrangement" mechanism. The 3'-O-protective groups which act as reversible terminators can also be cleaved off to enable addition of the next nucleotide. The invention contemplates the use of azidomethyl, aminooxy, methylaminoxy and allyl groups as reversible 3'-OH terminators.

I. Cleavable Linkers (CI)

Cleavable linkers are exemplified by trimethyl lock based linkers and 1,6-rearrangement linkers as further described below.

1. Trimethyl Lock Based Linkers

Cleavable linkers are the linkers linking the marker molecule M to the base and these can be selectively cleaved using specific cleaving agents. Specifically, this invention contemplates the use of a "trimethyl lock" structure as the cleavage mechanism. These structures are well known in the chemical arts and have been used before in controlled drug release applications. The general structures of cleavable trimethyl lock based linker utilized in particular embodiments of the present invention are shown below:

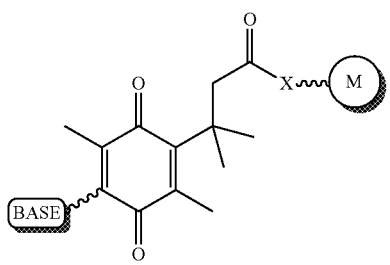

The above shows exemplary embodiment A where BASE is selected from any ribo- or deoxyribonucleobases: adenosine, cytidine, guanosine, thymidine and analogs, M is a detectable marker, and X is a divalent group selected from NH, O, S.

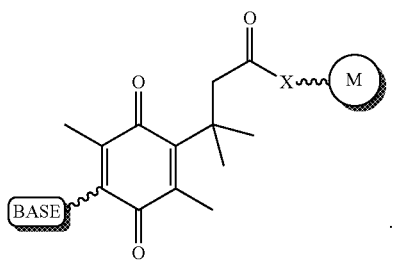

The above shows exemplary embodiment B where BASE is selected from any ribo- or deoxyribonucleobases: adenosine, cytidine, guanosine, thymidine and analogs, M is a detectable marker, and X is NH.

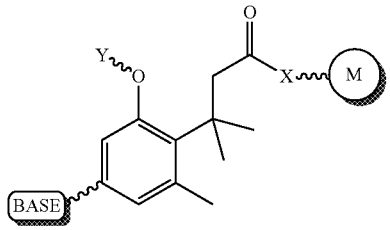

The above shows exemplary embodiment C where BASE is selected from any ribo- or deoxyribonucleobases: adenosine, cytidine, guanosine, thymidine and analogs, M is a detectable marker, and X is a divalent group selected from NH, O, S, and Y is a selectively removable protective group.

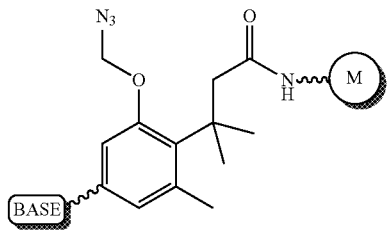

The above shows exemplary embodiment D where BASE is selected from any ribo- or deoxyribonucleobases: adenosine, cytidine, guanosine, thymidine and analogs, M is a detectable marker, X is NH, and Y is an azidomethyl group.

Figure 6:
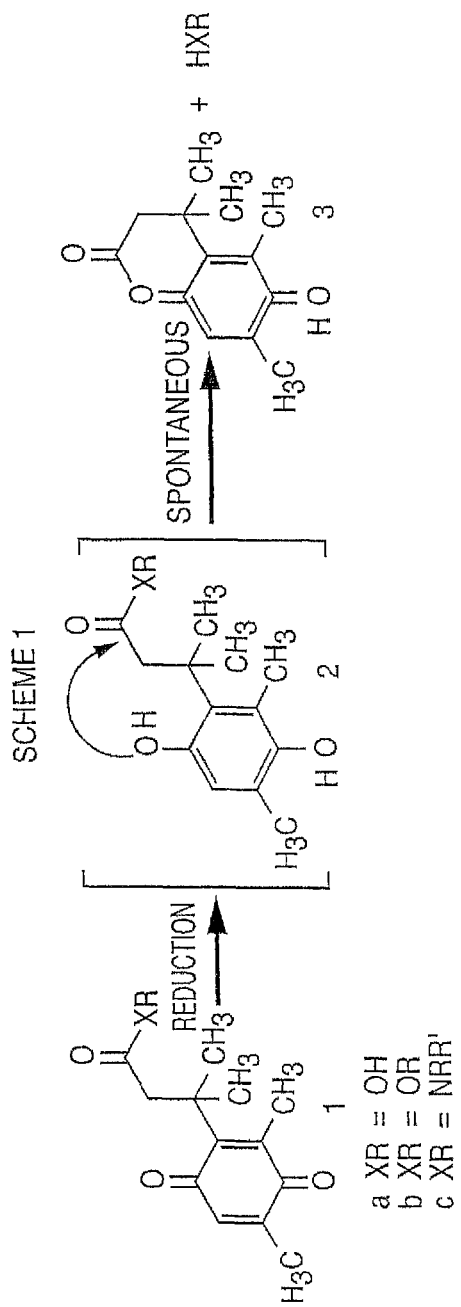
FIG. 6 shows a cleavage mechanism for trimethyl lock based compounds.

The cleavage mechanism for the trimethyl lock based compounds is shown schematically in FIG. 6. This phenomenon has been previously described in the chemical literature and used as for basic research studies (Borchardt and Cohen (1972). J. Am. Chem. Soc. 94(26): 9166-9174, Wang et al. (1996) Bioorg. Chem. 24: 39-49), as caging agents for controlled drug delivery (Wang et al. (1997). L Org. Chem. 62(5): 1363-1367) and as protective groups in organic synthesis (Wang et al. (1995). J. Org. Chem, 60(3): 539-543).

The linkers in the present invention leverage the ability of the trimethyl lock system to create cleavably linked nucleotides.

2. 1,6-Rearrangement Linkers

The invention contemplates another category of cleavable linkers linking the detectable marker moiety to the nucleotide that are based on 1,6 quinone methide rearrangement mechanism (Carl et al. (1981). J. Med. Chem. 24(5):479-480; Duimstra et al. (2005). J. Am. Chem. Soc. 127(37): 12847-12855). These structures are well known in the chemical arts and they have been used before for the controlled drug release applications and for chemical synthesis (Azoulay et al. (2006) Bioorganic & Medicinal Chemistry Letters 16(12): 3147-3149; Murata et al. (2006) Tetrahedron Letters 47(13): 2147-2150). The general structures of cleavable 1,6 rearrangement mechanism based linker utilized in some embodiments of the present invention are shown below:

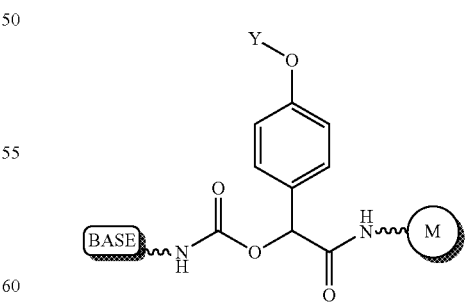

The above shows exemplary embodiment E, where BASE is selected from any ribo- or deoxyribonucleobases: adenosine, cytidine, guanosine, thymidine and analogs, M is a detectable marker and Y is a selectively removable protective group.

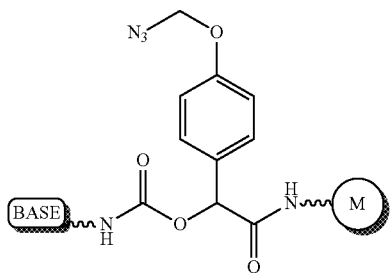

The above shows exemplary embodiment F, where BASE is selected from any ribo- or deoxyribonucleobases: adenosine, cytidine, guanosine, thymidine and analogs, M is a detectable marker.

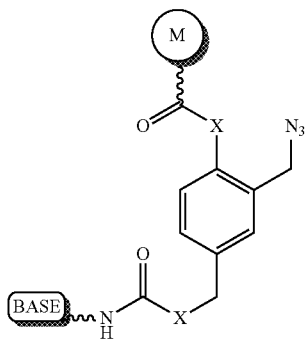

The above shows exemplary embodiment G where BASE is selected from any ribo- or deoxyribonucleobases: adenosine, cytidine, guanosine, thymidine and analogs, M is a detectable marker, and X is a divalent group selected from the following: NH, O, S.

Figure 7:
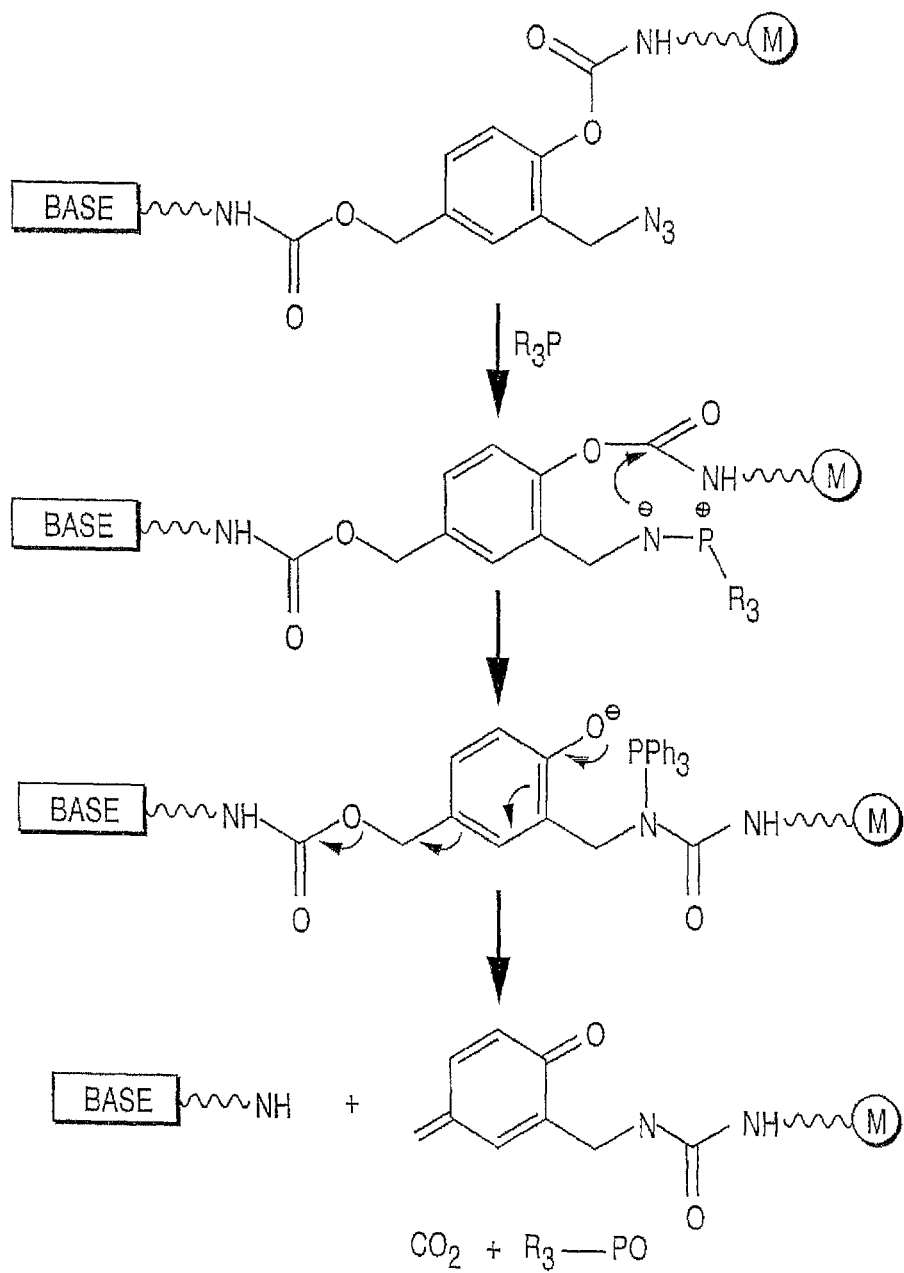
FIG. 7 shows a cleavage mechanism for 1,6-rearrangement based compounds.

FIG. 7 shows an exemplary cleavage mechanism for the cleavable linker described in the following exemplary embodiment G.

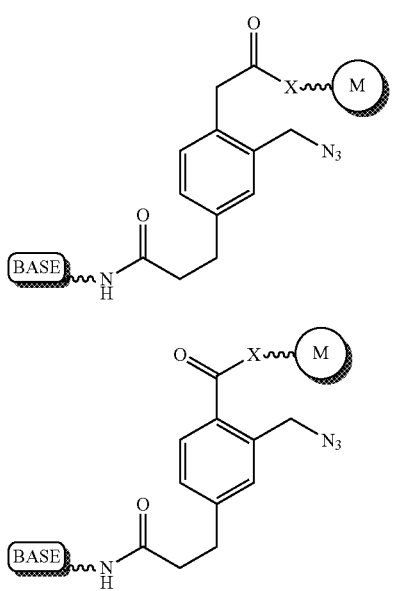

The above shows exemplary embodiment H where BASE is selected from any ribo- or deoxyribo- nucleobases: adenosine, cytidine, guanosine, thymidine and analogs, M is a detectable marker, and X is a divalent group selected from the following: NH, O, S. The cleavage is driven here by the reducing agent and nucleophilic attack of the resulting amino group on the carbonyl followed by cyclization. This mechanism has been used before for the development of protective groups for applications in the carbohydrate and nucleoside chemistry (Wada et al. (2001). Tetrahedron Letters 42(6): 1069-1072; Xu et al. (2002) Carbohydrate Research 337(2): 87-94

The cleavable linker attachment to the base moiety can be achieved in variety of ways that are well known in the art. Among these is the use of linkers based on 1) propargylamino nucleosides, 2) aminoallyl nucleosides, and 3) propargylhydroxy nucleosides.

ii. Protective Groups (PG1)

The invention contemplates nucleotide compositions comprising the following protective groups (PG1) that reside on the 3'-OH groups of the nucleotides: 1) 3'-O-Azidomethyl ethers, 2) 3'-O-disulfide, 3) 3'-O-methylaminoxy, and 4) 3'-O-allyl.

With respect to the 3'-O-Azidomethyl ethers, exemplary protective groups that reside on the 3'-OH groups of the nucleotides that are within the scope of this invention are 3'-O-azidomethyl groups. These groups can be removed using mild reducing agents, such as Tris(2-carboxyethyl)phosphine (TCEP).

With respect to the 3'-O-disulfide group, the 3'-O-disulfide group can be removed under mild oxidative conditions, for example using in using mild reducing agents, such as Tris(2-carboxy-ethyl)phosphine (TCEP).

With respect to the 3'-O-methylaminoxy group, the 3'-O-methylaminoxy (3'-O—CH2—NH2) group can be removed under mild oxidative conditions, for example using in situ generated nitrous acid (such as from sodium nitrite).

As to the 3'-O-allyl group, this protective group can be removed using a variety of reducing agents, including transition metal complexes (Pd, Rh).

c. 3'-O-Protected Nucleosides and Nucleotides

The invention contemplates compositions comprising compounds of the following general structure:

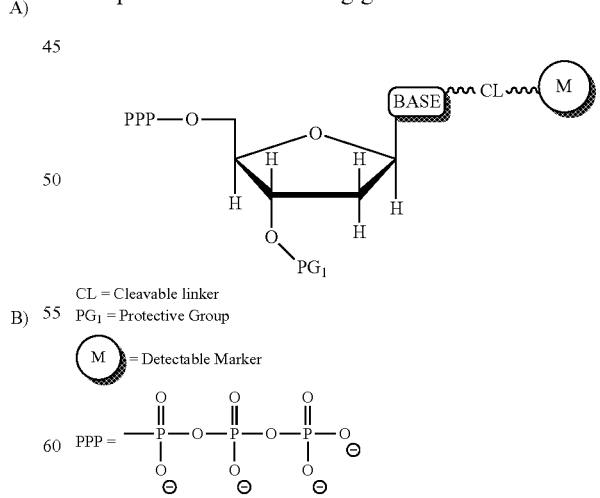

CL = Cleavable linker
PG1 = Protective Group
M = Detectable Marker

PG1 stands for protective group that is selectively removable and, and CL stands for cleavable linker, which is also selectively cleavable. In one embodiment these nucleotide compositions can be incorporated into the nucleic acid by nucleic acids modifying enzymes in a controlled fashion for example to decode the identity of the bases encoded by the marker moiety M. Once the identity of the base has been decoded, then the marker moiety can be cleaved off and removed. In one embodiment, the invention contemplates the use of cleavable protection for 3'-OH in nucleotides for reversible terminators for SBS.

Figure 28:
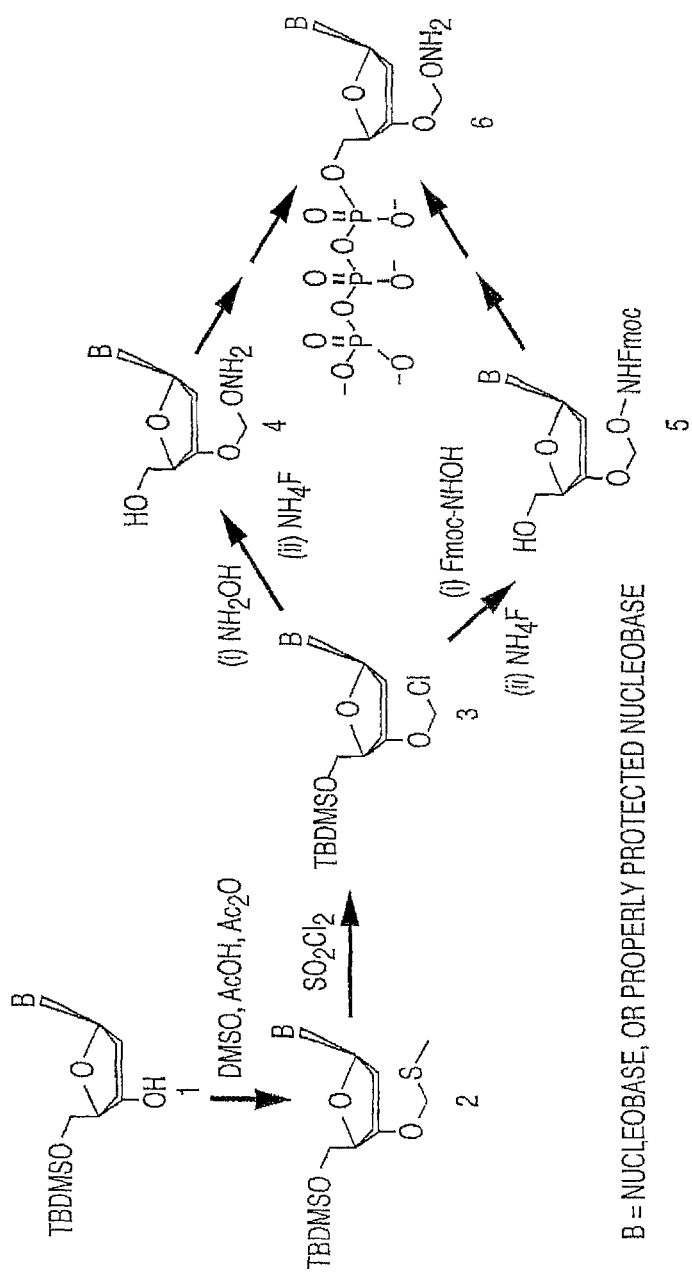
FIG. 28 shows an exemplary general synthetic pathway to install 3'-O amino hemiacetal group (—$CH_2ONH_2$) and conversion to nucleotides.
Figure 29:
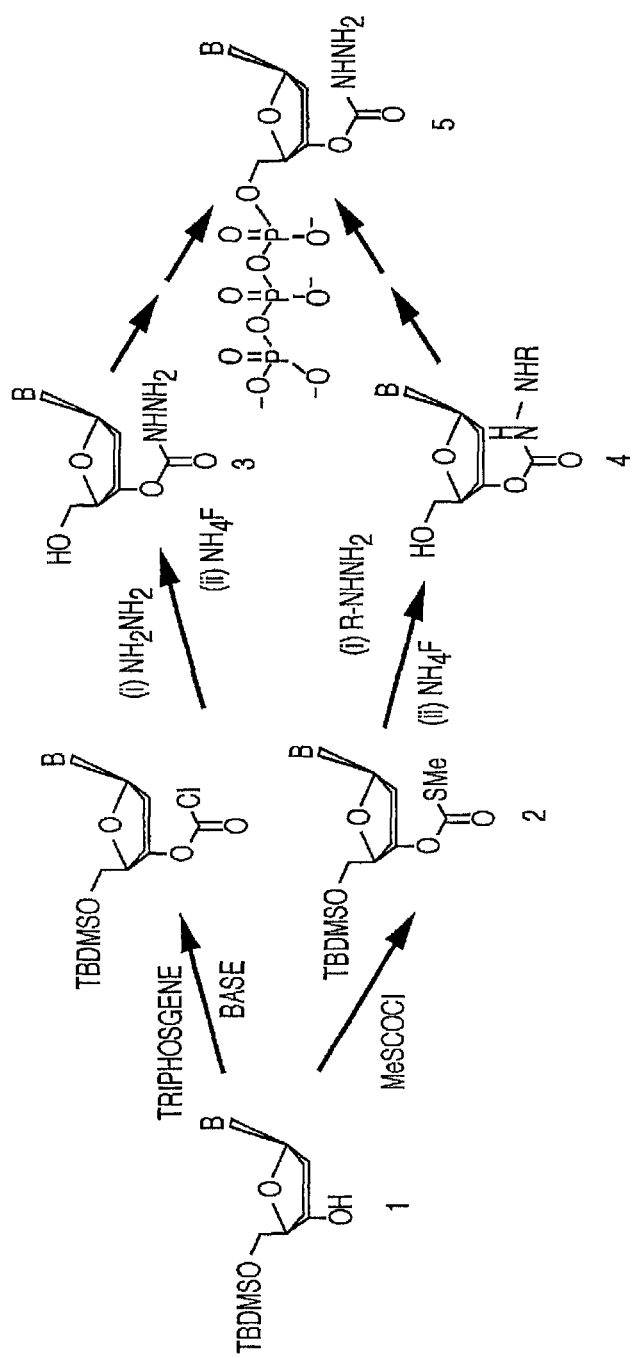
FIG. 29 shows an exemplary synthetic pathway to prepare 3'-O carbazate (—$CH_2ONH_2$) nucleotide analogues
Figure 30:
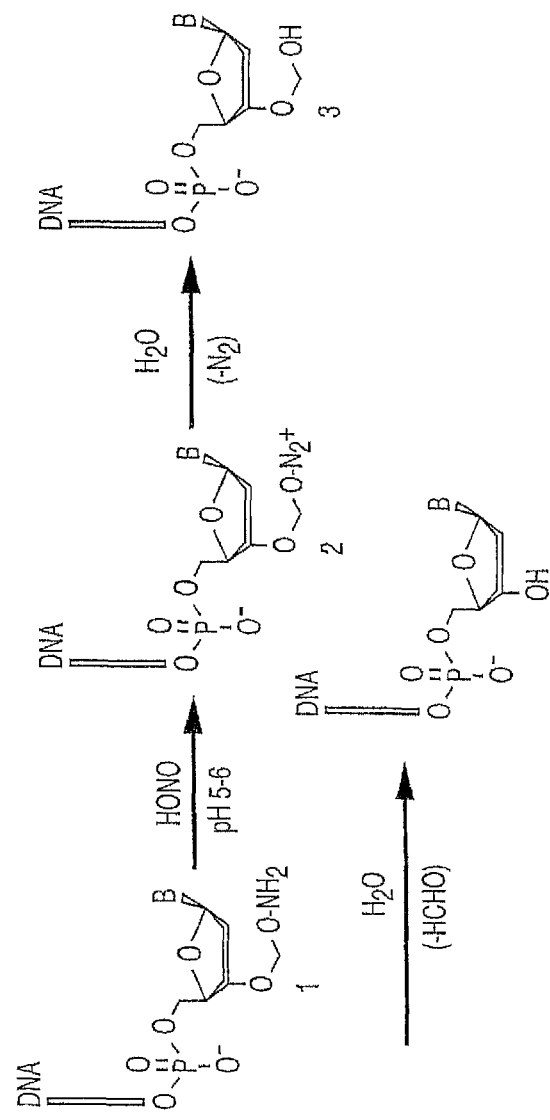
FIG. 30 shows an exemplary mechanism of 3'-O amino hemiacetal (—$CH_2ONH_2$) nucleotides deprotection reaction to generate free 3'-OH group.
Figure 31:
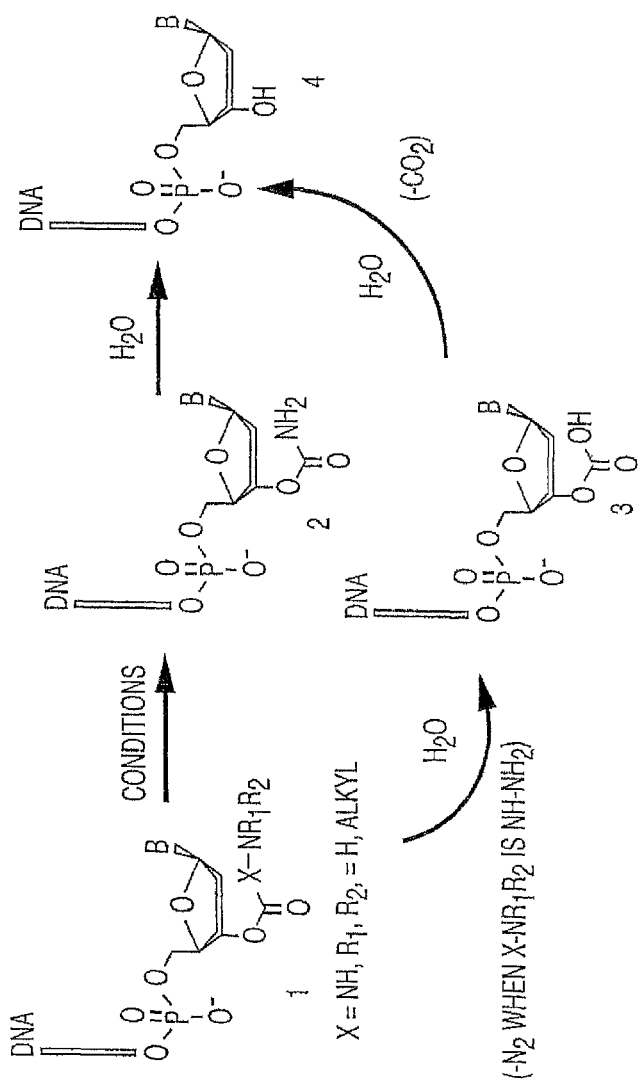
FIG. 31 shows an exemplary mechanism of 3'-O-carbazate (—$C(O)NHNH_2$) nucleotides deprotection. The reaction may be fast due to higher entropy contribution of the leaving molecular nitrogen and carbon dioxide gas.

Examples of PG1 protective groups are shown in FIG. 27. As an illustration, the synthesis of one of the embodiments in such classes of nucleotide-3'-O-($CH_2OH_2$)-dNTPs is presented in FIG. 28. Briefly, the protected 3'-methylthiomethyl nucleoside (1) upon treatment with $SO_2Cl_2$ produce activated product (2) which after reaction with hydroxylamine or its N-Fmoc protected compound install aminoxy group. The later compounds can be triphosphorylated to result in nucleotides. Other compounds and exemplary synthesis pathways within the scope of the invention are shown in FIGS. 29-31.

D. Reducing Lead and Lag

Figure 35:
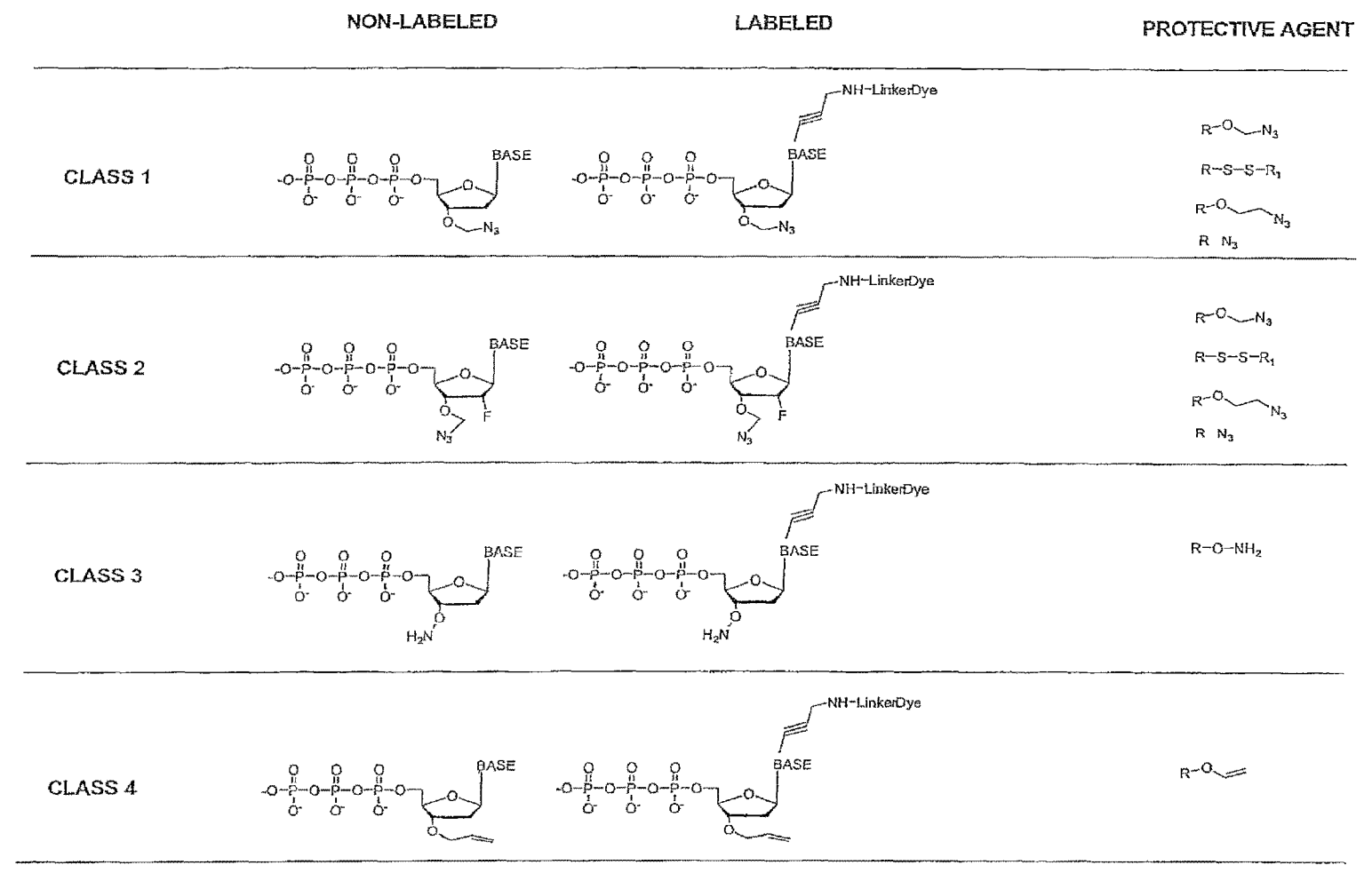
Figure 36:
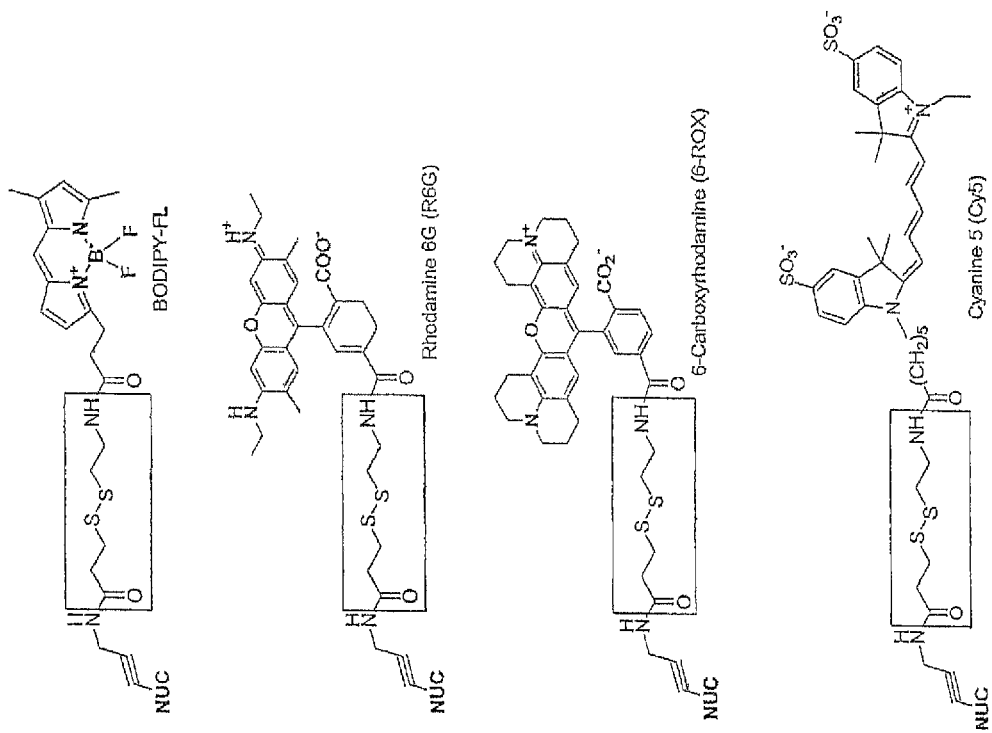
FIG. 36 provides examples of dyes conjugated to reversibly terminating nucleotides via a cleavable linker.

The cleaving agent is designed to cleave the 3'-OH or the dye attached to the nucleotide or both the 3'-OH and the dye, A variety of chemistries may be used for these attachments. FIG. 35 shows various possible chemistries for the 3'-OH group. FIG. 36 shows disulfide linkers for attaching the dye. Importantly, for any particular nucleotide, the chemistries may be same or may be different. For example, in one embodiment, the 3'-OH group can carry an azidomethyl ether and yet the dye can be attached via an azido linker. In another embodiment, however, the 3'-OH group can carry an azidomethyl ether and yet the dye can be attached via a disulfide linker. Both the azidomethyl ether and the disulfide linker are cleavable by TCEP (Tris-carboxyethyl)phosphine, although the disulfide linker cleaves much faster than the 3'-O-azidomethyl ether.

The cleaving agent is used at relatively high concentration (50-100 mM) to achieve fast cleavage. It is important for the sequencing process to remove any traces of cleaving agent in the wash steps, as these traces could interact with the Extend A and B solution (see the discussion of these solutions above) in the next cycle and create native nucleotides. This is highly undesirable as this leads to sequence dephasing (lead and lag) and limits useful read lengths.

One approach might be to increase the number of washes. However, it has been found empirically that increased washing cycles after cleavage step have only minimal effect on the sequencing performance unless very high numbers of washes are used (see Example 14). Such an approach would slow down the process considerably.

The present invention, in one embodiment, contemplates a different approach to solving the problem. In one embodiment, the present invention contemplates novel compositions to be used in one or more of the solutions employed in the sequencing by synthesis method (or in a new, additional separate solution) that reduce, minimize and/or inhibit the cleaving agent and the "pre-cleaving" effect. In one embodiment, a cleavage agent "scavenger" is contemplated. The cleavage agent scavenger is designed to react with any leftover cleaving reagent remaining in the flow cell or the fluidics (e.g. tubing) by inefficient or incomplete washing. In one preferred embodiment, the scavenger agent is added to the wash solution directly after the cleave step. In another embodiment the scavenger is added to the Extend A solution. In yet another embodiment the scavenger agent is added to Extend B solution. The scavenger requirements are as follows: 1) solubility; 2) fast and specific reaction with the cleaving agent. In the embodiments where the scavenger is added to Extend A or B solution, there is the additional requirement of lack of inhibition of polymerase reaction and lack of reactivity with functional groups on the nucleotides, dyes or polymerase.

Figure 37:
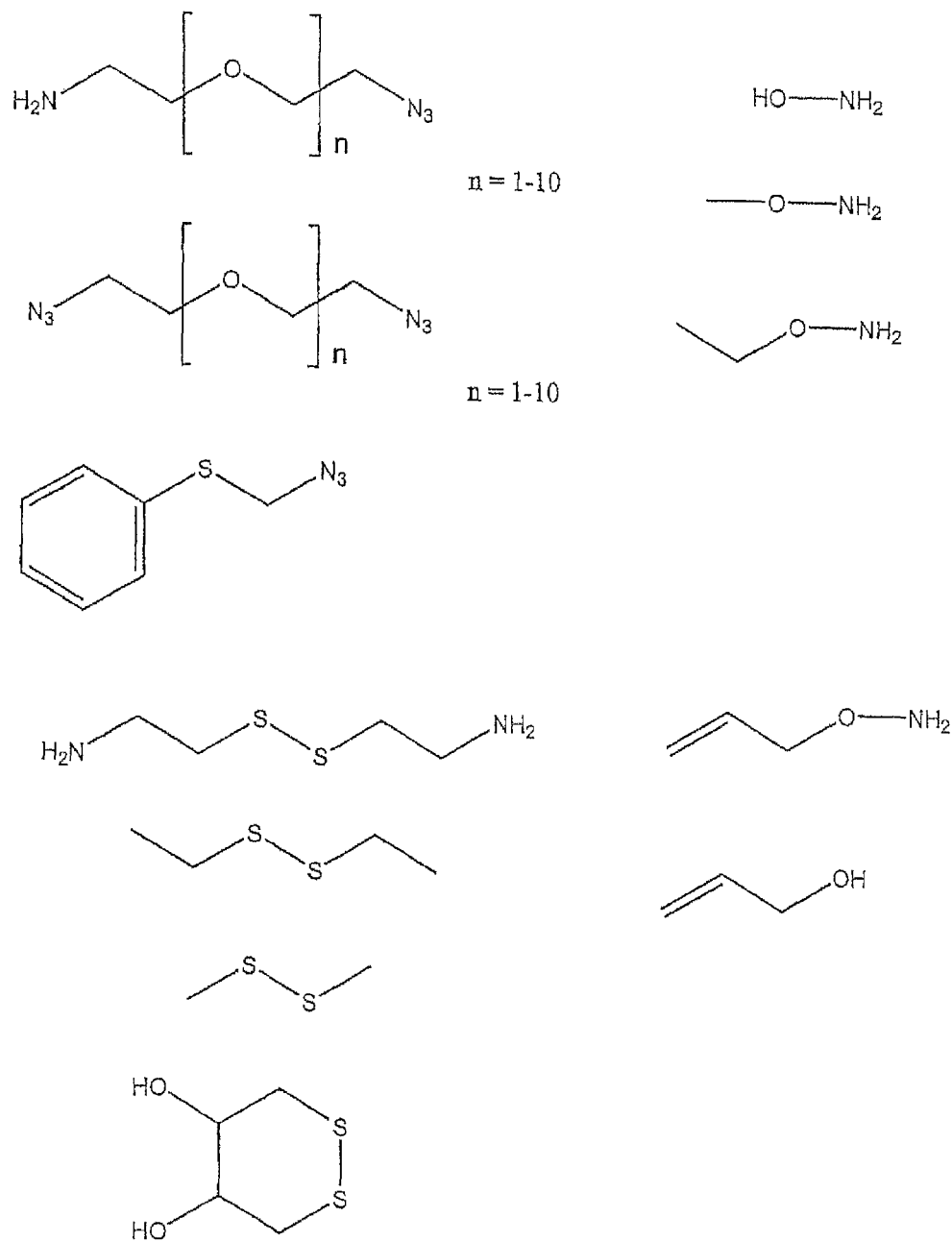
FIG. 37 provides examples of compounds useful as cleaving agent "scavengers."

In one particular embodiment, the scavenger agent mimicks the structure of the protective group present on the 3'-OH location of the nucleotide. In another embodiment, the scavenger mimicks only the reactivity of the protective group. For example, in case of 3'-O-azidomethyl nucleotides scavenger compounds could comprise azidomethyl, azidoethyl ethers or disulfide compounds. In case of 3'-O—NH2 nucleotides the scavengers could be any aminoxy compounds, such as hydroxylamine. In case of 3'-O-allyl nucleotides the scavengers could be any allyl ether or disulfide compounds. FIG. 37 provides examples of cleaving agent "scavengers." It has been found empirically (see Example 15), that the use of such compounds improves base calling accuracy, without the need for additional wash steps (and in particular, without the need for high numbers of wash cycles).

E. Dephasing

Many next-generation DNA sequencing systems read the sequence of millions of different single-stranded DNA fragments in parallel by using a polymerase enzyme to incorporate fluorescently labeled DNA nucleotides into the complementary strand one cycle at a time. However, incorporation errors can shift the phase of some of the templates, so base read outs may lead ahead or lag behind the cycle number. The invention provides a model and methods to account for incorporation errors and show how the model may be inverted to correct this dephasing and extend read lengths.

Although fluorescence-based, single-molecule sequencing on a chip has been demonstrated, it is very sensitive to polymerase incorporation errors. This may be reduced and therefore reliability of sequence read out may be increased if each spot on a chip is an ensemble of identical template molecules. Polymerase errors (such as the incorporation of the wrong complementary nucleotide or no incorporation at all) are inevitable, but infrequent. Therefore, the superposition of all of the fluorescent signals from template molecules within an ensemble will primarily be from the correct nucleotide. As the number of cycles gets large, however, certain errors can accumulate within an ensemble and contribute to possible miscalling of the correct nucleotide.

For our analysis, we assume that a set of reversibly terminated and cleavably labeled nucleotides with four different dye colors (one for each nucleotide type: A, C, G and T) are used for sequence read out. The methods described herein may also be applied to other types of SBS processes such as pyrosequencing. If the SBS process works without mis-incorporations, then for each cycle only a single nucleotide type is incorporated into every strand in an ensemble. During a read out phase, the color of each ensemble is measured, then during a cleavage phase, the terminator and dyes are cleaved off and the chip is ready for the next cycle. Thus, the position of the base being read out on every template on the chip is synchronized with the cycle number.

Figure 8:
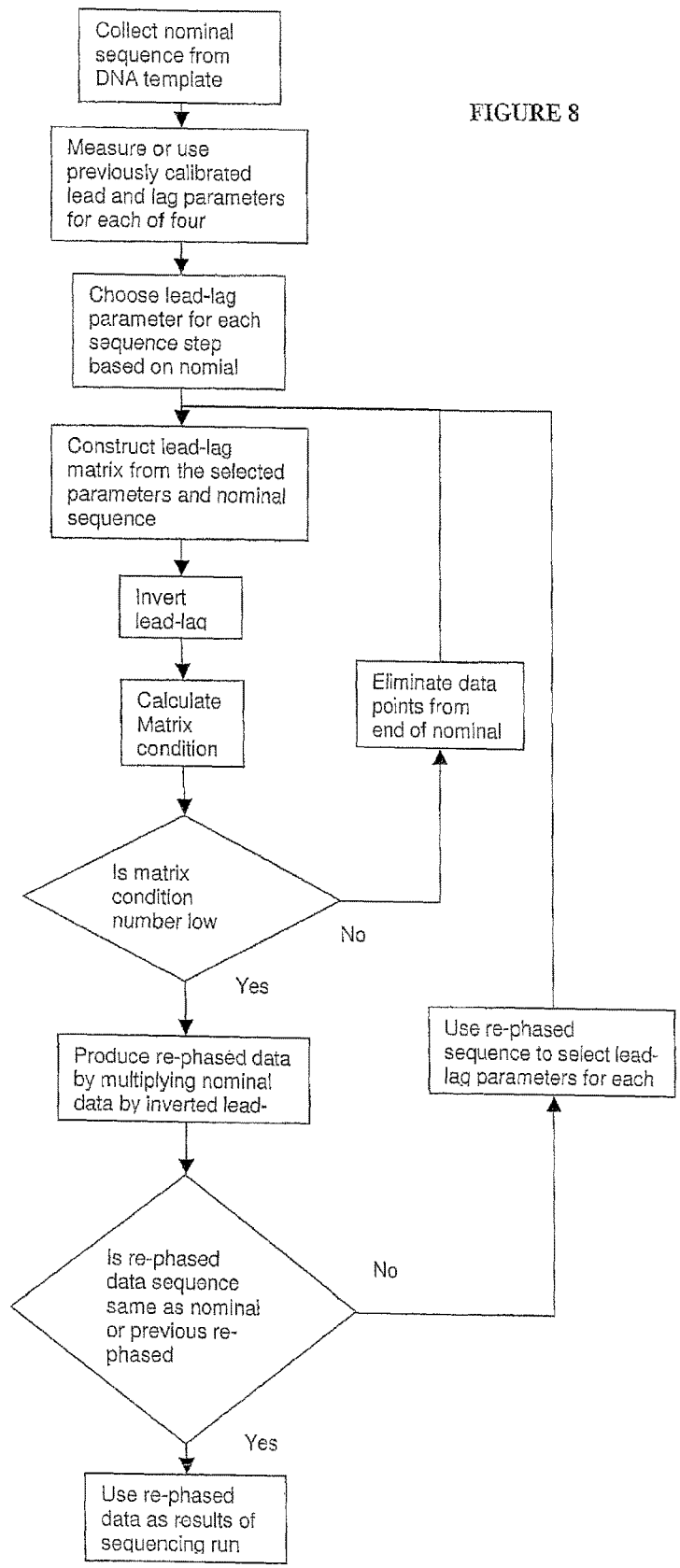
FIG. 8 is a schematic flow chart for re-phasing.
Figure 9A:
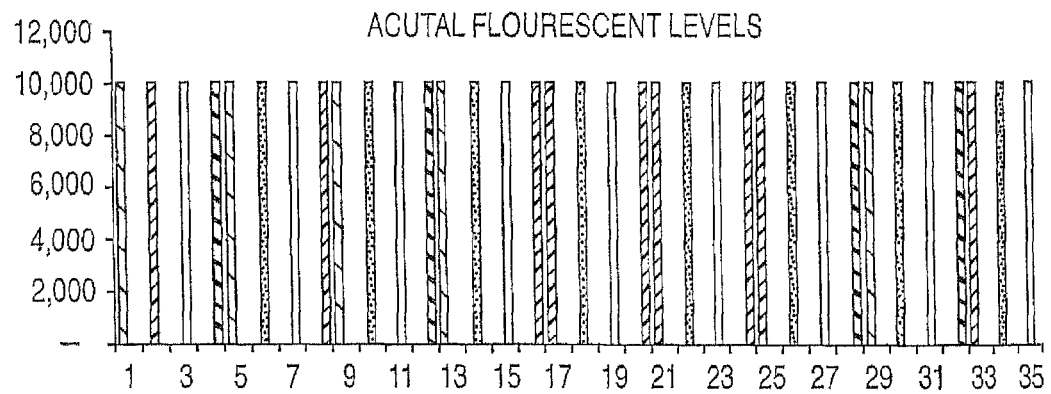
FIG. 9A-B shows simulated data showing sequence lead due to incorporation of small amounts of non-terminated nucleotides mixed with the reversibly terminated nucleotides. Panel 9A shows actual fluorescent levels, Panel 9B shows measured fluorescent levels.
Figure 9B:
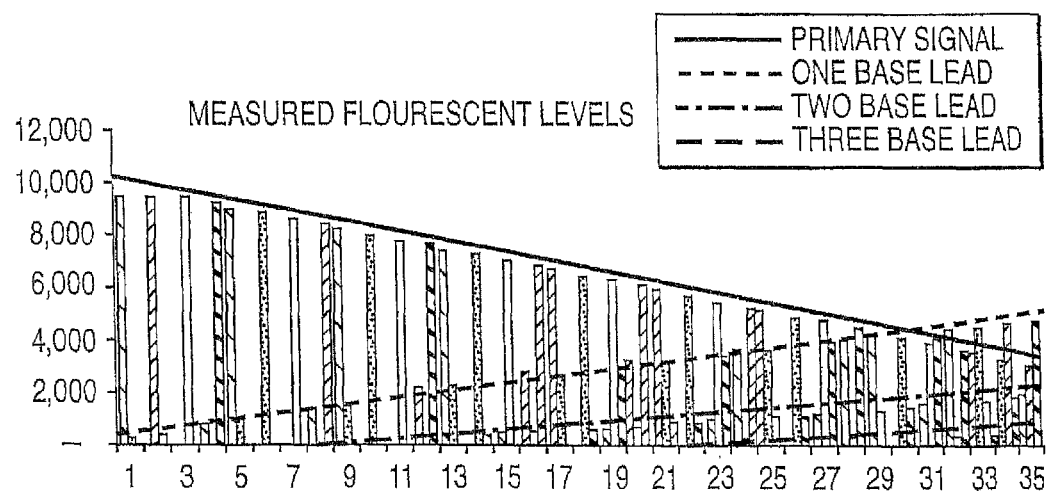

Because of impurities, limited polymerase efficiencies and other errors, some of the templates within an ensemble may get out of phase with the cycle number. For example, the base that is incorporated in the $i^{th}$ cycle may be complementary to the $i-1^{st}$ position or the $i+1^{st}$ position in the template rather than the expected $i^{th}$ position. The invention's methods provide computational re-phasing of the dephased data. FIG. 8 is a schematic flow chart for re-phasing. Additional data demonstrating the efficacy of the invention's methods is discussed below, including FIGS. 9-19 and Example 11 (FIGS. 33-34).

d. Sequence Lead

Polymerases that have an increased capacity for incorporating 3' reversibly terminated nucleotide analogs continue to have a preference for incorporating native nucleotides. This means that even though nucleotide analogs may be extremely pure, any residual nucleotides with 3'-OH (non-terminated) will be incorporated at a much higher rate and therefore appear to be more prevalent. The incorporation of non-terminated nucleotides has the effect of skipping a base, as a second incorporation (the next base) will occur in the same cycle. Thus, the fluorescent measurement for that template will exhibit the dye from the following base rather than the expected base at that cycle number. Since that template now exhibits a "lead," it will continue to do so, even if all future nucleotides are reversibly terminated. This effect is cumulative and shown in simulated 30 data in FIG. 9 for a non-terminated nucleotide incorporation rate of 2% as compared to the terminated nucleotide analog rate and a repeated 35 base sequence of the sequence ACTGACTGACTG [SEQ ID NO: 5]. Here we make the assumption that each of the nucleotides has the same nonterminated incorporation rate thereby allowing us to use a linear model. Again, the actual nucleotide purity may well be better than say 99.5%, but the apparent non-terminated incorporation rate may be 2% depending on the polymerase. In the example in FIG. 9, the model tells us the amount of signal due to the sequence lead effect. In cycle 20, the model calculates that we have 60% of the signal from the primary base at the 20th position (red), 32.4% of the signal from the base at the 21st position (blue), 6.7% of the signal from the base at the 22nd position (green), 0.8% of the signal from the base at the 23rd position (yellow), and 0.07% of the signal from the base at the 24th position (red). An interesting observation is that with the lead effect, the primary base signal (actual base at that cycle) does not have a 100% signal as some templates are already "reading out" subsequent bases on that strand, Thus at the end of a run, we can "look forward" and shift back the lead signals and correct the primary signals. We denote the contributions at the $i^{th}$ cycle as $R_{0Lead,i}$, $R_{+1Lead,i}$, $R_{+2Lead,i}$, $R_{+3Lead,i}$, etc. for the ratio between the reduced signal for the $i^{th}$ base to the actual $i^{th}$ base population, the ratio contribution to the $i^{th}$ base signal from the $i+1^{st}$ base, the ratio contribution to the $i^{th}$ base signal from the $i+2^{nd}$ base, etc. Because the amount of lead changes with each cycle, there will be a different set of ratios for each cycle.

e. Sequence Lag

Figure 10:
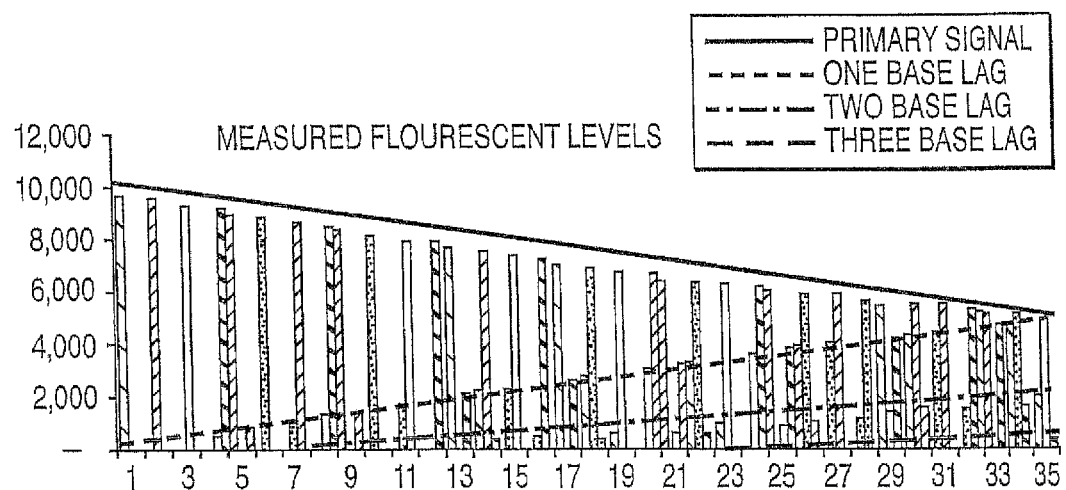
FIG. 10 shows simulated data showing sequence lag due to finite incorporation efficiency.

We developed a model for de-phasing due to sequence lag. This is caused by limited incorporation efficiency where some small percentage of the templates do not get a base incorporated in the cycle. FIG. 10 shows simulated data for a 98% incorporation efficiency for the same template sequence as in FIG. 9. We denote the contributions at the $i^{th}$ cycle as $R_{0Lag,i}$, $R_{-1Lag,i}$, $R_{-2Lag,i}$, $R_{-3Lag,i}$, etc., for the ratio between the reduced signal for the $i^{th}$ base to the actual $i^{th}$ base population, the ratio contribution to the $i^{th}$ base signal from the $i-1^{st}$ base, the ratio contribution to the $i^{th}$ base signal from the $i-2^{nd}$ base, etc.

f. Nucleotide Incorporation Events

As discussed above, every time there is an available site for the polymerase to incorporate a nucleotide on a template, there are three possible outcomes: First, no nucleotide is incorporated—Event No-I. If no nucleotide is incorporated due for example to polymerase inefficiency, then the site remains available for the next cycle. We term this a "lag" event as it has the effect of causing a readout in the next cycle that will from the position behind or lagging the cycle number. Second, a reversibly terminated nucleotide is incorporated—Event T-I. If as expected, a reversibly terminated nucleotide is incorporated, then the nucleotide readout is in sync with the cycle number. In the next cycle, the next consecutive template nucleotide position will be available for incorporation. Third, a non-terminated (native) nucleotide is incorporated—Event N-I. If a non-terminated nucleotide is incorporated, then during that same cycle, there is a second opportunity for another nucleotide to be incorporated at the subsequent position in the template strand. We term this a "lead" event as it has the effect of causing a readout of a nucleotide that is at a position that is ahead of or leading the cycle number. This second incorporation event is subject to the same three possible outcomes (No-I, T-I or N-I); thus, N-I events are recursive.

We will use the variable $G_i$ to represent the rate at which a lag occurs at template position i and similarly $D_i$ for the lead rate at position i. The analysis assumes that these rates may vary from position to position depending on the identity of the nucleotide that is to be incorporated, but we have assumed that all incorporation events for a particular nucleotide have the same lag and lead rates, even if the incorporation is not the first one in a cycle (it follows an N-I event). The fluorescent signal that will be generated from an incorporation event at a template location i is proportional to $(1-G_i-D_i)$, so at every $i^{th}$ incorporation event, the three types of events (No-I, T-I and N-I) will occur at the following rates: Event No-I at rate $G_i$, Event T-I at rate $(1-G_i-D_i)$, and Event N-I at rate $D_i$.

g. Signals Produced In Each Cycle

Figure 11:
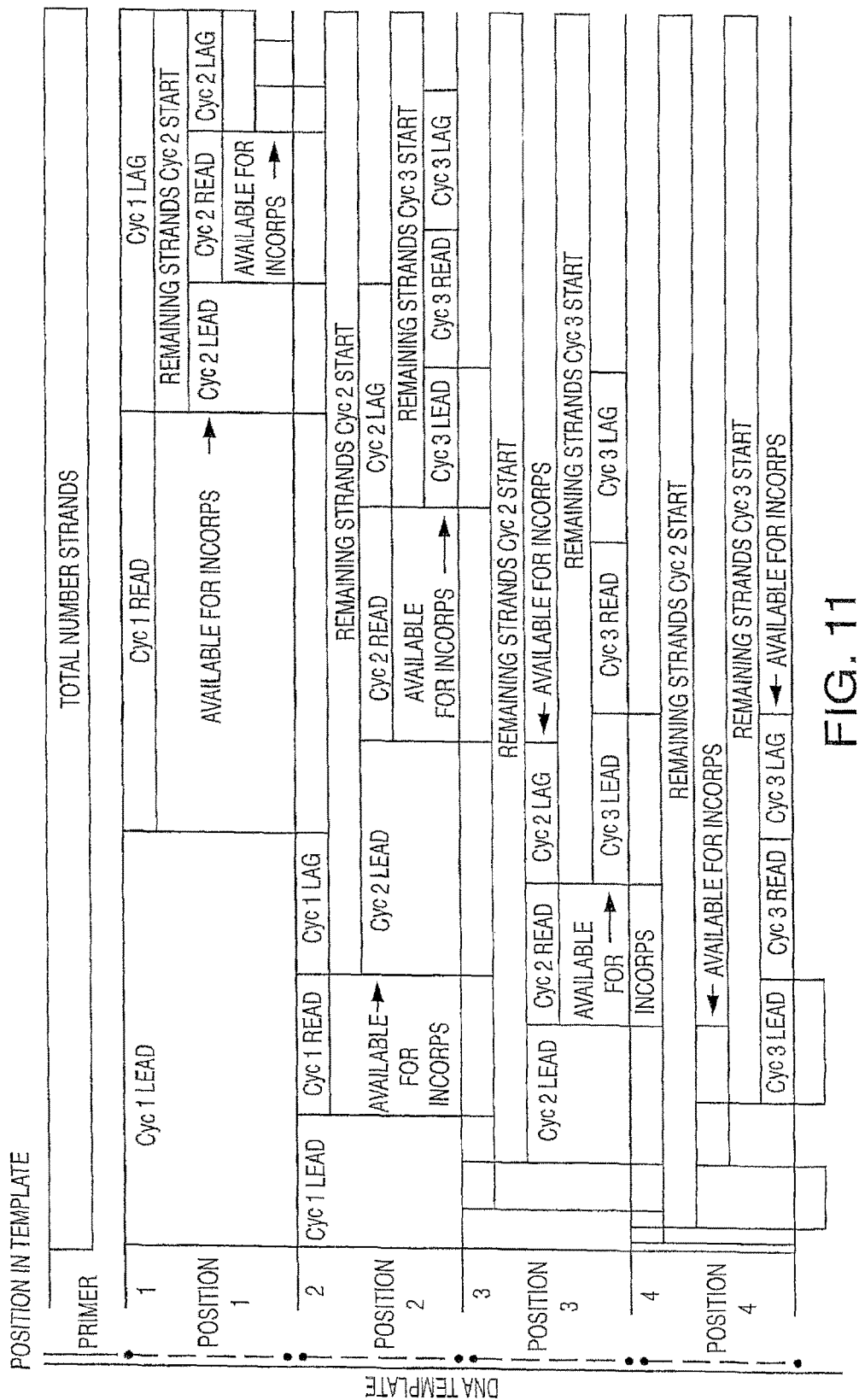
FIG. 11 is a chart of an exemplary sequence of extension events using an exemplary 4 templates positions and 3 cycles.
Figure 12:
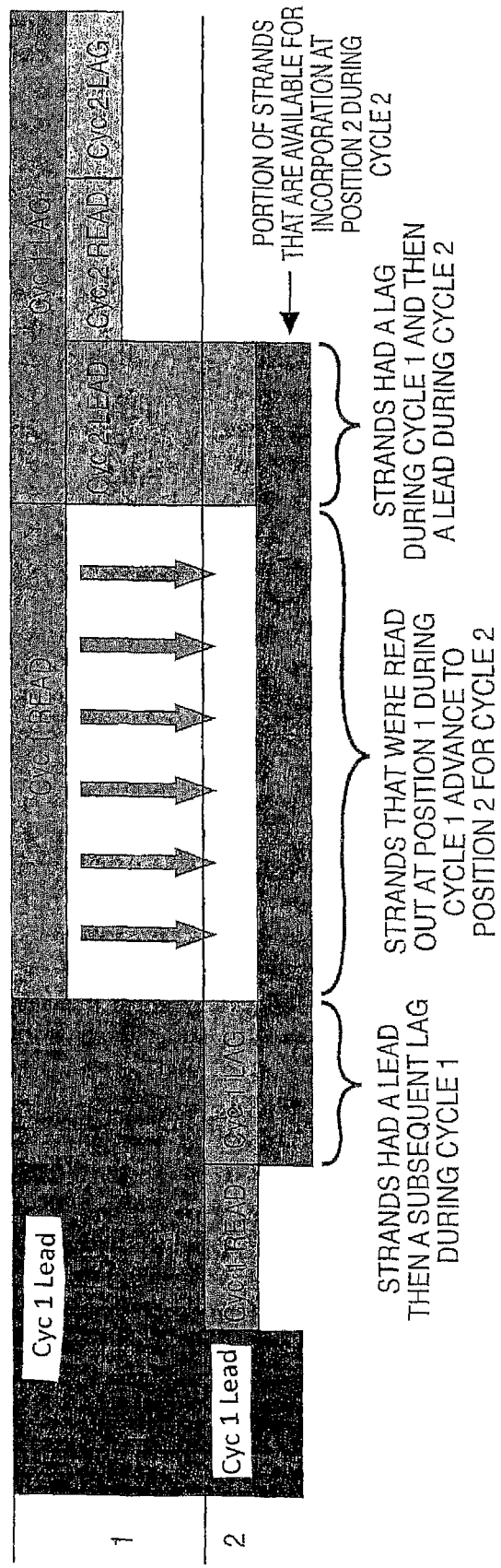
FIG. 12 is a chart of an exemplary sequence of extension events.

Although there are only three potential outcomes from an incorporation event, all of the combined events from multiple cycles in a template can be fairly complex. FIG. 11 may be used to better visualize the sequence of extension events. For simplicity, only 4 templates positions and only 3 cycles are illustrated in FIG. 11. The numbered regions in the vertical direction along the left edge indicate the nucleotide position along the strand. The horizontal direction symbolizes the relative number of strands in an ensemble that undergo events No-I, T-I or N-I (lag, readout or lead). The various events for cycle 1 in the sequence process are shown in shades of blue, events for cycle 2 are shown in red and events in cycle 3 are shown in green.

For clarity in FIG. 11, we have designated each of the three possible events (No-I, T-I and N-I) to occur at the same rate for every cycle. In an actual system, the lead and lag rate are both likely to be much smaller values. The chart is easier to understand if it is viewed one color at a time. The blue regions represent events that occur during the first cycle. At position 1 of the template, the entire ensemble of templates are available for extensions, thus (light blue) undergo a lag (no incorporation), (medium blue) are read out and (dark blue) undergo a lead. The portion of templates that experienced a lag (light blue) during the first cycle, remain available during the second cycle for incorporations. The portion of the templates that experienced a readout (medium blue) comprises the signal that is read during cycle 1 at position 1. This portion will progress in synchrony and allow incorporations to occur at position 2 during the second cycle. The portion of the templates that experienced a lead at position 1 will have a second incorporation event during cycle 1 at the second position of the template. This incorporation again will be split equally into the three possible events. A portion of the templates will remain. unextended (lag), a portion will generate a signal (readout) and a portion will undergo a lead and produce a third set of incorporation events at position 3. This process will continue during cycle 1. Although lead events may continue down the entire length of the template during cycle 1, in practical terms, the effects after about 4 lead events are negligible.

In cycle 2 (red colors), the only strands that are available to be extended at position 2 are those for which one of three events occurred (see FIG. 12): (1) strands that were read out at position 1 during cycle 1, (2) strands that experienced both a lead at position 1 and a lag at position 2 during cycle 1, and (3) strands that experienced a lag at position 1 during cycle 1 along with a subsequent lead at position 1 during cycle 2. A portion of these strands will also experience a cycle 2 lead to the third position, however, since they have "caught up" to the other strands with available sites at the second position, they are lumped together with them and further leads are considered as portions of the combined population.

Similar events occur at each template position during cycle 2. The events of cycle 3 (green shades) follow very similar patterns to those described for cycle 2.

h. Mathematical Models of Dephasing And Rephasing

We may derive general equations that describe all the incorporation events at each position and for each cycle. If we denote the relative magnitude (out of 1) of the number of strands that remain unincorporated for position i at the end of a cycle j as $R_{i,j}$, and the number of strands that are available for incorporation in the next cycle as $A_{i,j}$ then $$R_{i,j} = R_{i,j-1} - A_{i,j-1}(1-G_i) \quad (1)$$

and $$A_{I,j} = R_{I,j} - R_{I-1,j} + A_{I-1,j}D_{I-1} \quad (2)$$

Figure 13:
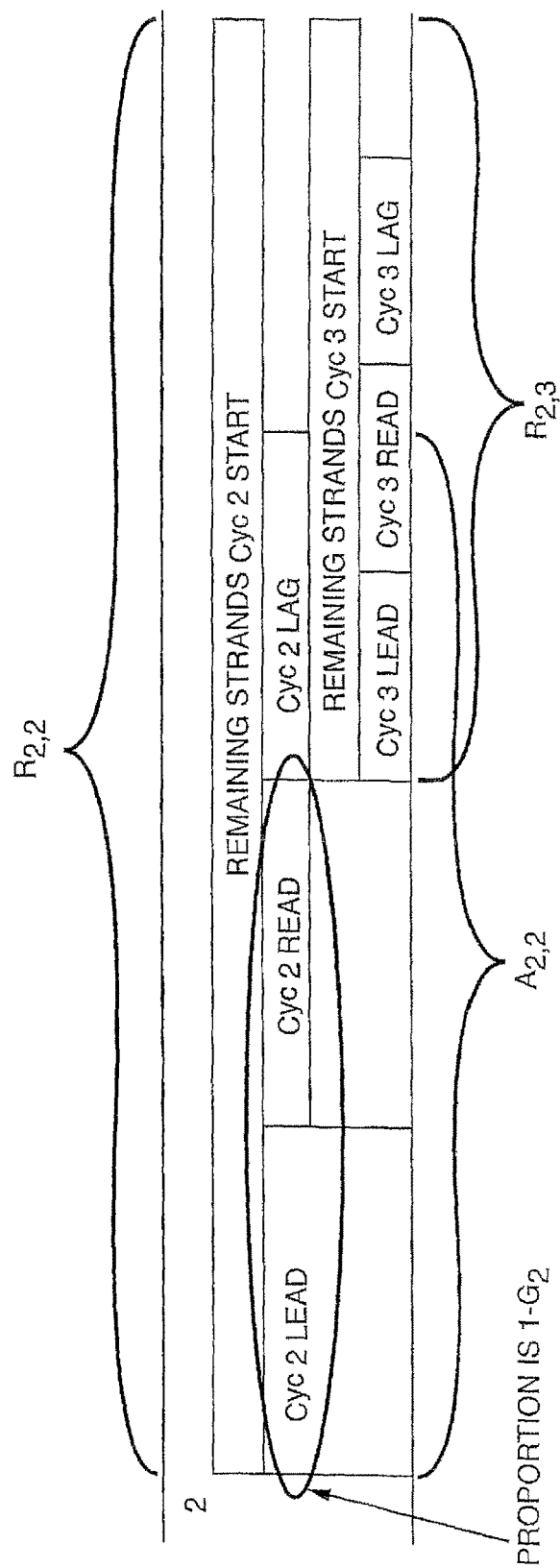
FIG. 13 shows a first portion of the chart of FIG. 11.

To explain the derivation of Equation 1, we use the example in FIG. 13, which shows a portion of the chart from FIG. 11. Only cycles 2 and 3 are shown for position 2. $R_{2,3}$ is comprised of $R_{2,2}$ minus a portion $(1-G_2)$ of $A_{2,2}$.

Figure 14:
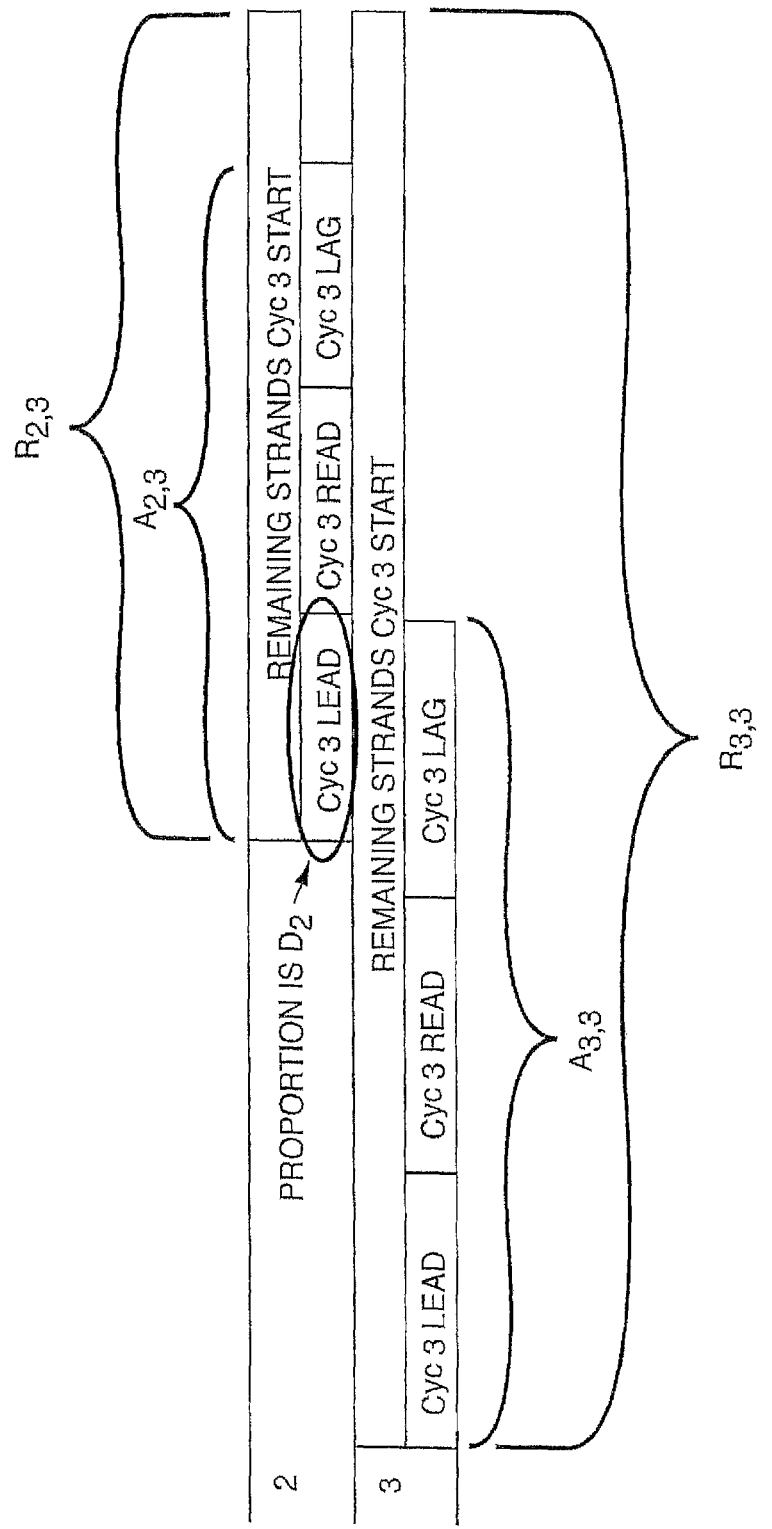
FIG. 14 shows a second portion of the chart of FIG. 11.

To explain the derivation of Equation 2, we use the example in FIG. 14, which shows a portion of the chart from FIG. 11. Only cycle 3 is shown for positions 2 and 3. $A_{3,3}$ is comprised of $R_{3,3}$ minus $R_{2,3}$ plus the lead portion $(D_2)$ of $A_{2,3}$.

It should be noted that for any particular cycle and position, the number of available strands, $A_{i,j}$, is generally fewer than the number of remaining strands, $R_{i,j}$, since some templates at the particular position are still lagging and unavailable, but may "catch up" in future cycles.

The signal that is produced, $S_{i,j}$, at the $i^{th}$ position at the end of the $j^{th}$ cycle comes from the proportion of the strands that are available, $A_{i,j}$, that undergo event T-I $$S_{i,j} = A_{i,j}(1-D_i-G_i) \quad (3).$$

In one embodiment, the model is used to apply the lead-lag compensation based on calibration of parameters, before or during the test, and to provide an initial estimate of the base identity at each location as determined during the sequencing run. In a particular embodiment, $G_i$ and $D_i$ for each nucleotide may be pre-calibrated or measured during the sequencing procedure. In general, the model is constructed with lag parameters that are applied to each cycle and lead parameters that are recursively applied to each cycle.

In a particular embodiment, the lead-lag matrix is formulated after an initial draft sequence is measured. This allows application of the proper set of $G_i$ and $D_i$ parameters to each cycle based on the nucleotides identified at each position in the draft sequence. In a further embodiment, the re-phasing of data is iterated using the result of one re-phasing calculation to select an updated set of $G_i$ and $D_i$ parameters for the next iteration.

i. Simulated Dephased Sequencing Data

Figure 15:
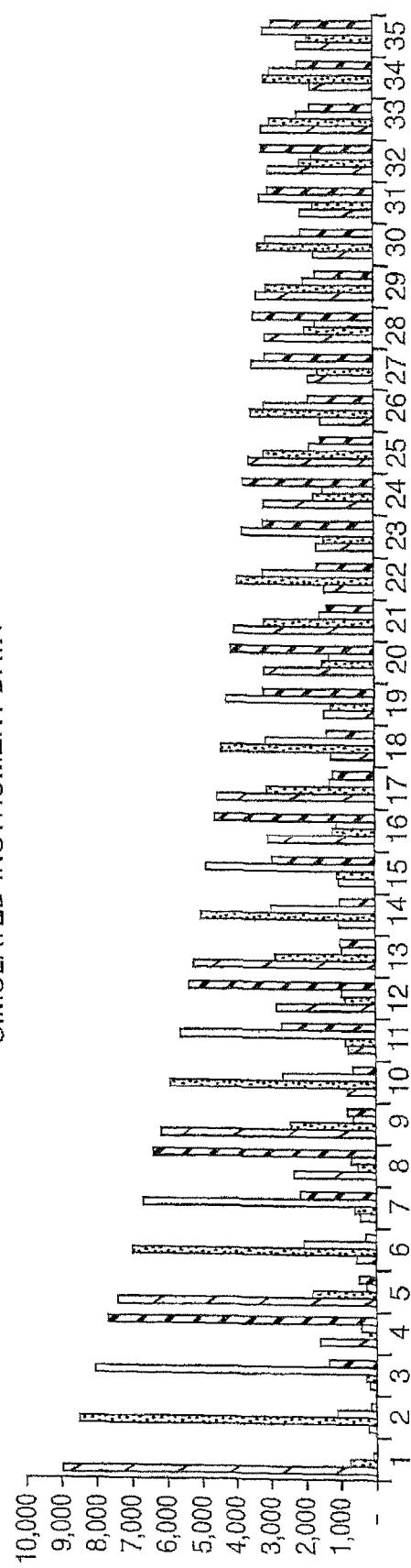
FIG. 15 shows data generated from the iterative application of equations 1-3 using parameters in Table 1.

We may use the relationships derived in the previous section to generate sequence data that simulate the signals that might occur when portions of every incorporation undergo a lead and a lag. As an example, we use the lead and lag factors below and generate simulated sequence data assuming the maximum signal from the template is 10,000 counts and the template has 35 base repeating sequence of the sequence AGCTAGCTAGCT [SEQ ID NO: 10]. FIG. 15 shows data generated from the iterative application of equations 1-3 using the parameters in Table 1.

TABLE 1

Lead Factors and Lag Factors for Nucleotides

| | A | G | C | T |
|---|---|---|---|---|
| Lead Factors | 4.10% | 4.20% | 4.30% | 4.40% |
| Lag Factors | 1.10% | 1.20% | 1.30% | 1.40% |

FIG. 15 shows that with the presence of a lead and lag component, there is a cumulative effect that reduces the signal from the expected nucleotide at a particular cycle and "spreads" some of the signal forwards and backwards. As the number of cycles increases, it becomes more and more difficult to directly read the correct base from the graph, thereby limiting the effective read length of the template.

ii. Re-Phasing Sequencing Data

Data herein (Example 11, FIGS. 33-34) demonstrate that applying the methods and the below described equations of the invention, exemplary 16-base and 25-base nucleotide sequences were sequenced with high fidelity. The high quality of the data, particularly in the last several bases in FIG. 34, demonstrates that the read length will not be limited by signal decline. Thus, it is contemplated that the invention's methods are applicable to sequences containing at least 16 nucleotides, at least 25 nucleotides, at least 35 nucleotides, at least 50 nucleotides, at least 100 nucleotides, at least 1,000 nucleotides, and at least 10,000 nucleotides. Further description of the equations used to re-phase sequencing data is described as follows.

We constructed a matrix equation that describes a model for the reduced measured signal, $I_{Mi}$, from the lead and lag effect in the $i^{th}$ cycle from the original template populations, $I_{Ai}$, for all cycles, i=1 to N. Here each of the intensity matrices ($[I_{Ai}]$ and $[I_{Mi}]$) have N rows (one for each cycle) and four columns (one for each color).

$$\begin{bmatrix} I_{M1} \\ I_{M2} \\ \vdots \\ I_{MN} \end{bmatrix} = K_{Lead/Lag} \begin{bmatrix} I_{A1} \\ I_{A2} \\ \vdots \\ I_{AN} \end{bmatrix}, \quad (4)$$

where the lead/lag matrix, $K_{Lead/Lag}$, is a square N×N matrix of the following form:

$$K_{Lead/Lag} = \begin{bmatrix} R_{Lag/Lead,1} & R_{+1Lead,1} & R_{+2Lead,1} & R_{+3Lead,1} & \cdots & R_{+(N-1)Lead,1} \\ R_{-1Lag,2} & R_{Lag/Lead,2} & R_{+1Lead,2} & R_{+2Lead,2} & \cdots & R_{+(N-2)Lead,2} \\ R_{-2Lag,3} & R_{-1Lag,3} & R_{Lag/Lead,3} & R_{+1Lead,3} & \cdots & R_{+(N-3)Lead,3} \\ R_{-3Lag,4} & R_{-2Lag,4} & R_{-1Lag,4} & R_{Lag/Lead,4} & \cdots & R_{+(N-4)Lead,4} \\ \vdots & \vdots & \vdots & \vdots & \ddots & \vdots \\ R_{-(N-1)Lag,N} & R_{-(N-2)Lag,N} & R_{-(N-3)Lag,N} & R_{-(N-4)Lag,N} & \cdots & R_{Lag/Lead,N} \end{bmatrix} \quad (5)$$

The diagonal terms, $R_{Lag/Lead,i}$, in the $K_{Lead/Lag}$ matrix above is the fractional remaining signal in the $i^{th}$ cycle from the $i^{th}$ position of the templates after all of the leads and lags to that point. Each of the terms in the upper triangular portion of the matrix, $R_{+kLead,i}$, is the fractional contribution to the signal in the $i^{th}$ cycle from k positions forward of the $i^{th}$ position. Each of the terms in the lower triangular portion of the matrix, $R_{-kLag,i}$, is the fractional contribution to the signal in the $i^{th}$ cycle from k positions before the position. In most systems, the terms with k greater than about 4 (5 positions or more away from the position corresponding to the cycle number) are negligible. The diagonal terms are close to 1 for the earlier cycles and do not drop below about 0.25 for the later cycles. Thus, this matrix is invertable.

In order to compensate for both sequence leads and lags, we solved for $[I_{AI}]$ in Equation 4 by taking the inverse, $K^{-1}_{Lead/Lag}$, of $K_{Lead/Lag}$ (Equation 5) to get an estimate of the actual template population $[L_{AI}]$:

$$\begin{bmatrix} I_{A1} \\ I_{A2} \\ \vdots \\ I_{AN} \end{bmatrix} = K^{-1}_{Lead/Lag} \begin{bmatrix} I_{M1} \\ I_{M2} \\ \vdots \\ I_{MN} \end{bmatrix}. \quad (6)$$

When the lead rates for all the nucleotides are identical and the lag rates for all of the nucleotides are identical, then the lead/lag matrix, $K_{Lead/Lag}$, does not depend on the sequence. This makes Equation 6 linear and the inverse of the matrix is deterministic. In this case the inverse of the lead/lag model gives the correction matrix, $K^{-1}_{Lead/Lag}$, which is applied just once at the end of a run and takes into account all of the signals from the first to the last base.

If on the other hand the lead and lag factors vary from one nucleotide to the next, then the lead/lag matrix, $K_{Lead/Lag}$, depends on the actual sequence (solution of $[I_{AI}]$ in Equation 6) and the problem is non linear. In other words, we need to determine an estimate for the true value of the intensities of each base in the sequence when the governing equations depend on this solution.

To solve the non-linear problem, one can estimate a solution and iterate until the solutions converge. We may use the raw out-of-phase sequence data to make an initial estimate of the sequence by taking the maximum value at each cycle, using this information to determine the lead and lag rates for each position, construct a lead/lag matrix ($K_{Lead/Lag}$), take the inverse of that matrix and solve for the corrected, re-phased sequence. We can then use the new sequence to make a new estimate of the lead/lag matrix, etc. As long as the various lead and lag factors are fairly close to one another, this method should converge in about two or three iterations.

iii. Additional Factors

The above method is a very powerful way of "cleaning up" sequence data that has been dephased due to the lead and lag phenomena. The matrix condition number determines when matrix manipulations will be sensitive to small numerical variations. A matrix condition near 1 means the matrix is well behaved, while a large condition number means the matrix is ill-conditioned or sensitive to small numerical inaccuracies.

Figure 16A:
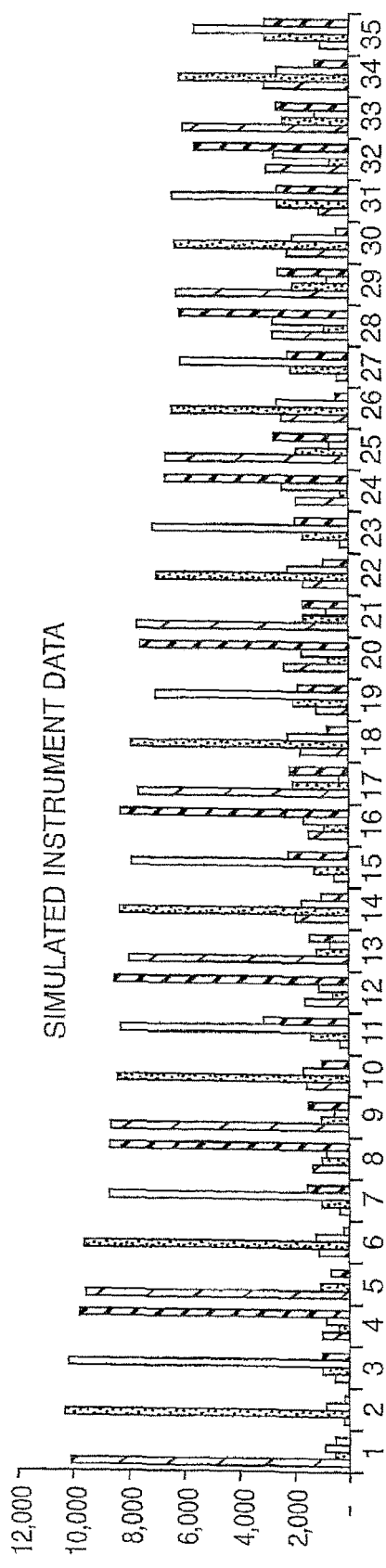
FIG. 16A-B panel 16A shows simulated base read data with 10% noise added and lead and lag factors of 1% each, and panel 16B shows reconstructed data with the lead and lag removed.
Figure 16B:
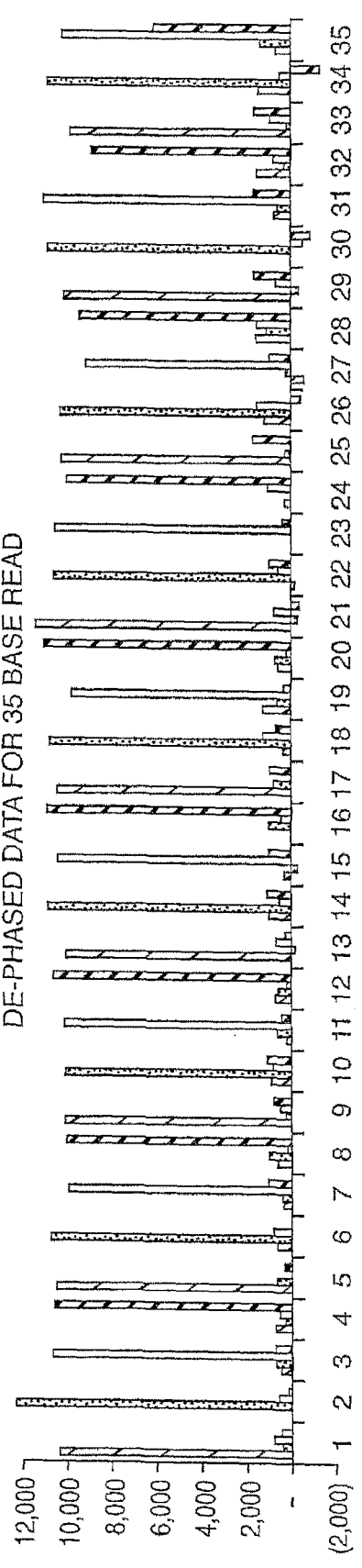
Figure 17A:
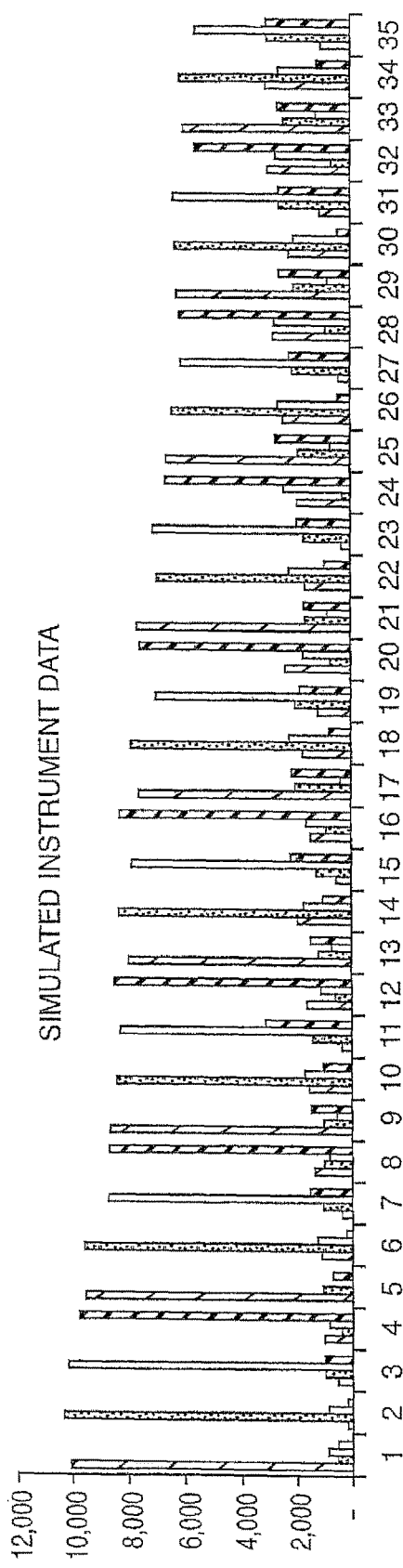
FIG. 17A-C panel 17A shows simulated base read data with 10% noise added and lead and lag factors of 1.75% each, and panel 17B shows that attempted reconstruction is poor as the lead/lag matrix is ill-conditioned, and 17C shows reconstructed data with the lead and lag removed for only the first 18 bases. The 18-base lead/lag matrix is relatively well behaved and a more precise reconstruction may be performed.
Figure 17B:
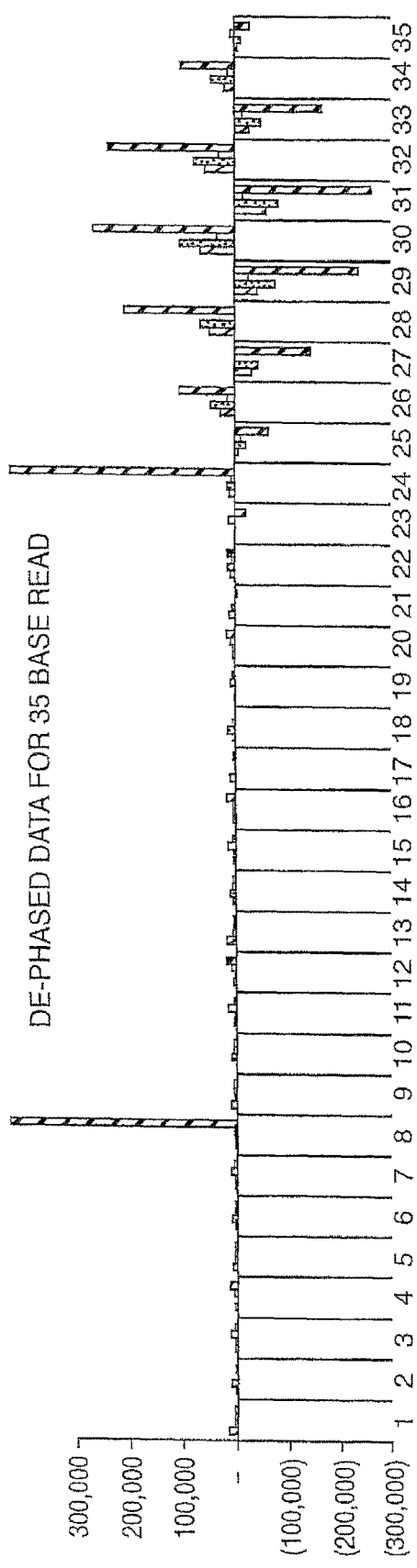
Figure 18:
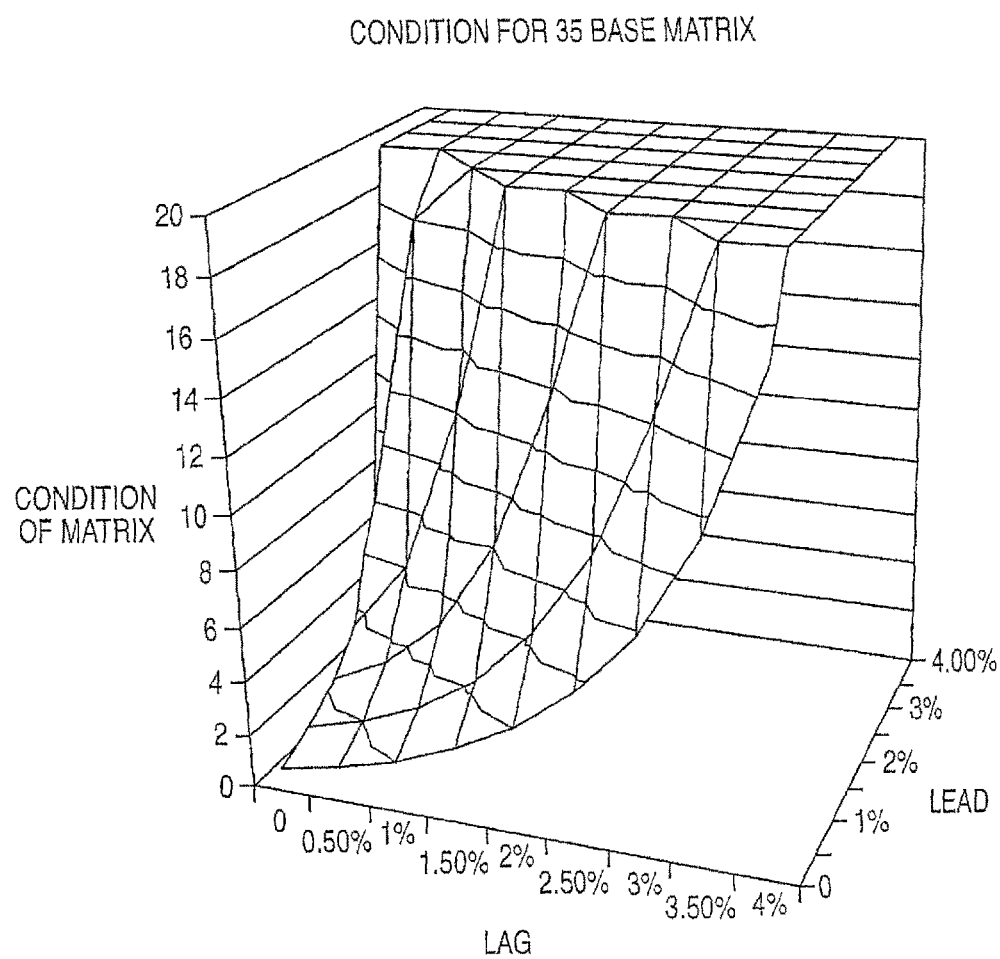
FIG. 18 shows lead/lag matrix conditions for various lead and lag parameters for a 35 Vase read. In one embodiment, a condition number below 20 produces accurate reconstruction.

FIG. 16A shows a simulated 35 base read data with 10% noise added and lead and lag factors of 1% each. FIG. 16B shows an accurate lead/lag compensation reconstruction using the inverse lead/lag matrix, $K^{-1}_{Lead/Lag}$. The condition number for this lead/lag matrix is 5. FIG. 17A shows the same exemplary 35 base sequence with 10% noise and a lead and lag factor of 1.75% each and FIG. 17B shows the reconstruction. Here, the condition number is 550 and reconstruction is poor. In order to have a fairly precise reconstruction of the data, lead/lag matrices desirably have a condition below about 20. FIG. 18 plots the matrix condition numbers below 20 for 35 base lead/lag matrices with various values of lead and lag. Because the lead/lag matrix is calculated independent of the DNA sequence in a template for the case where nucleotides all have equal lead ratios and equal lag ratios, we are able to determine our ability to accurately call bases without consideration of the A, C, T, and G content of the templates.

Figure 17C:
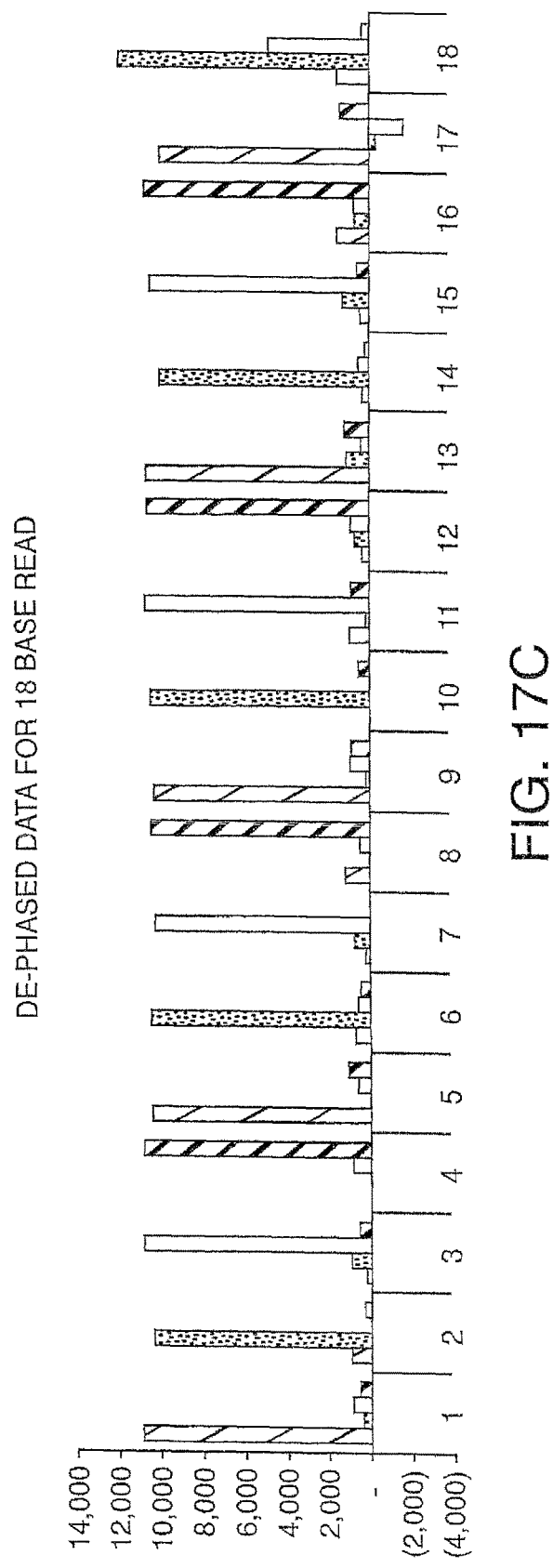

Even if a 35 base lead/lag matrix is ill-conditioned and produces poor reconstruction, smaller matrices from a portion of the same data may still be well behaved. For example, FIG. 17C shows the reconstruction of the first 18 bases for a lead and lag of 1.75% each (same conditions that produced the poor reconstruction for the 35 base read). Here the 18×18 lead/lag matrix has a condition number of 3.7. The matrix becomes ill-conditioning when cumulative contributions from the lead or lag or both generate signals that are on the order of the signal from the true base (where the position equals the cycle number).

Figure 19:
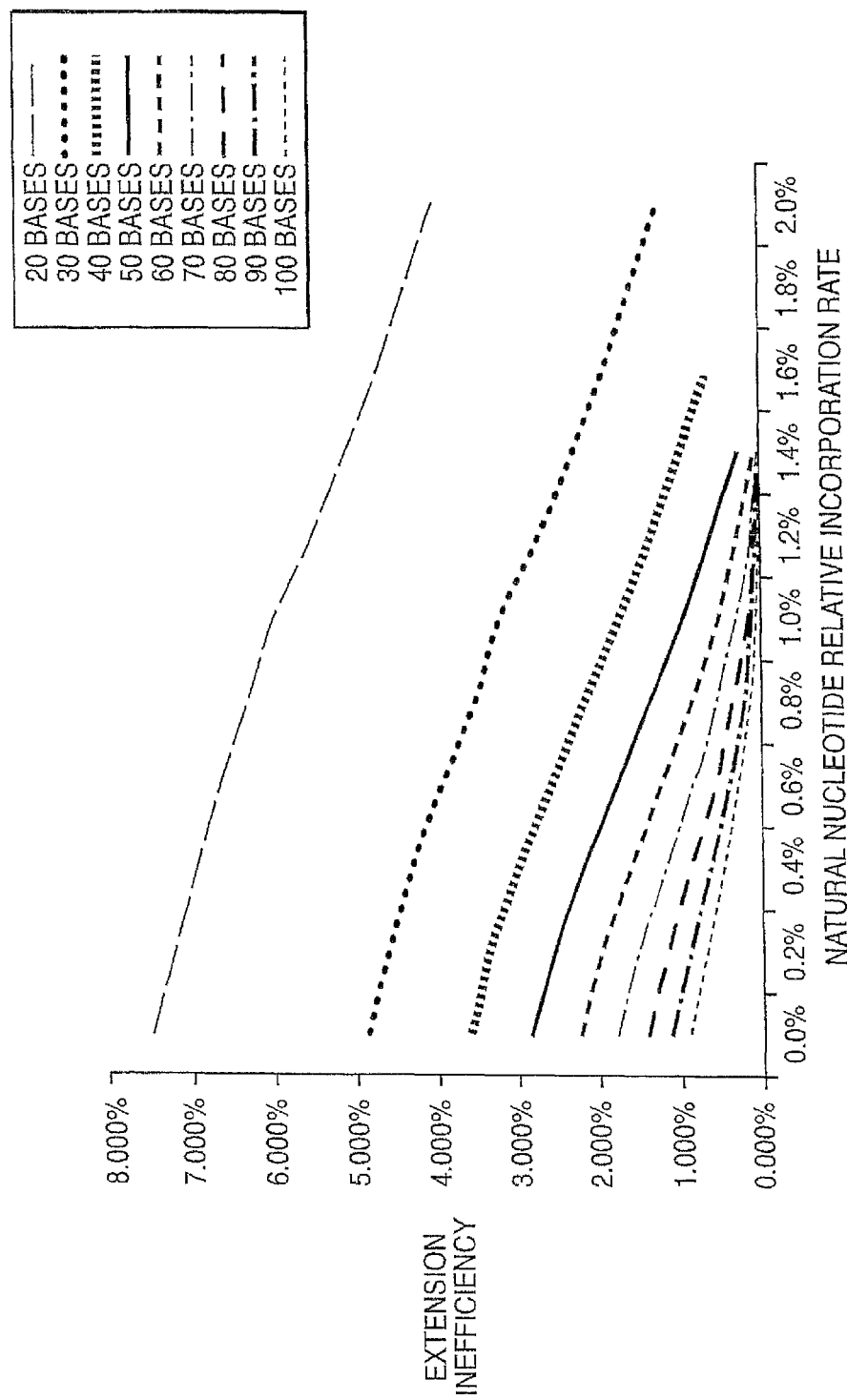
FIG. 19 shows exemplary read length fox various values of lead and lag.

The above shows that changing the read length can provide an accurate reconstruction of earlier portions of the data. Thus, we can plot the lead and lag factors that will cause matrices of different sizes (read lengths) to have a condition number of 20 (the point where matrices become too ill-conditioned for precise reconstruction). For example, if a 23×23 matrix produces a condition number of 20, then we would restrict the read length to a maximum of 23 as reconstruction using the 24th base (as well as any additional bases) would likely create a matrix that is too ill-conditioned to accurately reconstruct the data. FIG. 19 shows the read lengths for various lead and lag factors. This plot provides a method for predicting the read length obtainable from a sequencing system based on two factors: the purity of the nucleotides (major contributor to the lead) and the polymerase incorporation efficiency (major contributor to the lag). This result also shows that if both the lead and lag factors are below about 0.5%, this results in reconstruction of a 100-base read.

F. Field Flattening

In one embodiment, when a chip of uniform dye concentration is imaged, it may be desirable that all of the pixels in the resultant image have nearly the same intensity, with variations reflecting only the relatively small distribution inherent in the camera's optical system. In practice, however, the inventors have found that variations in illumination and filter response produce a significant spatially correlated pattern in an image. The inventors have also found that the pattern is highly reproducible and has a linear response to changes in dye concentration and camera exposure. These conditions lead to the following algorithm for removing this spatial correlation between pixel intensity and location of the pixel on the solid substrate.

First, for each machine and each filter, we image the pattern of a spatially uniform fluorescence on a dyed microscope slide. Second, the image is smoothed using a low-pass filter. In the resultant smoothed image, M, we choose an origin point, $M_{x0,y0}$. The choice of the point is fairly arbitrary but it is selected from a region in which the smoothed images of all of the filters have low intensity gradients to minimize the impact of changes in the system. Third, the intensity of each pixel at a point in a raw image ($R_{x,y}$) is replaced by its fold-flattening value, $F_{x,y}$, where $F_{x,y}=R_{x,y} M_{x0,y0}/M_{x,y}$, and $M_{x,y}$ is the value of the model image at the same spatial location as the raw image pixel. The resultant "Field Flattened" image, F, has intensities that are now solely dependent on the camera exposure and dye concentration, and do not have any correlation with the spatial location of the pixel in the image.

The invention's algorithms and equations for field flattening are distinguished from those described by, for example Eltoukhy et al. (2006), since the algorithms of Eltoukhy et al. relate to signal noise that is uncollrelated to system parameters (e.g., uneven light source). In contrast, the signal noise that is corrected by the invention's methods is correlated to the signal's position across the solid substrate. In one embodiment, each pixel is corrected (i.e., field flattened) based on a previously calibrated baseline intensity at that pixel position and a scaling factor based on for example a longer exposure time.

G. Spot Location in the Array

In one embodiment, the present invention contemplates a processing step (preferably in a series of processing steps as discussed above) for locating the spots in the array. In one embodiment, the spot locating image processing algorithm uses the fact that the spots on the chip are in a regular hexagonal pattern along vertical columns and diagonal rows. To find the columns of spots, image pixel values are summed along the vertical direction. This results in a one-dimensional set of data that resembles a sinusoidal pattern. The peaks of the pattern are measured and used to determine the period and phase of the pattern. There are then used to guide a search to determine a set of equations for vertical lines that approximately bisect each of the spots in a column. The result is a set of equations for parallel lines (slope, intercept and spacing) at regular spacing. A number of these lines are then probed to establish a second sinusoidal-like pattern of intensities along the lines. These are then used to determine the period, angle and phase of the diagonal lines that bisect each of the spots. These second set of lines are at a 60 degree angle from the vertical lines. The intersection of the diagonal set of lines and the vertical set of lines give an estimate for the subpixel locations of each of the spot centers.

H. Image Sharpening

In one embodiment, the present invention contemplates a processing step (preferably in a series of processing steps as discussed above) to sharpen the image of the spots on the array. This is particularly useful if chips are constructed with tightly packed spots. In such a case, it might be beneficial to run the images through a sharpening filter in order to reduce the amount of blur or spread for each of the spots. This will reduce the amount of light energy blooming into adjacent spots. Similarly, if the optics for the system cannot sufficiently resolve spots on the chip, then the application of a sharpening filter may also help to precisely analyze the images. A number of sharpening algorithms may be used to narrow the spread of the spots. One embodiment uses a Wiener filter (as described, for example, in The Image Processing Handbook, by John C. Russ, Published by CRC Press, 2006, ISBN 0849372542, 9780849372544, 817 pages) to make the diameter of the spots smaller and remove light energy from adjacent spots.

I. Spot Brightness Determination

In one embodiment, the present invention contemplates a processing step (preferably in a series of processing steps as discussed above) to determine spot brightness. In one embodiment, the pixels that surround each of the subpixel locations of the spots are summed to determine an estimate for the spot brightness. The local set of pixels that is selected depends on both the diameter of the spots and the location within the pixel of the subpixel center location. For example, if the subpixel location is close to the top of the pixel that contains the center, then more pixels above the pixel that contains the center are counted than pixels below the pixel containing the center.

In one embodiment, the above method for making spot brightness measurements is repeated independently for each of the four different color channels (four separate images) and the sharpening and neighbor influence (see below) correction calculations are applied, then the color crosstalk correction is applied (see below). In one embodiment, the result of the color crosstalk calculation produces a list of four values (one for each dye color) for each spot in the images that may be used to call the base for that sequencing cycle.

J. Neighbor Influence Elimination

In addition to each of the spots expanding beyond its physical bounds, the light from one spot (bead) may illuminate an adjacent spot and make it appear to have more of the color of its neighbors. This might happen because light being emitted from one bead make impinge on an adjacent bead, be reflected within the bead and then reemitted from that bead. This neighbor influence may be eliminated by, in one embodiment, constructing an influence or "spreading" matrix, then applying the inverse of this matrix to the data. To formulate the solution to the neighbor influence problem from spot data that is in hexagonal form, it is convenient to first put the data into a rectilinear array. This is done by shifting the even vertical columns up by ½ of pixel as shown below. Thus, a two-dimensional rectilinear matrix, whose elements represent the magnitude of each spot in the original image of the hexagonal array of spots, may be used. To further facilitate matrix manipulations, the rectilinear spot matrix may be made into a spot vector by stacking the columns from the two-dimensional matrix under one another to form a one dimensional array or vector. In other words, the second column is appended to the bottom of the first, the third to the bottom of the second, etc., thereby generating a $1 \times N^2$ vector formed from an N×N spot matrix.

In one embodiment, a "spreading matrix" is next formed that represents the magnitude of the influence from a spot to neighboring spot. In a general formulation, a central spot may be thought of as influencing the nearest six neighbors surrounding the central spot by a fraction, A, of the central spot brightness, the next nearest neighbors by a smaller fraction, B, etc. If the central spot is very bright, then its neighbors may appear to be emitting their own light of the same color as the central spot, even if they actually generate none of their own light in that color. The spreading matrix is formulated such that if it is applied to an ideal image of single element spots (each spot is an idealized point and does not extend beyond one element of the matrix), then the resultant matrix will have spots that have been spread across several elements due to the neighbor influence phenomenon. Thus, the spreading matrix is a model for the influence of any spot in the image to any other spot in the image.

For hexagonal arrayed spots that have been make into a one-dimensional vector with dimensions $N^2 \times 1$ (in other words, a concatenation of all the columns of the matrix), the spreading matrix, 5, may be formulated as a $N^2 \times N^2$ matrix. An example 25×25 spreading matrix corresponding to a 5×5 spot image that has the three levels of neighbor influence (A for the closest 6 neighbors, B for the next closest 6 and C for the third closest 6) is shown below.

and computer memory requirements for the calculation. It should be understood that the methods set forth above may be generalized in algorithms that are more efficient or operate on smaller portions of the image.

K. Spectral Crosstalk Calibration

In one embodiment, it may be desirable to correct the data to account for color crosstalk. This may be done using methods known in the art (e.g., U.S. Pat. No. 7,209,836 incorporated by reference) as well as methods disclosed herein (see Example 10, FIG. 32). For example, a four-color fluorescent detection system (for detection of the exemplary colors blue, green, yellow and red) has one detector channel for each of the four different color dyes. However, because the dyes have fairly broad spectra, there is some detection of dyes in adjacent color channels. For example, when exciting only a green dye, a signal is visible in the yellow channel as well as the green channel. If this spectral crosstalk is calibrated, it may be removed from subsequent measurements even if the dyes are mixed in unknown quantities. To determine actual fluorescent intensities for the four colors, A, B, C and D from measured detector outputs, $M_A$, $M_B$, $M_C$,

| 1 | A | C | 0 | 0 | A | A | B | 0 | 0 | B | C | 0 | 0 | 0 | 0 | 0 | 0 | 0 | 0 | 0 | 0 | 0 | 0 | 0 |
| A | 1 | A | C | 0 | B | A | A | B | 0 | C | B | C | 0 | 0 | 0 | 0 | 0 | 0 | 0 | 0 | 0 | 0 | 0 | 0 |
| C | A | 1 | A | C | 0 | B | A | A | B | 0 | C | B | C | 0 | 0 | 0 | 0 | 0 | 0 | 0 | 0 | 0 | 0 | 0 |
| 0 | C | A | 1 | A | 0 | 0 | B | A | A | 0 | 0 | C | B | C | 0 | 0 | 0 | 0 | 0 | 0 | 0 | 0 | 0 | 0 |
| 0 | 0 | C | A | 1 | 0 | 0 | 0 | B | A | 0 | 0 | 0 | C | B | 0 | 0 | 0 | 0 | 0 | 0 | 0 | 0 | 0 | 0 |
| A | B | 0 | 0 | 0 | 1 | A | C | 0 | 0 | A | B | 0 | 0 | 0 | B | C | 0 | 0 | 0 | 0 | 0 | 0 | 0 | 0 |
| A | A | B | 0 | 0 | A | 1 | A | C | 0 | A | A | B | 0 | 0 | C | B | C | 0 | 0 | 0 | 0 | 0 | 0 | 0 |
| B | A | A | B | 0 | C | A | 1 | A | C | B | A | A | B | 0 | 0 | C | B | C | 0 | 0 | 0 | 0 | 0 | 0 |
| 0 | B | A | A | B | 0 | C | A | 1 | A | 0 | B | A | A | B | 0 | 0 | C | B | C | 0 | 0 | 0 | 0 | 0 |
| 0 | 0 | B | A | A | 0 | 0 | C | A | 1 | 0 | 0 | B | A | A | 0 | 0 | 0 | C | B | 0 | 0 | 0 | 0 | 0 |
| B | C | 0 | 0 | 0 | A | A | B | 0 | 0 | 1 | A | C | 0 | 0 | A | A | B | 0 | 0 | B | C | 0 | 0 | 0 |
| C | B | C | 0 | 0 | B | A | A | B | 0 | A | 1 | A | C | 0 | B | A | A | B | 0 | C | B | C | 0 | 0 |
| 0 | C | B | C | 0 | 0 | B | A | A | B | C | A | 1 | A | C | 0 | B | A | A | B | 0 | C | B | C | 0 |
| 0 | 0 | C | B | C | 0 | 0 | B | A | A | 0 | C | A | 1 | A | 0 | 0 | B | A | A | 0 | 0 | C | B | C |
| 0 | 0 | 0 | C | B | 0 | 0 | 0 | B | A | 0 | 0 | C | A | 1 | 0 | 0 | 0 | B | A | 0 | 0 | 0 | C | B |
| 0 | 0 | 0 | 0 | 0 | B | C | 0 | 0 | 0 | A | B | 0 | 0 | 0 | 1 | A | C | 0 | 0 | A | B | 0 | 0 | 0 |
| 0 | 0 | 0 | 0 | 0 | C | B | C | 0 | 0 | A | A | B | 0 | 0 | A | 1 | A | C | 0 | A | A | B | 0 | 0 |
| 0 | 0 | 0 | 0 | 0 | 0 | C | B | C | 0 | B | A | A | B | 0 | C | A | 1 | A | C | B | A | A | B | 0 |
| 0 | 0 | 0 | 0 | 0 | 0 | 0 | C | B | C | 0 | B | A | A | B | 0 | C | A | 1 | A | 0 | B | A | A | B |
| 0 | 0 | 0 | 0 | 0 | 0 | 0 | 0 | C | B | 0 | 0 | B | A | A | 0 | 0 | C | A | 1 | 0 | 0 | B | A | A |
| 0 | 0 | 0 | 0 | 0 | 0 | 0 | 0 | 0 | 0 | B | C | 0 | 0 | 0 | A | A | B | 0 | 0 | 1 | A | C | 0 | 0 |
| 0 | 0 | 0 | 0 | 0 | 0 | 0 | 0 | 0 | 0 | C | B | C | 0 | 0 | B | A | A | B | 0 | A | 1 | A | C | 0 |
| 0 | 0 | 0 | 0 | 0 | 0 | 0 | 0 | 0 | 0 | 0 | C | B | C | 0 | 0 | B | A | A | B | C | A | 1 | A | C |
| 0 | 0 | 0 | 0 | 0 | 0 | 0 | 0 | 0 | 0 | 0 | 0 | C | B | C | 0 | 0 | B | A | A | 0 | C | A | 1 | A |
| 0 | 0 | 0 | 0 | 0 | 0 | 0 | 0 | 0 | 0 | 0 | 0 | 0 | C | B | 0 | 0 | 0 | B | A | 0 | 0 | C | A | 1 |

If the spreading matrix, S, is inverted, $S^{-1}$, it may be used to eliminate the neighbor influence modeled by the spreading matrix. If we multiply the measured spot matrix (in the form of a vector), $v_{spot}$, by the inverse of the spreading matrix, $S^{-1}$, we can generate an estimate for the spot matrix with the neighbor influence removed, $V_{uninfluenced}$ $$v_{uninfluenced} = S^{-1} v_{spot}.$$

The method described above for removing the neighbor influence can generate sizable spreading matrices on the order of $N^4$ and therefore may be computationally intensive for typical images. Since the influence of spots that are relatively far from the spot of interest have relatively negligible influence, it is possible to reduce the size of the spreading matrices used for the calculation and perform the calculation on smaller subsections of the image at a time. This can significantly reduce the computational complexity $M_D$ in corresponding channels, one needs to know all of the spectral crosstalk factors: $R_{AB}$, $R_{BA}$, $R_{BC}$, $R_{CB}$, $R_{CD}$, and $R_{DC}$. For example, $R_{AB}$ is the ratio between the portion of the signal in the A channel coming from the B dye and the actual intensity of the B dye. If for instance $R_{AB}$ is 20%, then the A channel will have an additional signal equal to 0.2 times the actual B dye intensity in the B channel. Thus for channel B, the observed measurement, $M_B$, is the direct measurement of B and the two contributions from the adjacent channels (if any): $M_B = B + R_{BA}A + R_{BC}C$ (6). For the four channels, this may be written in matrix form:

$$\begin{bmatrix} M_A \\ M_B \\ M_C \\ M_D \end{bmatrix} = K \begin{bmatrix} A \\ B \\ C \\ D \end{bmatrix} \quad (7)$$

where $$K = \begin{bmatrix} 1 & R_{AB} & 0 & 0 \\ R_{BA} & 1 & R_{BC} & 0 \\ 0 & R_{CB} & 1 & R_{CD} \\ 0 & 0 & R_{DC} & 1 \end{bmatrix}$$

Each of the six spectral crosstalk factors may be determined through an experiment with pure dyes. We want to solve for the actual fluorescent signals, A, B, C and D given the detector measurements, $M_A$, $M_B$, $M_c$, $M_D$. Thus, we want to solve the above matrix Equation (7). This is equation (8):

$$\begin{bmatrix} A \\ B \\ C \\ D \end{bmatrix} = K^{-1} \begin{bmatrix} M_A \\ M_B \\ M_C \\ M_D \end{bmatrix}$$

where $K^{-1}$ is the inverse of matrix K. Although the inverse of matrix K may be written out in terms of the six spectral crosstalk factors, it is somewhat complex and is best performed by plugging in the numbers and letting the computer take the inverse. The results are discussed in Example 10 which demonstrate that a base in the sequence would have been miscalled were the spectral crosstalk calibration not performed.

Any multicolor sequencing by synthesis device may be calibrated using the above equations and the resultant spectral crosstalk matrix may be used in all four color measurements from the device. In one embodiment, if we also include information on the relative magnitude of each of the four colors, then we can also correct for differences in perceived dye brightness from one channel to the next. Multiplying the matrix K by a diagonal matrix, whose diagonal terms are the relative brightness for each dye, produces a new matrix K whose inverse will automatically scale the dyes to be consistent with one another.

K. Base Calls

As discussed above, at each sequencing by synthesis cycle, the signals that are observed in the four color channels are used to both determine the most likely base at that cycle (base call) and to determine a quality score for the base call. Because of a number of factors, it may not always be the case that the brightest color in the raw data indicates the most likely base. Thus, it may be desirable to correct for at least on; and more particularly all, of the following phenomena that were discussed supra: field flattening, spectral crosstalk, sequence lead and sequence lag. After the correction factors (field flattening, spectral crosstalk and/or lead-lag compensation) have been applied, a base is called based on the maximum signal between the four channels. The output of the base calls may be a file similar to a FASTA format. In one embodiment, this file is also accompanied by a quality score file.

To optimize the alignment and assembly of the data into contigs, it is desirable to have a precise quality score associated with each base call. A quality file may be generated that encodes quality scores for each cycle. Preserving the information for all four bases is also desirable to allow the sequence alignment software to examine several likely calls instead of only the one with the highest signal.

EXPERIMENTAL

The following examples serve to illustrate certain exemplary embodiments and aspects of the present invention and are not to be construed as limiting the scope thereof.

Example 1

Materials and Methods

The following is a brief description of the exemplary materials and methods used in the following Examples. All solvents and reagents were reagent wades, purchased commercially and used without further purification. Protected nucleosides 5'-O-(tert-butyldimethylsilyl)-2'-deoxythymidine, $N^4$-benzoyl-5'-O-tert-butyldimethylsilyl-2'-deoxycytidine, $1V^6$-Benzoyl-5'-O-tert-butyldimethylsilyl-2'-deoxyadenosine, $N^2$-isobutyryl-5'-O-(tert-butyldimethylsilyl)-2'-deoxyguanosine were purchased from CNH Technologies, Inc. All other chemicals were purchased from Sigma-Aldrich.

Example 2

Synthesis of 3'-O-Azidomethyl Nucleotides

Figure 20:
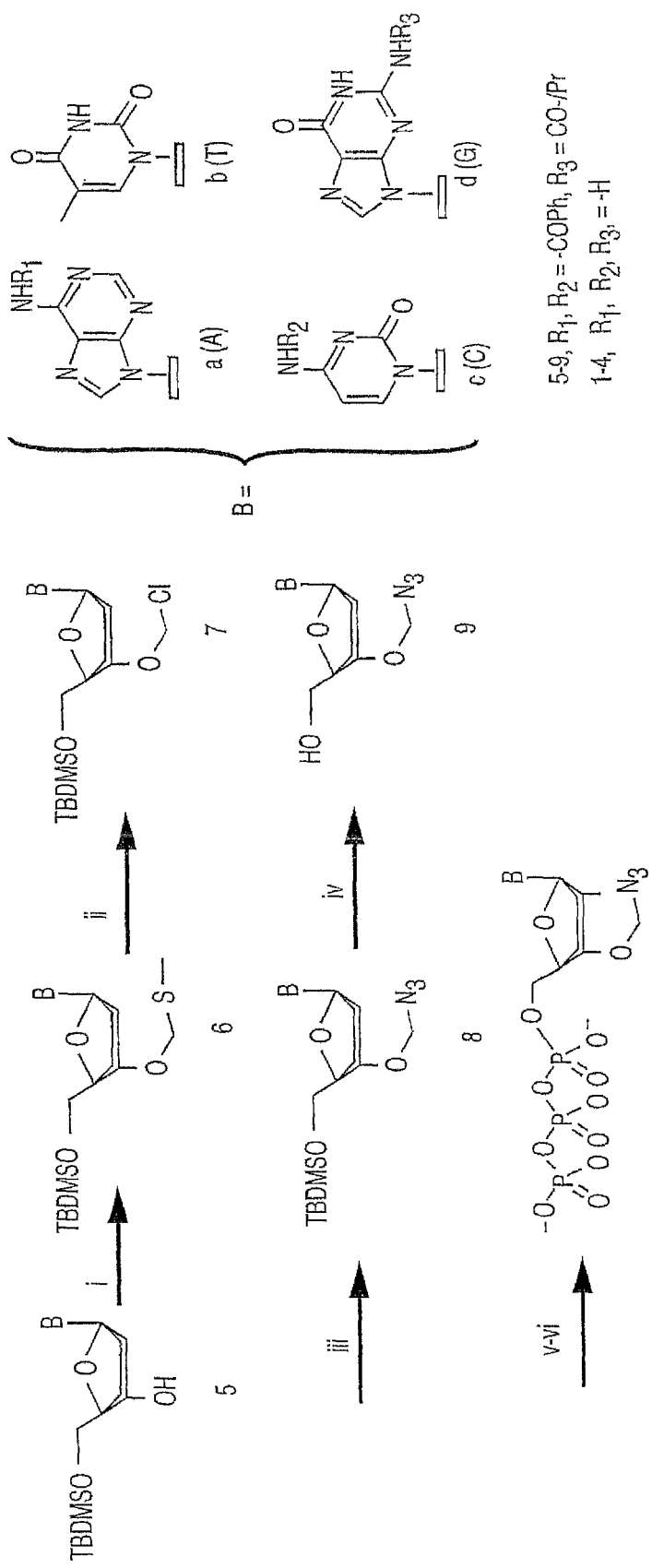
FIG. 20 shows synthesis of 3'-O-azidomethyl-dNTPs where the steps denote treatment with (i) DMSO, AcOH, $Ac_2O$, 48 h; (ii) $SO_2Cl_2$, dry $CH_2Cl_2$, 1-2 h; (iii) $NaN_3$ in DMF, 3 h; (iv) $NH_4F$ in MeOH, 16-20 h; (v) $(MeO)_3PO$, $POOCl_3$ then $(t-Bu_3NH)_4P_2O_7$, TEAB, 1 h; vi) $NH_4OH$.

The synthesis of 3'-O-azidomethyl-VPTs is described in FIG. 20. Briefly, reaction of 5'-O-TBDMS-2'-deoxynucleosides (5) with a mixture of DMSO, acetic acid, and acetic anhydride installed the 3'-O-methylthiomethyl group (3'-O-MTM, 6), which upon treatment with $SO_2Cl_2$ B. Synthesis of $N^6$-benzoyl-3'-O-(azidomethyl)-2'-deoxyadenosine (9a)

To 0.4 g $N^6$-benzoyl-3'-O-(methylthiomethyl)-5)-O-(tert-butyldimethylsilyl)-2'-deoxyadenosine (0.76 mmol) dissolved in 7 mL dry $CH_2Cl_2$ was treated with 0.4 mL cyclohexene and 155 μL $SO_2Cl_2$ (1.91 mmol) at 0° C. for 2 h. During this time the starting material completely converted to 7a which was shown by disappearance of the starting material and appearance of 3'-OH analog (5a) in TLC (EtOAC:Hex/7:3, $R_f$~0.3; the 3-$CH_2Cl$ (7a) could not detected in TLC due to decomposition in TLC plate to 5a). Then solvent was removed by rotary evaporation and kept about 10 minutes in high vacuum pump. Then dissolved in 5 mL dry DMF and treated with 400 mg $NaN_3$ (6.6 mmol) at room temperature for 3 h. Then the reaction mixture was partitioned in $H_2O/CH_2Cl_2$, the combined organic part was dried over $Na_2SO_4$ and concentrated by rotary evaporation. The crude sample was then dissolved in 5 mL MeOH and treated with 300 mg $NH_4F$ (8.1 mmol) more than 38 h, Then MeOH was removed by rotary evaporation. After partioning in $H_2O/EtOAc$, the combined organic part was dried over $Na_2SO_4$, concentrated, and purified by silica gel column chromatography (100% EtOAc to 98:2, EtOAc/MeOH) resulting 150 mg of 9a as white powder (48% yield in three steps). HR-MS: Obs. m/z 411.1530, calcd for $C_{18}H_{19}O_4N_8$ 411.1529 $[M+H]^+$. $^1$H-NMR ($CDC_3$): $\delta_H$ 8.84; (brs, 1H), 8.70; (brs, 1H), 8.08; (m, 1H), 7.76-7.54; (m, 5H), 6.47; (t, J=5.6 Hz, 1H), 4.83; (m, 4.78; (m, 1H), 4.39; (m, 1H), 4.09;

(d, 12.78 Hz, $H_5'$, 1H), 3.88; (d, J=12.78 Hz, $H_5''$, 1H), 3.09; (m, $H_2'$, 1H), and 2.65; (m, $H_2''$, 1H) ppm.

Example 4

Synthesis of 3'-O-azidomethyl-dT (9b)

The following describes exemplary synthesis steps for compounds shown in FIG. 20.

A. Preparation of 3'-O-(methylthiomethyl)-5'-O-(tert-butyldimethylsilyl)-2'-deoxythymidine (6b)

2.0 g 5'-O-(tert-butyldimethylsilyl)-2'-deoxythymidine (5b) (5.6 mmol) was dissolved in a mixture consisting of 10.5 mL DMSO, 4.8 mL, acetic acid, and 15.4 mL acetic anhydride and stirred for 48 h at room temperature, The mixture was then quenched by treating with a saturated $NaHCO_3$ solution and extracted with EtOAc (3×100 mL). The combined organic extract was then washed with a saturated solution of $NaHCO_3$ and dried over $Na_2SO_4$, concentrated under vacuum, and finally purified by silica gel column chromatography (Hex: EtOAc/7:3 to 1:1). The 3'-O-(methylthiomethyl)-5'-O-(tert-butyldimethylsilyl)-2'-deoxythymidine (6b) was obtained as white powder in 75% yield (1.75 g, $R_f$=0.6, hex: EtOAc/1:1). HR-MS: Obs. m/z 417.1890, cald. for $C_{18}H_{33}N_2O_5SSi$ 417.1879 [M+H]$^+$. $^1$H-NMR (CDCl$_3$): $\delta_H$ 8.16; (s, 1H), 7.48; (s, 1H), 6.28; (m, 1H), 4.62; (m, 2H), 4.46; (m, 1H), 4.10; (m, 1H), 3.78-3.90; (m, 2H), 2.39; (m, 1H), 2.14, 2.14; (s, 3H), 1.97; (m, 1H), 1.92; (s, 3H), 0.93; (s, 9H), and 0.13; (s, 3H) ppm.

B. Preparation of 3'-O-(azidomethyl)-2'-deoxythymidine (9h)

To 1.095 g 3'-O-(methylthiomethyl)-5'-O-(tert-butyldimethylsilyl)-2'-deoxythymidine (6b) (2.6 mmol) dissolved in 10 mL dry CH$_2$Cl$_2$ were added 1.33 mL, cyclohexene and 284 μl SO$_2$Cl$_2$ (3.5 mmol) at 0° C. and stirred at the ice-cold temperature for 1.5 h. Then the flask temperature was brought to room temperature and transferred to a round bottom flask. The volatiles were removed by rotary evaporation followed by high vacuum pump. Then the crude sample was dissolved in 5 mL dry DMF and 926 mg NaN$_3$ (15.4 mmol) was added to it and stirred for 3 h at room temperature. The crude sample was dispersed in 50 mL distilled water and extracted with CH$_2$Cl$_2$ (3×50 mL), the organic extracts were combined and dried over Na$_2$SO$_4$ and concentrated by rotary evaporation. The crude sample was then dissolved in MeOH (5 mL) and treated with NH$_4$F (600 mg, 16.2 mmol) for 24 h at room temperature. Then reaction mixture was concentrated and partitioned between H$_2$O/CH$_2$Cl$_2$ and the combined organic extract was dried over Na$_2$SO$_4$, concentrated, and purified the product by silica gel column chromatography using Hex: EtOAc/1:1 to 2:5 resulting the final product (9b) as white powders (~550 mg, 71% yield in three steps, $R_f$=0.3, Hex: EtOAc/1:1.5). HR-MS: Observed m/z 298.1146, calcd for $C_{11}H_{16}O_5N_5$ 298.1151 [M+H]$^+$, $^1$H-NMR (CDC$_3$): $\delta_H$ 8.30; (brs, 1H), 7.40; (s, 1H), 6.14; (t, J=6.8 Hz, 1H), 4.79-4.70; (m, 2H), 4.50; (m, 1H), 4.16; (m, 1H), 4.01-3.84; (m, 2H), 2.45; (m, 211) and 1.95; (s, 3H) ppm.

Example 5

Synthesis of N$^4$-Benzoyl-3'-O-(azidomethyl)-dC (9e)

The following describes exemplary synthesis steps for compounds shown in FIG. 20.

A. Preparation of N$^4$-Benzoyl-3'-O-(methylthiomethyl)-5'-O-(tert-butyldimethylsilyl)-2'-deoxycytidine (6e)

3.5 g N$^4$-benzoyl-5'-O-tert-butyldimethylsilyl-2'-deoxycytidine (5c) (7.65 mmol) was dissolved in a mixture consisting of 14.7 mL DMSO, 6.7 mL acetic acid, and 21.59 mL acetic anhydride and stirred for 48 h at room temperature. During this period of time, a complete conversion to product was observed by TLC ($R_f$=0.4, EtOAc:hex/10:1). The mixture was then neutralized with a saturated NaHCO$_3$ solution and extracted with CH$_2$Cl$_2$ (3×100 mL). The combined organic extract was then washed with saturated solution of NaHCO$_3$ and dried over Na$_2$SO$_4$, and concentrated under vacuum. The product was then purified by silica gel column chromatography (EtOAc: hex/2:1 to 9:1) to obtain N$^4$-benzoyl-3'-O-(methylthiomethyl)-5'-O-(tert-butyldimethylsilyl)-2'-deoxycytidine (6c) as white powder in 73% yield (2.9 g, $R_f$=0.6, EtOAc:hex/9:1). HR-MS: obs. m/z 506.2134, cald. for $C_{24}H_{36}O_5N_3SiS$ [M+H]$^+$. 506.2145. $^1$H-NMR (CDCl$_3$): $\delta_H$ 8.43; (d, J=7.1 Hz, 1H), 7.93; (m, 2H), 7.64; (m, 1H), 7.54; (m, 3H), 6.30; (m, 1H), 4.62 & 4.70; (2Xd, J=11.59 Hz, 2H), 4.50; (m, 1H), 4.19; (m, 1H), 3.84 & 3.99; (2Xdd, J=11.59 & 2.79 Hz, 2H), 2.72; (m, 1H), 2.21; (m, 1H), 2.14; (s, 3H), 0.99; (s, 9H), and 0.16; (s, 6H) ppm.

B. Preparation of N$^4$-Benzoyl-3''-O-(azidomethyl)-2'-deoxycytidine (9c). To 0.5580 g N$^4$-benzoyl-3'-O-(methylthiomethyl)-5'-O-(tert-butyldimethylsilyl)-2'-deoxycytidine (6c)

(1.04 mmol) dissolved in 8 mL dry CH$_2$Cl$_2$ were added 0.56 mL cyclohexene and 220 μl SO$_2$Cl$_2$ (2.7 mmol) at 0° C. and stirred at the ice-cold temperature for 1 h. During this time, the starting material converted to the chlorinated product as shown by the 3'-OH (5c) compound in the TLC. The volatiles were then removed under vacuum and resuspended in dry DMF (5 mL) and treated with NaN$_3$ (400 mg, 6.6 mmol) and stirred for 2 h at room temperature. The sample was then partitioned between water and CH$_2$Cl$_2$ and the organic extracts were combined and dried over Na$_2$SO$_4$ and concentrated under vacuum. The crude sample was then dissolved in MeOH (5 mL) and treated with NH$_4$F (600 mg, 16.2 mmol) for 20 h at room temperature. Then solvent was removed under vacuum and. extracted with CH$_2$Cl$_2$ and the organic extract was then dried over Na$_2$SO$_4$ and concentrated under vacuum. The sample was then purified by silica gel column chromatography (Hex:EtOAc 1:4 to 1:10), and the product (9c) was obtained as white powdery substance (~200 mg, 50% yield in three steps, $R_f$=0.5, EtOAc:Hex/5:0.5). HR-MS: Obs. m/z 387.1408, calcd. for $C_{17}H_{19}O_5N_6$ 387.1417 [M+H]$^+$. $^1$H-NMR (CDC$_3$): $\delta_H$ 8.30 (d, J=7.2 Hz, 1H), 7.93; (d, J=7.50 Hz 1H), 7.66-7.51; (m, 5H), 6.18; (t, J=6.4 Hz, 1H), 4.81-4.68; (m, 2H), 4.52; (m, 4.25 (m, 1H), 4.08-3.88; (m, 2H), 2.69; (m, 1H), and 2.50; (m, 2H) ppm.

Example 6

Synthesis of $N^2$-isobutyryl-$O^6$-diphenylcarbamoyl-3'-O-azidomethyl-dG (14)

Figure 21:
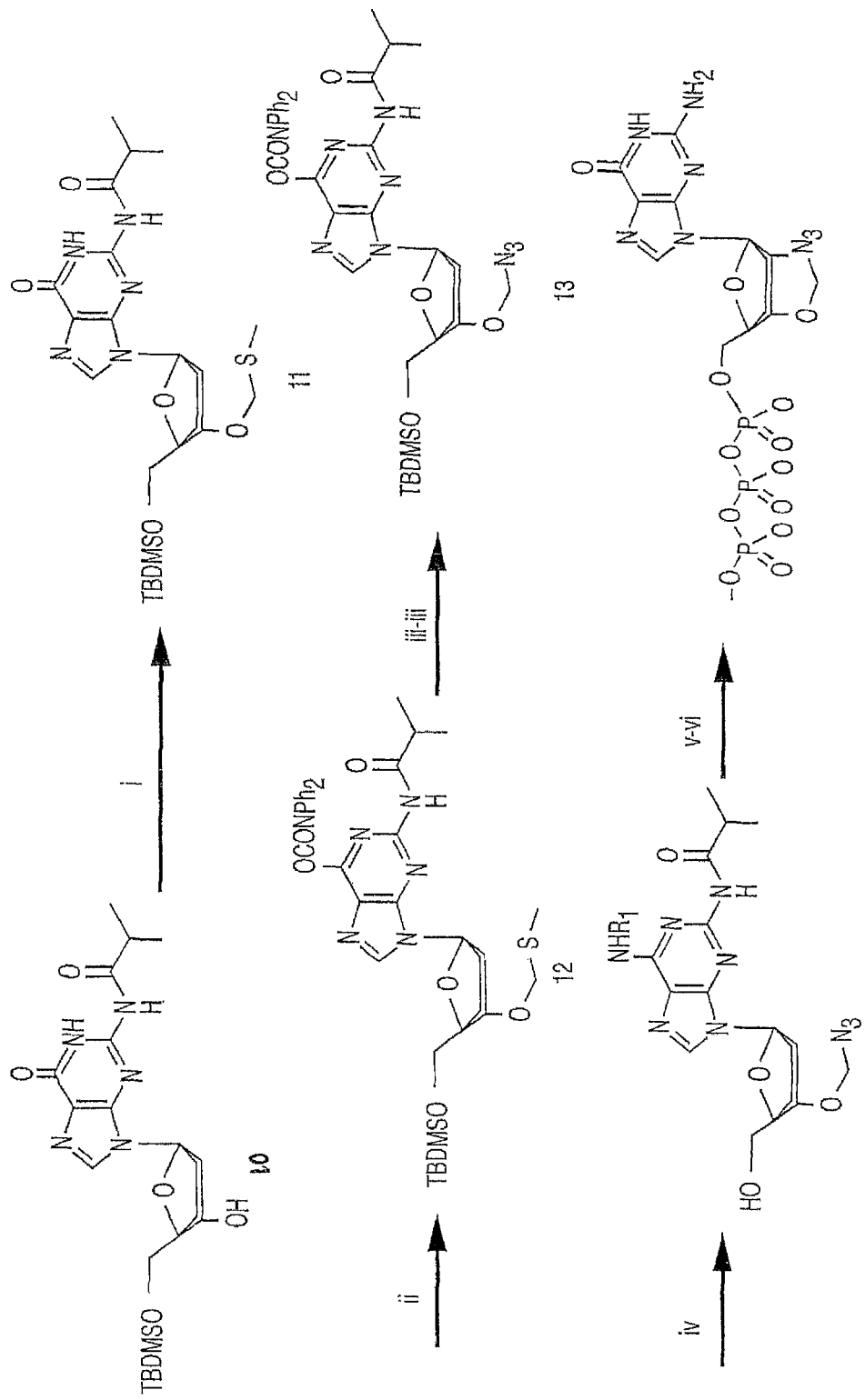
FIG. 21 shows synthesis of 3'-O-azidomethyl-dGTP where the steps denote treatment with (i) DMSO, AcOH, $Ae_2O$, 48 h; (ii) $Ph_2NCOCl$, DMA, Pyridine 3 h; (iii) $SO_2Cl_2$, dry $CH_2Cl_2$, 1-2 h; (iii) $NaN_3$ in DMF, 3 h; (iv) $NH_4F$ in MeOH, 24 h; (v) $(MeO)_3PO$, $POCl_3$ then $(t-Bu_3NH)_3P_2O_7H$, TEAB, 1 h; (vi) $NH_4OH$.
Figure 22A:
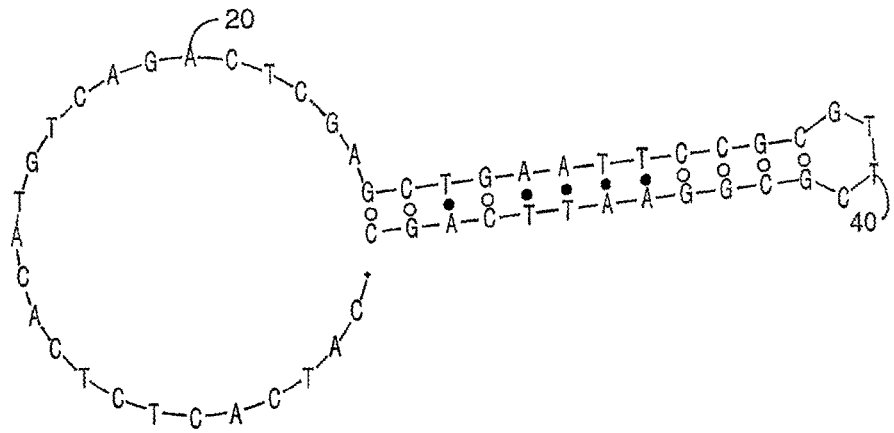
FIG. 22 shows synthetic DNA templates [SEO ID NOs: 1-4]used in exemplary sequencing experiments.
Figure 22B:
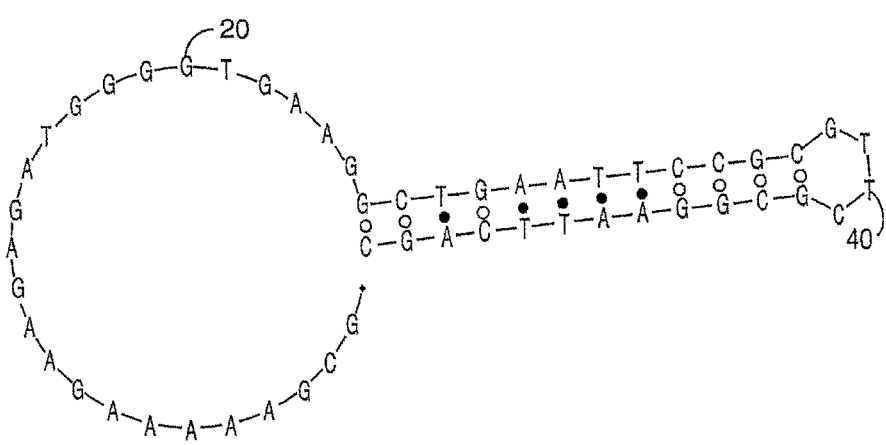
Figure 22C:
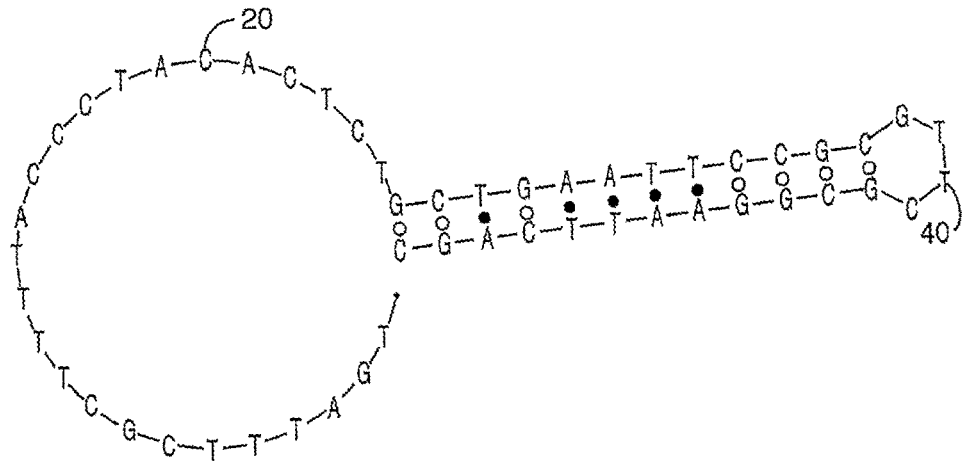
Figure 22D:
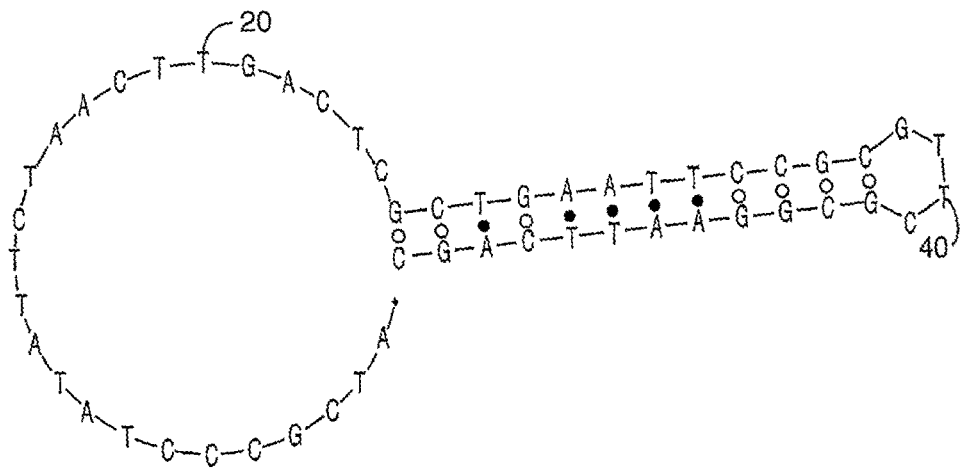
Figure 23A:
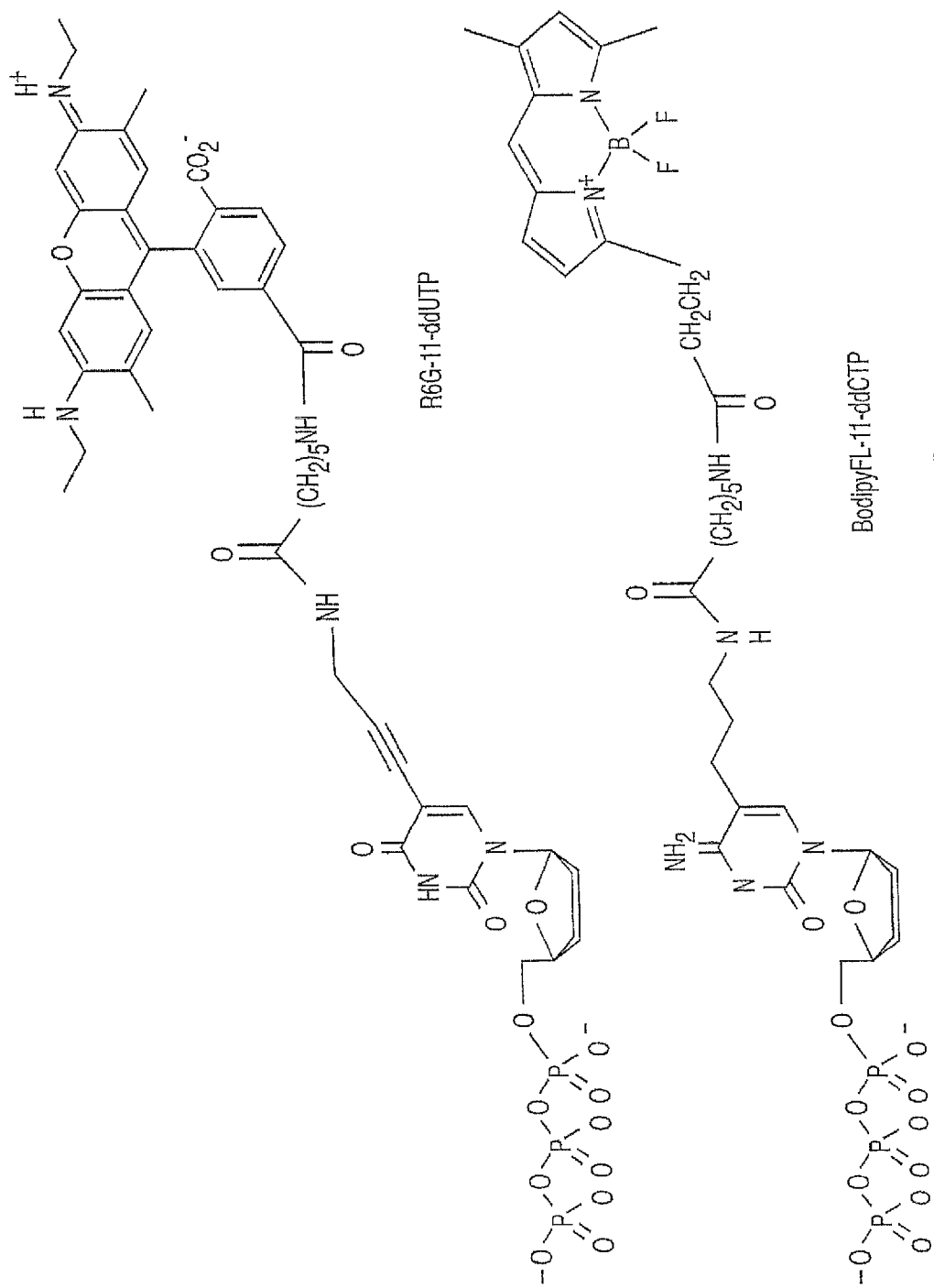
FIG. 23A-23B shows the structures of exemplary labeled 2,3-dideoxynucleotides used in the sequencing by synthesis.
Figure 23B:
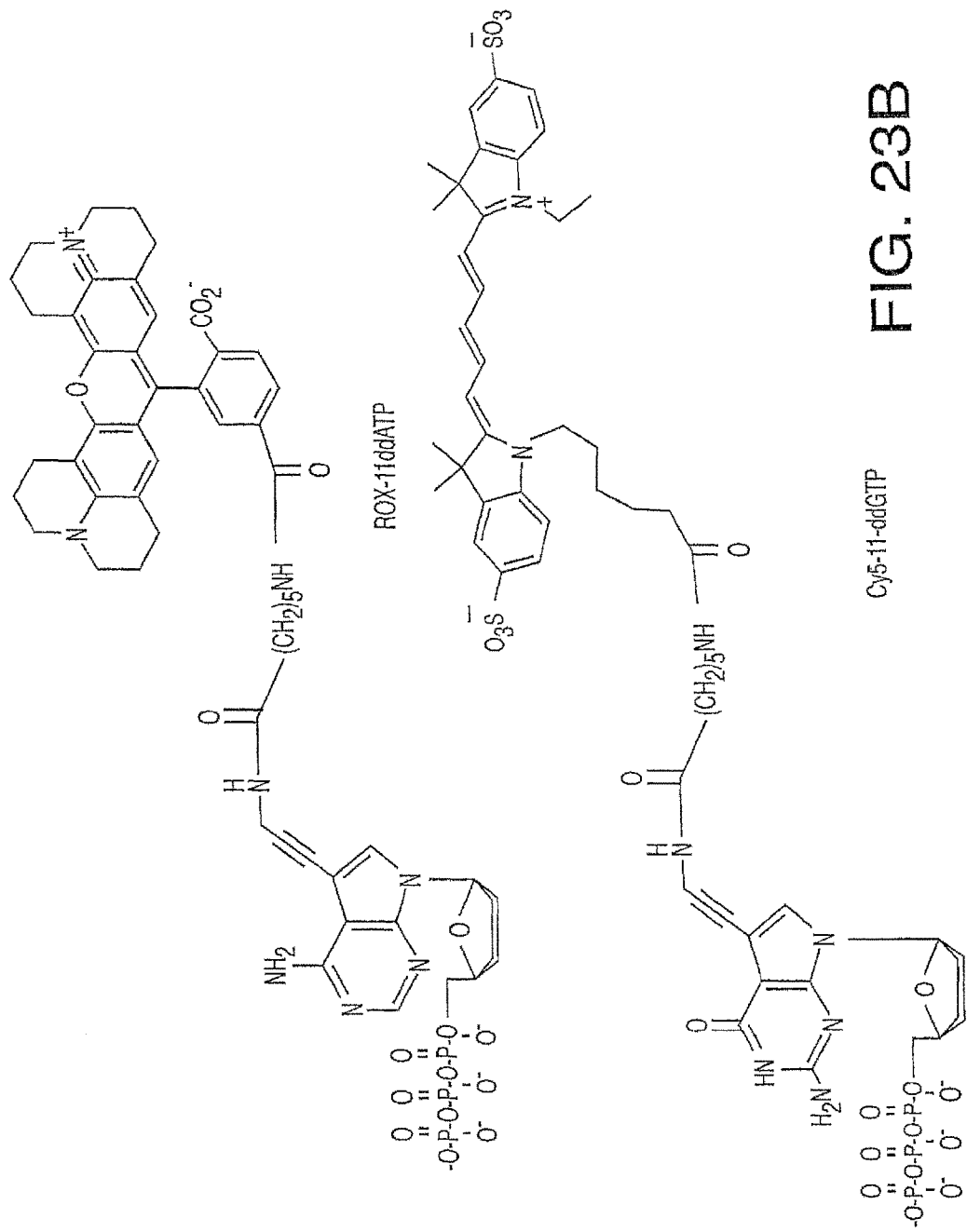

The following describes exemplary synthesis steps for compounds shown in FIG. 21.

A. Preparation of $N^2$-isobutyryl-3'-O-(methylthiomethyl)-5'-O-(tert-butyldimethylsilyl)-2'-deoxyguanosine (11)

5 g of $N^2$-isobutyryl-5'-O-(tert-butyldimethylsilyl)-2'-deoxyguanosine (11.0 mmol) dissolved in 21 mL dry DMSO was treated with 10 mL acetic, acid and 32 mL acetic anhydride, and stirred for 48 h at room temperature. The crude reaction mixture was then neutralized by adding a $K_2CO_3$ solution, and extracted with ethyl acetate (100×3 mL). The combined organic extract was then washed with saturated $NaHCO_3$ solution, dried over $Na_2SO_4$ and concentrated under vacuum. Then reaction mixture was purified by a silica gel column chromatography resulting the product 11 as white powder (3.9 g, 69% yield; $R_f$=0.35, $CH_2Cl_2$:MeOH/20:1). HR-MS: Obs. m/z 512.2344 cald. for $C_{22}H_{38}O_5N_5SiS$ 512.2363 [M+H]$^+$. $^1$H-NMR (CDCl$_3$): $\delta_H$ 12.0; (s, 1H), 8.95; (brs, 1H), 8.09; (s, 1H), 6.24; (t, J=6.8 Hz, 1H), 4.73; (m, 2H), 4.66; (m, 1H), 4.16; (m, 1H), 3.81; (m, 2H), 2.76; (m, 1H), 2.59; (m, 1H), 2.54; (m, 1H), 2.21; (s, 3H), 1.29; (m, 6H), 0.91; (s, 9H), and 0.10; (s, 6H) ppm.

B. Synthesis of $N^2$-isobutyryl-$O^6$-diphenylcarbamoyl-3'-O-(methylthiomethyl)-5'-O-(tert-butyldimethylsilyl)-2'-deoxyguanosine (12)

To 1.0 g $N^2$-isobutyryl-3'-O-(methylthimethyl)-5'-O-(tert-butyldimethylsilyl)-2'-deoxyguanosine (11, 1.95 mmol) dissolved in 22 mL dry pyridine were added diphenylcarbamoyl chloride (0.677 g, 2.92 mmol) and 1.02 mL N,N-diisopropylethylamine, and stirred at room temperature for 3 h under nitrogen atmosphere. The reaction mixture became dark red during this time. The solvent was removed under high vacuum, and product was then purified by silica gel column chromatography using EtOAc:hex/1:1 to 7:3 as mobile phase. The product 12 was isolated as yellowish powder (1.09 g, ~80% yield; $R_f$=0.7, EtOAc:hex (1:1)). HR-MS: Obs. m/z 707.3068 calcd. for $C_{35}H_{47}O_6N_6SiS$ 707.3047 [M+H]$^+$. $^1$H-NMR (CDCl$_3$): $\delta_H$ 8.25; (s, 1H), 7.94; (brs, 1H), 7.47-7.37; (m, 10H), 6.42; (m, 1H), 4.75; (m, 2H), 4.71; (m, 1H), 4.18; (m, 1H), 3.88-3.70; (m, 2H), 2.80; (m, 1H), 2.60; (m, 1H), 2.19; (s, 3H), 1.30; (d, J=7.2 Hz, 6H), 0.93; (s, 9H) and 0.14; (s, 6H) ppm.

C. Preparation of $N^2$-isobutyryl-$O^6$-diphenylcarbamoyl-3'-O-azidomethyl-2'-deoxyguanosine (14)

To 786 mg 12 (1.1 mmol) dissolved in 8 mL dry CH2Cl$_2$ was treated with 0.56 mL cyclohexene and 180 µL SO$_2$Cl$_2$ (2.2 mmol) at 0° C. and stirred for 1.5 h at the same temperature. The solvent was then removed by rotary evaporation, and farther dried under high vacuum for 10 minutes. The crude product was then dissolved in 5 mL dry DMF and reacted with 600 mg NaN$_3$ (10 mmol) at 0° C. and stirred at room temperature for 3 h. Reaction mixture was then partitioned H$_2$O/CH$_2$Cl$_2$, the combined organic extract was then dried over Na$_2$SO$_4$, and concentrated by rotary evaporation. The crude was then dissolved in 5 mL dry MeOH, treated with 500 mg NH$_4$F (13.5 mmol) at room temperature for more than 24 h. Then MeOH solvent was removed by rotary evaporation, and partitioned (H$_2$O/CH$_2$Cl$_2$). The combined organic part was dried over Na$_2$SO$_4$. and concentrated by rotary evaporation and purified by silica gel column chromatography resulting pure product of 14 as white powder (230 mg, ~36% yield in three steps; hex: EtOAc 1:1 to 1:5, ($R_f$=~0.3, Hex:EtOAc/1:4). HR-MS: Obs. m/z 588.2343, calcd for $C_{28}H_{30}O_6N_9$ 588.2319 [M+H]$^+$. $^1$H-NMR (DFM-d$_6$): $\delta_H$ 8.64 (brs, 1H), 7.48-7.34; (m, 10H), 6.36; (t, J=7.0 Hz), 4.93; (m, 2H), 4.76; (m, 1H), 4.04; (m, 1H), 3.57; (m, 1H), 3.34; (m, 2H), 2.97; (m, 1H), 2.81; (m, 1H), and 1.10; (m, 6H).

Example 7

General Method for the Preparation of 3'-O-Azidomethyl-Dntps

The protected 3'-O-azidomethyl nucleoside (0.3 mmol) and proton sponge (75.8 mg; 0.35 mmol) were dried in a vacuum desiccator over P$_2$O$_5$ overnight before dissolving in trimethyl phosphate (0.60 mL). Then freshly distilled POCl$_3$ (33 µL, 0.35 mmol) was added drop-wise at 0° C. and the mixture was stirred at 0° C. for 2 h. Subsequently, a well-vortexed mixture of tributylammonium pyrophosphate (552 mg) and tributylamine (0.55 mL; 2.31 mmol) in anhydrous DMF (2.33 mL) was added in one potion at room temperature and stirred for 30 min. Triethyl ammonium bicarbonate solution (TEAB) (0.1 M, 15 mL, pH 8.0) was then added and the mixture was stirred for 1 h at room temperature. Then 15 mL of NH$_4$OH was added and stirred overnight at room temperature. The resulting mixture was concentrated in vacuo and the residue was diluted with 5 mL of water. The crude mixture was then purified with anion exchange chromatography on DEAE-Sephadex A-25 at 4 ° C. using a gradient of TEAB (pH 8.0; 0.1-1.0 M). Further purification by RP HPLC to give corresponding target as colorless syrup:

Example 8

3'-O-Azidomethyl Nucleotides Cleavage

The 3'-O-azidomethyl group cleavage can be accomplished with a variety of reducing agents such as phosphines. The cleavage agents that are particularly desirable are those that are soluble in aqueous media and do not cause any damage to the DNA. One particularly desirable agent is tri(carboethoxy)phosphine (TCEP).

The 3'-O-azidomethyl nucleotides can be separated from native nucleotides using RP HPLC. In the next experiment, the kinetics of the 3'-O-azidomethyl TTP cleavage was studied. For this purpose, a 1 mM solution of nucleotide was prepared in water and mixed with 50 mM solution of TCEP/400 mM of Tris at pH 8.0 and incubated at 55 deg C. for various periods of time. After the incubation, the reaction was stopped by mixing with 4 M NaOAc at pH=4.3 and an aliquot of reaction mixture (0.5 nmole of nucleotide) was injected and separated on the RP HPLC column. The integrated peak area was then plotted against time.

Example 9

Sequencing by Synthesis Using 3'-O-Azidomethyl Nucleotides

We established conditions for sequencing by synthesis on the surface using 3'-O-azidomethyl nucleotides. For this purpose we used variants of the 9 deg N polymerase that were developed specifically to incorporate 3'-O-azidomethyl nucleotides. For these sequencing experiments we were using synthetic DNA templates that encompass self priming moieties. Examples of these DNA templates and their secondary structures are shown in FIG. 22.

These oligonucleotides carry a 5'-amino modification through which they are attached to assay surface. The surface constitutes any surface that is bio-compatible, has low fluorescent background and has functional groups on the surface which can be used to covalently attach the DNA. In the described case, pre-activated Codelink (from GE Healthcare) slides were used for this purpose. The solution of the oligonucleotides (50 uM) for spotting was prepared in 150 mM phosphate/bicarbonate spotting buffer (pH=7.5). The arrays were then spotted and incubated in the humid chamber at 25 deg C. overnight. After the incubation, the arrays were blocked by washing in the 1xTBST/2% BSA buffer, rinsed with nuclease free water and dried.

The sequencing was performed in a chambered slide (Grace Biolabs). In the experiment, each well was subjected to different number of cycles using the mixture of 3'-O-azidomethyl nucleotides with each extension cycle followed by a cleavage cycle. Extension cycle consisted of incubating the well with the solution containing: 3'-O-azidomethyl nucleotide mix—75 uM, 9 deg N polymerase mutant—250 ug/ml, 10 mM KCl, 10 mM (NH4)2SO4, 20 mM Tris-HCl, 4 mM MnSO4, 0.1% Triton-X-100, 0.1% acetylated BSA, pH 8.8. The incubation was carried out at 65 deg C. for 20 minutes. After the incubation the wells were washed with Thermopol II buffer 3.times. and then subjected to cleavage with TCEP (100 mM) in 400 mM Tris-HCl (pH=8.5) at 65 deg C. for 15 minutes. After the cleavage the wells were washed with the extension reaction buffer (3.times.) and subjected to the next extension reaction, The wells were read out with final readout mixture consisting of 2,3'-dideoxynucleotide mix (labeled)—2.mu.M, Therminator™ II polymerase—250 .mu.g/ml, 10 mM KCl, 10 mM (NH4)2SO.sub.4, 20 mM Tris-HCl, 2 mM MnSO.sub.4, 0.1% Triton-X-10. The structures of these nucleotides are presented in FIG. 23. After labeling cycle the slide was washed with wash/block buffer (5.times.SSC, 0.1% Tween®, 2% BSA), rinsed with water and dried before imaging. Each well was imaged using a prototype sequencing instrument and bases were then called based on the relative intensity of the observed signal. The result of the experiment is presented in FIG. 24.

Example 10

Synthesis Of 2'-Fluoro, 3'-O-Azidomethyl Nucleotides

Figure 25:
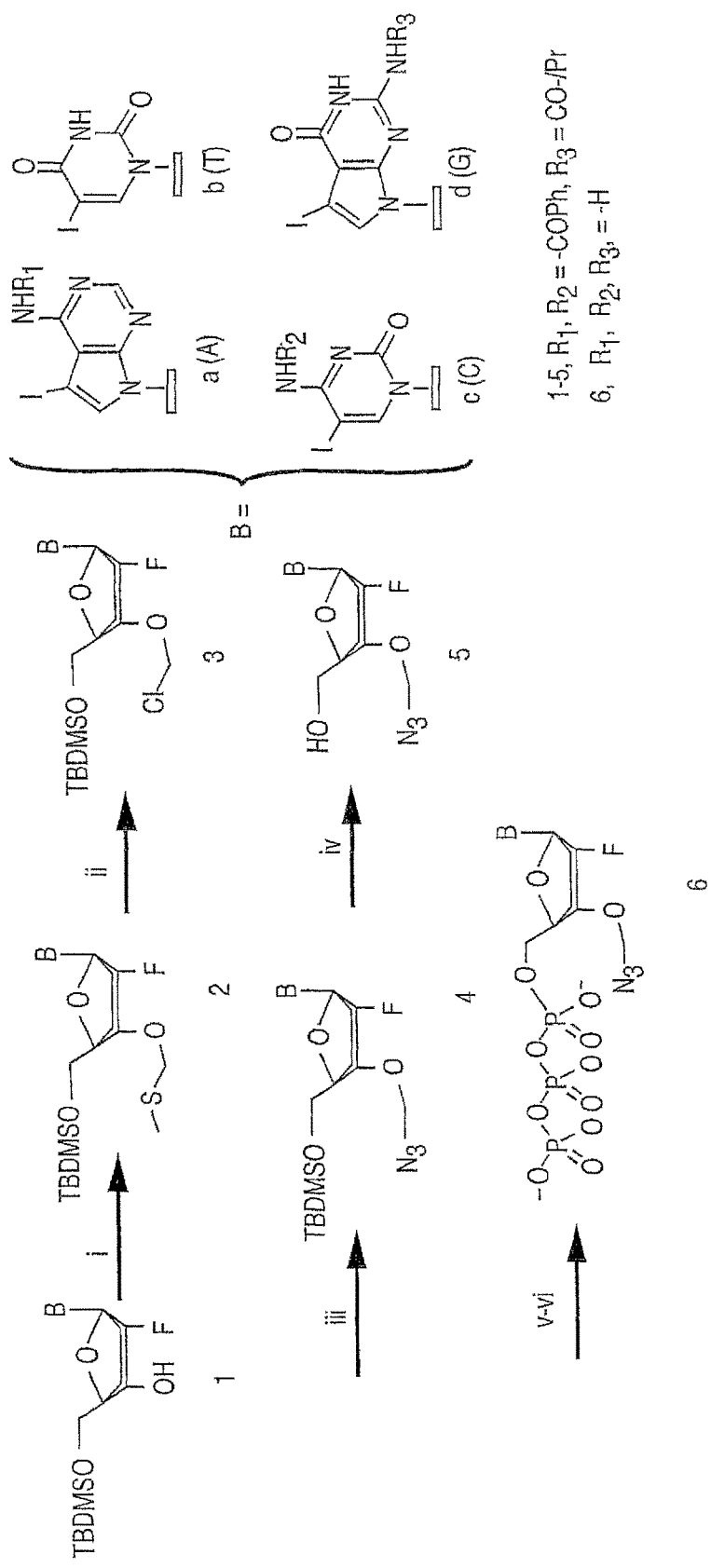
FIG. 25 shows synthesis steps for 2'-fluoro-3'-O-azidomethyl-dNTPs, where the steps comprise the following exemplary conditions (i) DMSO, AcOH, $Ac_2O$, 48 h, (ii) $SO_2Cl_2$, dry $CH_2Cl_2$, 1-2 h; $NaN_1$ in DMF, 3 h; (iv) $NH_4F$ in MeOH, 16-20 h; (v) $(MeO)_3PO$, $POCl_3$ then $(t-Bu_3NH)_4P_2O_7$, TEAB, 1 h; vi) $NH_4OH$.

The synthesis of 2-fluoro-3'-O-azidomethyl-dNTPs is described in FIG. 25. Briefly, reaction of 5'-O-TBDMS-2'-fluoro-2'-deoxynucleosides (1) with a mixture of DMSO, acetic acid, and acetic anhydride installed the 3'-O-methylthiomethyl group (3'-O-MTM, 2), which upon treatment with $SO_2Cl_2$ converted to activated 3'-O—$CH_2Cl$ (3). The 2'-fluoro-3'-O—$CH_2Cl_2$-2'-deoxynucleoside (3) is then treated with $NaN_3$ in dry DMF without purification to convert the 3'-O—$CH_2Cl$ to 3'-O—$CH_2N_3$ (4). 2"-fluoro-3'-O-azidomethyl-2'-deoxynucleosides of A,T, and C (5a-5c) can be obtained in good yield after deprotection of the 5'-O-TBDMS group as described in FIG. 25. In case of 2'-fluoro-3'-O-azidomethyl-2'-deoxybuanosine (G, 5d), the $O^6$-group is protected by diphenycarbamoyl group to increase yield. Finally, the respective nucleosides are phosphorylated using phosphorous oxychloride followed by tetrabutylammonium pyrophosphate in the presence of proton sponge (1,8-dimethylaminonaphthalene) and converted to their respective triphosphates (6).

Example 11

Synthesis Of 2'-Fluoro, 3'-O-Azidomethyl Propargylamino Nucleotides

Figure 26:
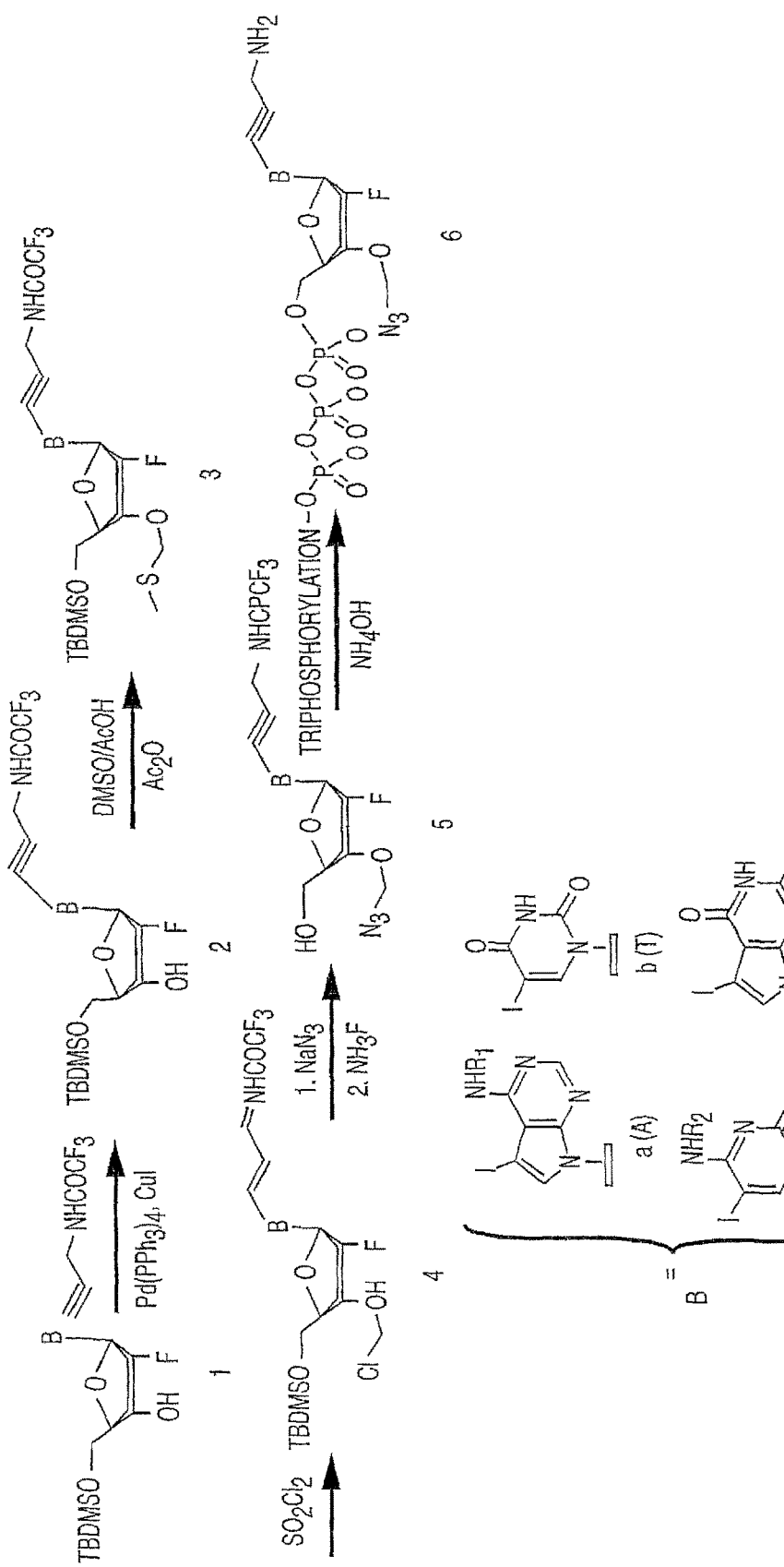
FIG. 26 shows synthesis steps for 2'-fluoro-3'-O-azidomethyl-(propargylamino)-dNTP synthesis.

Synthesis of 2'-fluoro-3'-O-azidomethyl-(propargylamino)-dNTPs is described in FIG. 26. Briefly, reaction of 5'-O-TBDMS-2'-fluoro-(5/7-iodo*)-2'-deoxynucleosides (1) with a mixture of N-trifluoroacetyl-propargylamine, tetraids (triphenylphosphine) palladium (0) and CuI resulted in the formation of 5/7-propargylamido substituted nucleosides (2). In the next step the mixture of DMSO, acetic acid, and acetic anhydride installed the 3'-O-methylthiomethyl group (3O-MTM, 3), which upon treatment with $SO_2Cl_2$ converted to activated 3'-O—$CH_2Cl$ (4). The 2'-fluoro-3'-O—$CH_2Cl$-5/7-propargylamido-2'-deoxynucleosides (4) were then treated with $NaN_3$ in dry DMF without purification to convert the 3'-O—$CH_2Cl$ to 3'-O—$CH_2N_3$. (5) 2'-fluoro-3'-O-azidomethyl-(propargylamino)-2'-deoxynucleosides of A,T, and C (5a-5c) can be obtained in good yield after deprotection of the 5'-O-TBDMS group as described in FIG. 26. In case of 2'-fluoro-3'-O-azidomethyl-2'-deoxybuanosine (G, 5d), the $O^6$-group is protected by diphenycarbamoyl group to increase yield. *5-iodo, 2'-fluoro-2'-deoxy purines and 7-iodo-7-deaza-2'-fluoro-2'-deoxy pyrimidines were used as starting material. The synthesis of these compounds is well known to those skilled in the art.

Example 12

Spectral Crosstalk Calibration

Figure 32A:
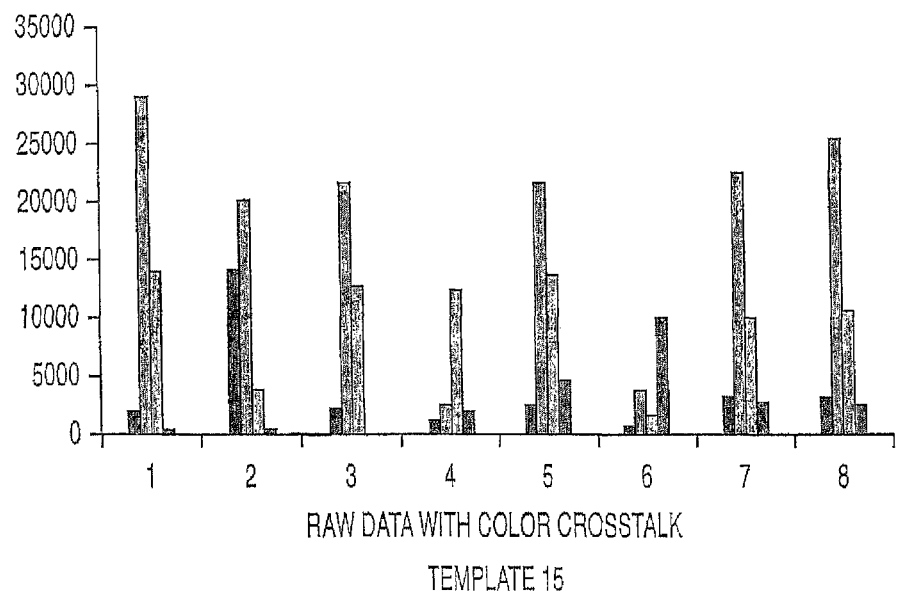
FIG. 32A-B shows sequencing by synthesis probe intensity in four channels (blue, green, yellow, and red) for a spot on a chip. Panel 32A is raw data, and panel 32B is data with the color crosstalk removed.
Figure 32B:
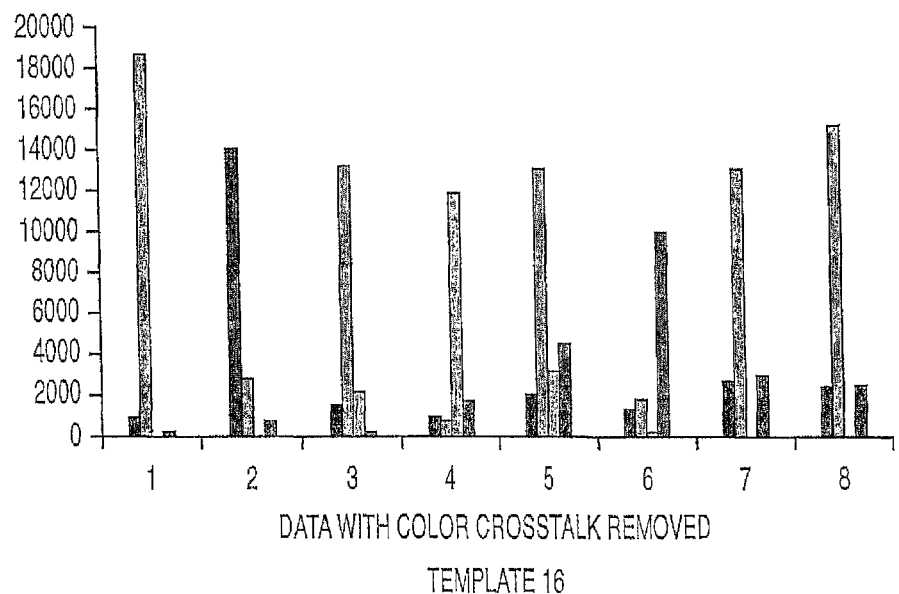

We calibrated the four color detection system of the above described exemplary SBS device using a chip spotted with four separate dyes, one in each of four spots. We then made measurements of the chip in all four channels, calculated the spectral crosstalk factors and constructed the K and $K^{-1}$ matrices. FIG. 32 shows the effect of applying the spectral crosstalk calibration matrix K-1 to raw sequencing data. The data demonstrates that the second base in the sequence would be miscalled as green were the spectral crosstalk calibration not performed.

Example 13

Re-Phasing Sequencing By Synthesis Data

Figure 33A:
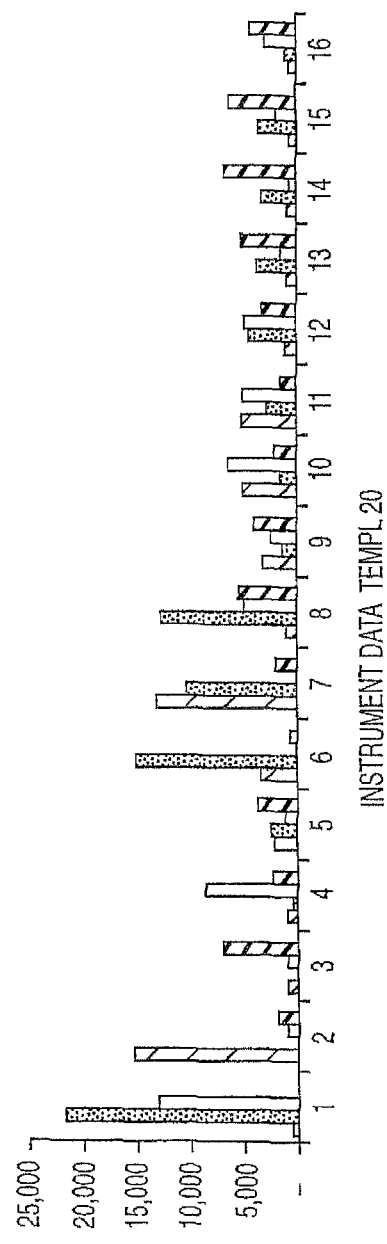
FIG. 33A-B panel 33A shows 16-base-long sequence data, and panel 33B shows the same data after applying the lead/lag compensation algorithm.
Figure 33B:
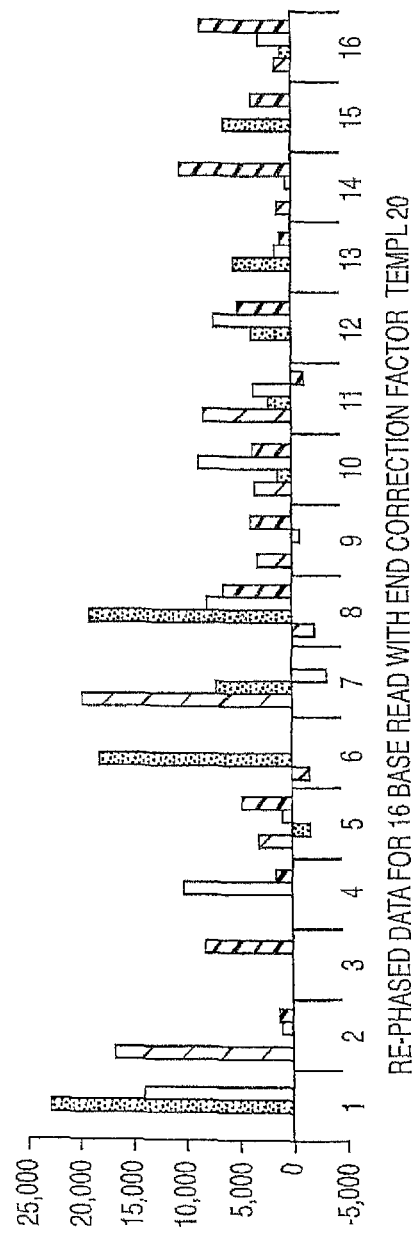

As discussed above, dephasing of sequence data is cumulative and can potentially be significant with longer read lengths. We applied the lead/lag compensation described above to both a 16-base and 25-base sequences containing an AGCT repeat. The results are shown in 33 and 34. FIG. 33A shows the original data captured by the fluorescent detection system and FIG. 33B shows the data after being multiplied by the lead/lag compensation matrix with a lead parameter of 4.5% and a lag parameter of 1%. The relatively high lead parameter was probably due to native nucleotide contamination in the polymerase preparation. FIG. 33 illustrates how the compensation helps to correct miscalls. For example, bases at locations 11, 13 and 15 would be a miscall in the original dephased data, but are correctly called (as are all the other bases) in the rephased data. For the 25-base read in FIG. 34, the lead and lag parameters were 1.2% and 1.5% respectively. Although the lead and lag for this sample were not large enough to create miscalls in the original data (FIG. 34A), the lead/lag correction does make the correct base a stronger signal compared to the other colors (FIG. 34B). While in both, corrected sequences (FIGS. 33B and 27B), the matrix multiplication produces some negative values, these are probably due to noise, and may be ignored as long as they are small values. FIG. 34 shows that we were able to generate data with high fidelity out to 25 bases.

Example 14

Sequencing By Synthesis Data: Extra Washing

In this example, additional washing was done in an attempt to completely remove the cleaving agent prior to the next cycle in sequencing by synthesis. Interestingly, increased washing cycles after cleavage step have only minimal effect on the sequencing performance, as illustrated in the Table below.

| | Rephased Data | | | | | |
|---|---|---|---|---|---|---|
| | 25 nt Templates | | 35 nt Templates | | % Correct | |
| Washes | Lead | Lag | Lead | Lag | Calls | Qa* |
| 24 | 2.56% | 1.69% | 1.75% | 1.12% | 92.0% | 0.822 |
| 48 | 1.55% | 2.32% | 1.20% | 1.80% | 96.0% | 0.862 |
| 100 | 1.40% | 2.80% | 0.95% | 1.65% | 95.5% | 0.826 |

*Qa = Intensity of the correct base signal/intensity of the second highest signal The metric used to measure the dephasing process is the lead percentage derived empirically to compensate for the lead observed in the run. Only at very high wash cycles (i.e. too many washes to be practical) can one improve the base calling accuracy.

Example 15

Sequencing by Synthesis Data: Using a Scavenger

In this example, scavengers were used in an attempt to inhibit any remaining cleaving agent prior to the next cycle in sequencing by synthesis. As noted above, such compounds can be included in the solutions used for sequencing by synthesis (or in a separate additional solution if desired). In this example, the suitable operating concentration for the scavenger in the Extend A/B solutions was explored. Two, different scavengers were used.

A. Cystamine Scavenger

3'-O-azidomethyl nucleotides labeled with dyes on a cleavable disulfide linker were used. A range of scavenger concentrations were tested to determine which concentration is acceptable by the polymerase. The table below shows lead and lag values, and percentage of correct calls for the 3'-O-azidomethy/disulfide chemistry in the absence and in the presence of a first scavenger (cystamine@ 1 mM).

| | AVG Lead [%] | AVG Lag [%] | Correct calls [%] |
|---|---|---|---|
| NO SCAVENGER | 2.0 | 3.1 | 93.7 |
| CYSTAMINE SCAVENGER | 1.1 | 1.9 | 98.7 |

Figure 38:
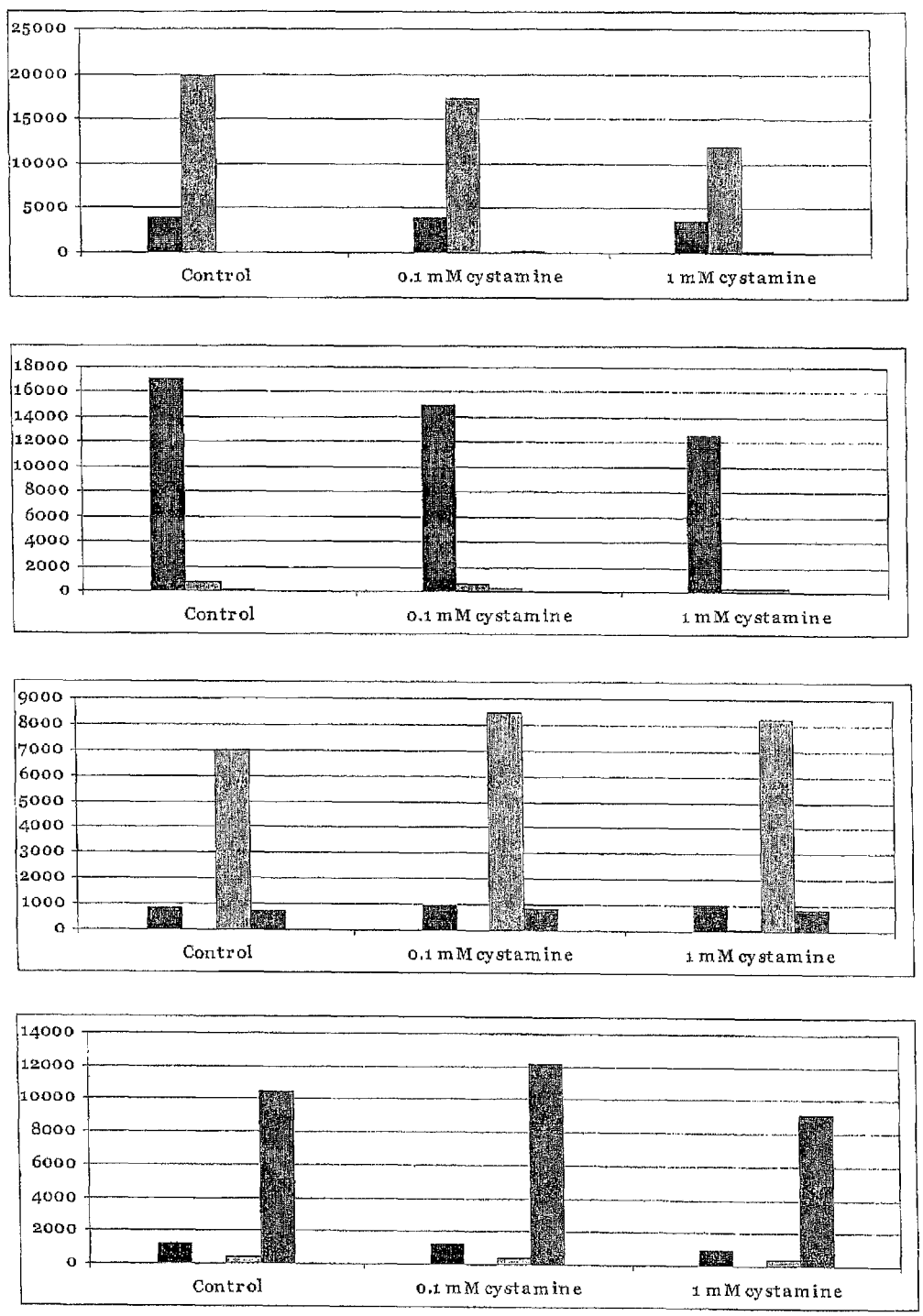
FIG. 38 shows detection of incorporated nucleotides in an extension reaction done in the presence of a first scavenger (cystamine).

It is clear from the data in the table that the use of a scavenger can improve the accuracy of base calling and reduce lead and lag. Importantly, extension reactions performed in the absence and in the presence of this disulfide based scavenger, cystamine, showed the additive does not significantly interfere with the extension reaction (FIG. 38).

B. ATA Scavenger

A second scavenger was also tested, i.e. the azido based scavenger, ATA (11-Azido-3,6,9-trioxaundecan-1-mine). Extension reactions performed in the absence and. in the presence of this azido based scavenger. Nucleotides with 3'-O-azidomethyl groups and with azido based cleavable linkers were used. The results (FIG. 39) show that the additive does not significantly interfere with the extension reaction, Example 16

Synthesis of Disulfide-Dye Labeled 3'-O-Azidomethyl Nucleotide

In this example, a method is described fox synthesizing a nucleotide analogue containing an azidomethyl group on the 3"-OH and a label attached via a disulfide linker (which is cleavable).

Figure 40:
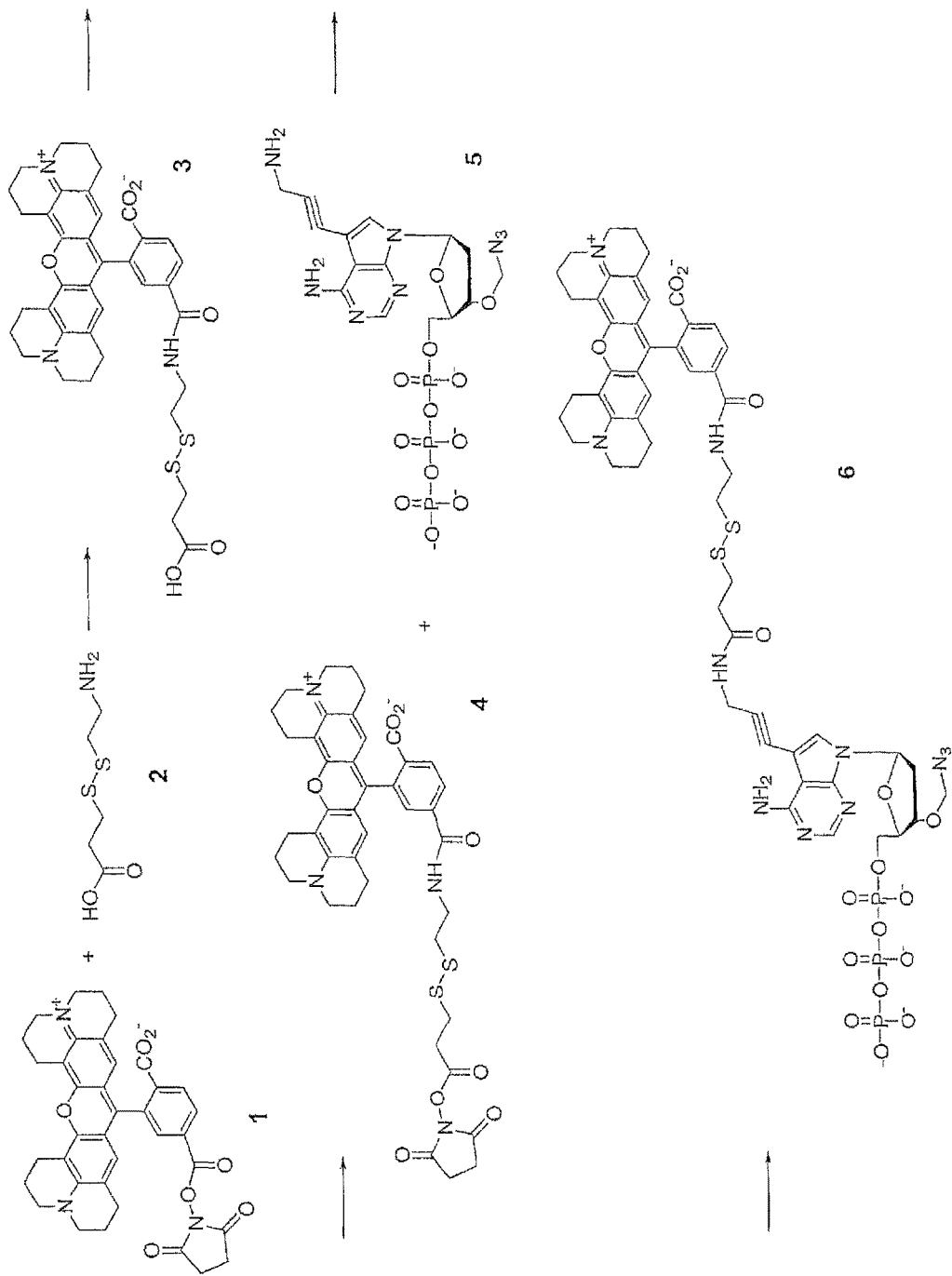
FIG. 40 is a schematic showing one embodiment for the synthesis of 3'-O-azidomethyl, 7-propargylamido-[3-((2-amidoethyl)dithio) propionamido]-6-carboxy-X-rhodamine deoxyadenosine triphosphate.
Figure 41A:
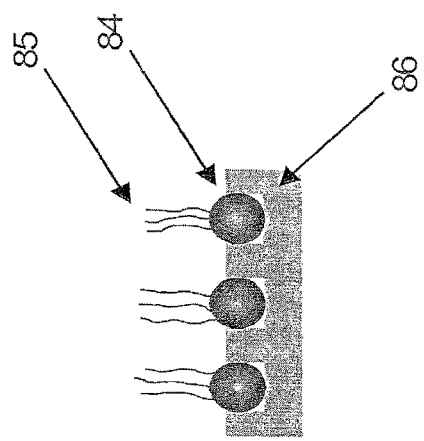
FIG. 41A-D is a schematic showing one embodiment of a hot embossing technique for making slide (or chips) with indentations (which can receive millions to billions of microbeads comprising nucleic acid).
Figure 41B:
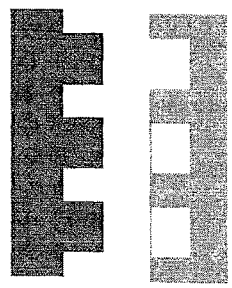
Figure 41C:
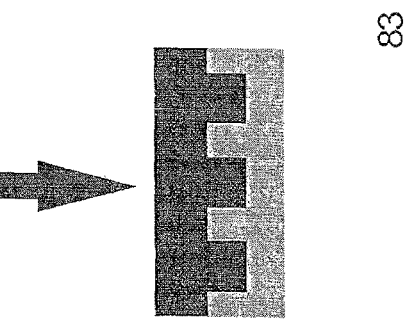
Figure 41D:
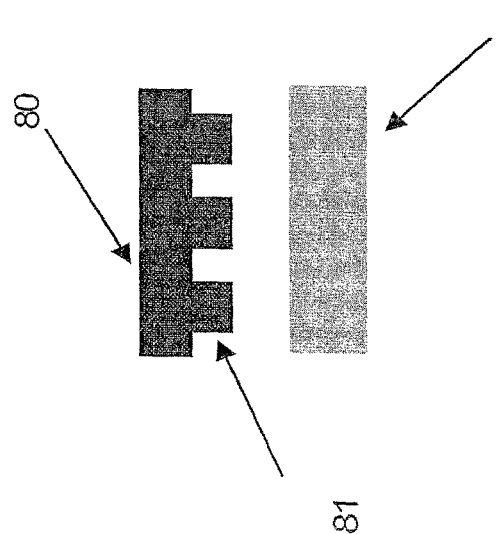

The scheme is shown in FIG. 40. Preparation of the linker buffer solution: 11 mg of 3-(2-aminoethyl)dithio) propionic acid hydrochloride (Prod #22101 from Pierce Biotech company, 2) was dissolved in 100 µl of 0.1 M sodium bicarbonate and 900 µl of acetonitrile. 14 µl of triethylamine was added. To a solution of 6-carboxy-X-rhodamine, succinimidyl ester (6-ROX SE, cat. #C6126, Invitrogen, 1) (158 µl L, 25 mM, 3.96 µmol) in DMF was added the above linker solution (500 µl, 50 mM, 25.0 µmol). The reaction mixture was stirred overnight at room temperature and then 800 µl of TEAB buffer (50 mM, pH 8) was added. The mixture was purified by HPLC and concentrated to give 0.51 µmol of product 3. HPLC method: A, 50 mM triethylammonium bicarbonate (TEAB) buffer, pH=8.0; B, acetonitrile and eluted with a linear gradient of 0-70% B over 35 minutes and at a flow rate of 2 ml/min. The column used was NoaPak C18, 8×100 mm. Retention time for product is 20.5 min. Retention time for hydrolysis of starting material is 18.2 min.

To the above linker-dye conjugate product 3 (0.51 µmol) in 300 µl of DMF was added a solution of 2,6-dimethylaminopyridine (DMAP) (25 mM, 31 µl, 0.77 µmol) and a solution of N,N'-disuccinimidyl carbonate (DSC) (25 mM, 31 µl, 0.77 µmol). The reaction mixture was stirred for one hour at room temperature. 7-propargylamino, 3'-O-azidomethyl-dATP 5 (1.5 µmol) was dissolved in 300 µl of water and 40 µl of tri-n-butylamine was added. All solvents were removed under vacuum and the residue dissolved in 300 µl of DMF. This solution was then added to the activated linker-dye conjugate 4 and the mixture was stirred overnight. The reaction mixture was diluted with 800 µl of TEAB buffer (50 mM, pH 8), purified by HPLC and concentrated. 198 nine! of product 6 was obtained (Retention time for product is 18.5 min).

Example 17

Hot Embossing: Millions to Billions of Beads on Slides or Chips

In one embodiment, the present invention contemplates such micro spheres or beads disposed at high density into microwells or indentations on a surface. It is not intended that the present invention be limited by the nature of the surface or the method of fabrication. Nonetheless, in one embodiment, the present invention contemplates methods of fabrication to generate beads on slides at high density.

In one preferred embodiment, the method relies on the use of a hot embossing technique as schematically shown in FIG. 41. Briefly, the process employs a stamp (80) having projections (81) that will create desired features (83) of desired dimensions when pressed into the polymer (82). The pressing step (B) is typically done with heat and pressure. Thereafter, the stamp is removed and the polymer is cooled (step C). Finally (step D), microspheres (84) containing biomolecules (85) are loaded into the microwells (86). In another embodiment, the method relies on the use of injection molding technique.

It is not intended that the present invention be limited by the nature of the polymer used in performing the hot embossing or molding process. A variety of polymers can be used including but not limited to: PMMA (polymethyl methacrylate), COP (cycloolefine polymer), and COC (cycloolefine copolymer). In the case of polymers that lack natural functional groups on the surface these groups can be grafted on the surface by performing ozonation, oxidation, corona discharge treatment, surface plasma or UV treatment or combination thereof. These fabrication methods allow one to generate substrates with varying features/wells density. Using standard size microscope slides casted out of PMMA or COP polymers one can create wells with 20 um, 5 um, and 1 um diameters. The slides with approximately 5 um features (e.g. between 4.8 um and 5.3 um) contain about 40 million micro wells per slide, while the 1 um feature slide contains about 1 billion features per slide. With the biomolecule-containing microspheres deposited within the microwells, a single slide with such features permits a variety of high throughput, robust assays (e.g. sequencing by synthesis, hybridization, etc.). Nucleic acid fragments representing a large portion of a genome (e.g. human genome) or even an entire genome can be placed on a single slide or handful of slides, and then assayed sequentially as simultaneously.

Example 18

Sequencing: Changing the Spacer Arm Groups or Charge

Figure 42:
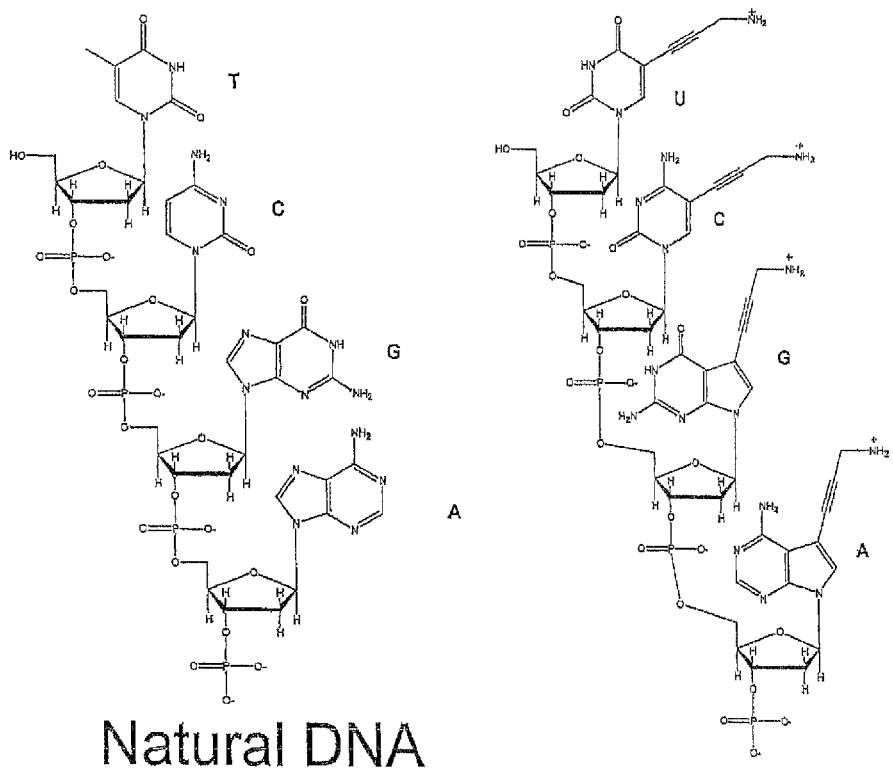
FIG. 42 is a schematic comparing the structure of natural DNA with DNA that was labeled with cleavable terminating nucleotides and then the label was removed. In this particular schematic, the example

When performing sequencing by synthesis process one needs to use labeled nucleotides to be able to read the signal. In most cases these labeled nucleotides after cleavage result in structures that is not of the native nucleotide. For example, if one uses only labeled nucleotides the DNA structure after cleavage of the dye looks like one shown in FIG. 42 (right side). As can be seen, the spacer arm used to attach the dye to the base still remains attached.

Figure 43:
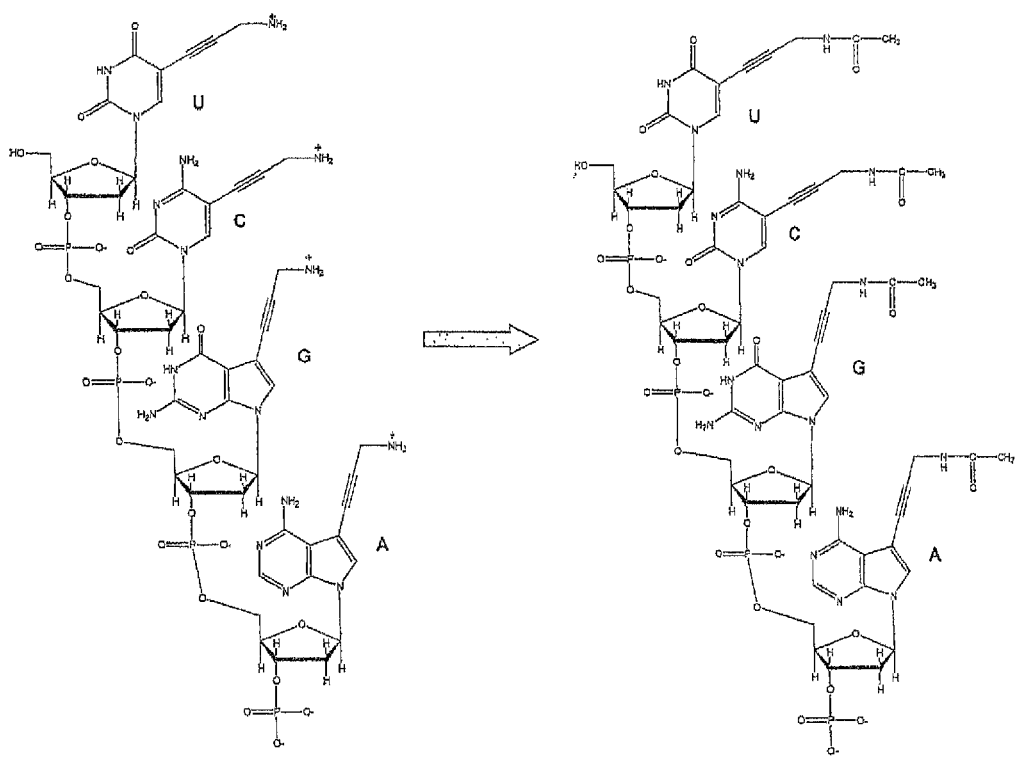
FIG. 43 is a schematic showing a capping step to neutralize the reactive groups after dye cleavage. For amines, one example that could be used is acetylation (such as acetic acid NHS ester); for the thiols (SH) N-methyl-maleimide or iodoacetamide can be used.

In some cases the spacer also carries a charge, such as for example when propargylamino nucleotides are used. In the case of disulfide bonds what remains after cleavage is the spacer arm with thiol (SH) group attached. The presence of these spacers and groups may affect the ability of the sequencing polymerases to incorporate the subsequent nucleotide. One approach to minimize or eliminate this undesirable effect is to change the reactivity of the spacer arm groups or their charge by performing a chemical "capping" step, where specific reagent is added to react only with groups on. the spacer arm. This is shown schematically in FIG. 43.

Example 19

Sequencing by Synthesis Data: Using Labeled and Unlabeled Nucleotides

As noted previously, the presence of the linkers, spacers and groups on nucleotides may affect the ability of the sequencing polymerases to incorporate the subsequent nucleotide. One approach to minimize or eliminate this undesirable effect is to reduce the amount of labeled nucleotides incorporated in the template. Reducing the amount of labeled nucleotides that are incorporated can be accomplished by reducing the concentration of labeled nucleotides in the extension solution, and/or mixing labeled nucleotides (reversible terminators) with non-labeled reversibly terminating nucleotides. In contrast to labeled nucleotides, non-labeled reversible terminator nucleotides after cleavage convert to native nucleotide.

Figure 44:
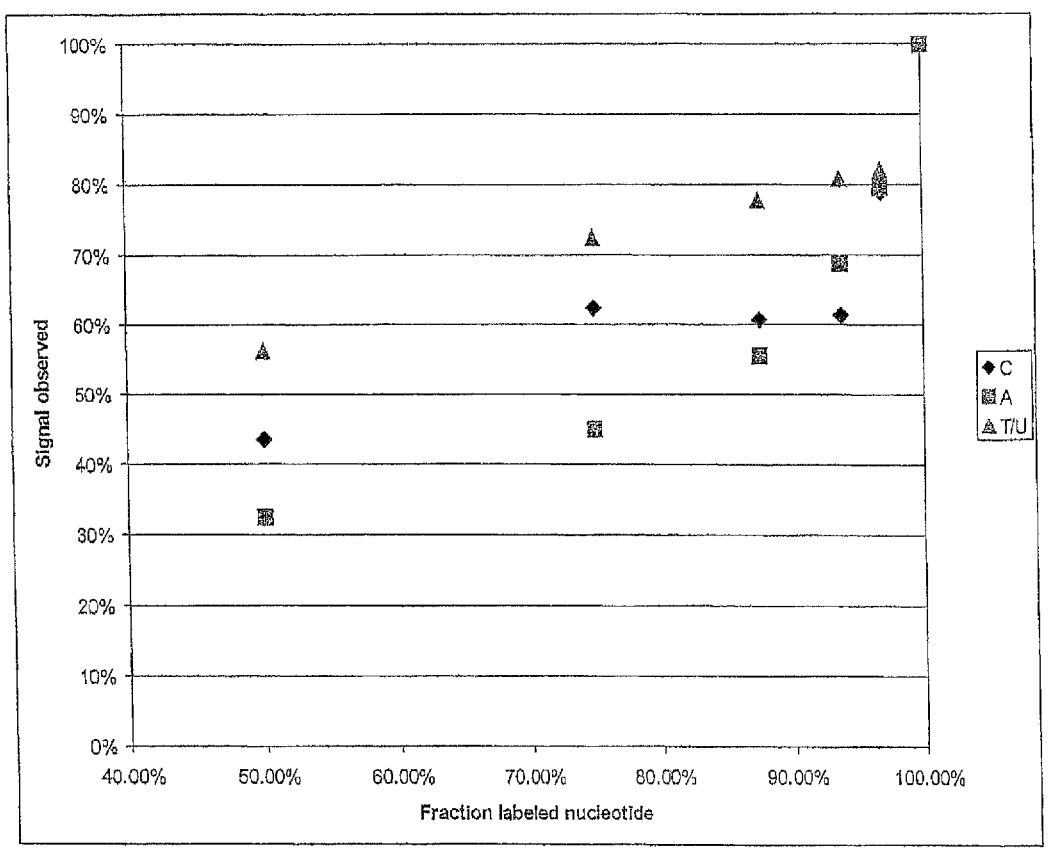
FIG. 44 shows the fluorescence signal from incorporated nucleotide analogues observed as a function of the composition of the extension mixture. In this case labeled nucleotides (3'-O-allyl) were supplemented with up to 1 equivalent of non-labeled terminators (also 3'-O-allyl). The extension was performed and the resulting signal measured. The response is different for different nucleotides tested and is a function of polymerase bias.
Figure 45A:
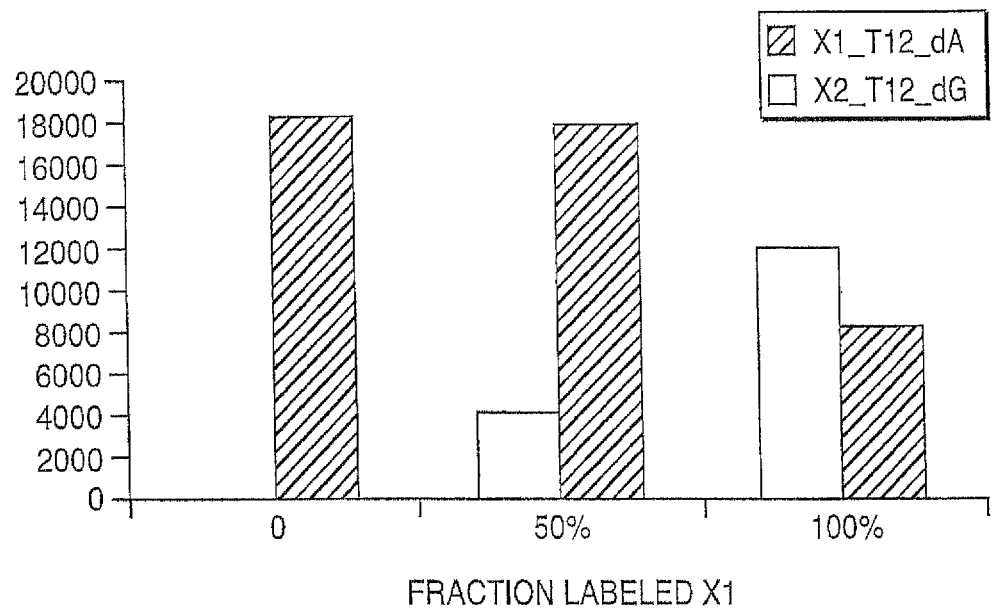
FIGS. 45A-D show the results for two subsequent extensions performed on 4 different DNA templates (FIGS. 45A, 45B, 45C, 45D). For extension 1, various amounts of labeled reversible terminating nucleotides were used (0, 50% and 100%). After cleavage, second extension was performed and the resulting signals were measured (bars on the right in each set). As can be seen the use of 100% labeled nucleotides in cycle 1 reduces the signal in subsequent cycle to by 50% compared to non-labeled reversible terminators.
Figure 45B:
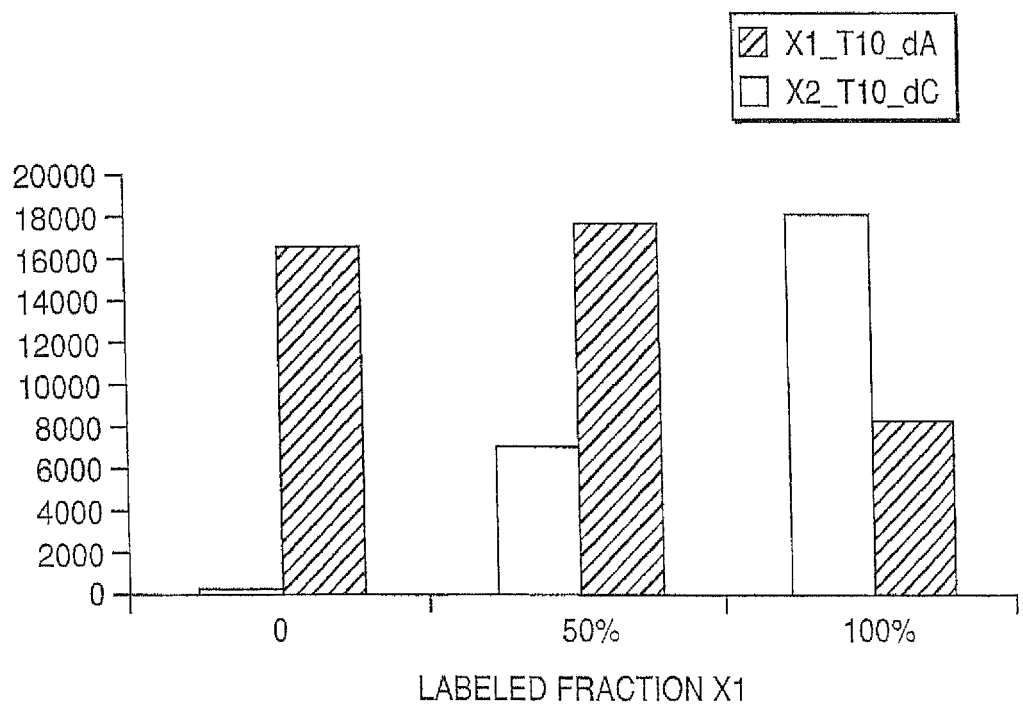
Figure 45C:
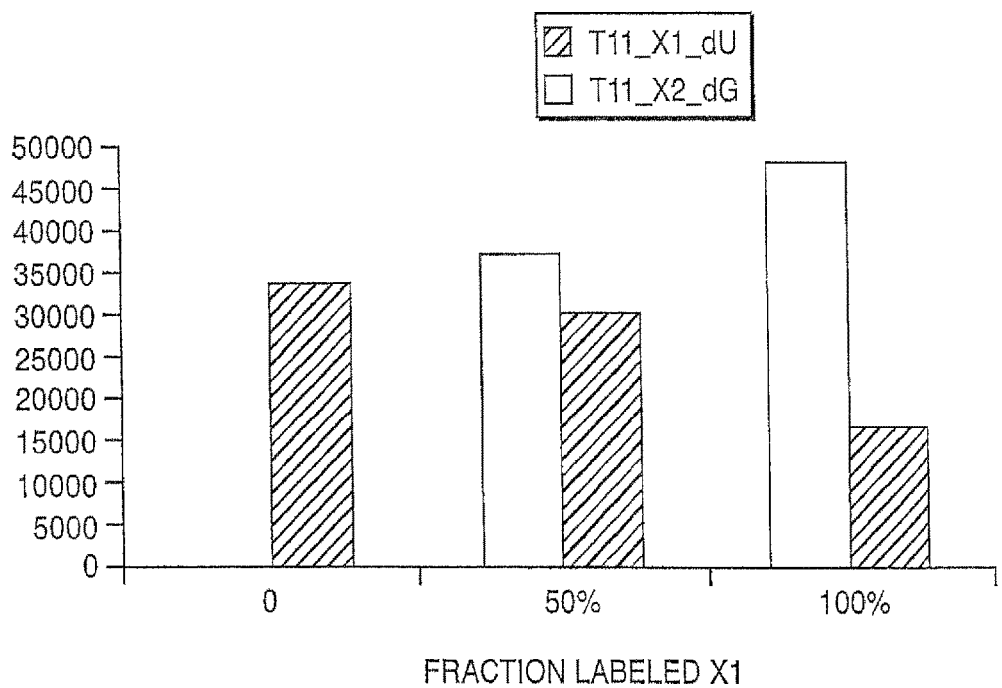
Figure 45D:
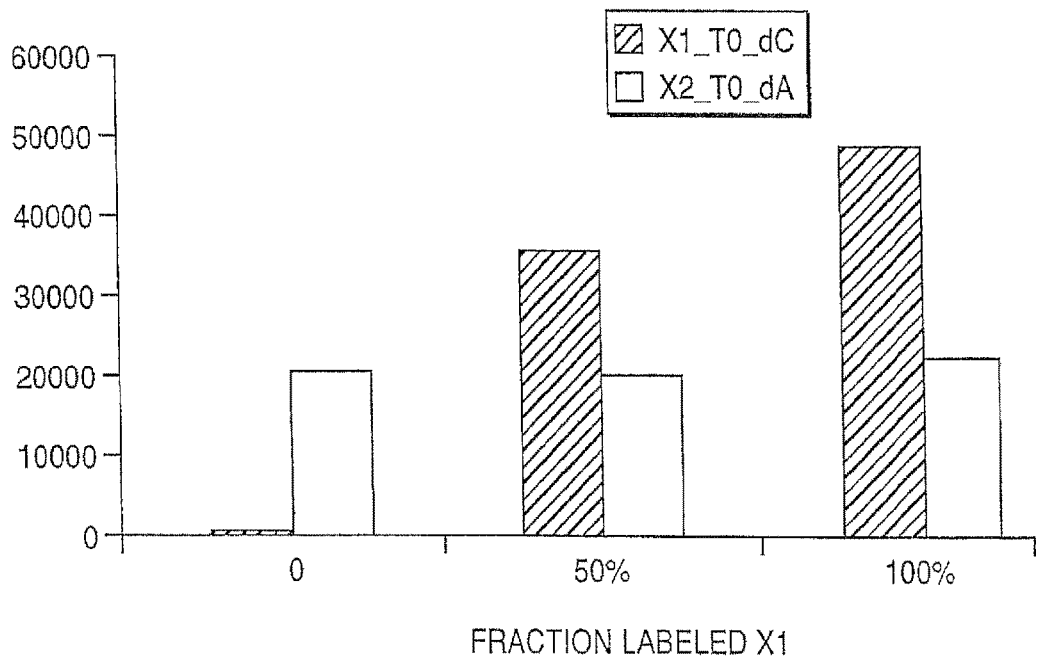
Figure 46:
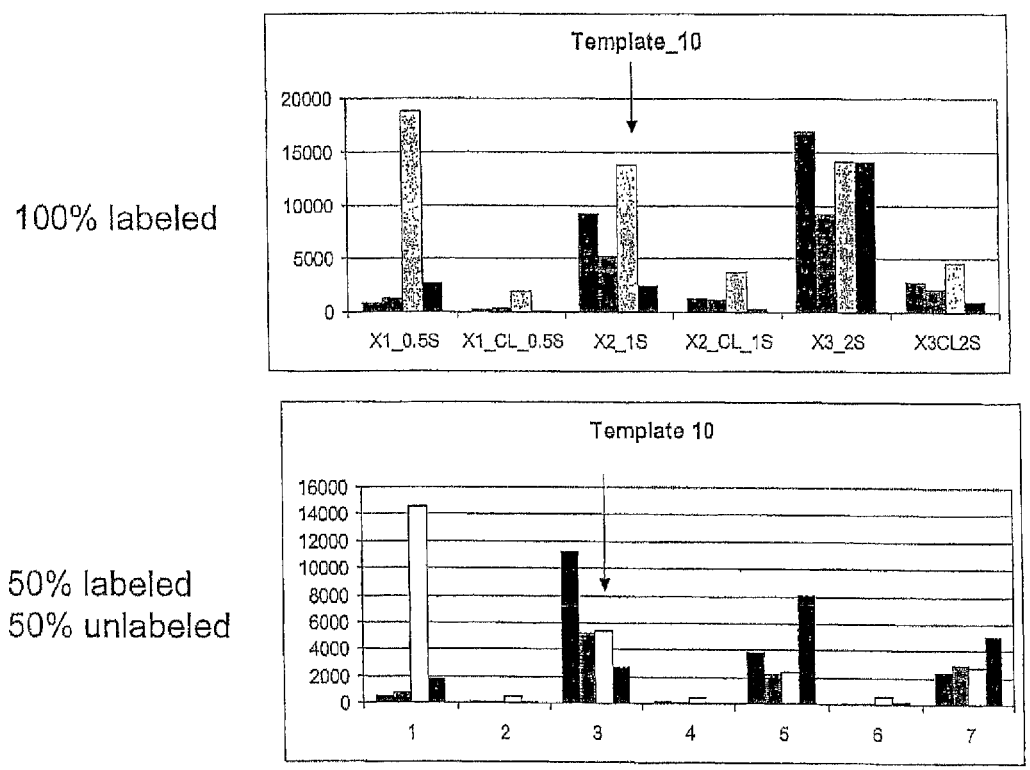
FIG. 46 shows that improvements in sequencing performance can be achieved with a mixture of labeled/unlabeled nucleotides. Using such a nucleotide mixture results in correct base calls.

The effect of reducing the concentration of labeled nucleotides can be best observed by measuring the ability of polymerase to incorporate the subsequent nucleotides efficiently and with high fidelity. This is shown in FIGS. 44, 45 and 46.

Figure 47:
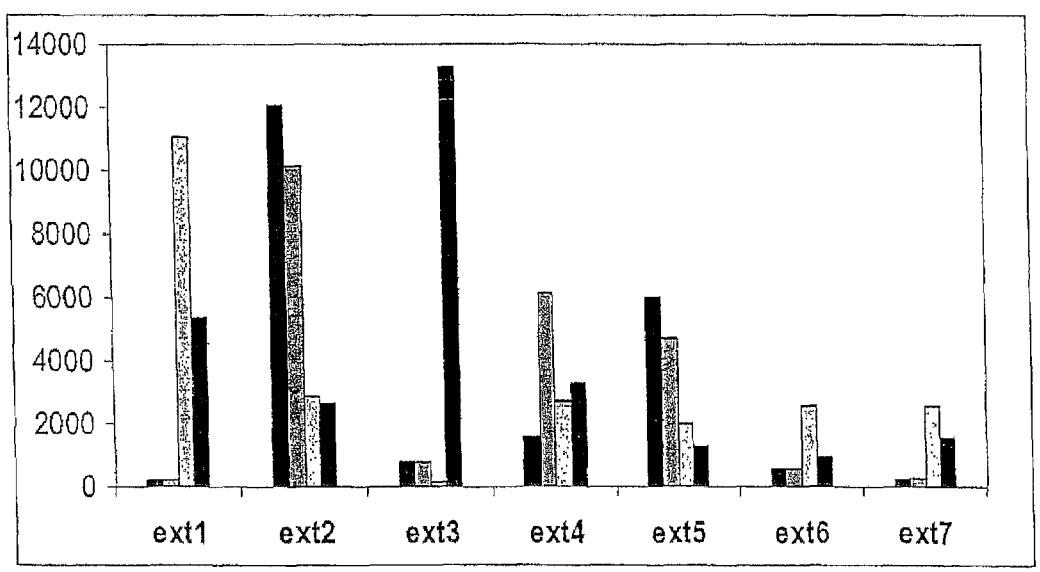
FIG. 47 shows the signal decline observed using labeled nucleotides in sequencing.
Figure 48A:
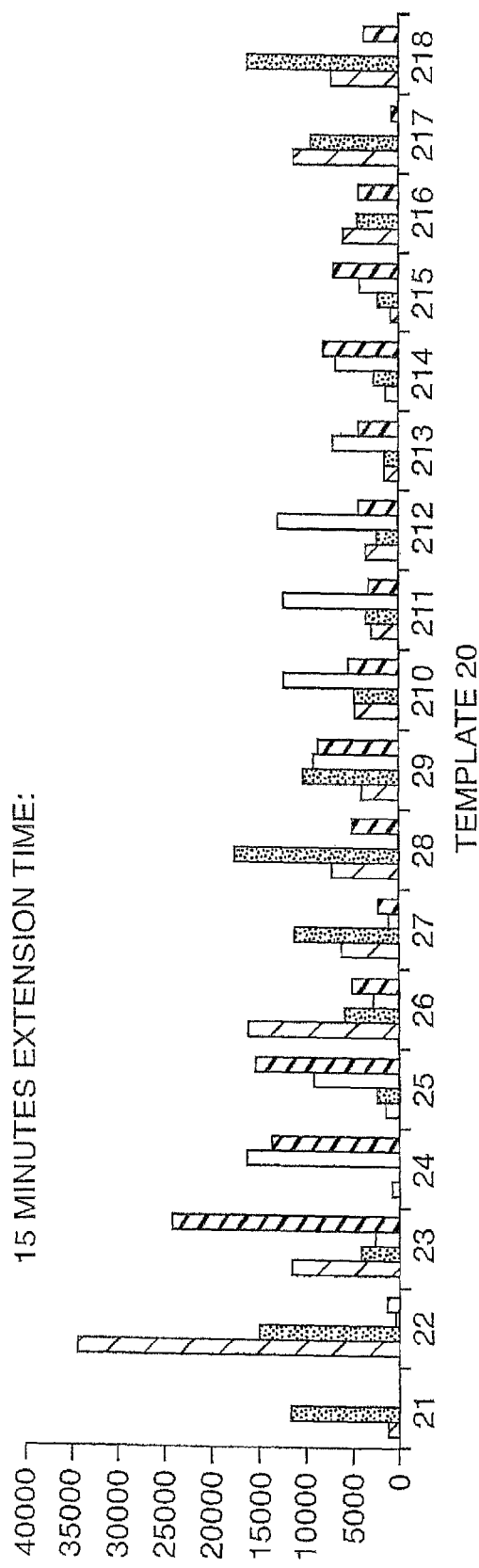
Figure 48B:
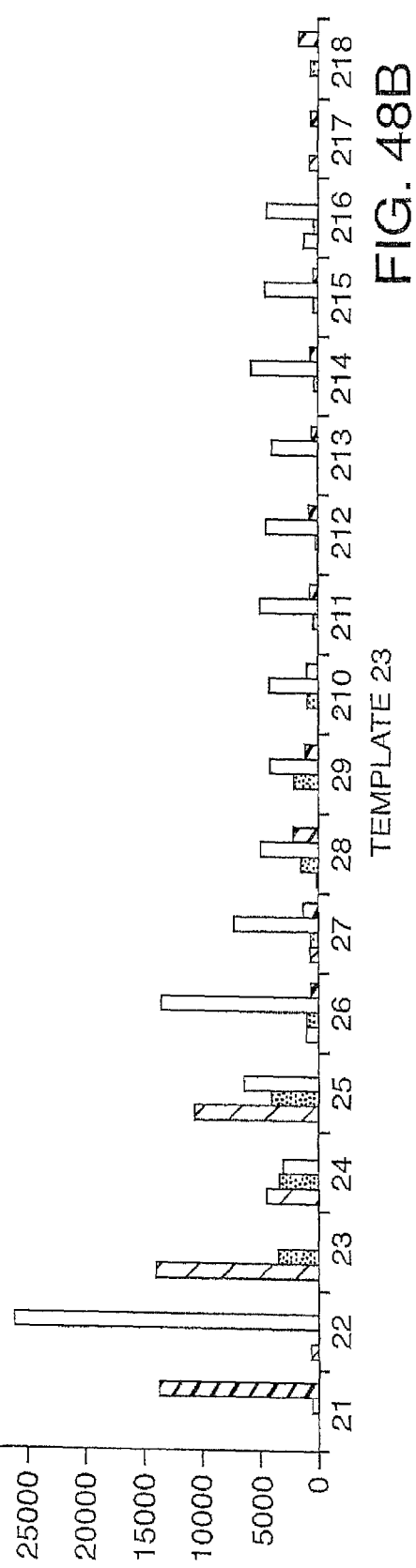
Figure 50:
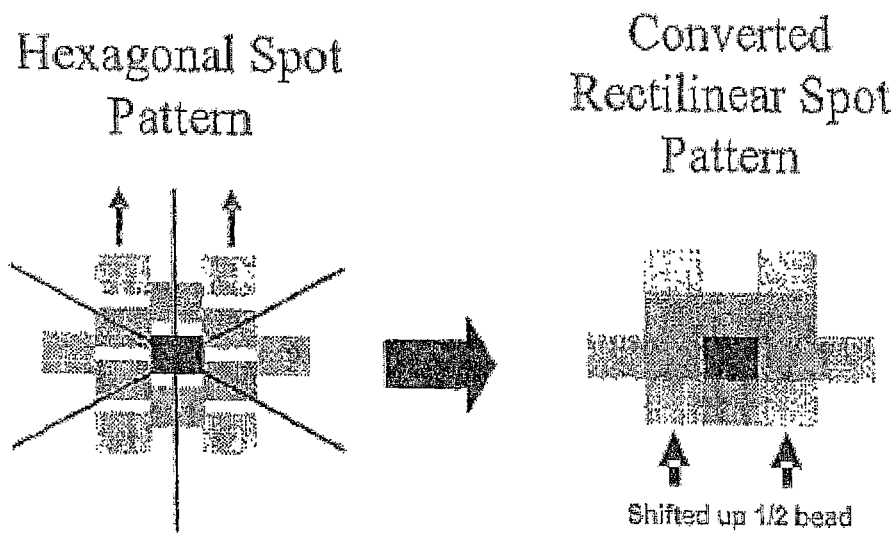
FIG. 50 shows a visual representation of a solution to the neighbor influence problem from spot data that is in hexagonal form. The data is first put into a rectilinear array by shifting the even vertical columns up by ½ of a pixel. A two-dimensional rectilinear matrix, whose elements represent the magnitude of each spot in the original image of the hexagonal array of spots, may be used.

When the amount of labeled nucleotides is reduced, this results in reduction of fluorescent signal as shown in FIG. 47 (where only labeled nucleotides are used in successive extension reactions). In principle only the amount of signal necessary to decode the nucleotide is required. In addition to changing the ratio of labeled and unlabeled nucleotides and optimizing it for particular polymerase, one can also adjust the time of extension (e.g. reduce extension times down to 1-2 minutes) to gain even better control on the signal/incorporation ratio of labeled nucleotides. This is shown in FIGS. 48 and 49 where additional performance improvement is achieved upon reducing extension time (to 2 minutes and 1 minute, respectively).

All publications and patents mentioned in the above specification are herein incorporated by reference. Various modifications and variations of the described methods and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled in the art and in fields related thereto are intended to be within the scope of the following claims.

We claim:

1. A labeled reversible terminator comprising a nucleotide analogue of dUTP having a 3'-O group and a label, wherein the label is Rhodamine 6G and is attached to the nucleotide analogue of dUTP though a cleavable linker comprising a disulfide bond, and wherein a removable chemical moiety caps the 3'-O group, wherein said labeled reversible terminator is in a mixture in solution with an unlabeled reversible terminator comprising a nucleotide analogue of dUTP, wherein the concentration of the unlabeled nucleotide analogue of dUTP is present in said solution at a higher concentration than the labeled nucleotide analogue of dUTP.

2. The labeled reversible terminator of claim 1, wherein said mixture further comprises labeled and unlabeled reversible terminator nucleotide analogues of dCTP and dGTP.

3. The labeled reversible terminator of claim 2, wherein said unlabeled nucleotide analogues are present at a concentration between 1 uM and 100 uM.

4. The labeled reversible terminator of claim 3, wherein said labeled nucleotide analogues are present at a concentration between 1 nM and 1 uM.

5. A labeled reversible terminator comprising a nucleotide analogue of dGTP having a 3'-O group and a label, wherein the label is Cy5 and is attached to the nucleotide analogue of dGTP though a cleavable linker comprising a disulfide bond, and wherein a removable chemical moiety caps the 3'-O group, wherein said labeled reversible terminator is in a mixture in solution with an unlabeled reversible terminator comprising a nucleotide analogue of dGTP, wherein the concentration of the unlabeled nucleotide analogue of dGTP is present in said solution at a higher concentration than the labeled nucleotide analogue of dGTP.

6. The labeled reversible terminator of claim 5, wherein said mixture further comprises labeled and unlabeled reversible terminator nucleotide analogues of dCTP and dATP.

7. The labeled reversible terminator of claim 6, wherein said unlabeled nucleotide analogues are present at a concentration between 1 uM and 100 uM.

8. The labeled reversible terminator of claim 7, wherein said labeled nucleotide analogues are present at a concentration between 1 nM and 1 uM.

\* \* \* \* \*

SEQUENCE LISTING

<160> NUMBER OF SEQ ID NOS: 12

<210> SEQ ID NO 1
<211> LENGTH: 53
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'NH2
<220> FEATURE:
<221> NAME/KEY: stem_loop
<222> LOCATION: (26)..(53)

<400> SEQUENCE: 1
catcactctc acatgtcaga ctcgagctga attccgcgtt cgcggaattc agc    53

<210> SEQ ID NO 2
<211> LENGTH: 53
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'NH2
<220> FEATURE:
<221> NAME/KEY: stem_loop
<222> LOCATION: (26)..(53)

<400> SEQUENCE: 2
gcgaaaaaga agagatgggg tgaaggctga attccgcgtt cgcggaattc agc    53

<210> SEQ ID NO 3
<211> LENGTH: 53
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'NH2
<220> FEATURE:
<221> NAME/KEY: stem_loop
<222> LOCATION: (26)..(53)

<400> SEQUENCE: 3
tgatttcgct tttaccctac actctgctga attccgcgtt cgcggaattc agc    53

<210> SEQ ID NO 4
<211> LENGTH: 53
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'NH2
<220> FEATURE:
<221> NAME/KEY: stem_loop
<222> LOCATION: (26)..(53)

<400> SEQUENCE: 4
atcgccctat attctaactt gactcgctga attccgcgtt cgcggaattc agc    53

```
<210> SEQ ID NO 5
<211> LENGTH: 12
<212> TYPE: DNA
<213> ORGANISM: Artificial Sequence
<220> FEATURE:
<223> OTHER INFORMATION: Synthetic

<400> SEQUENCE: 5
actgactgac tg                                                        12

<210> SEQ ID NO 6
<211> LENGTH: 25
<212> TYPE: DNA
<213> ORGANISM: Artificial Sequence
<220> FEATURE:
<223> OTHER INFORMATION: Synthetic

<400> SEQUENCE: 6
tcgagtctga catgtgagag tgatg                                          25

<210> SEQ ID NO 7
<211> LENGTH: 25
<212> TYPE: DNA
<213> ORGANISM: Artificial Sequence
<220> FEATURE:
<223> OTHER INFORMATION: Synthetic

<400> SEQUENCE: 7
cttcacccca tctcttcttt ttcgc                                          25

<210> SEQ ID NO 8
<211> LENGTH: 25
<212> TYPE: DNA
<213> ORGANISM: Artificial Sequence
<220> FEATURE:
<223> OTHER INFORMATION: Synthetic

<400> SEQUENCE: 8
agagtgtagg gtaaaagcga aatca                                          25

<210> SEQ ID NO 9
<211> LENGTH: 25
<212> TYPE: DNA
<213> ORGANISM: Artificial Sequence
<220> FEATURE:
<223> OTHER INFORMATION: Synthetic

<400> SEQUENCE: 9
gagtcaagtt agaatatagg gcgat                                          25

<210> SEQ ID NO 10
<211> LENGTH: 12
<212> TYPE: DNA
<213> ORGANISM: Artificial Sequence
<220> FEATURE:
<223> OTHER INFORMATION: Synthetic

<400> SEQUENCE: 10
agctagctag ct                                                        12

<210> SEQ ID NO 11
<211> LENGTH: 10
<212> TYPE: DNA
<213> ORGANISM: Artificial Sequence
<220> FEATURE:
<223> OTHER INFORMATION: Synthetic
```

```
<400> SEQUENCE: 11
tcgtcgtcga                                                              10

<210> SEQ ID NO 12
<211> LENGTH: 18
<212> TYPE: DNA
<213> ORGANISM: Artificial Sequence
<220> FEATURE:
<223> OTHER INFORMATION: Synthetic

<400> SEQUENCE: 12
tctcgacgtc gacgacga                                                     18
```